United States Patent
Laurent et al.

(10) Patent No.: US 9,284,350 B2
(45) Date of Patent: Mar. 15, 2016

(54) IAP BIR DOMAIN BINDING COMPOUNDS

(75) Inventors: Alain Laurent, Montreal (CA); Melanie Proulx, Montreal (CA); Yannick Rose, Montreal (CA); Irina Denissova, Montreal (CA); Kenza Dairi, Cambridgeshire (GB); Scott Jarvis, Longueuil (CA); James B. Jaquith, Pincourt (CA)

(73) Assignee: Pharmascience Inc., Montréal, Québec (CA)

( * ) Notice: Subject to any disclaimer, the term of this patent is extended or adjusted under 35 U.S.C. 154(b) by 116 days.

(21) Appl. No.: 13/578,574

(22) PCT Filed: Feb. 11, 2011

(86) PCT No.: PCT/IB2011/000264
§ 371 (c)(1),
(2), (4) Date: Oct. 29, 2012

(87) PCT Pub. No.: WO2011/098904
PCT Pub. Date: Aug. 18, 2011

(65) Prior Publication Data
US 2013/0040892 A1 Feb. 14, 2013

Related U.S. Application Data

(60) Provisional application No. 61/303,809, filed on Feb. 12, 2010, provisional application No. 61/415,638, filed on Nov. 19, 2010.

(51) Int. Cl.
*C07K 5/062* (2006.01)
*A61K 38/00* (2006.01)

(52) U.S. Cl.
CPC .......... *C07K 5/06026* (2013.01); *C07K 5/06034* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,750,646 A | 5/1998 | Coy et al. | |
| 6,110,691 A | 8/2000 | Wang et al. | |
| 6,423,689 B1 | 7/2002 | Booth et al. | |
| 6,608,026 B1 | 8/2003 | Wang et al. | |
| 6,992,063 B2 | 1/2006 | Shi | |
| 7,041,784 B2 | 5/2006 | Wang et al. | |
| 7,094,758 B2 | 8/2006 | Wang et al. | |
| 7,229,617 B2 | 6/2007 | Nasoff et al. | |
| 7,244,851 B2 | 7/2007 | Cohen et al. | |
| 7,309,792 B2 | 12/2007 | Harran et al. | |
| 7,419,975 B2 | 9/2008 | Palermo et al. | |
| 7,456,209 B2 | 11/2008 | Condon et al. | |
| 7,517,906 B2 | 4/2009 | Condon et al. | |
| 7,772,177 B2 | 8/2010 | Jarvis et al. | |
| 2004/0180828 A1 | 9/2004 | Shi et al. | |
| 2005/0234042 A1 | 10/2005 | Palermo et al. | |
| 2006/0025347 A1 | 2/2006 | Condon et al. | |
| 2006/0194741 A1 | 8/2006 | Condon et al. | |
| 2006/0211627 A1 | 9/2006 | Reed et al. | |
| 2006/0258581 A1 | 11/2006 | Reed et al. | |
| 2006/0264379 A1 * | 11/2006 | Jarvis et al. | 514/18 |
| 2007/0032437 A1 | 2/2007 | Shi et al. | |
| 2007/0042428 A1 | 2/2007 | Springs et al. | |
| 2007/0093428 A1 * | 4/2007 | Laurent | 514/17 |
| 2007/0093429 A1 | 4/2007 | Laurent et al. | |
| 2007/0219140 A1 | 9/2007 | Laurent et al. | |
| 2008/0069812 A1 | 3/2008 | Boudreault et al. | |
| 2008/0089896 A1 | 4/2008 | Wang et al. | |
| 2008/0207525 A1 | 8/2008 | Boudreault et al. | |
| 2009/0192140 A1 * | 7/2009 | Laurent et al. | 514/212.04 |

(Continued)

FOREIGN PATENT DOCUMENTS

| CA | 2491041 A1 | 1/2004 |
|---|---|---|
| CA | 2582734 A1 | 9/2005 |

(Continued)

OTHER PUBLICATIONS

Arnt et al., "Synthetic Smac/DIABLO peptides enhance the effects of chemotherapeutic agents by binding XIAP and cIAP1 in Situ," *J. Biol. Chem.*, 277(46): 44236-44243 (2002).
Bertrand et al., "cIAP1 and cIAP2 facilitate cancer cell survival by functioning as E3 ligases that promote RIP1 ubiquitination," *Mol. Cell*, 30: 689-700 (2008).
Bucher et al., *Helv. Chim. Acta.*, 78(4):935-46 (1995).
Chai et al., "Structural and biochemical basis of apoptotic activation by Smac/DIABLO," *Nature*, 406: 855-62 (2000).
Chauhan et al., "Targeting mitochondrial factor Smac/DIABLO as therapy for multiple myeloma (MM)," *Blood*, 109(3): 1220-7 (2007).
Chen et al., "Design, synthesis, and characterization of new embelin derivatives as potent inhibitors of X-linked inhibitor of apoptosis protein," *Bioorg. Med. Chem. Lett.*, 16(22): 5805-5808 (2006).

(Continued)

Primary Examiner — Maury Audet
(74) Attorney, Agent, or Firm — Leydig, Voit & Mayer, Ltd.

(57) ABSTRACT

A compound of Formula 1: (I) or salt thereof, as well as methods of making compounds of Formula 1, methods of using compounds of Formula 1 to treat proliferative disorders such as cancer, and related compounds, composition, and methods.

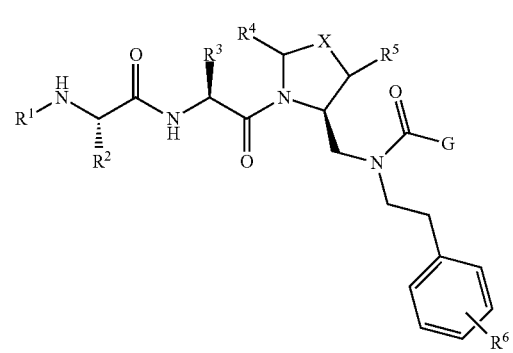

39 Claims, No Drawings

(56) References Cited

U.S. PATENT DOCUMENTS

| | | | |
|---|---|---|---|
| 2011/0117081 A1* | 5/2011 | Laurent et al. | 424/130.1 |
| 2011/0171171 A1* | 7/2011 | Laurent et al. | 424/85.2 |
| 2013/0040892 A1* | 2/2013 | Laurent et al. | 514/18.9 |

FOREIGN PATENT DOCUMENTS

| | | | |
|---|---|---|---|
| CA | 2560162 A1 | | 10/2005 |
| CA | 2574040 A1 | | 2/2006 |
| EP | 1883627 | * | 2/2008 |
| JP | 61-183297 A | | 8/1986 |
| JP | 04-208299 A | | 7/1992 |
| WO | WO 92/02545 A1 | | 2/1992 |
| WO | WO 92/12168 A1 | | 7/1992 |
| WO | WO 00/17263 A1 | | 1/2000 |
| WO | WO 02/26775 A2 | | 4/2002 |
| WO | WO 02/30959 A2 | | 4/2002 |
| WO | WO 02/096930 A2 | | 12/2002 |
| WO | WO 03/086470 A2 | | 10/2003 |
| WO | WO 2004/005248 A1 | | 1/2004 |
| WO | WO 2005/069888 A2 | | 8/2005 |
| WO | WO 2005/074989 A2 | | 8/2005 |
| WO | WO 2005/084317 A2 | | 9/2005 |
| WO | WO 2005/094818 A1 | | 10/2005 |
| WO | WO 2005/097791 A1 | | 10/2005 |
| WO | WO 2006/010118 A2 | | 1/2006 |
| WO | WO 2006/014361 A1 | | 2/2006 |
| WO | WO 2006/017295 A2 | | 2/2006 |
| WO | WO 2006/020060 A2 | | 2/2006 |
| WO | WO 2006/069063 A1 | | 6/2006 |
| WO | WO 2006/113376 A1 | | 10/2006 |
| WO | WO 2006/122408 A1 | | 11/2006 |
| WO | WO 2006/128455 A2 | | 12/2006 |
| WO | WO 2006/133147 A2 | | 12/2006 |
| WO | WO 2007/048224 A1 | | 5/2007 |
| WO | WO 2007/075525 A2 | | 7/2007 |
| WO | WO 2007/101347 A1 | | 9/2007 |
| WO | WO 2007/104162 A1 | | 9/2007 |
| WO | WO 2007/106192 A2 | | 9/2007 |
| WO | WO 2007/130626 A2 | | 11/2007 |
| WO | WO 2007/131366 A1 | | 11/2007 |
| WO | WO 2007/136921 A2 | | 11/2007 |
| WO | WO 2008/014229 A2 | | 1/2008 |
| WO | WO 2008/014236 A1 | | 1/2008 |
| WO | WO 2008/014238 A2 | | 1/2008 |
| WO | WO 2008/014240 A2 | | 1/2008 |
| WO | WO 2008/014252 A2 | | 1/2008 |
| WO | WO 2008/014263 A2 | | 1/2008 |
| WO | WO 2008/016893 A1 | | 2/2008 |
| WO | WO 2008/045905 A1 | | 4/2008 |
| WO | WO 2008/057172 A2 | | 5/2008 |
| WO | WO 2008/067280 A2 | | 6/2008 |
| WO | WO 2008/073306 A1 | | 6/2008 |
| WO | WO 2008/079735 A1 | | 7/2008 |
| WO | WO 2008/085610 A1 | | 7/2008 |
| WO | WO 2008/128121 A1 | | 10/2008 |
| WO | WO 2008/128171 A2 | | 10/2008 |
| WO | WO 2008/134679 A1 | | 11/2008 |
| WO | WO 2008/144925 A1 | | 12/2008 |
| WO | WO 2009/060292 A2 | | 5/2009 |
| WO | WO 2009/136290 A1 | | 11/2009 |
| WO | WO 2009/140447 A1 | | 11/2009 |
| WO | WO 2009/152824 A1 | | 12/2009 |
| WO | WO 2009/155709 A1 | | 12/2009 |
| WO | WO 2010/015090 A1 | | 2/2010 |
| WO | WO 2010/019035 A2 | | 2/2010 |
| WO | WO 2010/031171 A1 | | 3/2010 |

OTHER PUBLICATIONS

Eckelman et al., "The mechanism of peptide-binding specificity of IAP BIR domains," *Cell Death Differ.*, 15(5): 920-8 (2008).
Elmore et al., "Inhibitors of Anti-apoptotic Proteins for Cancer Therapy," *Annual Rep. Med. Chem.*, 40: 245-62 (2006).
Franklin et al., "Structure and function analysis of peptide antagonists of melanoma inhibitor of apoptosis (ML-IAP)," *Biochemistry*, 42: 8223-31 (2003).
Fulda et al., "Smac agonists sensitize for Apo2L/TRAIL—or anticancer drug-induced apoptosis and induce regression of malignant glioma in vivo," *Nature Medicine*, 8: 808-15 (2002).
Gao et al., "A dimeric Smac/Diablo peptide directly relieves caspase-3 inhibition by XIAP. Dynamic and cooperative regulation of XIAP by Smac/Diablo," *J. Biol. Chem.*, 282(42): 30718-27 (2007).
Glover et al., "A High-Throughput screen for identification," *Anal. Biochem.*, 320: 157-169 (2003).
Haining et al., "The proapoptotic function of Drosophila HID is conserved in mammalian cells," *Proc. Natl. Acad. Sci. USA*, 96(9): 4936-41 (1999).
Kipp et al., "Molecular targeting of inhibitor of apoptosis proteins based on small molecule mimics of natural binding partners," *Biochemistry*, 41: 7344-9 (2002).
Leban et al., "Potent Gastrin-Releasing Peptide (GRP) Antagonists Derived from GRP(19-27) with a C-Terminal DPro.PSI.[CH.sub.2NH]Phe-NH.sub.2 and N-Terminal Aromatic Residues," *J. Med. Chem.*, 37(4): 439-445 (1994).
Li et al., "A small molecule Smac mimic potentiates TRAIL- and TNFalpha-mediated cell death," *Science*, 305(5689): 1471-4 (2004).
Liu et al., "Structural basis for binding of Smac/DIABLO to the XIAP BIR3 domain," *Nature*, 408: 1004-8 (2000).
Marik et al., "Synthesis and effect of shortened oostatic decapeptide (TMOF) analogs with isosteric structures on reproduction of Neobellieria bullata," *J. Peptide. Res.*, 57(5): 401-8 (2001).
McCarthy et al., "Apoptosis induced by Drosophila reaper and grim in a human system. Attenuation by inhibitor of apoptosis proteins (cIAPs)," *J. Biol. Chem.*, 273(37): 24009-15 (1998).
Nikolovska-Coleska et al., "Development and optimization of a binding assay for the XIAP BIR3 domain using fluorescence polarization," *Anal. Biochem.*, 332: 261-273 (2004).
Nikolovska-Coleska et al., "Discovery of embelin as a cell-permeable, small-molecular weight inhibitor of XIAP through structure-based computational screening of a traditional herbal medicine three-dimensional structure database," *J. Med. Chem.*, 47(10): 2430-40 (2004).
Nikolovska-Coleska et al., "Design and characterization of bivalent Smac-based peptides as antagonists of XIAP and development and validation of a fluorescence polarization assay for XIAP containing both BIR2 and BIR3 domains," *Anal. Biochem.*, 374(1): 87-98 (2008).
Oost et al., "Discovery of potent antagonists of the antiapoptotic protein XIAP for the treatment of cancer," *J. Med. Chem.*, 47(18): 4417-26 (2004).
Park et al., "Non-peptidic small molecule inhibitors of XIAP," *Bioorg. Med. Chem. Lett.*, 15(3): 771-5 (2005).
Petersen et al., "Autocrine TNFalpha signaling renders human cancer cells susceptible to Smac-mimetic-induced apoptosis," *Cancer Cell*, 12(5): 445-56 (2007).
Probst et al., "Smac mimetics increase cancer cell response to chemotherapeutics in a TNF-.alpha.-dependent manner," *Cell Death Differ.*, 1-10 (2010).
Richard et al., "Agonism, inverse agonism, and neutral antagonism at the constitutively active human neurotensin receptor 2," *Mol. Pharmacol.*, 60(6): 1392-1398 (2001).
Sporn et al. "Chemoprevention of cancer," *Carcinogenesis*, 21:3 (2000), pp. 525-530.
Srinivasula et al., "Molecular determinants of the caspase-promoting activity of Smac/DIABLO and its role in the death receptor pathway," *J. Biol. Chem.*, 275(46): 36152-7 (2000).
Sun et al., "Structure-Based Design of Potent, Conformationally Constrained Smac Mimetics," *J. Am. Chem. Soc.*, 126(51): 16686-87 (2004).
Sun et al., "Structure-based design, synthesis, and evaluation of conformationally constrained mimetics of the second mitochondria-derived activator of caspase that target the X-linked inhibitor of apoptosis protein/caspase-9 interaction site," *J. Med. Chem.*, 47(17): 4147-50 (2004).
Sun et al., "Structure-based design, synthesis and biochemical testing of novel and potent Smac peptido-mimetics," *Biorg. Med. Chem. Lett.*, 15(3): 793-97 (2005).
Sun et al., "Design and synthesis of a potent biotinylated Smac mimetic," *Tetrahedron Letters*, 46: 7015-18 (2005).

(56) References Cited

OTHER PUBLICATIONS

Sun et al., "Design, synthesis, and evaluation of a potent, cell-permeable, conformationally constrained second mitochondria derived activator of caspase (Smac) mimetic," *J. Med. Chem.*, 49(26): 7916-20 (2006).

Sun et al., "Design, synthesis, and characterization of a potent, nonpeptide, cell-permeable, bivalent Smac mimetic that concurrently targets both the BIR2 and BIR3 domains in XIAP," *J. Am. Chem. Soc.*, 129(49): 15279-94 (2007).

Sweeney et al., "Determination of the sequence specificity of XIAP BIR domains by screening a combinatorial peptide library," *Biochemistry*, 45(49): 14740-8 (2006).

Terui et al., "NH2-terminal pentapeptide of endothelial interleukin 8 is responsible for the induction of apoptosis in leukemic cells and has an antitumor effect in vivo," *Cancer Res.*, Cancer Res 59(22): 5651-5 (1999).

Varfolomeev et al., "IAP antagonists induce autoubiquitination of c-IAPs, NF-kappaB activation, and TNFalpha-dependent apoptosis," *Cell*, 131(4): 669-81 (2007).

Vince et al., "IAP antagonists target cIAP1 to induce TNFalpha-dependent apoptosis," *Cell*, 131(4): 682-93 (2007).

Voskoglou-Nomikos et al., *Clin. Cancer Res.*, "Clinical Predictive Value of the in vitro Cell Line, Human Xenograft, and Mouse Allograft Preclinical Cancer Models," 9: 4227-4239 (2003).

Vucic et al., "Inhibitor of apoptosis proteins physically interact with and block apoptosis induced by Drosophila proteins HID and GRIM," *Mol. Cell. Biol.*, 18(6): 3300-9 (1998).

Weber et al., "A bombesin receptor subtype-3 peptide increases nuclear oncogene expression in a MEK-1 dependent manner in human lung cancer cells," *Eur. J. Pharmacol.*, 412(1): 13-20 (2001).

Wist et al., "Structure-activity based study of the Smac-binding pocket within the BIR3 domain of XIAP," *Bioorg. Med. Chem.*, 15(8): 2935-43 (2007).

Wu et al., *Nature*, "Structural basis of IAP recognition by Smac/DIABLO," 408: 1008-12 (2000).

Wu et al., *Chem. Biol.*, "Development and characterization of nonpeptidic small molecule inhibitors of the XIAP/caspase-3 interaction," 10(8): 759-67 (2003).

Zobel et al., ACS Chem. Biol., "Design, Synthesis, and Biological Activity of a Potent Smac Mimetic That Sensitizes Cancer Cells to Apoptosis by Antagonizing IAPs," 1(8): 525-33 (2006).

Zips et al., "New Anticancer Agents: In Vitro and In Vivo Evaluation: Review," *In vivo*, 19, pp. 1-8 (2005).

IAP from GenBank Accession No. Q13490, pp. 1-6. Accessed Jul. 1, 2008.

Interferon Gamma from GenBank Accession No. NP.sub.-776511, pp. 1-3. Accessed Jul. 1, 2008.

XIAP from GenBank Accession No. CAB95312, pp. 1-3. Accessed Jul. 1, 2008.

CIPO, International Search Report in Patent International Application No. PCT/CA2006/000797, 3 pp. (Sep. 6, 2006).

CIPO, Written Opinion in International Patent Application No. PCT/CA2006/000797, 6 pp. (Aug. 16, 2006).

CIPO, International Search Report in International Patent Application No. PCT/IB2011/000264, 4 pp. (Jul. 8, 2011).

CIPO, Written Opinion in International Patent Application No. PCT/IB2011/000264, 10 pp. (Jul. 5, 2011).

EPO, Extended European Search Report in European Patent Application No. 11741951.5, 9 pp. (Mar. 27, 2014).

\* cited by examiner

IAP BIR DOMAIN BINDING COMPOUNDS

CROSS-REFERENCE TO RELATED APPLICATIONS

This application claims priority to U.S. Provisional Patent Applications 61/303,809 filed Feb. 12, 2010 and 61/415,638 filed Nov. 19, 2010.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 810 bytes ASCII (Text) file named "510465_ST25.TXT," created on Jan. 30, 2015.

BACKGROUND OF THE INVENTION

Apoptosis, or programmed cell death, typically occurs in the normal development and maintenance of healthy tissues in multicellular organisms. It is a complex process which results in the removal of damaged, diseased or developmentally redundant cells, in the absence of signs of inflammation or necrosis.

Intrinsic apoptotic pathways are known to be dysregulated in a variety of disorders, including cancer and lymphoproliferative disorders, neurodegenerative diseases, and autoimmune and inflammatory conditions such as multiple sclerosis and rheumatoid arthritis. Cancer cells, for instance, gain the ability to overcome or circumvent apoptosis and continue with inappropriate proliferation despite strong pro-apoptotic signals such as hypoxia, endogenous cytokines, radiation treatments and chemotherapy. Abnormally apoptotic resistant cells also have been linked to autoimmune and inflammatory disease. For instance, apoptosis-resistance has been observed in fibroblast-like synoviocytes in connection with rheumatoid arthritis (RA), and in keratinocytes in connection with psoriasis. Abnormally apoptotic resistant T-cells also have been observed in several autoimmune or inflammatory diseases such as multiple sclerosis, rheumatoid arthritis, idiopathic thrombocytopenic purpura, and alopecia areata. Pathogenic effector cells also have demonstrated resistance to normal apoptotic cues. It is believed that resistance to normal apoptosis is caused, at least in part, by increased activity of anti-apoptotic pathways or expression of anti-apoptotic genes.

The caspases are an integral part of the apoptotic pathway. The caspases are a family of proteolytic enzymes from the class of cysteine proteases, which are known to initiate and execute apoptosis. In normal cells, the caspases are present as inactive zymogens, but are catalytically activated by any of several external signals. Caspase-activating signals include, for example, the release of cytokines or immunological agents following ligand-driven Death Receptor activation, or the release of mitochondrial factors, such as cytochrome C, following genotoxic, chemotoxic, or radiation-induced cellular injury.

The Inhibitors of Apoptosis Proteins (IAPs) constitute a family of proteins that inhibit the caspases, thereby suppressing cellular apoptosis. Because of their central role in regulating caspase activity, the IAPs are capable of inhibiting programmed cell death from a wide variety of triggers. The IAPs are believed to play a role in the loss of homeostatic or endogenous cellular growth control mechanisms, as well as resistance chemotherapeutic drugs and radiation therapy.

The IAPs contain one to three homologous structural domains known as baculovirus IAP repeat (BIR) domains. They may also contain a RING zinc finger domain at the C-terminus, with a capability of inducing ubiquitinylation of IAP-binding molecules via its E3 ligase function. The human IAPs known as XIAP, HIAP1 (also referred to as cIAP2), and HIAP2 (cIAP1) each have three BIR domains, and a carboxy terminal RING zinc finger. Another IAP known as NAIP, has three BIR domains (BIR1, BIR2 and BIR3), but no RING domain. Still other IAPs known as Livin, TsIAP and MLIAP have only a single BIR domain and a single RING domain.

The X chromosome-linked inhibitor of apoptosis (XIAP) is an example of an IAP which can inhibit, by direct binding, the initiator caspase, known as caspase-9, and the effector caspases, known as Caspase-3 and Caspase-7. It is via the BIR3 domain that XIAP binds to and inhibits caspase-9. The linker-BIR2 domain of XIAP inhibits the activity of caspases-3 and -7. The BIR domains have also been associated with the interactions of IAPs with tumor necrosis factor-receptor associated factor (TRAFs)-1 and -2, and to TAB1, as adaptor proteins effecting survival signaling through NFkB activation. XIAP also can induce the removal of caspases by way of the E3 ligase activity of the RING zinc finger domain, which induces ubiquitinylation-mediated proteasomal degradation.

The IAPs thus function as a direct brake on the apoptosis cascade by inhibiting active caspases and re-directing cellular signaling to a pro-survival mode. The sustained over-expression of one or more members of the IAP family of proteins, therefore, allows diseased cells, such as cancer cells and cells involved in autoimmune disease, to avoid apoptosis. In fact, IAP overexpression has been demonstrated to be prognostic of poor clinical outcome in multiple cancers. Furthermore, suppressing IAP expression through RNA antisense or siRNA strategies sensitizes tumor cells to a wide variety of apoptotic insults including chemotherapy, radiotherapy, and ligand-mediated activation of the death receptors. In the case of XIAP, this has been shown in cancers as diverse as leukemia and ovarian cancer. Over expression of cIAP1 and cIAP2 also has been observed in a diverse variety of malignancies, including medulloblastomas, renal cell carcinomas, glioblastomas, and gastric carcinomas. For these reasons, the IAPs are valid therapeutic targets and compounds that inhibit their expression or function are believed to have significant utility in the treatment of proliferative diseases associated with dysregulated apoptosis, including cancer, autoimmune, and inflammatory diseases.

SUMMARY OF THE INVENTION

Provided herein is a compound of Formula 1

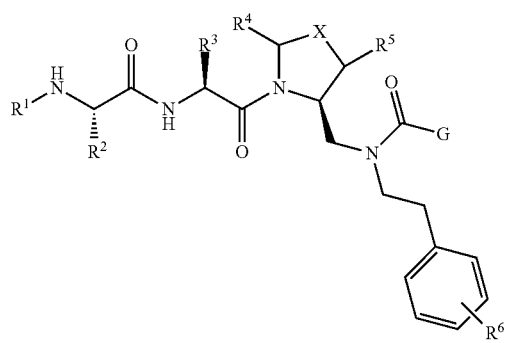

or a salt thereof, wherein $R^1$ is H or alkyl;

$R^2$ is methyl or ethyl;

R³ is alkyl, cycloalkyl, heterocyclyl, heteroaryl, or aryl, any of which can be optionally further substituted with an amino, alkylamino, or alkoxy;

R⁴ and R⁵ are each, independently, H or alkyl;

R⁶ is H, halogen, or alkoxy;

X is O, S, CH₂, —(CH₂)₂— or CH—R⁷, wherein R⁷ is NR⁸, OR⁸, NC(O)OR⁸, NHC(O)R⁸ or NHSO₂R⁸, wherein R⁸ is alkyl, cycloalkyl, heterocyclyl, aryl, arylalkyl, or heteroaryl, any of which can be optionally further substituted with an alkyl or halogen;

and G is (1)

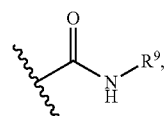

wherein R⁹ is substituted or unsubstituted alkyl, cycloalkyl, heterocyclyl, aryl or heteroaryl; or (2) a substituted or unsubstituted azole or pyrrole ring, optionally fused to a substituted or unsubstituted aryl, heteroaryl, cycloalkyl or heterocyclyl. Also provided herein are methods for preparing a compound of Formula 1 or salt thereof, as well as compounds useful as intermediates in the preparation of a compound of Formula 1 or salt thereof.

In another aspect, the invention provides a pharmaceutical composition comprising a compound of Formula 1 or salt thereof and a pharmaceutically acceptable carrier, as well as a method of preparing same comprising combining a compound of Formula 1 or salt thereof with a pharmaceutically acceptable carrier.

The invention further provides a method of enhancing apoptosis in a cell, the method comprising contacting a cell with a compound of Formula 1 or salt thereof. A method of treating a disease or disorder characterized by insufficient apoptosis also is provided herein, the method comprising administering to a subject in need thereof a compound or pharmaceutical composition, as described above, so as to treat the disease or disorder.

Also provided herein is a probe comprising a compound of Formula 1 or salt thereof and a detectable label, as well as a method of using the probe to identify a compound that binds to an IAP BIR domain, the method comprising: (a) contacting an IAP BIR domain with the probe to form a probe:BIR domain complex, the probe being displaceable by a test compound; (b) measuring a signal from the probe so as to establish a reference level; (c) contacting the probe:BIR domain complex with a test compound; (d) measuring the signal from the probe; and (e) comparing the signal from step (d) with the reference level, wherein a modulation of the signal (e.g., an increase or decrease in the signal relative to the reference level) indicates that the test compound binds to the BIR domain.

DETAILED DESCRIPTION OF THE INVENTION

Provided herein is a compound of Formula 1:

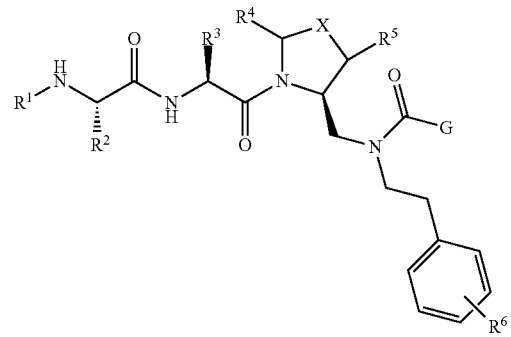

or a salt thereof. The invention encompasses all compounds described by Formula 1 and salts thereof without limitation. However, for the purposes of further illustration, preferred aspects and elements of the invention are discussed herein.

In accordance with Formula 1, G can be a group with the structure

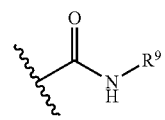

wherein R⁹ is substituted or unsubstituted alkyl, cycloalkyl, heterocyclyl, aryl or heteroaryl. For example, R⁹ can be a phenyl group optionally substituted with a halogen or alkoxy.

Alternatively, G can be a substituted or unsubstituted azole or pyrrole ring, optionally fused to a substituted or unsubstituted aryl, heteroaryl, cycloalkyl, or heterocyclic ring. For instance, G can be

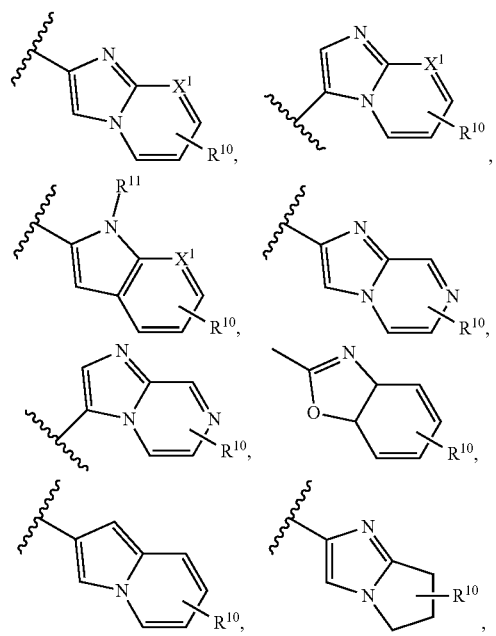

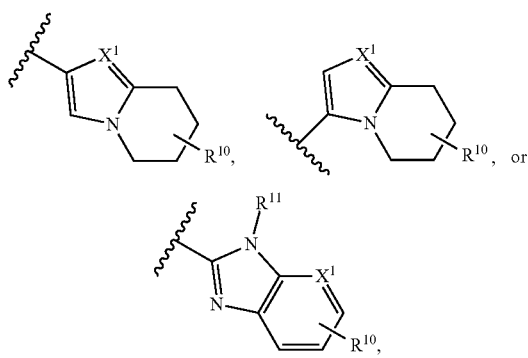

wherein $X^1$ is CH or N, $R^{10}$ is H, halogen, hydroxyl, alkyl, alkoxy, aryl, amino, or NHC(O)-alkyl, and $R^{11}$ is hydrogen, alkyl, or NHC(O)CH$_3$. G also can be

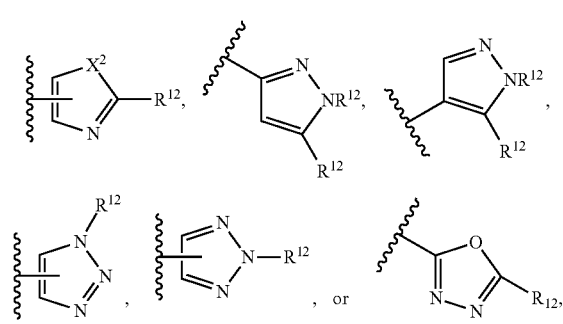

wherein $X^2$ is NH, $NR^{12}$, O, or S, and each $R^{12}$ is independently hydrogen, alkyl, cycloalkyl, heterocyclyl, NHC(O)CH$_3$, or phenyl optionally substituted with one or more alkyl, alkoxy, or halogen groups.

According to one embodiment G is:

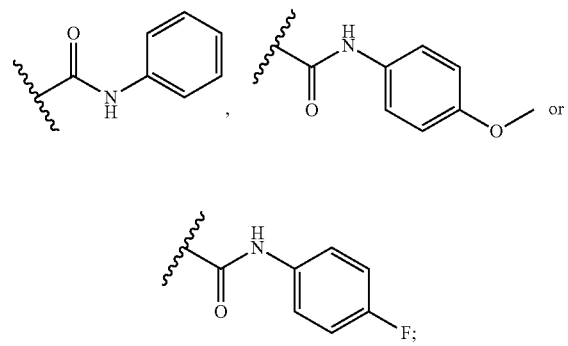

or a substituted or unsubstituted pyrrole, specific examples of which include, without limitation:

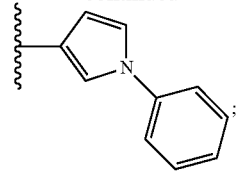

or a substituted or unsubstituted imidazole, specific examples of which include, without limitation:

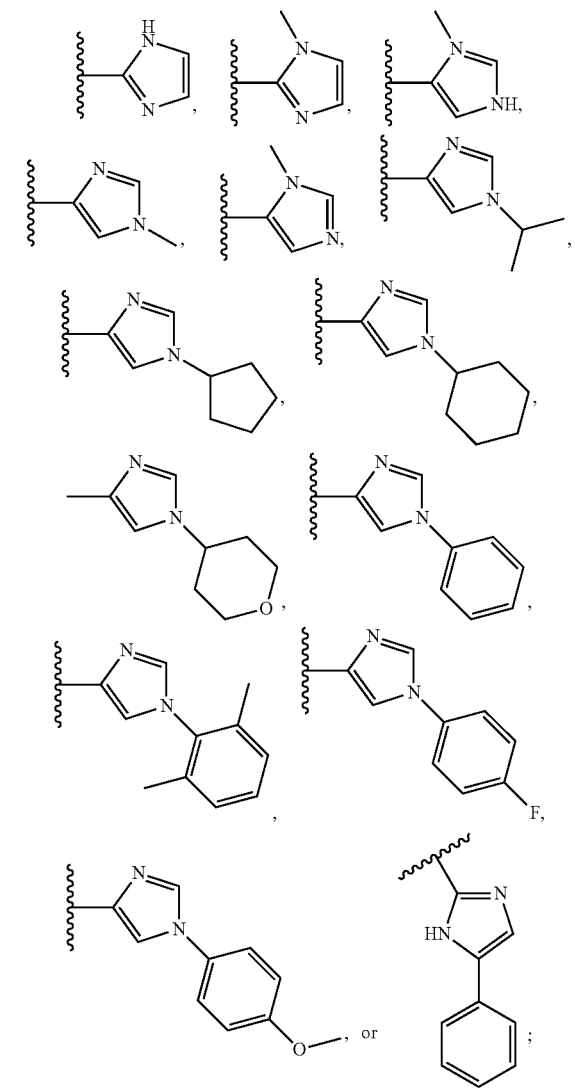

or a substituted or unsubstituted pyrazole, specific examples of which include, without limitation:

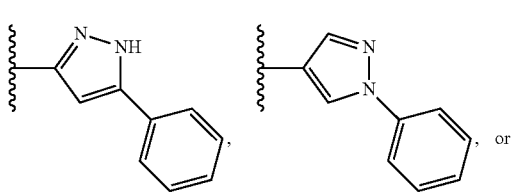

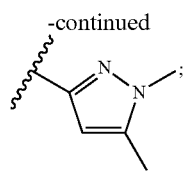

or a substituted or unsubstituted triazole, specific examples of which include, without limitation:

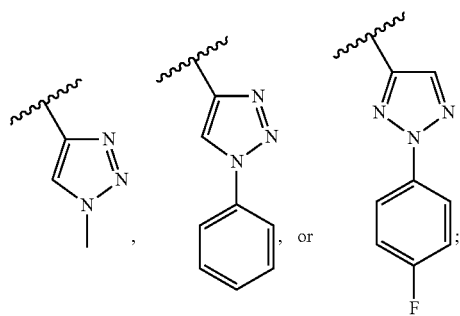

or a substituted or unsubstituted thiazole, specific examples of which include, without limitation:

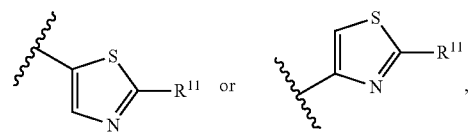

wherein $R^{11}$ is NHC(O)CH$_3$ or phenyl;
or a substituted or unsubstituted tetrazole, specific examples of which include, without limitation:

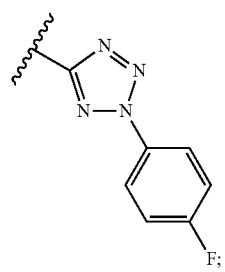 [SMILES: *c1nnn(-c2ccc(F)cc2)n1]

or a substituted or unsubstituted oxazole, specific examples of which include, without limitation:

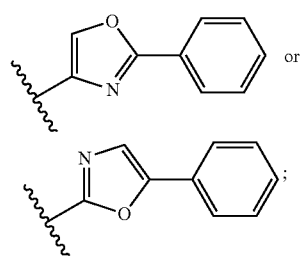

or a substituted or unsubstituted isoxazole, specific examples of which include, without limitation:

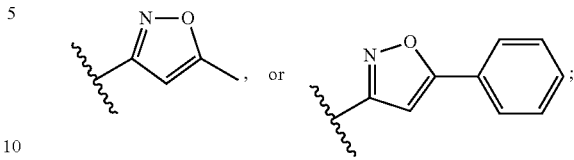

or a substituted or unsubstituted oxadiazole, specific examples of which include, without limitation:

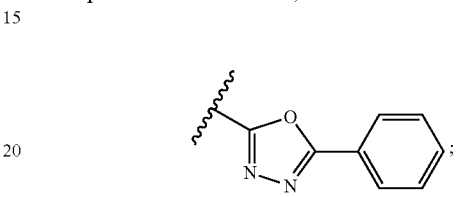

or a substituted or unsubstituted indole, specific examples of which include, without limitation:

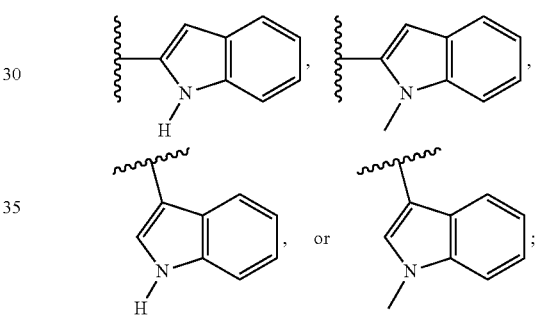

or a substituted or unsubstituted imidazo[1,2-a]pyridine, specific examples of which include, without limitation:

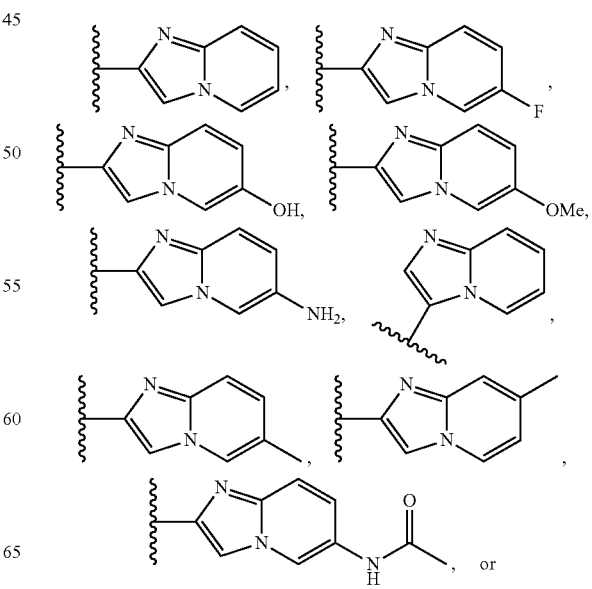

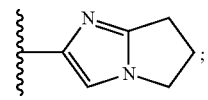 [SMILES: *c1cn2c(n1)CCC2]

or a substituted or unsubstituted imidazo[1,2-a]pyrimidine, specific examples of which include, without limitation:

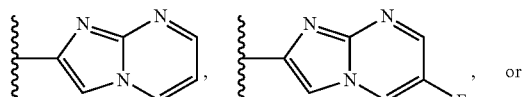

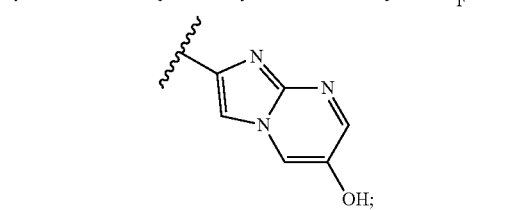

or a substituted or unsubstituted indolizine, specific examples of which include, without limitation:

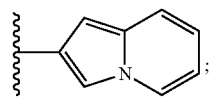 [SMILES: *c1cc2ccccn2c1]

or a substituted or unsubstituted tetrahydroindolizine, specific examples of which include, without limitation:

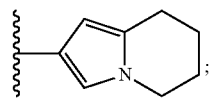 [SMILES: *c1cc2n(c1)CCCC2]

or a substituted or unsubstituted tetrahydroimidazo[1,2-a]pyridine, specific examples of which include, without limitation:

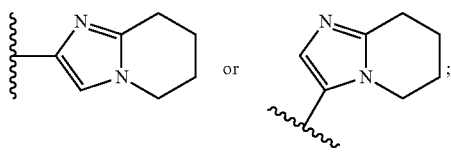 [SMILES: *c1cn2c(n1)CCCC2 ; *c1cnc2n1CCCC2]

or a substituted or unsubstituted 1H-benzo[d]imidazole, specific examples of which include, without limitation:

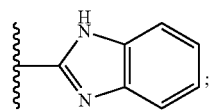 [SMILES: *c1nc2ccccc2[nH]1]

or a substituted or unsubstituted 6,7-dihydro-5H-pyrrolo[1,2-a]imidazole, specific examples of which include, without limitation:

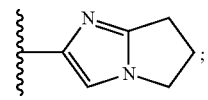 [SMILES: *c1cn2c(n1)CCC2]

or a substituted or unsubstituted benzo[d]oxazole, specific examples of which include, without limitation:

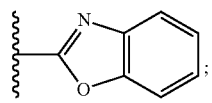 [SMILES: *c1nc2ccccc2o1]

or a substituted or unsubstituted imidazo[1,2-a]pyrazine, specific examples of which include, without limitation

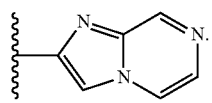 [SMILES: *c1cn2ccncc2n1]

$R^1$ can be any alkyl, such as a $C_1$-$C_3$ alkyl (e.g., methyl, ethyl, or propyl, including isopropyl), preferably methyl, and $R^2$ is methyl or ethyl.

$R^3$ can be alkyl, cycloalkyl, heterocyclyl, heteroaryl, or aryl, and can be optionally further substituted with an amino, alkylamino, or alkoxy. Non-limiting examples of suitable $R^3$ groups include $C_1$-$C_6$ or $C_1$-$C_4$ alkyl (e.g., methyl, ethyl, propyl, isopropyl, butyl, isobutyl, t-butyl, etc.), cyclohexyl, cyclopropyl, and tetrahydro-2H-pyranyl. For example, $R^3$ can be:

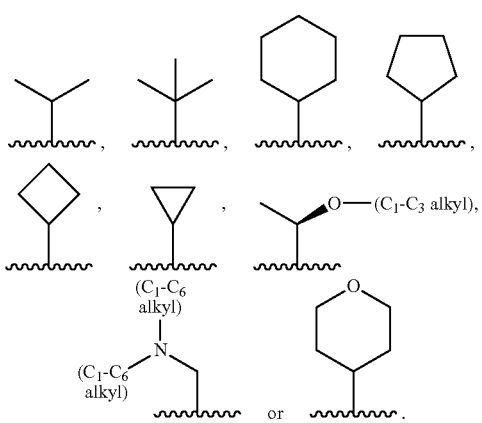

Desirably, $R^3$ is tert-butyl, cyclohexyl, tetrahydropyranyl,

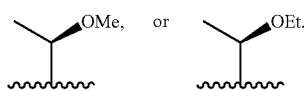

$R^4$ and $R^5$ are, independently, hydrogen or alkyl, such as a $C_1$-$C_6$ alkyl. $R^6$ can be hydrogen, halogen, or an alkoxy, such as a $C_1$-$C_6$ alkoxy. Desirably, $R^6$ is hydrogen, fluorine, or a $C_1$-$C_3$ alkoxy, such as methoxy or ethoxy.

X can be O, S, $CH_2$, —$(CH_2)_2$— or CH—$R^7$, wherein $R^7$ is $NR^8$, $OR^8$, $NHC(O)OR^8$, $NHC(O)R^8$ or $NHSO_2R^8$, and $R^8$ is alkyl, cycloalkyl, heterocyclyl, aryl, arylalkyl, or heteroaryl. $R^8$ can be further substituted with an alkyl, alkoxy, haloalkyl, or halogen. According to some embodiments, X is $CH_2$. In other embodiments, X is CH—$NHC(O)R^8$, and $R^8$ is alkyl, aryl, arylalkyl, alkoxy or heteroaryl, any of which can be optionally further substituted with an alkyl, alkoxy, haloalkyl, or halogen. In yet other embodiments, X is CH—$OR^8$ and $R^8$ is aryl or arylalkyl. which can be optionally further substituted with halogen. Specific examples of X include, without limitation:

or, more particularly:

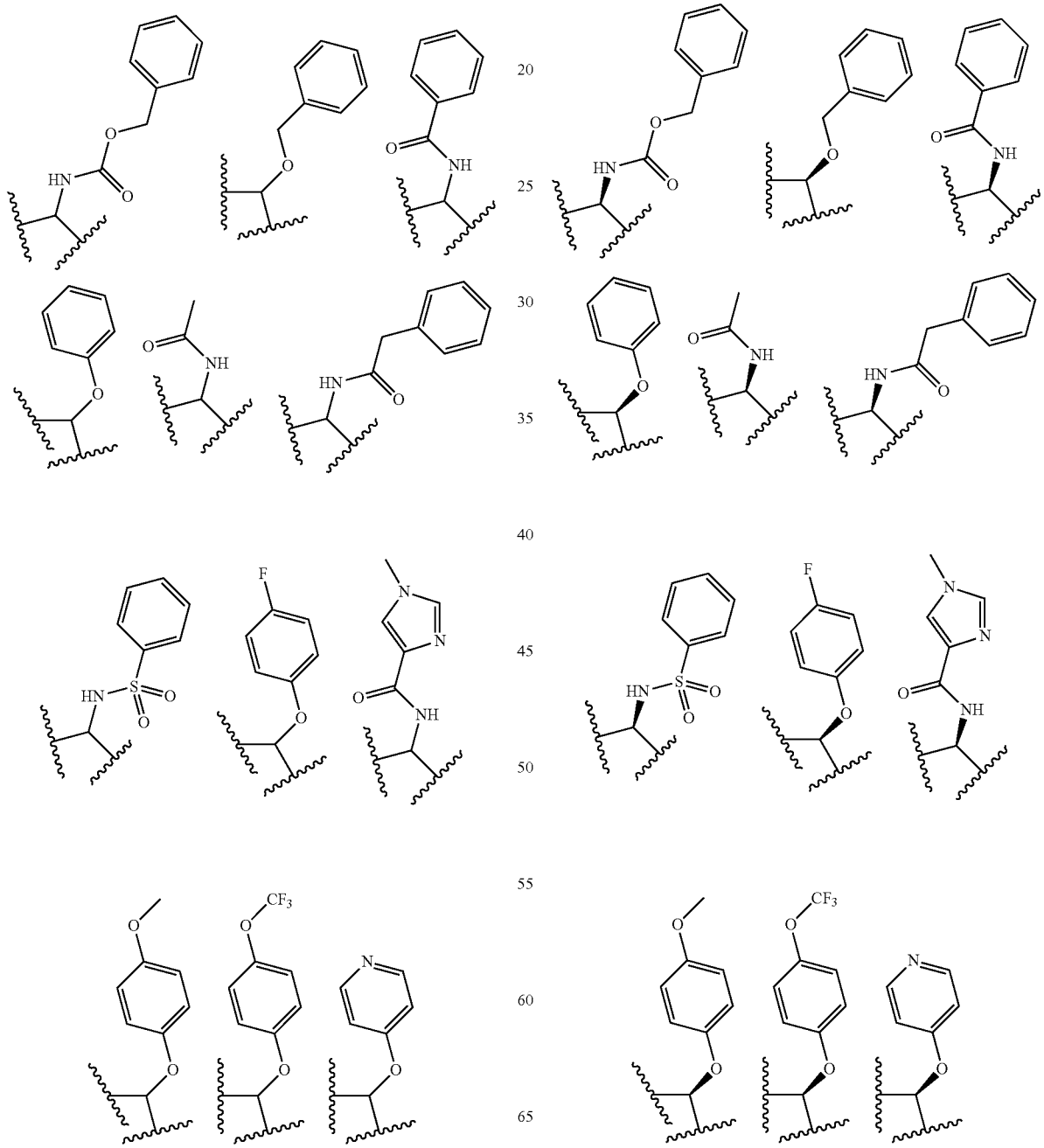

-continued

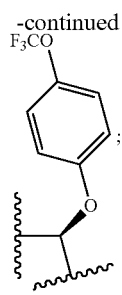

Any of the foregoing substituent groups, in both general and preferred aspects, can be employed in any combination to provide a compound of Formula 1 or salt thereof. Specific examples of compounds of Formula 1 or salts thereof are provided in Table 1 and the Examples.

Whenever a range of the number of atoms in a structure is indicated (e.g., a $C_1$-$C_8$, $C_1$-$C_6$, $C_1$-$C_4$, or $C_1$-$C_3$ alkyl, haloalkyl, alkylamino, alkenyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, haloalkyl, alkylamino, alkenyl, etc.) referenced herein encompasses and specifically describes 1, 2, 3, 4, 5, 6, 7, or 8 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 2-3 carbon atoms, 2-4 carbon atoms, 2-5 carbon atoms, 2-6 carbon atoms, 2-7 carbon atoms, 2-8 carbon atoms, 3-4 carbon atoms, 3-5 carbon atoms, 3-6 carbon atoms, 3-7 carbon atoms, 3-8 carbon atoms, 4-5 carbon atoms, 4-6 carbon atoms, 4-7 carbon atoms, 4-8 carbon atoms, 5-6 carbon atoms, 5-7 carbon atoms, 5-8 carbon atoms, 6-7 carbon atoms, or 6-8 carbon atoms, as appropriate).

As used herein, unless otherwise specified, the term "substituted" means a group substituted by one to four or more substituents. Examples of substitutents include, for instance, alkyl, alkenyl, alkynyl, cycloalkyl, cycloalkenyl, aroyl, halo, haloalkyl (e.g., trifluoromethyl), haloalkoxy (e.g., trifluoromethoxy), hydroxy, alkoxy, alkylthioether, cycloalkyloxy, heterocyclooxy, oxo, alkanoyl, aryl, arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloamino, mono- and di-substituted amino (in which the two substituents on the amino group are selected from alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido (e.g., $SO_2NH_2$), substituted sulfonamido, nitro, cyano, carboxy, carbamyl (e.g., $CONH_2$), substituted carbamyl (e.g., CONH-alkyl, CONH-aryl, CONH-arylalkyl or instances where there are two substituents on the nitrogen selected from alkyl or arylalkyl), alkoxycarbonyl, aryl, substituted aryl, guanidino, substituted or unsubstituted heterocycloalkyl, substituted or unsubstituted heteroaryl (such as, indolyl, imidazolyl, furyl, thienyl, thiazolyl, pyrrolidyl, pyridyl, pyrimidyl and the like).

As used herein, the term "azole" is intended to include a five-membered nitrogen-containing ring that contains at least one other ring-member nitrogen, sulfur, or oxygen. Non-limiting examples of azoles include pyrazole, imidazole, triazole, tetrazole, pentazole, thiazole, isothiazole, oxazole, and isoxazole.

As used herein, the term "pyrrole" is intended to include a five-membered aromatic heterocyclic ring containing one nitrogen atom. Pyrrole, as used herein, also encompass the hydrogenated derivatives 1-, 2-, and 3-pyrroline.

As used herein, the term "alkyl" is intended to include both branched and straight chain saturated aliphatic hydrocarbon groups having the specified number of carbon atoms (e.g., $C_1$-$C_{20}$ alkyl, $C_1$-$C_8$ alkyl, $C_1$-$C_6$ alkyl, etc.). For example, a $C_1$-$C_6$-alkyl includes alkyl groups with 1, 2, 3, 4, 5 or 6 carbons in a linear or branched arrangement. Similarly, a $C_1$-$C_4$ alkyl includes alkyl groups having 1, 2, 3, or 4 carbons in a linear or branched arrangement, and a $C_1$-$C_{20}$-alkyl includes alkyl groups having 1, 2, 3, 4, 5, 6, 7, 8, 9, 10, 11, 12, 13, 14, 15, 16, 17, 18, 19 or 20 carbons in a linear or branched arrangement. Representative saturated straight chain alkyls include -methyl, -ethyl, -n-propyl, -n-butyl, -n-pentyl, -n-hexyl, -n-heptyl, -n-octyl, -n-nonyl and -n-decyl; while representative saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-dimethylpentyl, 3,3-diethylhexyl, 2,2-diethylhexyl, 3,3-diethylhexyl and the like. An alkyl group can be unsubstituted or substituted. For the purposes of describing the invention, the term "alkyl" encompasses an "alkylene" where appropriate.

As used herein, the term, "alkenyl" is intended to mean an unsaturated straight or branched chain hydrocarbon group having the specified number of carbon atoms, in which at least two of the carbon atoms are bonded to each other by a double bond, and having either E or Z regiochemistry or combination thereof. For example, a $C_2$-$C_6$ alkenyl group includes hydrocarbon groups having 2, 3, 4, 5, or 6 carbons in a linear or branched arrangement, at least two of the carbon atoms being bonded together by a double bond. Examples of $C_2$-$C_6$ alkenyl include ethenyl(vinyl), 1-propenyl, 2-propenyl, 1-butenyl-2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. An alkenyl group can be unsubstituted or substituted. For the purposes of describing the invention, the term "alkenyl" encompasses an "alkenylene" where appropriate.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_4$ as in $C_2$-$C_4$ alkynyl is defined as including groups having 2, 3, or 4 carbon atoms in a chain, at least two of the carbon atoms being bonded together by a triple bond. Examples of such alkynyls include ethynyl, 1-propynyl, 2-propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. An alkynyl group can be unsubstituted or substituted. For the purposes of describing the invention, the term "alkynyl" encompasses an "alkynylene."

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6, or 7 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl. For the purposes of describing the invention, the term "cycloalkyl" encompasses a "cycloalkylene."

As used herein, the term "cycloalkenyl" is intended to mean a monocyclic unsaturated aliphatic hydrocarbon group having the specified number of carbon atoms therein, for example, $C_3$-$C_7$ as in $C_3$-$C_7$ cycloalkenyl is defined as including groups having 3, 4, 5, 6, or 7 carbons in a monocyclic arrangement. Examples of $C_3$-$C_7$ cycloalkenyl as defined above include, but are not limited to, cyclopentenyl, and cyclohexenyl. For the purposes of describing the invention, the term "cycloalkenyl" encompasses a "cycloalkenylene."

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term "aryl", either alone or in combination with another radical, means a carbocyclic aromatic monocyclic group containing 6 carbon atoms which may be further fused to a second or a third 5- or 6-membered carbocyclic group which may be aromatic, saturated or unsaturated. Aryl includes, but is not limited to, phenyl, indanyl, 1-naphthyl, 2-naphthyl, tetrahydronaphthyl, 1-anthracenyl, 2-anthracenyl, 9-anthracenyl, 1-phenanthryl, 2-phenanthryl, 3-phenanthryl, 4-phenanthryl, and 5-phenanthryl. The aryls may be connected to another group either at a suitable position on the cycloalkyl ring or the aromatic ring. For example:

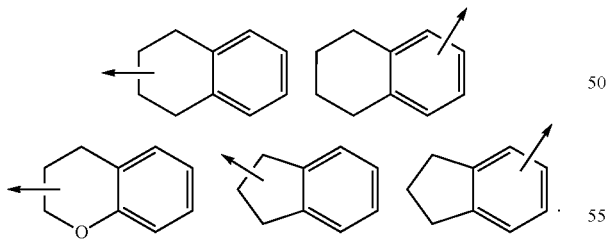

Lines drawn perpendicular to a bond between members of a ring, such as the arrowed lines above, indicate a bond that may be attached to any of the suitable ring atoms (e.g., an attachment point at any suitable member of the ring). For the purposes of describing the invention, the term "aryl" encompasses an "arylene" where appropriate.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, and fluoroscein derivatives such as:

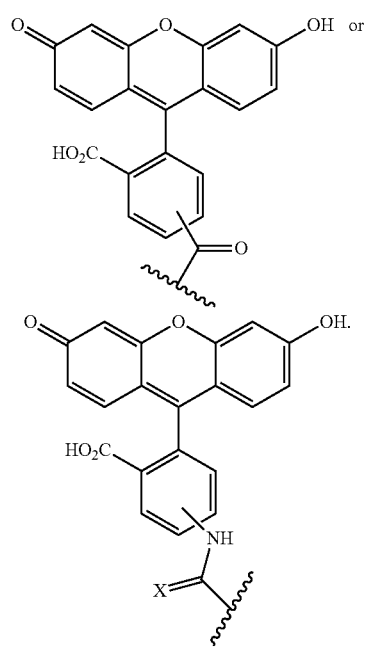

For the purposes of describing the invention, the term "heteroaryl" encompasses a "heteroarylene."

As used herein, the term "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, pyrazolinyl, and

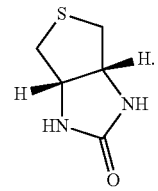

For the purposes of describing the invention, the term "heterocyclyl" encompasses a "heterocyclylene."

As used herein, the term "heterobicycle" either alone or in combination with another radical, is intended to mean a heterocycle as defined above fused to another cyclic group, be it a heterocycle, an aryl or any other cyclic group defined herein. Examples of such heterobicycles include, but are not limited to, coumarin, benzo[d][1,3]dioxole, 2,3-dihydrobenzo[b][1,4]dioxine and 3,4-dihydro-2H-benzo[b][1,4]dioxepine.

As used herein, the term "heteroatom" is intended to mean O, S or N.

To the extent any indicated substituent groups may be incompatible with the synthetic methods described herein, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Examples of protecting groups used throughout include, but are not limited to Fmoc, Bn, Boc, CBz and COCF$_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

The invention encompasses any salt of a compound described herein, especially pharmaceutically acceptable salts. Pharmaceutically acceptable salts include both acid and base addition salts. Acid additional salts encompass, for instance, salts formed with inorganic acids such as hydrochloric acid, hydrobromic acid, sulfuric acid, nitric acid, phosphoric acid and the like, or organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Base addition salts include those prepared from addition of an inorganic base or an organic base to a free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Preferably, the salt retains the desirable biological effectiveness and properties of the free acid or base form of the compound.

The compound of Formula 1 or salt thereof preferably binds a BIR domain of an IAP. Examples of BIR binding proteins include, but are not limited to, caspases and mitochondrially derived BIR binding proteins such as Smac, Omi/WTR2A and the like. Examples of IAPs include, but are not limited to human or mouse NAIP (Birc 1), HIAP-1 (cIAP2, Birc 3), HIAP-2 (cIAP1, Birc 2), XIAP (Birc 4), survivin (Birc 5), livin (ML-IAP, Birc 7), ILP-2 (Birc 8) and Apollon/BRUCE (Birc 6) (see for example U.S. Pat. Nos. 6,107,041; 6,133,437; 6,156,535; 6,541,457; 6,656,704; 6,689,562; Deveraux and Reed, Genes Dev. 13, 239-252, 1999; Kasof and Gomes, J. Biol. Chem., 276, 3238-3246, 2001; Vucic et al., Curr. Biol. 10, 1359-1366, 2000; Ashab et al. FEBS Lett., 495, 56-60, 2001, the contents of which are hereby incorporated by reference). The BIR domains of the IAPs are documented in the relevant literature, typically characterized by a number of invariant amino acid residue including conserved cysteines and one conserved histidine residue within a particular sequence. The BIR domain residues for some human IAPs are include, for instance, residues 21-93 (BIR1), 159-230 (BIR2), and 258-330 (BIR3) of XIAP (Referencing Swiss-Prot P98170), residues 41-113 (BIR1), 179-250 (BIR2), and 264-336 (BIR3) of HIAP-1 (Referencing XP-006266), and residues 24-96 (BIR1), 164-235 (BIR2), and 250-322 (BIR3) of HIAP-2 (Referencing XP-006267) (see Verhagen et al., *Genome Biology*, 2(7): reviews 3009.1-3009.10 (2001)).

Desirably, the compound of Formula 1 or salt thereof binds to a BIR domain of XIAP, more preferably human XIAP. BIR domain binding can be detected by any suitable technique. For instance, BIR domain binding can be detected on the basis of a test compounds ability to compete with the binding of a known BIR-domain binding protein (e.g., inhibiting or preventing the binding of a known BIR-domain binding protein to a given BIR domain). Naturally occurring and synthetic BIR domain binding proteins are known in the art. In some embodiments, the compound of Formula 1 or salt thereof binds one or more IAPs (such as NAIP, HIAP-1, HIAP-2, XIAP, survivin, livin, ILP-2, or Apollon/BRUCE) with a $K_i$ of less then or about 500 µM, 250 µM, 100 µM, 50 µM, 25 µM, 10 µM, 1 µM, 500 nM, 250 nM, 100 nM, or 50 nM (wherein a lower $K_i$ value represents a greater binding affinity). In some embodiments, the compound of Formula 1 or salt thereof binds one or more IAPs with a $K_i$ between about 500 µM to about 50 nM, such as about 250 µM to about 50 nM, about 100 µM to about 1 µM, or about 1 µM to about 50 nM. In some embodiments, the compound of Formula 1 or salt thereof binds both XIAP and HIAP2 with a $K_i$ in one of the above ranges.

The compounds described herein may contain one or more asymmetric centers, chiral axes, and chiral planes. These compounds may, thus, give rise to enantiomers, diastereomers, and other stereoisomeric forms and may be defined in terms of absolute stereochemistry, such as (R)- or (S)- or, as (D)- or (L)- for amino acids, and/or by optical activity, such as (+) and (−). The present invention is intended to encompass any and all such possible stereoisomers, whether present in a pure or substantially form (e.g, an optically pure form) or as a mixture of isomers in any proportion, including racemic mixtures. Optically active (+) and (−), (R)- and (S)-, or (D)- and (L)-isomers may be prepared by chiral (asymmetric) synthesis using optically active reagents, substrates, catalysts, or solvents (chiral synthons or chiral reagents), or by converting one enantiomer to another by asymmetric transformation. Alternatively, isomers can be resolved from mixtures of isomeric forms (e.g., racemic mixtures) using conventional techniques, including without limitation reverse-phase HPLC, formation of diastereoisomeric salts that can be separated by crystallization, gas-liquid or liquid chromatography, selective reaction of one stereoisomer with an enantiomer-specific reagent. When the desired enantiomer is converted into another chemical entity by a separation technique, an additional step may be required to form the desired enantiomeric form.

Certain compounds of the present invention also may exist under certain conditions in anionic, cationic, or Zwitterionic forms. Compounds of Formula 1 and other formulas described herein specifically encompass such alternative forms.

According to a preferred embodiment, the compound of Formula 1 or salt thereof provides oral bioavailability when administered to a mammal, particularly a human. Desirably, the compound of Formula 1 or salt thereof exhibits an oral bioavailability of about 10% or more, about 15% or more, or about 20% or more. More preferably, the compound of Formula 1 or salt thereof, exhibits an oral bioavailability of about 25% or more, about 30% or more, about 50% or more, or even about 75% or more (e.g., about 80% or more, about 90% or more, or about 95% or more). In some embodiments, the compound of Formula 1 or salt thereof exhibits an oral bioavailability of between about 25% to about 50%, about 50% to about 75%, or about 75% to about 100%.

Synthesis Methods

The compounds of the invention described herein can be prepared by any of several techniques. According to one aspect of the invention, the compounds can be prepared in accordance with any of Methods A-C illustrated by Schemes 1-4.

Method A provides a method of preparing a compound of Formula 1 or salt thereof, as well as methods for preparing intermediate compounds associated therewith, comprising one or more of the following steps: (1) combining a prolinal derivative (1-i) with an amine having the formula

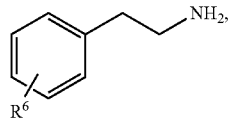

followed by reduction with a hydride, to provide intermediate compound 1-ii, wherein $PG^1$ is a protecting group; (2) protecting the amine group of intermediate compound 1-ii with a protecting group ($PG^2$) that is different from $PG^1$, followed by deprotection of $PG^1$ to provide intermediate compound 1-iii; (3) coupling intermediate compound 1-iii with $PG^3$(H)N($R^3$)CHCO$_2$H using amino acid coupling agents, wherein $PG^3$ is a protecting group that is different from $PG^2$, followed by deprotection of $PG^3$ to provide intermediate compound 1-iv; (4) coupling intermediate compound 1-iv with $PG^4$($R^1$)N($R^2$)CHCO$_2$H using amino acid coupling agents, wherein $PG^4$ is a protecting group that is different from $PG^2$, to provide intermediate compound 1-v; (5) deprotection of $PG^2$ of intermediate compound 1-v to provide intermediate compound 1-vi; and (6) acylation of intermediate compound 1-vi by combining intermediate compound 1-vi with a compound of formula LG-C(O)-G, wherein "LG" is a leaving group, followed by deprotection of $PG^4$ to provide a compound of Formula 1 or salt thereof. Method A is illustrated in Scheme 1, below. Each intermediate compound of Method A, as well as each individual process step for preparing the intermediate compound, is considered to be an additional aspect of the invention. Thus, provided herein is a compound of any one of Formulas 1-i through 1-v of Scheme 1, including salts thereof. Also provided herein is a method of preparing a compound of Formula 1 or salt thereof, or an intermediate compound of any of Formulas 1-i through 1-vi of Scheme 1, including salts thereof, comprising one or more of steps (1) through (6) of Method A described above.

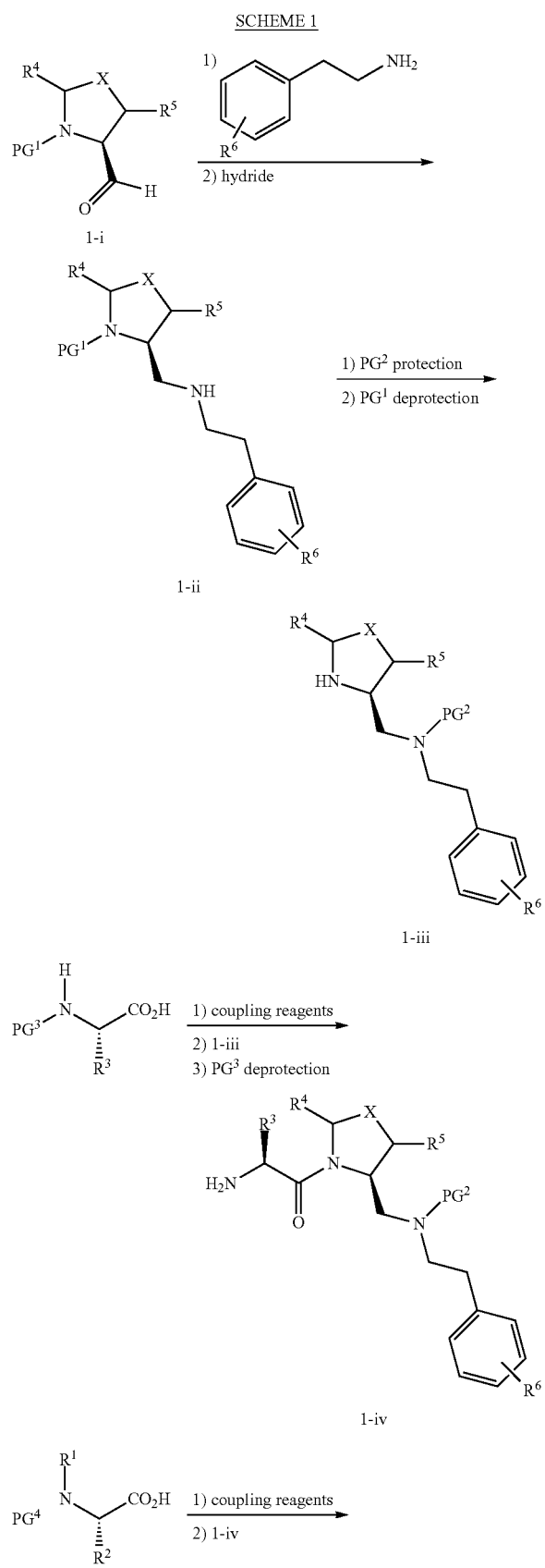

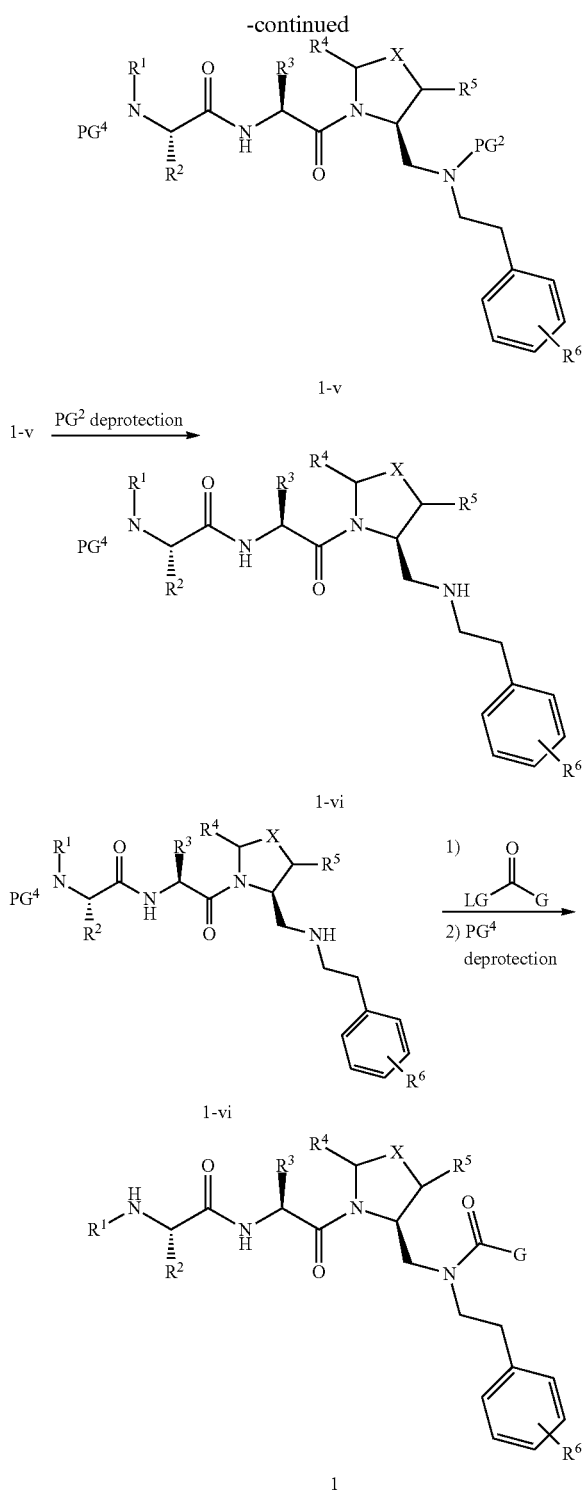

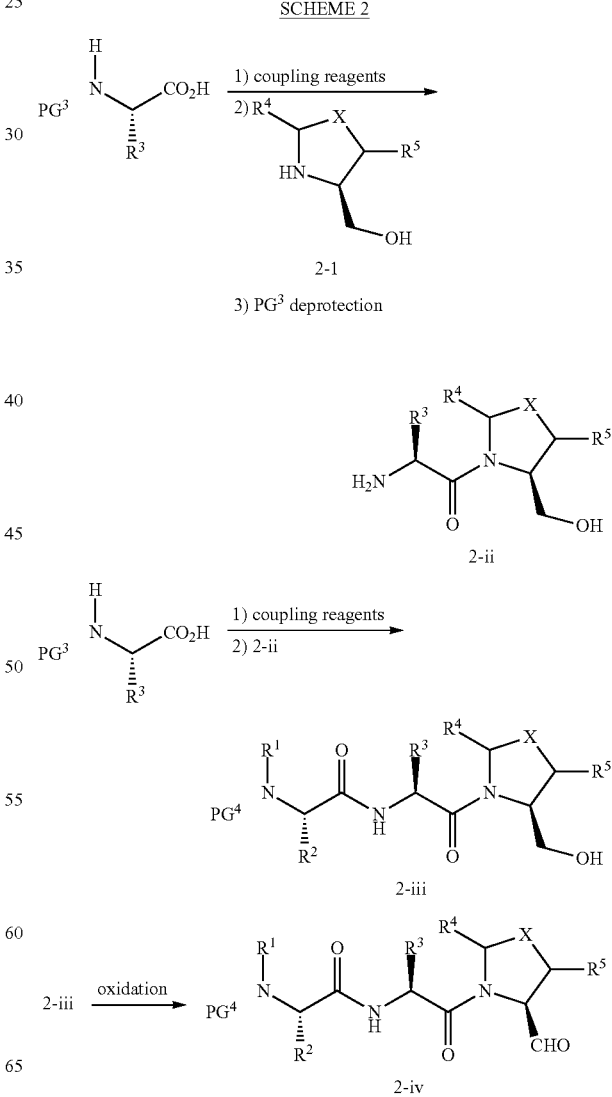

vide intermediate compound 2-iii, wherein $PG^4$ is a protecting group; (3) oxidizing intermediate compound 2-iii to provide the corresponding aldehyde, intermediate compound 2-iv; (4) reductive amination of compound 2-iv, for example, by combining compound 2-iv with an amine followed by reduction with an appropriate hydride, to provide intermediate compound 1-vi; (5) acylation of compound 1-vi by combining compound 1-vi with a compound of formula LG-C(O)-G, wherein LG is a leaving group, followed by deprotection of $PG^4$, to provide a compound of Formula 1 or salt thereof. Method B is illustrated in Scheme 2, below. Each intermediate compound of Method B, as well as each individual process step for preparing the intermediate compound, is considered to be an additional aspect of the invention. Thus, provided herein is a compound of any one of Formulas 2-i through 2-iv or Formula 1-vi of Scheme 2, including salts thereof. Also provided herein is a method of preparing a compound of Formula 1 or salt thereof, or an intermediate compound of any of Formulas 2-i through 2-iv or Formula 1-vi of Scheme 2, including salts thereof, comprising one or more of steps (1) through (5) of Method B described above.

Method B provides an alternative method of preparing a compound of Formula 1 or salt thereof, as well as methods for preparing intermediate compounds associated therewith, comprising one or more of the following steps: (1) coupling a prolinol derivative (intermediate compound 2-i) with a compound of the formula $PG^3(H)N(R^3)CHCO_2H$ using amino acid coupling agents, wherein $PG^3$ is a protecting group, followed by deprotection of $PG^3$ to provide intermediate compound 2-ii; (2) coupling intermediate compound 2-ii with a compound of the formula $PG^4(R^1)N(R^2)CHCO_2H$ to pro-

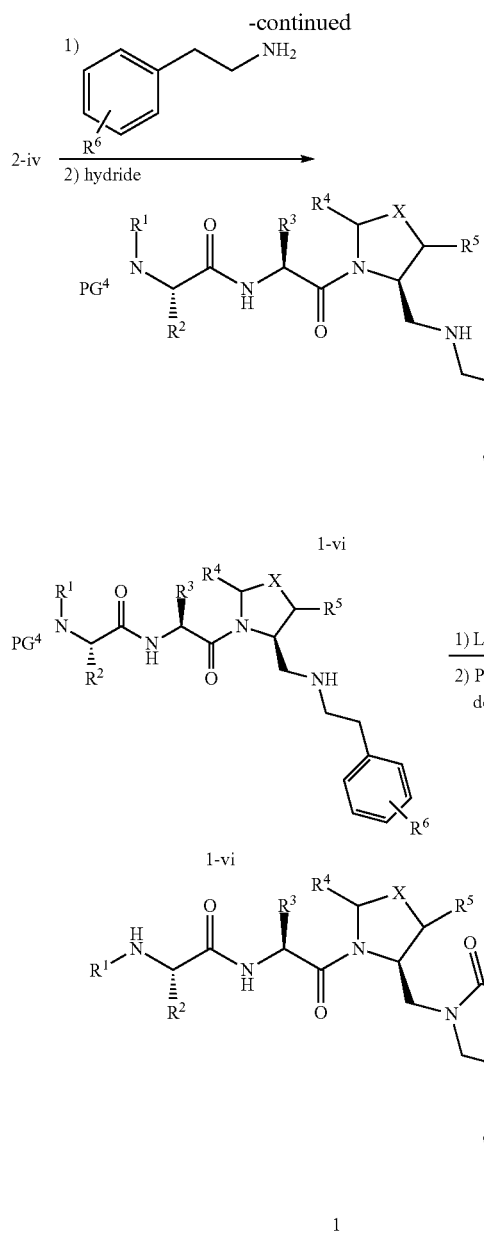

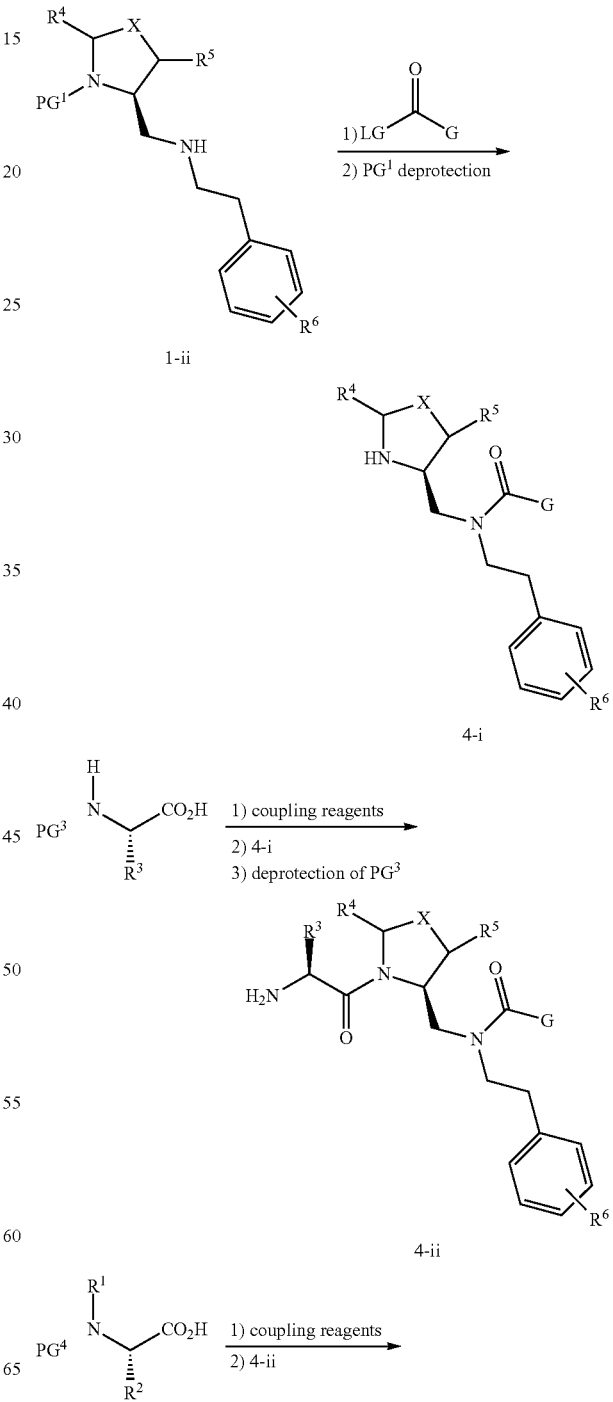

SCHEME 3

Method C provides another alternative method of preparing a compound of Formula 1 or salt thereof, as well as methods for preparing intermediate compounds associated therewith, comprising one or more of the following steps: (1) acylation of intermediate compound 1-ii (prepared as described in Method A, or by other methods) by combining intermediate compound 1-ii with a compound of formula LG-C(O)-G, wherein $PG^1$ is a protecting group, followed by deprotection of $PG^1$ to provide intermediate compound 4-i; (2) coupling compound 4-i with a compound having the formula $PG^3(H)N(R^3)CHCO_2H$ using amino acid coupling agents, wherein $PG^3$ is a protecting group, followed by deprotection of $PG^3$ to provide intermediate compound 4-ii; (3) coupling intermediate compound 4-ii with a compound having the formula $PG^4(R^1)N(R^2)CHCO_2H$ using amino acid coupling agents to provide intermediate compound 1-vi, wherein $PG^4$ is a protecting group, followed by deprotection of $PG^4$ to provide a compound of Formula 1 or salt thereof. Method C is illustrated in Scheme 3, below. Each intermediate compound of Method C, as well as each individual process step for preparing the intermediate compound, is considered to be an additional aspect of the invention. Thus, provided herein is a compound of Formula 4-i or 4-ii of Scheme 3, including salts thereof. Also provided herein is a method of preparing a compound of Formula 1 or salt thereof, or an intermediate compound of Formula 4-i or 4-ii of Scheme 3, including salts thereof, comprising one or more of steps (1) through (3) of Method C described above.

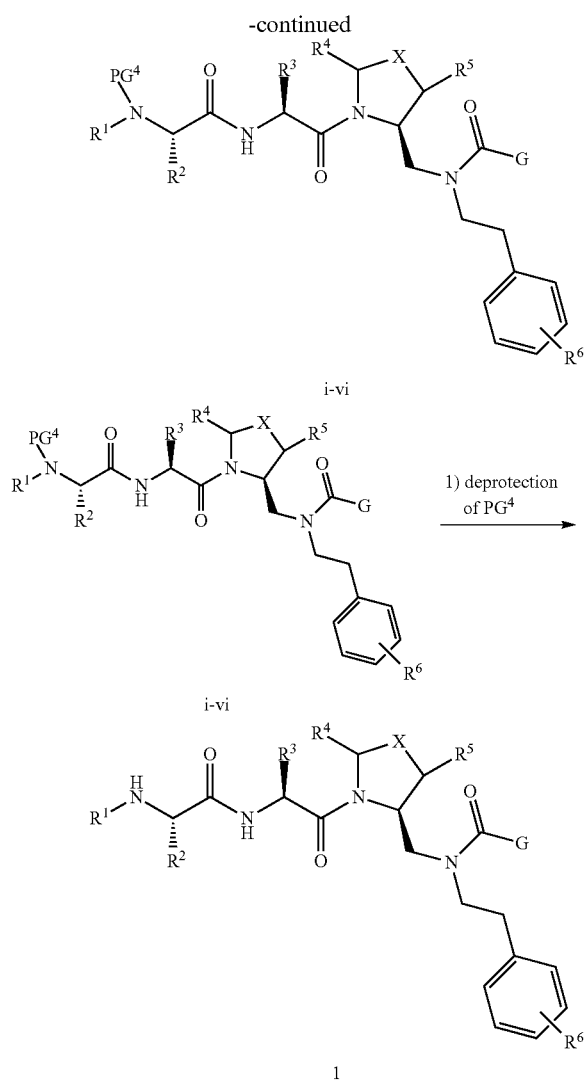

Utilities

The compounds of the present invention can be used for any purpose. However, compounds of Formula 1 and salts thereof as provided herein are believed to be especially useful as IAP BIR domain binding compounds. As such the compounds of Formula 1 and salts thereof described herein can be used to enhance apoptosis in a cell or subject, particularly in cells that exhibit abnormally low levels of apoptosis or in subjects afflicted with, or having a predisposition towards, a disease or condition associated with insufficient apoptosis. Insufficient apoptosis means a level or degree of apoptosis that is abnormal under given conditions, or otherwise leads to or causes a pathological state. Thus, insufficient apoptosis encompasses, for instance, a state wherein a disease is caused or continues because cells deleterious to the subject have not apoptosed. Conditions or diseases associated with insufficient apoptosis encompass cell-proliferative diseases and disorders including, without limitation cancer, autoimmune diseases, inflammatory disorders, and cell proliferation induced by medical procedures, including, but not limited to, surgery, angioplasty, and the like.

Thus provided herein is a method of enhancing or inducing apoptosis in a cell comprising administering a compound of Formula 1 or salt thereof to a cell. Compounds of Formula 1 or salt thereof can be administered to a cell by any suitable method, for instance, contacting the cell with a compound of Formula 1 or salt thereof or a composition comprising a compound of Formula 1 or salt thereof. Target cells can include cells of any type that exhibits insufficient apoptosis, in other words, are characterized by resistance to apoptosis or which exert pathological functions that can be abrogated by apoptosis, including but not limited to cancerous and inflammatory cells. Cancerous cells can be any type of malignancy including, but not limited to, ovarian, colorectal, hematological, breast, lung or pancreatic cancer cells. Inflammatory cells can be any type including, but not limited to, B-cells, T-cells, macrophage, dendritic cells, and granulocytes. Additional examples of target cells include ectopic endometrial cells and psoriatic keratinocytes.

Apoptosis of a cell, or a population of cells, is enhanced if the level of apoptosis is increased by any degree in the presence of the compound of Formula 1 or salt thereof as compared to the level of apoptosis exhibited in the absence of the compound of Formula 1 or salt thereof. Enhancement of apoptosis, thus, encompasses inducing apoptosis in a cell that otherwise would not apoptose, as well as increasing the rate at which a cell undergoes apoptosis, increasing the number of apoptosing cells in a cell population, or increasing the sensitivity of a cell to apoptotic stimuli. When measured in a population of cells, preferably the number of cells undergoing apoptosis is increased by at least about 25%, more preferably at least about 50%, at least about 75%, or at least about 100% (e.g., at least a 1-fold or 2-fold increase). Any technique for measuring and comparing the level of apoptosis in cells can be used to detect enhancement of apoptosis. Such techniques may be based, for instance, upon changes in cell proliferation, increases in cell membrane permeability, reduction in metabolic activity of mitochondria, fragmentation of DNA (DNA laddering) or chromatin condensation, alterations in membrane asymmetry (e.g., translocation phosphatoylserine from the cytoplasmic to the extracellular side of the membrane), activation of apoptotic caspases, release of cytochrome C or apoptosis inhibitory factor (AIF) into the cytoplasm by mitochondria, or any other basis known to be an indicator of apoptosis.

The compounds of Formula 1 and salts thereof also can be used to alter the release of inflammatory cytokines from an immune system cell, thereby reducing the inflammatory potential of the cell. Inflammatory cytokines include pro-inflammatory cytokines and anti-inflammatory cytokines. The release of cytokines is altered if the amount or rate of release of any one or more cytokines is increased or decreased by any degree in the presence of the compound of Formula 1 or salt thereof as compared to the amount or rate of release of the same one or more cytokines in the absence of the compound of Formula 1 or salt thereof. Desirably, the amount or rate of release of any one or more cytokines is altered (increased or decreased) by at least about 25%, more preferably at least about 50%, at least about 75%, or at least about 100% (e.g., at least a 1-fold or 2-fold increase). Any technique for measuring and comparing the level of cytokine release in cells can be used to detect alteration in the release of the inflammatory cytokines. Such techniques may be based, for instance, directly upon changes in the amount of cytokine in a sample or cell culture, or indirectly by detecting cellular responses to increased or decreased cytokine concentration.

Without wishing to be bound by any particular theory or mechanism, it is believed that the compounds of Formula 1 bind to or otherwise inhibit XIAP, cIAP-1, and/or cIAP-2. Thus, in a related aspect, the invention provides a method of reducing the activity or protein levels of XIAP, cIAP-1, and/or cIAP-2 in a cell comprising contacting the cell with a compound of Formula 1 or salt thereof. The activity and protein levels of XIAP, cIAP-1, and/or cIAP-2 can be measured by known assays and protein quantification techniques. All other aspects of the method are as previously described.

The compounds of the invention described herein can be administered to a cell in vitro. As used herein, the term "in vitro" means that the cell is not in a living organism. The compounds of the invention also can be administered to a cell in vivo or ex vivo. As used herein, the term "in vivo" means that the cell is a part of a living organism, for instance, when the cell is in a host subject. The term "ex vivo" as used herein refers to the administration of a compound to a cell or a population of cells in vitro, followed by administration of the cell or population of cells to a host subject. Often the cells are autologous to the subject.

When the compound is administered to a cell in a subject, the subject desirably is a mammal, especially a human. The methods, in accordance with this aspect of the invention, are most suitable for use in conjunction with a subject that is afflicted with a disease, or at risk for developing a disease, associated with insufficient apoptosis or an autoimmune or inflammatory disease. When the cell is in a subject, the compound of Formula 1 or salt thereof can be administered to the cell by administering the compound of Formula 1 or salt thereof, or composition comprising same (e.g., pharmaceutical composition) to the subject. Preferably, the administration of a compound of Formula 1 or salt thereof to a cell in a subject afflicted with a disease associated with insufficient apoptosis or an autoimmune or inflammatory disease is effective to treat the disease. Thus, the invention also provides a method of treating a disease associated with insufficient apoptosis or an autoimmune or inflammatory disease comprising administering to a subject in need thereof a compound of Formula 1 or salt thereof. As used herein, the term "treat" is intended to encompass alleviating to any degree, or preventing the onset of, any symptom of the disease or condition. The term "treat" also encompasses inhibiting, arresting, or reversing the growth or proliferation of diseased cells or the progression or spread (metastasis) of the disease or condition, or altering the release of inflammatory cytokines. Treatment includes preventative treatment, such as treatment of a patient after surgical removal of cancer or tumor cells to prevent regrowth of the cancer or tumor, or treatment to prevent pathogenic cell-survival, for instance, under conditions that lead to diseases such as asthma, MS, and the like.

Diseases and conditions associated with insufficient apoptosis encompass proliferative diseases characterized by inappropriately high levels of cell division, inappropriately low levels of apoptosis, or both. Such disease may include those in which there is a defect in normally programmed cell-death or the cellular apoptotic machinery (TRAIL, FAS, apoptosome).

Examples of autoimmune of inflammatory disorders where apoptotic resistance contributes to pathology or where increased apoptosis may be therapeutically beneficial include multiple sclerosis, atherosclerosis, arthritis (e.g., rheumatoid arthritis (RA)) and the like. Another aspect of the present invention provides a method of inducing apoptosis in a cell such as a rheumatoid arthritis fibroblast-like synoviocyte with a compound of Formula 1 or salt thereof alone or in combination with cytokines or death-receptor ligands such as Fas, TRAIL or TRAIL-receptor angonist antibodies.

Diseases where apoptotic resistance contributes to pathology or where increased apoptosis may be therapeutically beneficial include all types of cancer including lung, colorectal, breast and prostate cancer. Other cancers that may be treated by compounds, compositions and methods of the invention include but are not limited those listed in the following table.

| Tissue | Example |
| --- | --- |
| Adrenal gland | neuroblastoma |
| Bone | osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors |
| Cardiac | sarcoma (angiosarcoma, fibrosarcoma, rhabdomyosarcoma, liposarcoma), myxoma, rhabdomyoma, fibroma, lipoma and teratoma |
| Gastrointestinal | esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) |
| Genitourinary tract | kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) |
| Gynecological | uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) |
| Hematologic | blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] |
| Liver | hepatoma (hepatocellular carcinoma), cholangiocarcinoma, hepatoblastoma, angiosarcoma, hepatocellular adenoma, hemangioma |
| Lung | bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma |
| Nervous system | skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma) |
| Skin | malignant melanoma, basal cell carcinoma, squamous cell carcinoma, Karposi's sarcoma, moles dysplastic nevi, lipoma, angioma, dermatofibroma, keloids |

The compound of Formula 1 or salt thereof can be used in a pure or substantially pure form, or as part of a composition comprising the compound of Formula 1 or salt thereof and a suitable carrier. When the composition is to be administered to a subject or patient, especially a human subject or patient, the carrier should be a pharmaceutically acceptable carrier. As used herein, the terms "subject" and "patient" are intended to mean humans as well as non-human mammals such as primates, cats, dogs, swine, cattle, sheep, goats, horses, rabbits, rats, mice and the like.

The pharmaceutical compositions of the present invention can be prepared by combining a compound of the present invention with an appropriate carrier. The carrier can be any of those conventionally used and is limited only by physiochemical considerations, such as solubility and lack of reactivity with the active compound, and by the route of administration. It will be appreciated by one of skill in the art that, in addition to the following described pharmaceutical composition, the active compounds of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

There are a variety of suitable formulations of the pharmaceutical composition of the present inventive methods. The formulation can be, for instance, a solid, semi-solid, or liquid, including tablets, capsules, powders, granules, ointments, solutions, suppositories, injections, inhalants, gels, microspheres, and aerosols.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the present invention, or a pharmaceutically acceptable salt thereof, for treatment of a disease-state as described above.

The pharmaceutical composition can be formulated for any route of administration, including, for instance, oral, topical, transdermal, transmucosal, aerosol/inhalation, parenteral (including without limitation subcutaneous, intravenous, intramuscular, intrasernal, interperitoneal, intracerebral, intraosseous, and intradermal), rectal, sublingual, ocular, intranasal, and vaginal administration. One skilled in the art will appreciate that these routes of administering the compound of the invention are known, and, although more than one route can be used to administer a particular compound, a particular route can provide a more immediate and more effective response than another route. The following formulations are describe for the purposes of further illustration, and are in no way intended to limit the invention.

Injectable formulations are among those formulations that may be suitable in accordance with the present invention. The requirements for effective pharmaceutical carriers for injectable compositions are well-known to those of ordinary skill in the art (See, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)). Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants including pegylated or fatty acid modified glycerols and triglycerides.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.01% to about 10% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations are well-known to those of skill in the art. Such formulations are particularly suitable in the context of the present invention for application to the skin. The carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the present invention from about 0.1% to about 10% w/v (weight per unit volume).

Formulations suitable for oral administration can consist of (a) liquid solutions, such as an effective amount of the active compound dissolved in diluents, (b) capsules, sachets, tablets, lozenges, and troches, each containing a predetermined amount of the active ingredient, as solids or granules; (c) powders; (d) suspensions in an appropriate liquid; and (e)

suitable emulsions. Liquid formulations may include diluents, such as water, saline, and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art. The oral formulations will typically contain from about 0.1% to about 70% by weight of the active ingredient.

The compounds of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Additionally, the compounds of the invention, or compositions comprising such compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

Alternatively, the compounds of the invention described herein can be modified into a depot form, such that the manner in which the compound of the invention is released into the body to which it is administered is controlled with respect to time and location within the body (see, e.g., U.S. Pat. No. 4,450,150). Depot forms of the active compound can be, for example, an implantable composition comprising the compound and a porous material, such as a polymer, wherein the compound is encapsulated by or diffused throughout the porous material. The depot is then implanted into the desired location within the body and the compound is released from the implant at a predetermined rate by diffusing through the porous material.

In some contexts, the compounds of the invention can be advantageously administered via an implanted pump that allows intrathecal delivery. Such a delivery method is especially useful for delivery of drugs to the CNS when the drugs administered do not otherwise sufficiently penetrate the blood-brain barrier.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered should, in any event, contain a therapeutically effective amount of a compound of the present invention, or a pharmaceutically acceptable salt thereof, for treatment of a disease-state as described above.

One of ordinary skill in the art will readily appreciate that the compounds of the invention described herein can be modified in any number of ways to increase the therapeutic efficacy of the compound. For instance, the compound or inhibitor could be conjugated either directly or indirectly through a linker to a targeting moiety. The practice of conjugating compounds or inhibitors to targeting moieties is known in the art. The term "targeting moiety" as used herein, refers to any molecule or agent that specifically recognizes and binds to a cell-surface receptor, such that the targeting moiety directs the delivery of the compound or inhibitor to a population of cells on which surface the receptor is expressed. Targeting moieties include, but are not limited to, antibodies, or fragments thereof, peptides, hormones, growth factors, cytokines, and any other naturally- or non-naturally-existing ligands, which bind to cell surface receptors. The term "linker" as used herein, refers to any agent or molecule that bridges the compound or inhibitor to the targeting moiety. One of ordinary skill in the art recognizes that sites on the compounds or inhibitors, which are not necessary for the function of the compound or inhibitor, are ideal sites for attaching a linker and/or a targeting moiety, provided that the linker and/or targeting moiety, once attached to the compound or inhibitor, do(es) not interfere with the function of the compound or inhibitor.

The amount considered to be therapeutically effective will vary depending upon a variety of factors including the specific compound employed, the precise type and severity of the condition to be treated, and the age, body weight, general health, sex, and diet of the patient; and the mode of administration. Generally, a therapeutically effective daily dose may be from about 0.1 mg to about 40 mg/kg of body weight per day or twice per day.

Combination Therapy

The compound of Formula 1 or salt thereof, or composition comprising same, can be used in accordance with the methods described herein alone or in combination with one or more additional active ingredients. For instance, two or more different compounds of Formula 1 or salts thereof can be used together, or one or more compounds of Formula 1 or salts thereof can be used in conjunction with one or more other therapeutically effective compounds. When the compound of Formula 1 or salt thereof is used in conjunction with one or more additional active compounds (whether another compound of Formula 1 or a different compound), the one or more additional compounds can be administered simultaneously with, prior to, or after administration of the compound of Formula 1 or salt thereof. Furthermore, when administered simultaneously, the one or more additional compounds can be administered in the same composition as the compound of Formula 1 or salt thereof, or in a different composition.

The selection of additional therapeutic agents for use in combination with a compound of Formula 1 or salt thereof will depend, at least in part, on the particular disease or condition to be treated. According to one aspect of the invention, the compound of Formula 1 or salt thereof is administered in combination with an agent that directly or indirectly stimulates the death receptor apoptotic pathway. Without wishing to be bound by any particular theory, it is believed that the combined use of a compound of Formula 1 or salt thereof and an agent that stimulates the death receptor apoptotic pathway (e.g., a death receptor agonist) produces an enhanced, and in some cases synergistic, effect. The death receptor agonist can be any agent capable of stimulating the pro apoptotic response mediated by the death-receptors. Such agents include soluble TRAIL, TRAIL receptor agonists, and any agent that increases the circulating level of TRAIL in a subject, including immune system modulators such as interferon-alpha or ionizing radiation (e.g., UVB) that can induce the release of cytokines, such as the interleukins, or TNF.

TRAIL receptor agonists include any compound that mimics TRAIL by stimulating the TRAIL death receptor. Such compounds may include, for instance, a small molecule or an antibody agonist of the TRAIL receptor. Agonist antibodies directed against the death receptors TRAIL-R1 and/or TRAIL-R2 are preferred, particularly antibodies known as HGS-ETR1 and HGS-ETR2. Exemplary agonist antibodies include those described in U.S. Pat. No. 7,244,429; in U.S. Patent Application Publication Nos. 2007/0179086, 2002/0004227, 2006/0269554, 2005/0079172, 2007/0292411, 2006/0270837 (now U.S. Pat. No. 7,361,341), 2009/0026429, 2006/0269555, 2004/0214235, and 2007/0298039; and in International Patent Publications WO2006/017961 and WO98/51793. Each of these publications is hereby incorporated by reference in its entirety. In preferred embodiments, compounds of the invention are used in combination with one or more of these TRAIL receptor agonist antibodies for the treatment of cancer and other neoplasms.

Other agents useful in combination with a compound of Formula 1 or salt thereof include, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, angiogenesis inhibitors, PPAR-γ agonists, PPAR-δ agonists, inhibitors of inherent multidrug resistance, anti-emetic agents, agents used to treat anemia or neutropenia, immunologic-enhancing drugs, proteasome inhibitors such as Velcade and MG132 (7-Leu-Leu-aldehyde) (see He at al., *Oncogene* (2004) 23, 2554-2558), HDAC inhibitors such as sodium butyrate, phenyl butyrate, hydroamic acids, cyclin tetrapeptide and the like (see Rosato et al., *Molecular Cancer Therapeutics* (2003), 1273-1284), inhibitors of the chymotrypsin-like activity in the proteasome, and E3 ligase inhibitors. Other such agents are described in WO 03/099211 (PCT/US03/15861).

Other known chemotherapeutic agents can be used in combination with a compound of Formula 1 or salt thereof, especially for the treatment of cancers or other proliferative disease susceptible to chemotherapy. Any chemotherapeutic agent can be used in combination with the compound of Formula 1 or salt thereof. The selection of a chemotherapeutic agent may depend, in part, on the particular type of cancer or proliferative disease being treated. Exemplary chemotherapeutic agents are described in the following paragraphs. The chemotherapeutic agents described herein are merely illustrative, and are in no way limiting.

Vinca Alkaloids and Microtubule-Disrupting Compounds:

Vinca alkaloids include vincristine, vinblastine, vindesine, vinflunine, vinorelbine, and anhydrovinblastine. Dolastatins are oligopeptides that primarily interfere with tubulin at the vinca alkaloid binding domain. Dolastatins include dolastatin-10 (NCS 376128), dolastatin-15, ILX651, TZT-1027, symplostatin 1, symplostatin 3, and LU103793 (cemadotin). Cryptophycins (e.g., cryptophycin 1 and cryptophycin 52 (LY355703)) bind tubulin within the vinca alkaloid-binding domain and induce G2/M arrest and apoptosis.

Other microtubule disrupting compounds are described in U.S. Pat. Nos. 6,458,765; 6,433,187; 6,323,315; 6,258,841; 6,143,721; 6,127,377; 6,103,698; 6,023,626; 5,985,837; 5,965,537; 5,955,423; 5,952,298; 5,939,527; 5,886,025; 5,831,002; 5,741,892; 5,665,860; 5,654,399; 5,635,483; 5,599,902; 5,530,097; 5,521,284; 5,504,191; 4,879,278; and 4,816,444, and U.S. patent application Publication Nos. 2003/0153505 A1; 2003/0083263 A1; and 2003/0055002 A1.

Taxanes and Other Microtubule Stabilizing Compounds:

Taxanes include paclitaxel, docetaxel, RPR 109881A, SB-T-1213, SB-T-1250, SB-T-101187, BMS-275183, BRT 216, DJ-927, MAC-321, IDN5109, and IDN5390. Taxane analogs include BMS-184476, BMS-188797, and functionally related non-taxanes include epothilones (e.g., epothilone A, epothilone B (EP0906), deoxyepothilone B, and epothilone B lactam (BMS-247550)), eleutherobin, discodermolide, 2-epi-discodermolide, 2-des-methyldiscodermolide, 5-hydroxymethyldiscodermolide, 19-des-aminocarbonyldiscodermolide, 9(13)-cyclodiscodermolide, and laulimalide.

Other microtubule stabilizing compounds are described in U.S. Pat. Nos. 6,624,317; 6,610,736; 6,605,599; 6,589,968; 6,583,290; 6,576,658; 6,515,017; 6,531,497; 6,500,858; 6,498,257; 6,495,594; 6,489,314; 6,458,976; 6,441,186; 6,441,025; 6,414,015; 6,387,927; 6,380,395; 6,380,394; 6,362,217; 6,359,140; 6,306,893; 6,302,838; 6,300,355; 6,291,690; 6,291,684; 6,268,381; 6,262,107; 6,262,094; 6,147,234; 6,136,808; 6,127,406; 6,100,411; 6,096,909; 6,025,385; 6,011,056; 5,965,718; 5,955,489; 5,919,815; 5,912,263; 5,840,750; 5,821,263; 5,767,297; 5,728,725; 5,721,268; 5,719,177; 5,714,513; 5,587,489; 5,473,057; 5,407,674; 5,250,722; 5,010,099; and 4,939,168; and U.S. patent application Publication Nos. 2003/0186965 A1; 2003/0176710 A1; 2003/0176473 A1; 2003/0144523 A1; 2003/0134883 A1; 2003/0087888 A1; 2003/0060623 A1; 2003/0045711 A1; 2003/0023082 A1; 2002/0198256 A1; 2002/0193361 A1; 2002/0188014 A1; 2002/0165257 A1; 2002/0156110 A1; 2002/0128471 A1; 2002/0045609 A1; 2002/0022651 A1; 2002/0016356 A1; 2002/0002292 A1, each of which is hereby incorporated by reference.

Other chemotherapeutic agents that may be administered with a compound of the present invention are listed in the following table:

| | | |
|---|---|---|
| Alkylating agents | cyclophosphamide | mechlorethamine |
| | lomustine | thiotepa |
| | busulfan | streptozocin |
| | procarbazine | chlorambucil |
| | ifosfamide | temozolomide |
| | altretamine | dacarbazine |
| | melphalan | semustine |
| | estramustine phosphate | carmustine |
| | hexamethylmelamine | |
| Platinum agents | cisplatin | tetraplatin |
| | carboplatinum | BBR-3464 |
| | oxaliplatin | Ormiplatin |
| | ZD-0473 | SM-11355 |
| | spiroplatinum | iproplatin |

-continued

| | | |
|---|---|---|
| | lobaplatin | AP-5280 |
| | carboxyphthalatoplatinum | |
| | satraplatin | |
| Antimetabolites | azacytidine | 6-mercaptopurine |
| | tomudex | hydroxyurea |
| | gemcitabine | 6-thioguanine |
| | trimetrexate | decitabine |
| | capecitabine | cytarabin |
| | deoxycoformycin | clofarabine |
| | 5-fluorouracil | 2-fluorodeoxy |
| | fludarabine | cytidine |
| | floxuridine | irofulven methotrexate |
| | pentostatin | DMDC idatrexate |
| | 2-chlorodeoxyadenosine | ethynylcytidine |
| | raltitrexed | |
| Topoisomerase inhibitors | amsacrine | TAS-103 |
| | rubitecan | Topotecan |
| | epirubicin | elsamitrucin dexrazoxanet |
| | exatecan mesylate | J-107088 |
| | etoposide | pixantrone |
| | quinamed | BNP-1350 rebeccamycin |
| | teniposide or mitoxantrone | analogues |
| | gimatecan | CKD-602 ( |
| | irinotecan (CPT-11) | BBR-3576 |
| | diflomotecan (Beaufour-Ipsen) | KW-2170 |
| | 7-ethyl-10-hydroxy-campto-thecin | |
| Antitumor antibiotics | dactinomycin (actinomycin D) | bleomycinic acid |
| | amonafide | idarubicin |
| | doxorubicin (adriamycin) | bleomycin A |
| | azonafide | rubidazone |
| | deoxyrubicin | bleomycin B |
| | anthrapyrazole | plicamycinp |
| | valrubicin | mitomycin C |
| | oxantrazole | porfiromycin |
| | daunorubicin (daunomycin) | MEN-10755 |
| | losoxantrone | cyanomorpholinodoxorubicin |
| | epirubicin | GPX-100 mitoxantrone |
| | bleomycin sulfate (blenoxane) | (novantrone) |
| | therarubicin | |
| Antimitotic agents | paclitaxel | RPR 109881A |
| | SB 408075 docetaxel | ZD 6126 |
| | E7010 | TXD 258 |
| | Colchicines | PEG-paclitaxel |
| | PG-TXL vinblastine | epothilone B |
| | IDN 5109 | AZ10992 |
| | Vincristine | T 900607 |
| | A 105972 | IDN-5109 |
| | Vinorelbine | T 138067 |
| | A 204197 | AVLB |
| | Vindesine | cryptophycin 52 azaepothilone B |
| | LU 223651 | vinflunine |
| | dolastatin 10 | BNP-7787 |
| | D 24851 | auristatin PE |
| | rhizoxin | CA-4 prodrug |
| | ER-86526 | BMS 247550 |
| | mivobulin combretastatin A4 | dolastatin-10 |
| | cemadotin | BMS 184476 |
| | isohomohalichondrin-B | CA-4 |
| | | BMS 188797 |
| | | taxoprexin |
| Aromatase inhibitors | Aminoglutethimide | anastrazole |
| | Exemestane | YM-511 |
| | Letrozole | formestane |
| | atamestane | |
| Thymidylate synthase inhibitors | pemetrexed | ZD-9331 |
| | nolatrexed | CoFactor$^{TM}$ |
| DNA antagonists | trabectedin mafosfamide | albumin + 32P |
| | glufosfamide | O6 benzyl guanine thymectacin |
| | apaziquone | edotreotide |
| Farnesyl-transferase inhibitors | arglabin tipifarnib lonafarnib | perillyl alcohol |
| Pump inhibitors | CBT-1 | tariquidar |
| | zosuquidar trihydrochloride | biricodar dicitrate |
| | | MS-209 ) |
| Histone acetyltransferase | tacedinaline pivaloyloxymethyl butyrate | depsipeptide MS-275 |

| | | |
|---|---|---|
| inhibitors | SAHA | |
| Metallo-proteinase inhibitors | Neovastat CMT-3 | marimastat BMS-275291 |
| Ribonucleoside reductase inhibitors | gallium maltolate tezacitabine | triapine didox |
| TNF alpha agonists/ antagonists | virulizin revimid | CDC-394 |
| Endothelin A receptor antagonist | atrasentan YM-598 | ZD-4054 |
| Retinoic acid receptor agonists | fenretinide alitretinoin | LGD-1550 |
| Immuno-modulators | Interferon dexosome therapy oncophage pentrix GMK ISF-154 adenocarcinoma vaccine cancer vaccine (Intercell) CTP-37 | norelin IRX-2 BLP-25 PEP-005 MGV synchrovax vaccines beta.-alethine melanoma vaccine CLL therapy p21 RAS vaccine |
| Hormonal and antihormonal agents | estrogens Prednisone conjugated estrogens methylprednisolone ethinyl estradiol prednisolone chlortrianisen aminoglutethimide idenestrol leuprolide hydroxyprogesterone caproate goserelin medroxyprogesterone leuporelin testosterone | bicalutamide testosterone propionate; fluoxymesterone flutamide methyltestosterone octreotide diethylstilbestrol nilutamide megestrol mitotane tamoxifen P-04 (Novogen) Toremofine 2-methoxyestradiol dexamethasone arzoxifene |
| Photodynamic agents | talaporfin Pd-bacteriopheophorbide Theralux lutetium texaphyrin | motexafin gadolinium hypericin |
| Kinase Inhibitors | imatinib kahalide F leflunomide CEP-701 ZD1839 CEP-751 erlotinib MLN518 canertinib PKC412 squalamine phenoxodiol SU5416 trastuzumab SU6668 Sorafenib Cetuximab ZD1839 PKI 166 | C225 ZD4190 rhu-Mab ZD6474 MDX-H210 vatalanib 2C4 PKI166 MDX-447 GW2016 ABX-EGF EKB-509 IMC-1C11 EKB-569 CI-1033 EKB-569 Semaxanib ZD6474 PTK-787 INC-1C11 |

Miscellaneous agents

SR-27897 (CCK A inhibitor), Sanofi-Synthelabo)
BCX-1777 (PNP inhibitor, BioCryst)
tocladesine (cyclic AMP agonist, Ribapharm)
ranpirnase (ribonuclease stimulant, Alfacell)
alvocidib (CDK inhibitor, Aventis)
galarubicin (RNA synthesis inhibitor, Dong-A)
CV-247 (COX-2 inhibitor, Ivy Medical)
tirapazamine (reducing agent, SRI International)
P54 (COX-2 inhibitor, Phytopharm)

gemtuzumab (CD33 antibody, Wyeth Ayerst)
CCI-779 (mTOR kinase inhibitor, Wyeth)
PG2 (hematopoiesis enhancer, Pharmagenesis)
exisulind (PDE V inhibitor, Cell Pathways)
Immunol$^{TM}$ (triclosan oral rinse, Endo)
CP-461 (PDE V inhibitor, Cell Pathways)
triacetyluridine (uridine prodrug, Wellstat)
AG-2037 (GART inhibitor, Pfizer)
SN-4071 (sarcoma agent, Signature BioScience WX-UK1 (plasminogen activator inhibitor, Wilex)

| | |
|---|---|
| N-acetylcysteine (reducing agent, Zambon) | TransMID-107 .TM. (immunotoxin, KS Biomedix) |
| CapCell™ (CYP450 stimulant, Bavarian Nordic) | PBI-1402 (PMN stimulant, ProMetic LifeSciences) |
| R-flurbiprofen (NF-kappaB inhibitor, Encore) | PCK-3145 (apoptosis promotor, Procyon) |
| GCS-100 (gal3 antagonist, GlycoGenesys) | bortezomib (proteasome inhibitor, Millennium) |
| 3CPA (NF-kappaB inhibitor, Active Biotech) | doranidazole (apoptosis promotor, Pola) |
| G17DT immunogen (gastrin inhibitor, Aphton) | SRL-172 (T cell stimulant, SR Pharma) |
| seocalcitol (vitamin D receptor agonist, Leo) | CHS-828 (cytotoxic agent, Leo) |
| efaproxiral (oxygenator, Allos Therapeutics) | TLK-286 (glutathione S transferase inhibitor, Telik) |
| 131-I-TM-601 (DNA antagonist, TransMolecular) | trans-retinoic acid (differentiator, NIH) |
| PI-88 (heparanase inhibitor, Progen) | PT-100 (growth factor agonist, Point Therapeutics) |
| eflornithine (ODC inhibitor, ILEX Oncology) | |
| tesmilifene (histamine antagonist, YM BioSciences) | MX6 (apoptosis promotor, MAXIA) |
| | midostaurin (PKC inhibitor, Novartis) |
| minodronic acid (osteoclast inhibitor, Yamanouchi) | apomine (apoptosis promotor, ILEX Oncology) |
| histamine (histamine H2 receptor agonist, Maxim) | bryostatin-1 (PKC stimulant, GPC Biotech) |
| | urocidin (apoptosis promotor, Bioniche) |
| indisulam (p53 stimulant, Eisai) | CDA-II (apoptosis promotor, Everlife) |
| tiazofurin (IMPDH inhibitor, Ribapharm) | Ro-31-7453 (apoptosis promotor, La Roche) |
| aplidine (PPT inhibitor, PharmaMar) | |
| cilengitide (integrin antagonist, Merck KGaA) | SDX-101 (apoptosis promotor, Salmedix) |
| | brostallicin (apoptosis promotor, Pharmacia) |
| rituximab (CD20 antibody, Genentech) | |
| SR-31747 (IL-1 antagonist, Sanofi-Synthelabo) | ceflatonin (apoptosis promotor, ChemGenex) |
| | Herceptin |

When the disease or disorder to be treated is an inflammatory or autoimmune disorder, especially rheumatoid arthritis (RA), the compound of Formula 1 or salt thereof can be administered in combination with one or more non-steroidal anti-inflammatory drugs (NSAIDs), analgesics, corticosteroids and disease-modifying antirheumatic drugs. Other agents which may be useful in combination with Formula 1 or salt thereof for such applications include interleukin-1 (IL-1) receptor antagonist therapy such as anakinra (Kineret™), tocilizumab (Actemra™), hydroxychloroquine (Plaquenil™), sulfasalazine (Azulfidine™), leflunomide (Arava™), tumor necrosis factor inhibitors such as etanercept (Enbrel™), adalimumab (Humira™), and infliximab (Remicade™), T-cell costimulatory blocking agents such as abatacept (Orencia™), B cell depleting agents such as rituximab (Rituxan™), natalizumab (Tysabri™), intramuscular gold and other immunomodulatory and cytotoxic agents such as azathioprine (Imuran™), cyclophosphamide and cyclosporine A (Neoral™, Sandimmune™).

Still other agents which may be useful in combination with a compound of Formula 1 or salt thereof for the treatment of RA include methotrexate, alemtuzumab (Campath™), anti-RANKL MAb (denosumab), anti-Blys MAb belimumab (LymphoStat-B™), certolizumab pegol (Cimzia™), p38 inhibitors, JAK inhibitors, anti-TNF agents, anti-CD20 MAbs, anti-IL/ILR targeting agents such as those which target IL-1, IL-5, IL-6 (toclizumab), II-4, IL-13, and IL-23.

Additional combinations may also include agents which reduce the toxicity of the aforesaid agents, such as hepatic toxicity, neuronal toxicity, nephrotoxicity and the like.

Screening Assays

The compounds of the present invention may also be used in a method to screen for other compounds that bind to an IAP BIR domain. Generally speaking, to use the compounds of the invention in a method of identifying compounds that bind to an IAP BIR domain, the IAP is bound to a support, and a compound of the invention is added to the assay. Alternatively, the compound of the invention may be bound to the support and the IAP is added.

There are a number of ways in which to determine the binding of a compound of the present invention to the BIR domain. In one way, the compound of the invention, for example, may be fluorescently or radioactively labeled and binding determined directly. For example, this may be done by attaching the IAP to a solid support, adding a detectably labeled compound of the invention, washing off excess reagent, and determining whether the amount of the detectable label is that present on the solid support. Numerous blocking and washing steps may be used, which are known to those skilled in the art.

In some cases, only one of the components is labeled. For example, specific residues in the BIR domain may be labeled. Alternatively, more than one component may be labeled with different labels; for example, using $I^{125}$ for the BIR domain, and a fluorescent label for the probe.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity. The compounds may be capable of directly or indirectly altering the IAP biological activity.

Drug candidates can include various chemical classes, although typically they are small organic molecules having a molecular weight of more than 100 and less than about 2,500 Daltons. Candidate agents typically include functional groups necessary for structural interaction with proteins, for example, hydrogen bonding and lipophilic binding, and typically include at least an amine, carbonyl, hydroxyl, ether, or carboxyl group. The drug candidates often include cyclical carbon or heterocyclic structures and/or aromatic or polyaromatic structures substituted with one or more functional groups.

Drug candidates can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Competitive screening assays may be done by combining an IAP BIR domain and a probe to form a probe:BIR domain complex in a first sample followed by adding a test compound from a second sample. The binding of the test is determined, and a change or difference in binding between the two samples indicates the presence of a test compound capable of binding to the BIR domain and potentially modulating the IAP's activity.

Thus, provided herein as an aspect of the invention is a probe comprising a compound of the invention and a detectable label or affinity tag. Detectable labels include any chemical moiety that may be linked to a compound of the present invention such that when the compound comprising the label is associated with the BIR domain, the label allows either direct or indirect detection of the compound. Preferably, the label also allows for quantification. Affinity tags are moieties that facilitate isolation or purification of compounds to which they are attached.

As used herein, the term "probe" is intended to mean a compound of Formula 1 or salt thereof which is labeled with either a detectable label or an affinity tag, and which is capable of binding, either covalently or non-covalently, to an IAP BIR domain. When, for example, the probe is non-covalently bound, it may be displaced by a test compound. When, for example, the probe is bound covalently, it may be used to form cross-linked adducts, which may be quantified and inhibited by a test compound.

In one case, the binding of the test compound is determined through the use of competitive binding assays. In this embodiment, the probe is labeled with a fluorescent label. Under certain circumstances, there may be competitive binding between the test compound and the probe. Test compounds which display the probe, resulting in a change in fluorescence as compared to control, are considered to bind to the BIR region.

In one case, the test compound may be labeled. Either the test compound, or a compound of the present invention, or both, is added first to the IAP BIR domain for a time sufficient to allow binding to form a complex.

Formation of the probe:BIR domain complex typically require incubations of between 4° C. and 40° C. for between 10 minutes to about 1 hour to allow for high-throughput screening. Any excess of reagents are generally removed or washed away. The test compound is then added, and the presence or absence of the labeled component is followed, to indicate binding to the BIR domain.

In one case, the probe is added first, followed by the test compound. Displacement of the probe is an indication the test compound is binding to the BIR domain and thus is capable of binding to, and potentially modulating, the activity of IAP. Either component can be labeled. For example, the presence of probe in the wash solution indicates displacement by the test compound. Alternatively, if the test compound is labeled, the presence of the probe on the support indicates displacement.

In one case, the test compound may be added first, with incubation and washing, followed by the probe. The absence of binding by the probe may indicate the test compound is bound to the BIR domain with a higher affinity. Thus, if the probe is detected on the support, coupled with a lack of test compound binding, may indicate the test compound is capable of binding to the BIR domain.

Modulation is tested by screening for a test compound's ability to modulate the activity of IAP and includes combining a test compound with an IAP BIR domain, as described above, and determining an alteration in the biological activity of the IAP. Therefore in this case, the test compound should both bind to the BIR domain (although this may not be necessary), and alter its biological activity as defined herein.

Positive controls and negative controls may be used in the assays. All control and test samples are performed multiple times to obtain statistically significant results. Following incubation, all samples are washed free of non-specifically bound material and the amount of bound probe determined. For example, where a radiolabel is employed, the samples may be counted in a scintillation counter to determine the amount of bound compound.

Typically, the signals that are detected in the assay may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; a chemiluminescent label such as luciferase; colorimetric labels; enzymatic markers; or radioisotopes such as tritium, $I^{125}$ and the like. Affinity tags, which may be useful in performing the screening assays of the present invention include be biotin, polyhistidine and the like.

EXAMPLES

The following terms and abbreviations, constructs, and general procedures are used in the Examples:

ABBREVIATIONS AND TERMS

Boc: t-butoxycarbonyl;
Boc-Chg-OH: Boc-L-2(cyclohexyl)glycine
Boc-N-MeAla-OH: N-Boc-N-methylalanine
CBz: benzyloxycarbonyl;
DIPEA: diisopropylethylamine;
DMAP: 4-(dimethylamino)pyridine;
DMF: N,N-dimethylformamide;
DTT: dithiothreitol;
EDC: 3-(dimethylaminopropyl)-3-ethylcarbodiimide hydrochloride;
EDTA: ethylenediaminetetracetic acid;
Fmoc: N-(9-fluorenylmethoxycarbonyl);
HBTU: O-(benzotriazol-1-yl)-N,N,N',N'-tetramethyluronium hexafluorophosphate;
HCl: hydrochloric acid;
HOAc: acetic acid;
HOBt: 1-hydroxybenzotriazole;
HPLC: high performance liquid chromatography;
LCMS: liquid chromatography-mass spectrometer;
MeOH: methanol;
$MgSO_4$: magnesium sulfate;
MS: mass spectrum;
Ms: methanesulfonyl;
$NaHCO_3$: sodium hydrogen carbonate;
Pd/C: palladium on carbon;
TEA: triethylamine;
TFA: trifluoroacetic acid;
THF: tetrahydrofuran;

TMEDA: N,N,N,N-tetramethylethylenediamine;
Ts: para-toluenesulfonyl.
$IC_{50}$: The amount, concentration, or dosage of a particular compound that achieves 50% of a maximum response.
$EC_{50}$ The amount, concentration, or dosage of a particular compound that achieves 50% inhibition of cell survival.

Molecular Constructs for Expression

GST-XIAP linked BIR3RING: XIAP coding sequence amino acids 246-497 cloned into PGEX4T3 via BamH1 and AVA I. The plasmid was transformed into E. coli DH5α for use in protein expression and purification.

GST-HIAP2 (cIAP-1) linker BIR 3: HIAP2 coding sequence from amino acids 251-363 cloned into PGex4T3 via BamH1 and XhoI. The plasmid was transformed into E. coli DH5α for use in protein expression and purification.

GST-HIAP1(cIAP-2) linker BIR 3: HIAP1 coding sequence from amino acids 236-349, cloned into PGex4T3 via BamH1 and XhoI. The plasmid was transformed into E. coli DH5α for use in protein expression and purification.

GST-linker BIR 2 BIR3Ring: XIAP coding sequence from amino acids 93-497 cloned into PGex4T1 via BamH1 and XhoI. Amino acids 93-497 were amplified from full length XIAP in pGex4t3, using the primers: TTAATAGGATCCAT-CAACGGCTTTTATC (SEQ ID NO: 1) and GCTGCATGT-GTGTCAGAGG (SEQ ID NO: 2), using standard PCR conditions. The PCR fragment was TA cloned into pCR-2.1 (Invitrogen). Linker BIR 2 BIR 3Ring was subcloned into pGex4T1 by BamHI/XhoI digestion. The plasmid was transformed into E. coli DH5α for use in protein expression and purification.

Full-length human XIAP, AEG plasmid number 23. XIAP coding sequence amino acids 1-497 cloned into GST fusion vector, PGEX4T3 via BamH1 and Xho I restriction sites. The plasmid was transformed into E. coli DH5α for use in protein purification.

GST-XIAP linker BIR 2: XIAP linker BIR 2 coding sequence from amino acids 93-497 cloned into pGex4T3 via BamHI and XhoI. The plasmid was transformed into E. coli DH5α for use in protein expression and purification.

Expression of Recombinant Proteins

Glutathione S-transferase (GST) tagged proteins were expressed in *Escherichia coli* strains DH5-alpha. For expression of full length XIAP, individual or combinations of XIAP-BIR domains, cIAP-1, cIAP-2 and Livin transformed bacteria were cultured overnight at 37° C. in Luria Broth (LB) medium supplemented with 50 ug/ml of ampicillin. The overnight culture was then diluted 25 fold into fresh LB ampicillin supplemented media and bacteria were grown up to $A_{600}$=0.6 then induced with 1 mM isopropyl-D-1-thiogalactopyranoside for 3 hours. Upon induction, cells were centrifuged at 5000 RPM for 10 minutes and the media was removed. Each pellet obtained from a 1 liter culture received 10 ml of lysis buffer (50 mM Tris-HCl, 200 mM NaCl, 1 mM DTT, 1 mM PMSF, 2 mg/ml of lysosyme, 100 μg/ml)), was incubated at 4° C. with gentle shaking. After 20 minutes of incubation, the cell suspension was placed at −80° C. overnight or until needed.

Purification of Recombinant Proteins

For purification of recombinant proteins, the pellet was thaw on ice and resuspended with 25 mL of lysis buffer (50 mM Tris-HCl pH 7.6, 0.1 mM EDTA, 100 mM NaCl, 100 μg/mL of lysozyme)/500 mL of original culture and incubated on ice for 15 min. and 5 cycles of freeze/thaw cycles were performed in liquid nitrogen and 37° C. water bath. The mixture was sonicated using a probe sonicator until the suspension is no longer viscous and centrifuged at 13000 g for 20 minutes to collect soluble fraction (supernatant).

The resulting supernatant was mixed with 3 mL of glutathione-Sepharose beads (Pharmacia) for 20 min. at 4° C. Afterwards, the beads were washed 3 times with 1× Tris-Buffered Saline (TBS) to remove unbound proteins. The retained proteins were eluted with 2 washes of 1 mL of 50 mM TRIS pH 8.0 containing 10 mM reduced glutathione. The eluted proteins were kept separately and appropriate reagents were added to them for storage at −80° C. As judged by SDS-PAGE the purified proteins were >90% pure. The protein concentration of purified proteins was determined from the Bradford method.

His-tag proteins were expressed in the E. Coli strain in E. coli AD494 cells using a pet28ACPP32 construct. The soluble protein fraction was prepared as described above. For protein purification, the supernatant was purified by affinity chromatography using chelating-Sepharose (Pharmacia) charged with $NiSO_4$ according to the manufacturer's instructions. Briefly, the supernatant were loaded into the $NiSO_4$ charged sepharose with 2 mL of sepharose for 20 min. at 4° C. Afterwards, the beads were washed 3 times with 10 mM MOPS, pH 7.0 containing 500 mM NaCl to remove unbound proteins. The retained proteins were eluted with 2 mL of elution buffer (500 mM imidazole in Tris pH 8.0) and appropriate reagents were added to them for storage at −80° C. Purity of the eluted protein was >90% pure as determined by SDS-PAGE. The protein concentration of purified proteins was determined from the Bradford assay.

Preparation of Probes P1 and P2

A fluorescent peptide probe P1, Fmoc-Ala-Val-Pro-Phe-Tyr(t-Bu)-Leu-Pro-Gly(t-Bu)-Gly-OH (SEQ ID NO: 3), was prepared using standard Fmoc chemistry on 2-chlorotrityl chloride resin (see Int. J. Pept. Prot. Res. 38:555-561, 1991). Cleavage from the resin was performed using 20% acetic acid in dichloromethane (dichloromethane), which left the side chain still blocked. The C-terminal protected carboxylic acid was coupled to 4'-(aminomethy)fluorescein (Molecular Probes, A-1351; Eugene, Oreg.) using excess diisopropylcarbodiimide (DIC) in dimethylformamide (DMF) at room temperature and was purified by silica gel chromatography (10% methanol in dichloromethane). The N-terminal Fmoc protecting group was removed using piperidine (20%) in DMF, and purified by silica gel chromatography (20% methanol in dichloromethane, 0.5% HOAc). Finally, the t-butyl side chain protective groups were removed using 95% trifluoroacetic acid containing 2.5% water and 2.5% triisopropyl silane, to provide probe P1 (>95% pure, HPLC).

Probe P2 was prepared using methods as described in WO 2007/131,366.

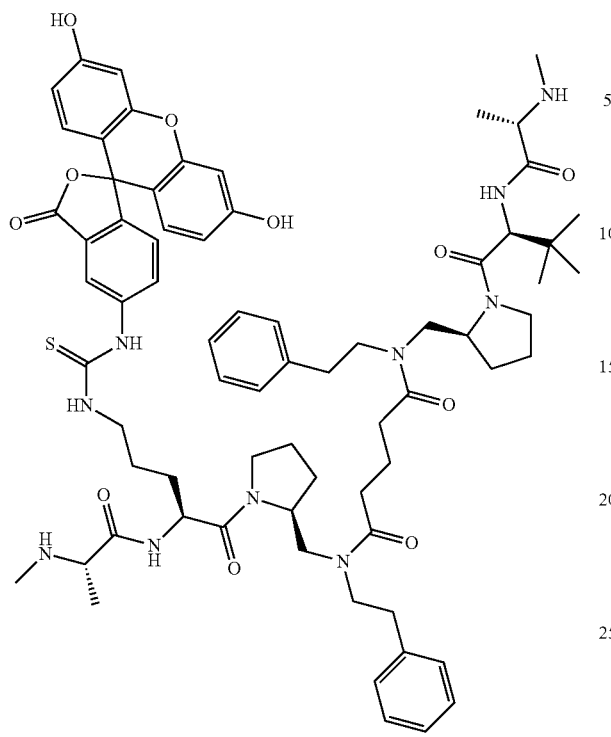

Probe P2

Example 1

The following example illustrates the preparation of compound 5-e, which can be used as an intermediate in the preparation of a compound of Formula 1 or salt thereof.

Scheme 5: Synthesis of Intermediate 5-e

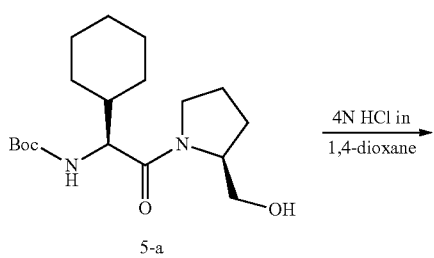

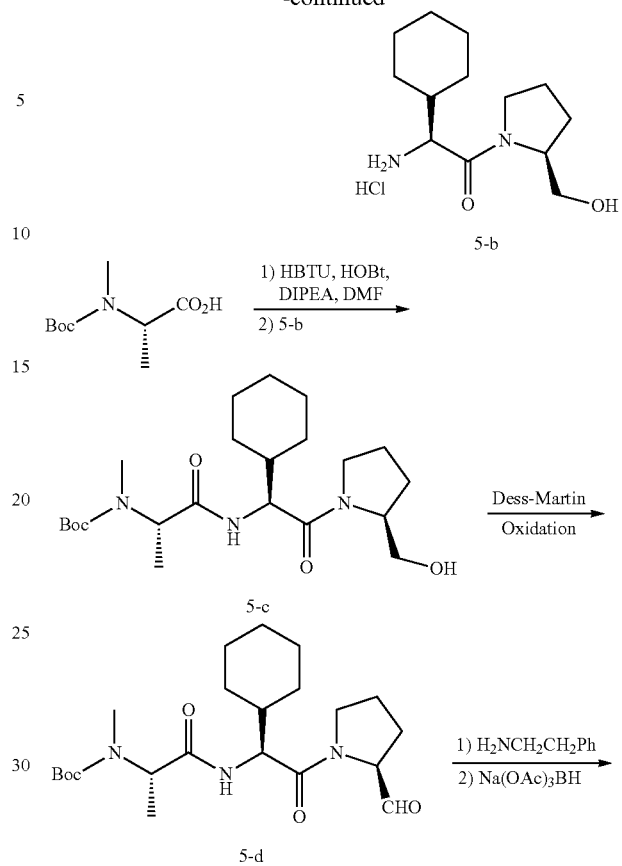

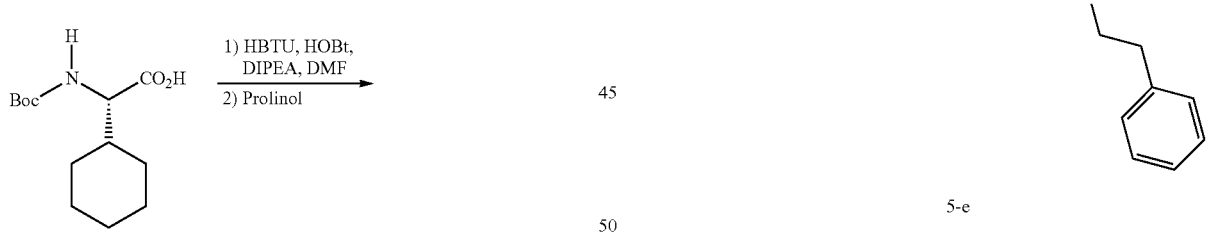

Step 1:

To a solution of Boc-Chg-OH (9.16 g, 35.6 mmol) in DMF cooled to 0° C. were sequentially added DIPEA (10.33 mL, 59.3 mmol), HOBt (4.81 g, 35.6 mmol) and HBTU (13.50 g, 35.6 mmol). After stirring for 10 minutes (S)-prolinol (3.0 g, 29.7 mmol) was added and the reaction mixture was stirred overnight at room temperature. Water and ethyl acetate were added, the organic layer was separated, washed with 10% citric acid, aqueous $NaHCO_3$ and brine, dried over anhydrous $MgSO_4$, filtered and concentrated in vacuo. Purification by silica gel chromatography provided intermediate 5-a as colorless oil.

Step 2:

4N HCl in 1,4-dioxane (30 mL) was added to intermediate 5-a (10.10 g, 29.7 mmol) and the solution was stirred for 1 hour at room temperature. Volatiles were removed under reduced pressure and the residue was triturated with diethyl ether to provide intermediate 5-b.HCl as a white solid. MS (m/z) M+1=240.2

Step 3:

To a solution of Boc-N-Me-Ala-OH (6.02 g, 29.6 mmol) in DMF cooled to 0° C. were sequentially added DIPEA (20.70 mL, 118 mmol), HOBt (6.35 g, 41.5 mmol) and HBTU (14.61 g, 38.5 mmol). After stirring for 10 minutes intermediate 5-b.HCl (8.20 g, 29.6 mmol) was added and the reaction mixture was stirred overnight at room temperature. Water and ethyl acetate were added, the organic layer was separated, washed with 10% citric acid, aqueous NaHCO₃ and brine, dried over anhydrous MgSO₄, filtered and concentrated in vacuo. Purification by silica gel chromatography provided intermediate 5-c as colorless oil.

Step 4:

To a solution of intermediate 5-c (1.20 g, 2.82 mmol) in CH₂Cl₂ cooled to 0° C. were sequentially added sodium hydrogencarbonate (2.36 g, 28.2 mmol) and Dess-Martin periodinane (1.49 g, 3.52 mmol) and the reaction was then stirred for 2 hours at 10° C. Aqueous NaHCO₃ and ethyl acetate were added, the organic layer was separated, dried over anhydrous. MgSO₄, filtered and concentrated in vacuo to provide intermediate 5-d as colorless oil.

Step 5:

To a solution of intermediate 5-d (500 mg, 1.18 mmol) in CH₂Cl₂ was added phenethylamine (283 uL, 1.88 mmol). After stirring for 2 hours at room temperature sodium triacetoxyborohydride (300 mg, 1.41 mmol) and methanol were added and the reaction was stirred at room temperature overnight. Saturated aqueous NaHCO₃ and ethyl acetate were added, the organic layer was separated, washed with brine, dried over MgSO₄, filtered and concentrated in vacuo to provide intermediate 5-e as colorless oil. MS (m/z) M+1=528.4.

Example 2

The following example illustrates the preparation of compound 6-h, which can be used as an intermediate in the preparation of a compound of Formula 1 or salt thereof.

Scheme 6: Synthesis of Intermediate 6-h

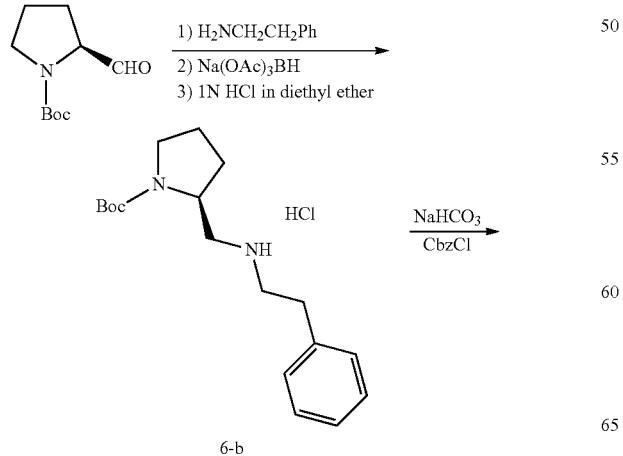

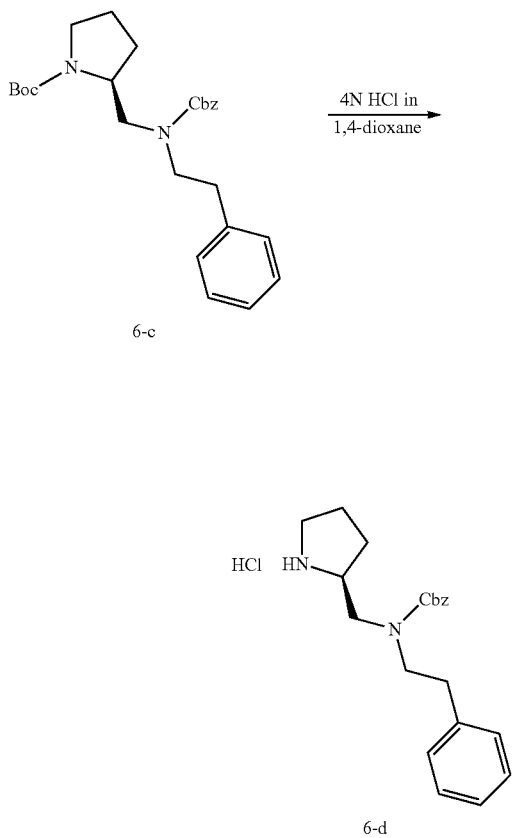

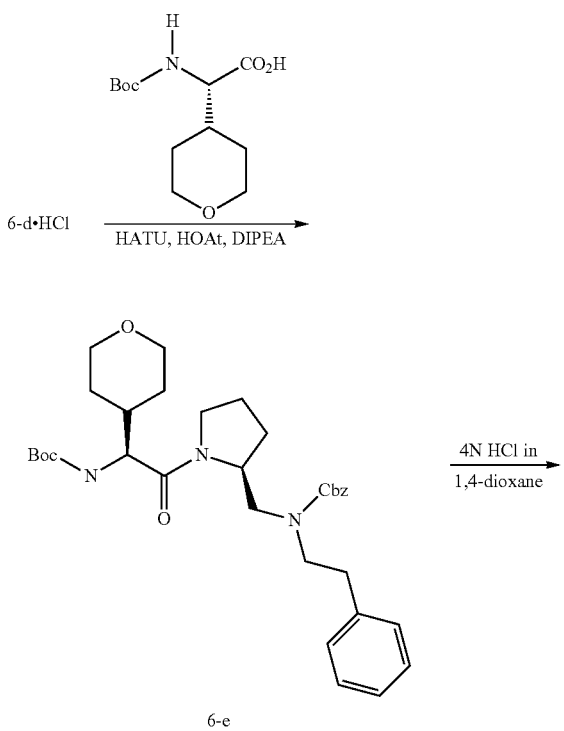

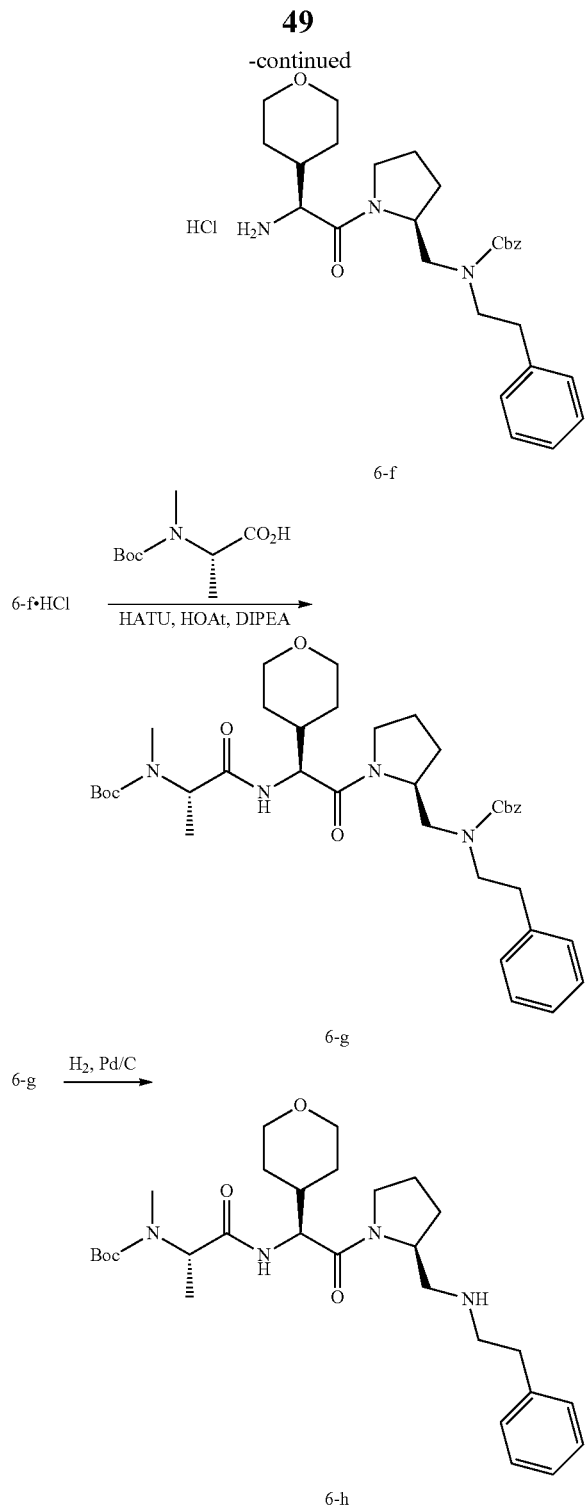

Step 1:

To a solution of N-(tert-butoxycarbonyl)-L-prolinal 6-a (10.0 g, 50.2 mmol) in dichloromethane (300 mL) was added phenethylamine (6.52 mL, 50.2 mmol). After stirring for 2 hours at room temperature, the reaction was cooled to 0° C., sodium triacetoxyborohydride (21.0 g, 100.3 mmol) was added portionwise and the reaction mixture was then stirred at room temperature overnight. 10% aqueous $Na_2CO_3$ was added, the organic layer was separated, the aqueous phase was extracted with dichloromethane, the combined organic extracts were washed with brine, dried over anhydrous $MgSO_4$, filtered and concentrated in vacuo to provide intermediate 6-b as a colorless oil. Intermediate 6-b was dissolved in diethyl ether (125 mL), the solution was cooled to 0° C. and 1N HCl in diethyl ether (50.0 mL, 50.0 mmol) was added. A precipitate formed and intermediate 6-b.HCl was collected by filtration as a white solid. MS (m/z) M+1=305.2

Step 2:

To a solution of intermediate 6-b (6.11 g, 20.08 mmol) in 1,4-dioxane (50.0 mL) and water (50 mL) cooled to 0° C. was added $NaHCO_3$ (8.43 g, 100.0 mmol). After stirring for 15 minutes benzyl chloroformate (3.43 mL, 24.10 mmol) was added and the reaction was then stirred at room temperature for 2 hours. Water and ethyl acetate were added, the organic layer was separated, washed with brine, dried over anhydrous $MgSO_4$, filtered and concentrated in vacuo. Purification by silica gel chromatography provided intermediate 6-c as a colorless oil.

Step 3:

4N HCl in 1,4-dioxane (67.1 mL) was added to intermediate 6-c (8.41 g, 19.18 mmol) at 0° C. and the solution was stirred for 2 hours at room temperature. Volatiles were removed under reduced pressure and the residue was triturated with diethyl ether to provide intermediate 6-d.HCl as a beige solid. MS (m/z) M+1=339.3

Step 4:

To a solution of intermediate 6-d (394 mg, 1.05 mmol) in DMF cooled to 0° C. were sequentially added (S)-2-Boc-2-(tetrahydro-2H-pyran-4-yl)acetic acid (300 mg, 1.15 mmol), HATU (520 mg, 1.36 mmol), HOAt (48 uL, 0.21 mmol) and DIPEA (733 uL, 4.21 mmol) and the reaction was then stirred at room temperature overnight. Saturated aqueous ammonium chloride and ethyl acetate were added; the organic layer was separated, washed with saturated aqueous ammonium chloride, saturated aqueous $NaHCO_3$ and brine, dried over anhydrous $MgSO_4$, filtered and concentrated in vacuo. Purification by silica gel chromatography provided the expected intermediate 6-e as a yellowish oil.

Step 5:

4N HCl in 1,4-dioxane (3.68 mL) was added to intermediate 6-e (610 mg, 1.05 mmol) at 0° C. and the solution was stirred at 0° C. for 4 hours. Volatiles were removed under reduced pressure and the residue was triturated with diethyl ether to provide the expected intermediate 6-f.HCl as a white solid. MS (m/z) M+1=480.4

Step 6:

To a solution of intermediate 6-f.HCl (271 mg, 0.52 mmol) in DMF cooled to 0° C. were sequentially added Boc-N-Me-Ala-OH (117 mg, 0.58 mmol), HATU (240 mg, 0.63 mmol), HOAt (175 uL, 0.10 mmol) and DIPEA (366 uL, 2.10 mmol) and the reaction was then stirred at room temperature for 2 hours. Saturated aqueous ammonium chloride and ethyl acetate were added; the organic layer was separated, washed with saturated aqueous ammonium chloride, saturated aqueous $NaHCO_3$ and brine, dried over $MgSO_4$, filtered and concentrated in vacuo. Purification by silica gel chromatography provided the expected intermediate 6-g as a light yellow oil.

Step 7:

To a solution of intermediate 6-g (277 mg, 0.41 mmol) in THF and stirred under $N_2$ was added 10% Pd/C (50% w/w water content) (89 mg). The reaction mixture was purged with $H_2$ and stirred for 3 hours. The reaction was then filtered through celite and the filtrate was concentrated in vacuo. Purification by silica gel chromatography provided intermediate 6-h as colorless oil. MS (m/z) M+1=531.5.

Example 3

The following example illustrates the preparation of compound 7-d, which can be used as an intermediate in the preparation of a compound of Formula 1 or salt thereof.

Scheme 7: Synthesis of Intermediate 7-d

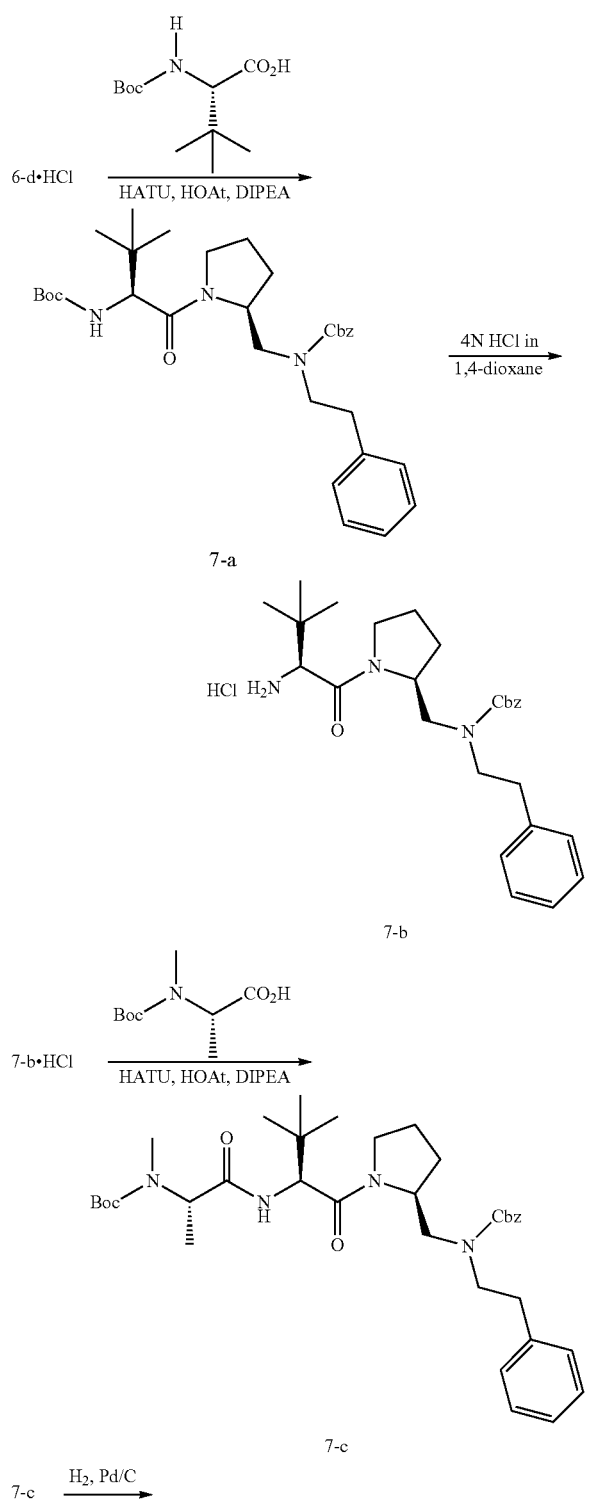

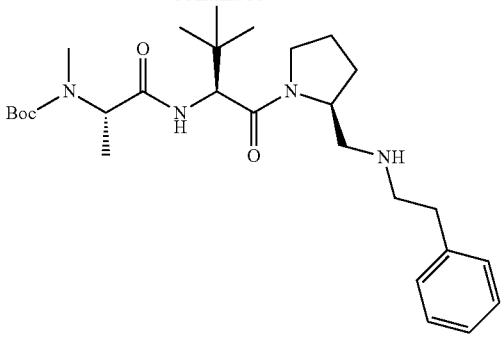

Step 1:

To a solution of intermediate 6-d.HCl (95.90 g, 256 mmol) in DMF (1300 mL) cooled to 0° C. were sequentially added Boc-tBu-gly-OH (65.10 g, 281 mmol), HOAt (42.6 mL, 25.6 mmol), HATU (107 g, 281 mmol) and DIPEA (179 mL, 1023 mmol) and the reaction was then stirred at 0° C. for 30 min. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 7-a as a colorless oil.

Step 2:

4N HCl in 1,4-dioxane (480 mL) was added to intermediate 7-a (141.00 g, 256 mmol) in methanol (130 mL) at 0° C. and the solution was stirred for 30 minutes at 0° C. followed by 3 hours at room temperature. Volatiles were removed under reduced pressure and the residue was triturated with diethyl ether to provide intermediate 7-b.HCl as a white solid. MS (m/z) M+1=452.4

Step 3:

To a solution of intermediate 7-b.HCl (85.00 g, 174 mmol) in DMF (870 mL) cooled to 0° C. were sequentially added Boc-N-Me-Ala-OH (38.90 g, 192 mmol), HOAt (37.70, 22.64 mmol), HATU (72.80 g, 56.3 mmol) and DIPEA (122 mL, 192 mmol) and the reaction was then stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 7-c as white foam.

Step 4:

To a solution of intermediate 7-c (1.56 g, 2.45 mmol) in methanol and stirred under N$_2$ was added 10% Pd/C (50% w/w water content) (500 mg). The reaction mixture was purged with H$_2$ and stirred for 3 hours. The reaction was then filtered through celite and the filtrate was concentrated in vacuo to give intermediate 7-d as a colorless oil. MS (m/z) M+1=503.5.

Example 4

The following example illustrates the preparation of compound 5, which is a compound of Formula 1 or salt thereof.

Scheme 8: Synthesis of compound 5

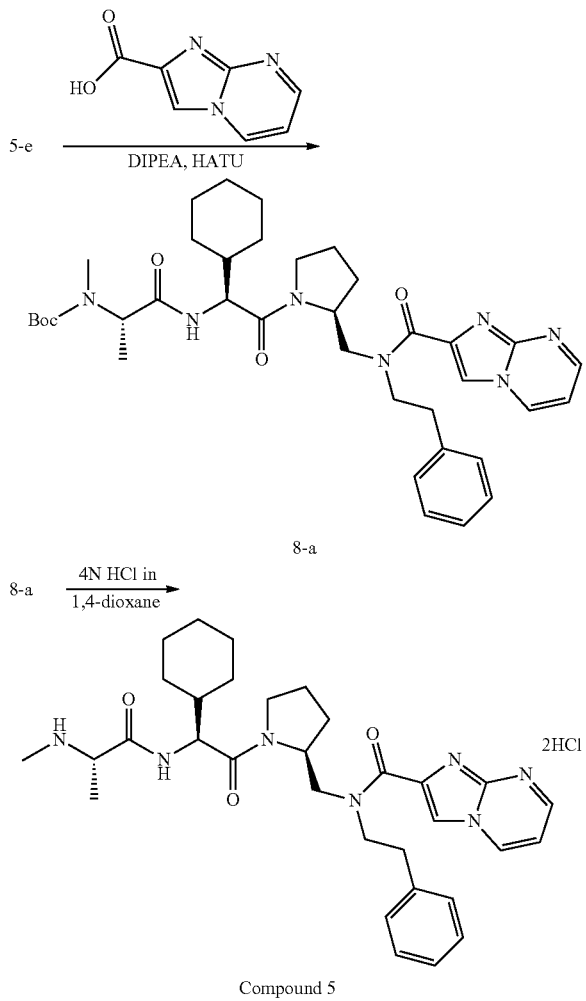

Scheme 9: Synthesis of compound 3

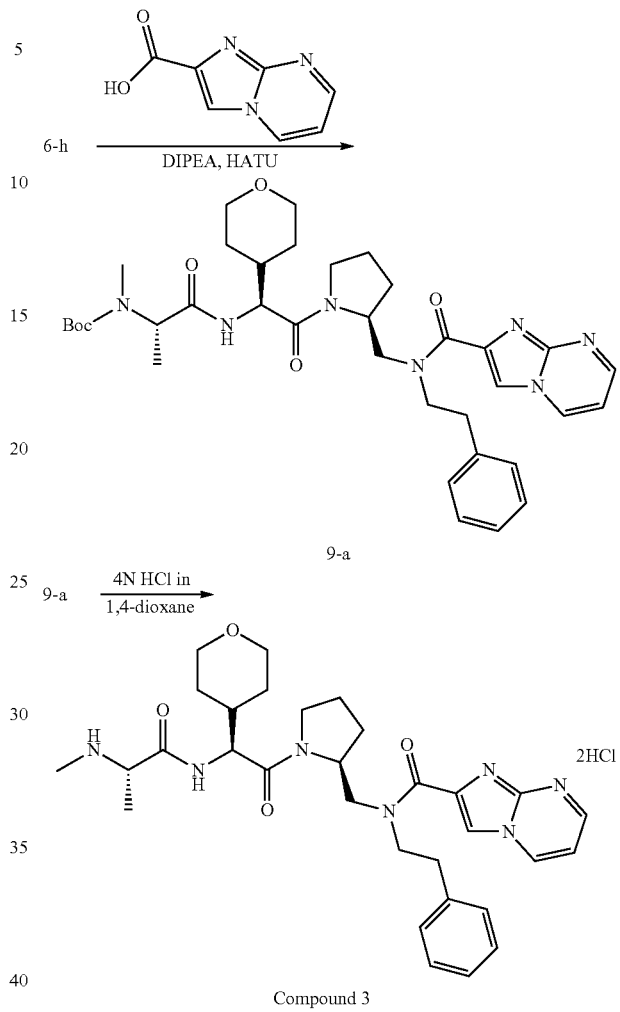

Step 1:

To a solution of intermediate 5-e (150 mg, 0.28 mmol) in DMF, cooled to 0° C., were sequentially added imidazo[1,2-a]pyrimidine-2-carboxylic acid (56 mg, 0.34 mmol), HATU (162 mg, 0.42 mmol) and DIPEA (500 uL, 2.87 mmol). The reaction mixture was stirred for 2 hours at room temperature. Water and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 8-a as a white solid.

Step 2:

4N HCl in 1,4-dioxane (1.8 mL) was added to intermediate 8-a (99 mg, 0.14 mmol) in ethyl acetate (0.5 mL) and the solution was stirred for 1 hour at room temperature. Volatiles were removed under reduced pressure and the residue was triturated with diethyl ether to provide compound 5.2HCl as a white solid. MS (m/z) M+1=574.4.

Example 5

The following example illustrates the preparation of compound 3, which is a compound of Formula 1 or salt thereof.

Step 1:

To a solution of intermediate 6-h (221 mg, 0.41 mmol) in DMF cooled to 0° C. were sequentially added imidazo[1,2-a]pyrimidine-2-carboxylic acid (74.7 mg, 0.45 mmol), HATU (206 mg, 0.54 mmol) and DIPEA (218 uL, 1.24 mmol). The reaction mixture was stirred for 2 hours at room temperature. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 9-a as a colorless oil.

Step 2:

4N HCl in 1,4-dioxane (554 uL) was added to intermediate 9-a (107 mg, 0.15 mmol) in ethyl acetate (0.5 mL) at 0° C. and the solution was stirred for 1 hour at 0° C. Volatiles were removed under reduced pressure and the residue was triturated with diethyl ether to provide compound 3.2HCl as a white solid. MS (m/z) M+1=576.4.

Example 6

The following example illustrates the preparation of compound 6, which is a compound of Formula 1 or salt thereof.

Scheme 10: Synthesis of compound 6

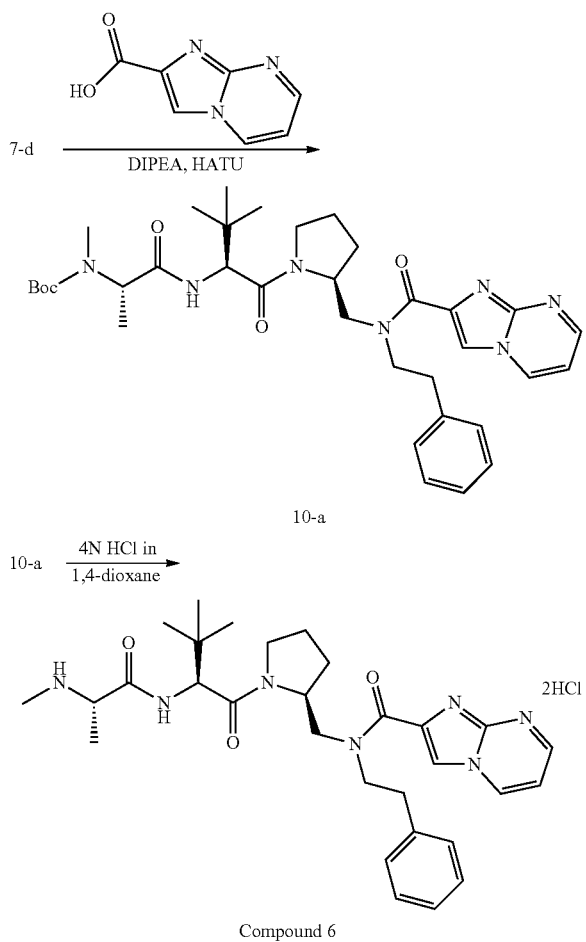

Scheme 11: Synthesis of compound 9

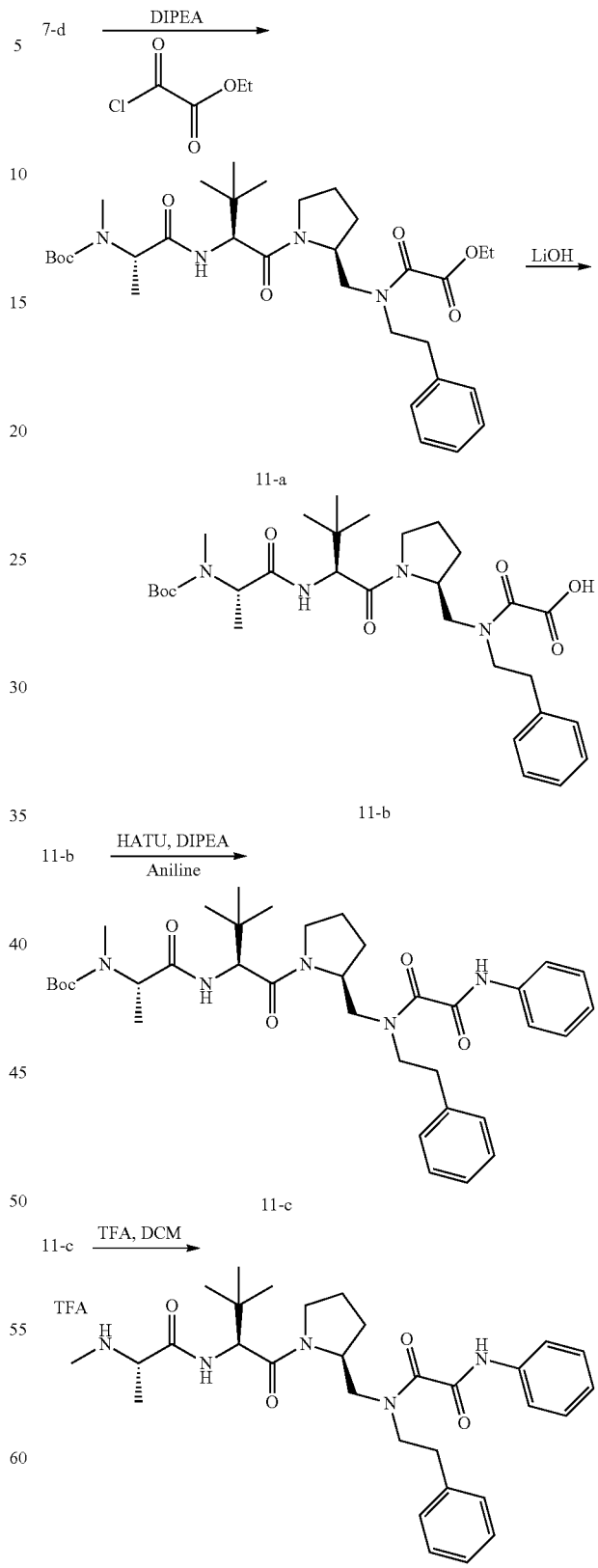

Step 1:

To a solution of intermediate 7-d (1.97 g, 3.94 mmol) in DMF cooled to 0° C. were sequentially added imidazo[1,2-a]pyrimidine-2-carboxylic acid (642 mg, 3.94 mmol), HATU (1.94 g, 5.12 mmol) and DIPEA (2.05 mL, 11.81 mmol). The reaction mixture was stirred for 2 hours at room temperature. Saturated aqueous ammonium chloride and ethyl acetate were added; the organic layer was separated, washed with saturated aqueous ammonium chloride, saturated aqueous $NaHCO_3$ and brine, dried over anhydrous $MgSO_4$, filtered and concentrated in vacuo. Purification by silica gel chromatography provided intermediate 10-a as a white solid.

Step 2:

4N HCl in 1,4-dioxane (9.40 mL) was added to intermediate 10-a (1.74 g, 2.69 mmol) in ethyl acetate (5 mL) at 0° C. and the solution was stirred for 3 hours at 0° C. Volatiles were removed under reduced pressure and the residue was triturated with diethyl ether to provide compound 6.2HCl as a white solid. MS (m/z) M+1=548.4

Example 7

The following example illustrates the preparation of compound 9, which is a compound of Formula 1 or salt thereof.

57

Step 1:

To a solution of intermediate 7-d (200 mg, 0.39 mmol) in dichloromethane cooled to 0° C. were sequentially added DIPEA (174 uL, 0.99 mmol) and ethyl 2-chloro-2-oxoacetate (109 mg, 0.79 mmol). The reaction mixture was stirred for 3 hours at room temperature. 1N HCl and ethyl acetate were added; the organic layer was separated, washed saturated aqueous $NaHCO_3$ and brine, dried over anhydrous $MgSO_4$, filtered and concentrated in vacuo. Purification by silica gel chromatography provided intermediate 11-a as a white solid.

Step 2:

To a solution of intermediate 11-a (215 mg, 0.35 mmol) in THF cooled to 0° C. was added 2N aqueous LiOH (1.0 mL, 2.0 mmol) and the reaction was stirred for 1 hour at room temperature. 1N HCl and ethyl acetate were added; the organic layer was separated, washed with brine, dried over anhydrous $MgSO_4$, filtered and concentrated in vacuo to provide intermediate 11-b as a white solid.

Step 3:

To a solution of intermediate 11-b (200 mg, 0.34 mmol) in DMF cooled to 0° C. were sequentially added aniline (41 uL, 0.45 mmol), DIPEA (61 uL, 0.34 mmol) and HATU (172 mg, 0.45 mmol) and the reaction mixture was stirred for 2 hours at 0° C. Water and ethyl acetate were added; the organic layer was separated, washed with 1N aqueous HCl, saturated aqueous $NaHCO_3$ and brine, dried over anhydrous $MgSO_4$, filtered and concentrated in vacuo. Purification by silica gel chromatography provided intermediate 11-c as a white solid.

Step 4:

To a solution of intermediate 11-c (230 mg, 0.35 mmol) in dichloromethane (2 mL) cooled to 0° C. was added TFA (2 mL) and the reaction was then stirred at 0° C. for 1 hour. Volatiles were removed under reduced pressure and the residue was triturated with diethyl ether to provide compound 9.TFA as a white solid. MS (m/z) M+1=550.1

Example 8

The following example illustrates the preparation of compound 12-g, which can be used as an intermediate in the preparation of a compound of Formula 1 or salt thereof.

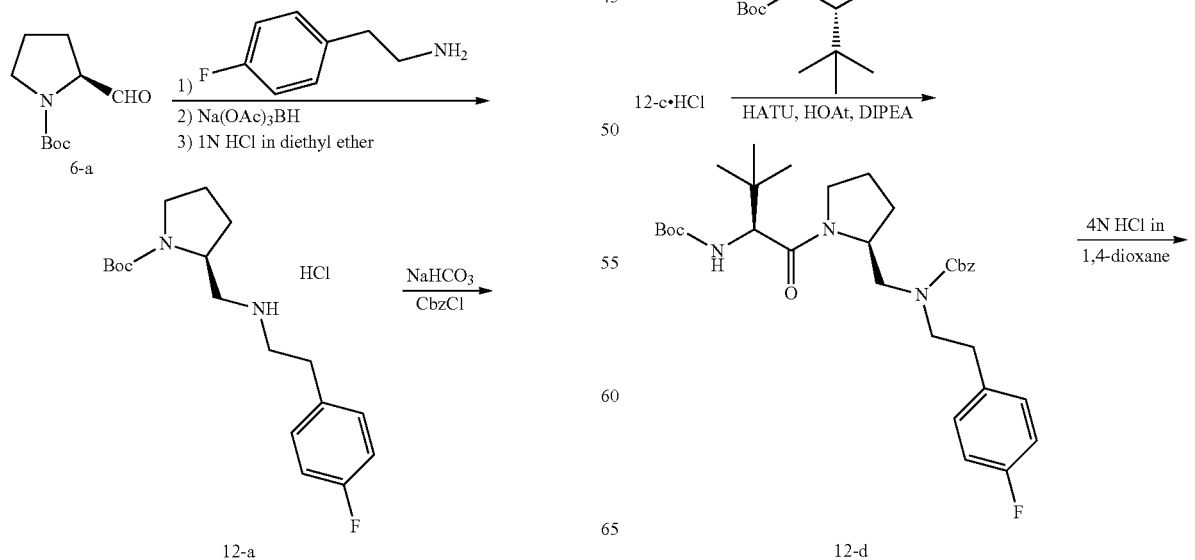

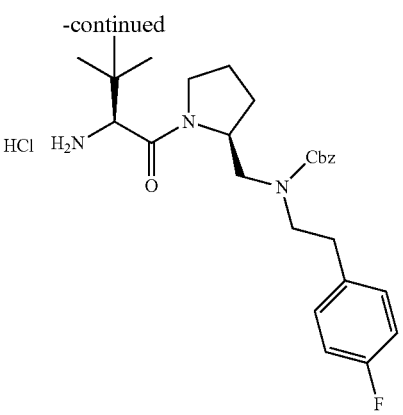

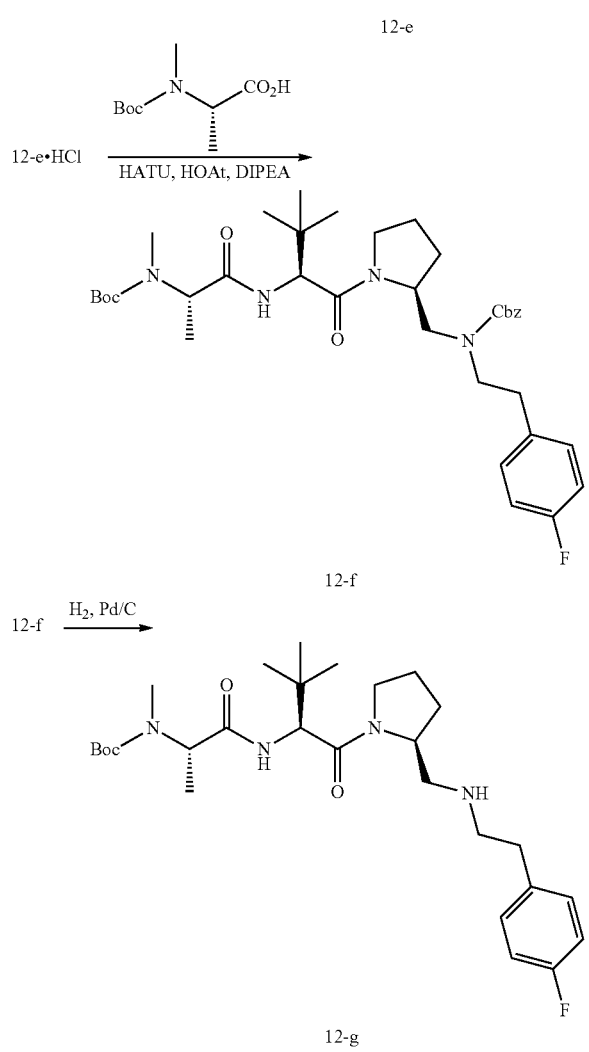

Step 1:

To a solution of N-(tert-butoxycarbonyl)-L-prolinal 6-a (30.0 g, 151.0 mmol) in dichloromethane (1000 mL) was added 2-(4-fluorophenyl)ethanamine (19.79 mL, 151.0 mmol). After stirring for 2 hours at room temperature, the reaction was cooled to 0° C., sodium triacetoxyborohydride (38.3 g, 181.0 mmol) was added portionwise and the reaction mixture was then stirred at room temperature overnight. 10% aqueous Na$_2$CO$_3$ (800 mL) was added, the organic layer was separated, the aqueous phase was extracted with dichloromethane, the combined organic extracts were washed with brine, dried over MgSO$_4$, filtered and concentrated in vacuo to provide intermediate 12-a as a colorless oil. Intermediate 12-a was dissolved in diethyl ether (400 mL), the solution was cooled to 0° C. and 1N HCl in diethyl ether (151.0 mL, 151.0 mmol) was added. A precipitate formed and intermediate 12-a.HCl was collected by filtration as a white solid. MS (m/z) M+1=323.3

Step 2:

To a solution of intermediate 12-a.HCl (40.0 g, 111.0 mmol) in 1,4-dioxane (300 mL) and water (300 mL) cooled to 0° C. was added NaHCO$_3$ (46.8 g, 557.0 mmol). After stirring for 15 minutes benzyl chloroformate (17.50 mL, 123.0 mmol) was added and the reaction was then stirred at room temperature for 1.5 hour. Water and ethyl acetate were added, the organic layer was separated, washed with brine, dried over anhydrous MgSO$_4$, filtered and concentrated in vacuo to provide intermediate 12-b as a colorless oil.

Step 3:

4N HCl in 1,4-dioxane (139 mL) was added to intermediate 12-b (50.7 g, 111.0 mmol) at 0° C. and the solution was stirred for 2.5 hours at 0° C. Volatiles were removed under reduced pressure and the residue was triturated with diethyl ether and hexanes to provide intermediate 12-c.HCl as a white foam. MS (m/z) M+1=357.3

Step 4:

To a solution of intermediate 12-c.HCl (38.9 g, 99.0 mmol) in DMF cooled to 0° C. were sequentially added Boc-tBu-gly-OH (15.07 g, 65.1 mmol), HATU (48.9 g, 129.0 mmol), HOAt (24.75 mL, 14.85 mmol) and DIPEA (69.0 mL, 396.0 mmol) dropwise over a period of 30 minutes and the reaction was then stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over MgSO$_4$, filtered and concentrated in vacuo. Purification by silica gel chromatography provided the expected intermediate 12-d as white foam.

Step 5:

4N HCl in 1,4-dioxane (108 mL) was added to a solution of intermediate 12-d (49.0 g, 86.0 mmol) in ethyl acetate (10 mL) at 0° C. and the reaction mixture was stirred for 4 hours at 0° C. Volatiles were removed under reduced pressure and the residue was triturated with diethyl ether to provide intermediate 12-e.HCl as a white foam. MS (m/z) M+1=470.5

Step 6:

To a solution of intermediate 12-e.HCl (10.4 g, 20.55 mmol) in DMF cooled to 0° C. were sequentially added Boc-NMe-Ala-OH (5.01 g, 24.66 mmol), HATU (10.94 g, 28.8 mmol), HOAt (5.14 mL, 3.08 mmol) and DIPEA (14.32 mL, 82.0 mmol) dropwise over a period of 30 minutes and the reaction was then stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over MgSO$_4$, filtered and concentrated in vacuo. Purification by silica gel chromatography provided the expected intermediate 12-f as white foam.

Step 7:

To a solution of intermediate 12-f (8.50 g, 16.32 mmol) in MeOH (100 mL) under N$_2$ was added 10% Pd/C (50% w/w water content) (3.4 g). The reaction mixture was purged with H$_2$ and stirred for 1 hour. The reaction was then filtered through celite and the filtrate was concentrated in vacuo.

Purification by silica gel chromatography provided intermediate 12-g as a colorless oil. MS (m/z) M+1=521.5

Example 9

The following example illustrates the preparation of compound 40, which is a compound of Formula 1 or salt thereof.

Scheme 13: Synthesis of compound 40

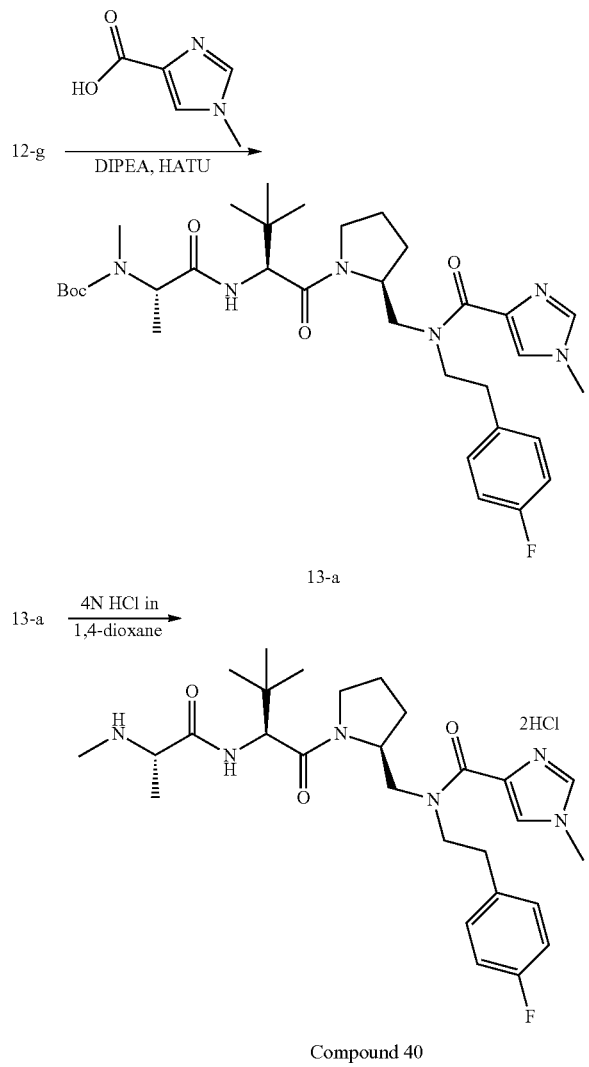

Compound 40

Step 1:

To a solution of intermediate 12-g (610 mg, 1.17 mmol) in DMF, cooled to 0° C., were sequentially added 1-methyl-1H-imidazole-4-carboxylic acid (177 mg, 1.40 mmol), HATU (624 mg, 1.64 mmol) and DIPEA (816 uL, 4.69 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 13-a as a white foam.

Step 2:

4N HCl in 1,4-dioxane (2.3 mL) was added to a solution of intermediate 13-a (590 mg, 0.93 mmol) in ethyl acetate (0.5 mL) and the mixture was stirred for 3 hours at 0° C. Volatiles were removed under reduced pressure and the residue was triturated with diethyl ether to provide compound 40.2HCl as a white solid. MS (m/z) M+1=529.5

Example 10

The following example illustrates the preparation of compound 50, which is a compound of Formula 1 or salt thereof.

Scheme 14: Synthesis of compound 50

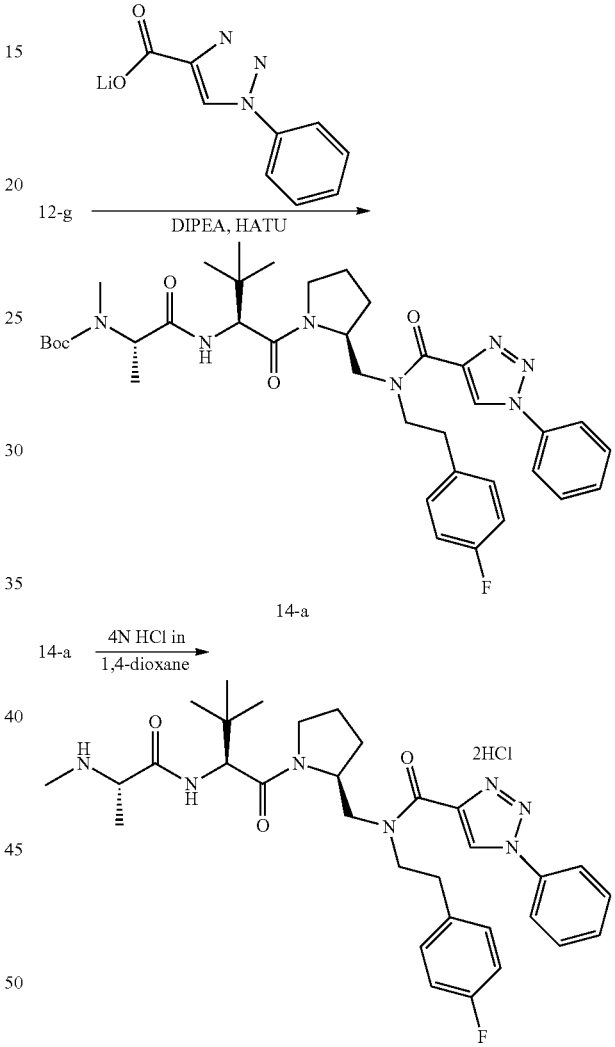

Compound 50

Step 1:

To a solution of intermediate 12-g (400 mg, 0.76 mmol) in DMF, cooled to 0° C., were sequentially added 1-phenyl-1H-1,2,3-triazole-4-carboxylic acid, lithium salt (226 mg, 1.15 mmol), HATU (467 mg, 1.23 mmol) and DIPEA (535 uL, 3.07 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 14-a as a white foam.

Step 2:

4N HCl in 1,4-dioxane (1.0 mL) was added to intermediate 14-a (282 mg, 0.40 mmol) in ethyl acetate (1.0 mL) and the solution was stirred for 5 hours at 0° C. Volatiles were removed under reduced pressure and the residue was triturated with diethyl ether to provide compound 50.2HCl as a white solid. MS (m/z) M+1=592.5

Example 11

The following example illustrates the preparation of compound 63, which is a compound of Formula 1 or salt thereof.

Scheme 15: Synthesis of compound 63

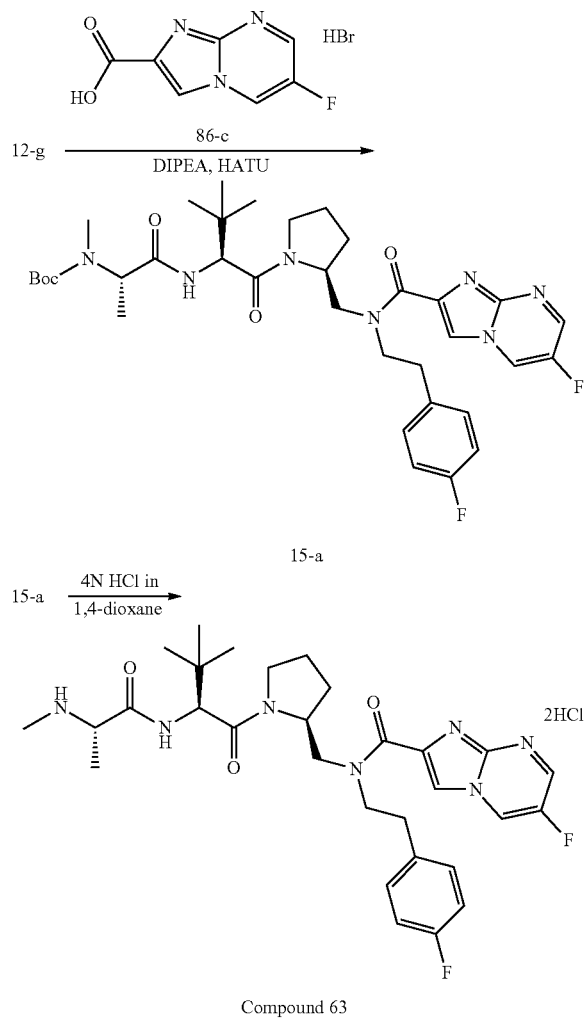

Compound 63

Step 1:

To a solution of intermediate 12-g (15.17 g, 29.1 mmol) in DMF, cooled to 0° C., were sequentially added 6-fluoroimidazo[1,2-a]pyrimidine-2-carboxylic acid, HBr salt (86-c) (9.16 g, 35.0 mmol), HATU (13.29 g, 35.0 mmol) and DIPEA (20.0 mL, 117 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 15-a as a white foam.

Step 2:

4N HCl in 1,4-dioxane (82.0 mL) was added to intermediate 15-a (14.96 g, 21.88 mmol) in ethyl acetate (11 mL) and the solution was stirred for 3 hours at 0° C. Diethyl ether was added, a precipitate formed and compound 63.2HCl was collected by filtration as a white solid. MS (m/z) M+1=584.5.

Example 12

The following example illustrates the preparation of compound 66, which is a compound of Formula 1 or salt thereof.

Scheme 16: Synthesis of compound 66

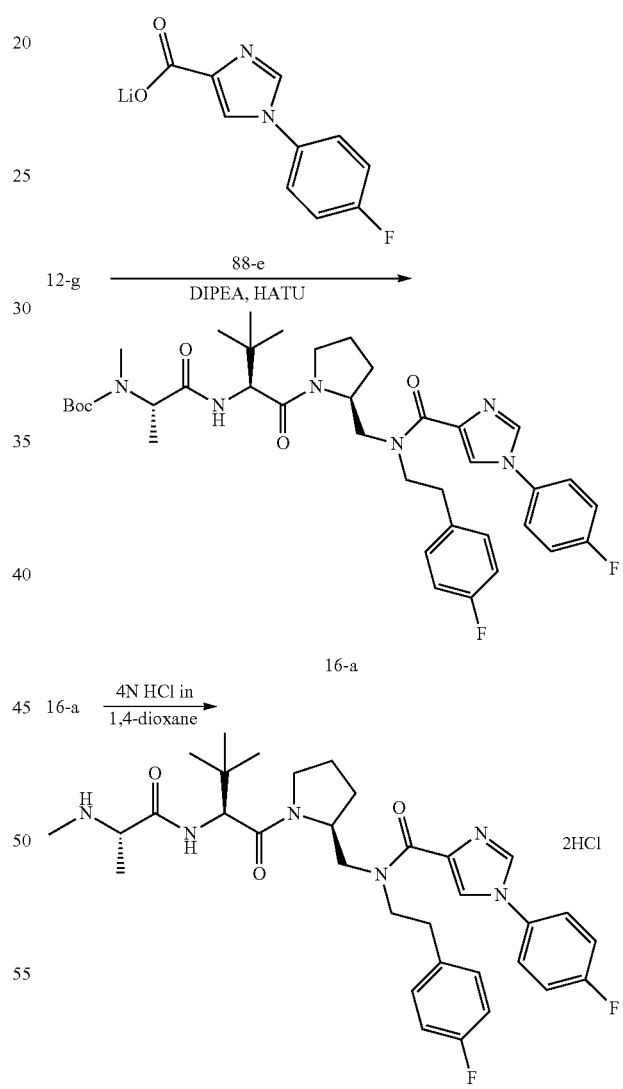

Compound 66

Step 1:

To a solution of intermediate 12-g (350 mg, 0.67 mmol) in DMF, cooled to 0° C., were sequentially added 1-(4-fluorophenyl)-1H-imidazole-4-carboxylic acid, lithium salt (88-e) (208 mg, 1.0 mmol), HATU (435 mg, 1.14 mmol) and DIPEA (468 uL, 2.69 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 16-a as a white foam.

Step 2:

4N HCl in 1,4-dioxane (1.0 mL) was added to intermediate 16-a (515 mg, 0.78 mmol) in MeOH (0.5 mL) and the solution was stirred for 2 hours at 0° C. Volatiles were removed under reduced pressure and the residue was triturated with diethyl ether to provide compound 66.2HCl as a white solid. MS (m/z) M+1=609.5

Example 13

The following example illustrates the preparation of compound 67, which is a compound of Formula 1 or salt thereof.

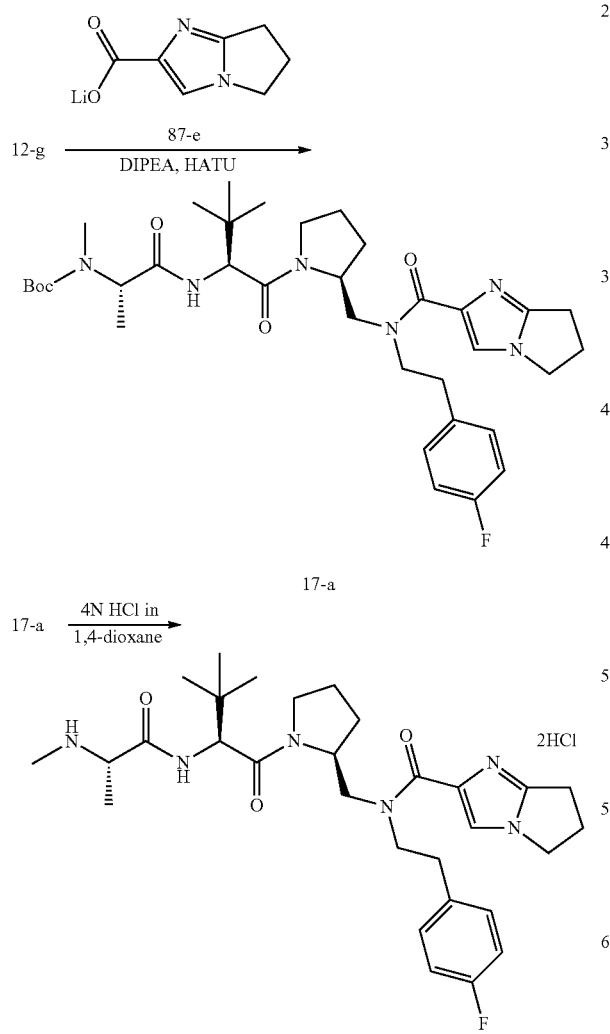

Compound 67

Step 1:

To a solution of intermediate 12-g (856 mg, 1.64 mmol) in DMF, cooled to 0° C., were sequentially added 6,7-dihydro-5H-pyrrolo[1,2-a]imidazole-2-carboxylic acid, lithium salt (87-e) (340 mg, 2.13 mmol), HATU (875 mg, 2.30 mmol) and DIPEA (859 uL, 4.93 mmol) and the reaction mixture was stirred at 0° C. for 30 minutes. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 17-a as a white foam.

Step 2:

4N HCl in 1,4-dioxane (1.0 mL) was added to intermediate 17-a (515 mg, 0.78 mmol) in ethyl acetate (0.5 mL) and the solution was stirred for 2 hours at 0° C. Volatiles were removed under reduced pressure and the residue was triturated with diethyl ether to provide compound 67.2HCl as a white solid. MS (m/z) M+1=555.6

Example 14

The following example illustrates the preparation of compound 68, which is a compound of Formula 1 or salt thereof.

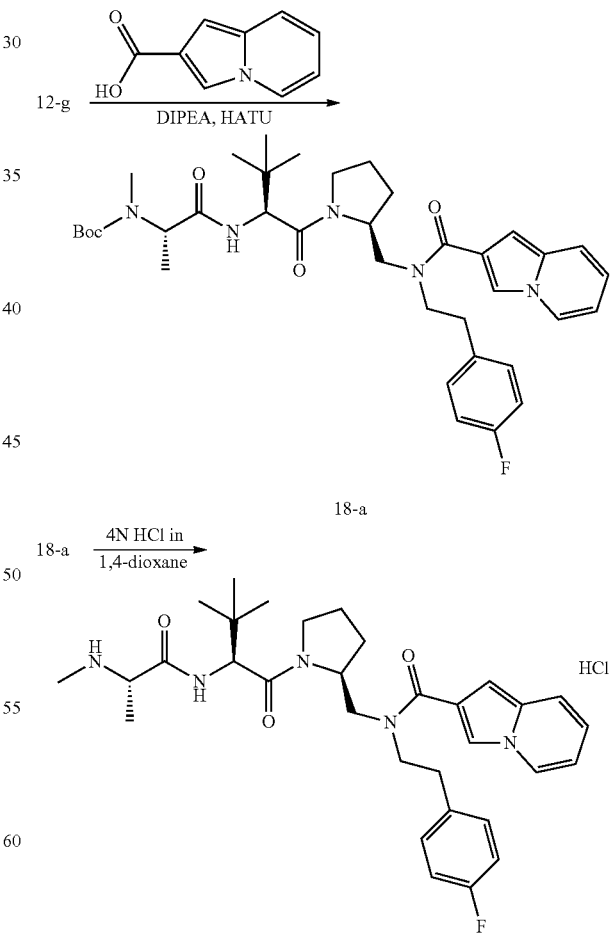

Compound 68

Step 1:

To a solution of intermediate 12-g (300 mg, 0.57 mmol) in DMF, cooled to 0° C., were sequentially added indolizine-2-carboxylic acid (107 mg, 0.66 mmol), HATU (285 mg, 0.75 mmol) and DIPEA (301 uL, 1.72 mmol) and the reaction mixture was stirred at 0° C. for 30 minutes. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 18-a as a white foam.

Step 2:

4N HCl in 1,4-dioxane (1.0 mL) was added to intermediate 18-a (360 mg, 0.54 mmol) in ethyl acetate (0.5 mL) and the solution was stirred for 2 hours at 0° C. Volatiles were removed under reduced pressure and the residue was triturated with diethyl ether to provide compound 68.HCl as a white solid. MS (m/z) M+1=564.5

Example 15

The following example illustrates the preparation of compound 62, which is a compound of Formula 1 or salt thereof.

Step 1:

To a solution of intermediate 12-g (300 mg, 0.57 mmol) in DMF, cooled to 0° C., were sequentially added sodium benzo[d]oxazole-2-carboxylate (139 mg, 0.74 mmol), HATU (263 mg, 0.69 mmol) and DIPEA (401 uL, 2.30 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 19-a as a white foam.

Step 2:

4N HCl in 1,4-dioxane (1.20 mL) was added to intermediate 19-a (294 mg, 0.44 mmol) and the solution was stirred for 2 hours at 0° C. Volatiles were removed under reduced pressure and the residue was triturated with diethyl ether to provide compound 62.HCl as a white solid. MS (m/z) M+1=566.5

Example 16

The following example illustrates the preparation of compound 53, which is a compound of Formula 1 or salt thereof.

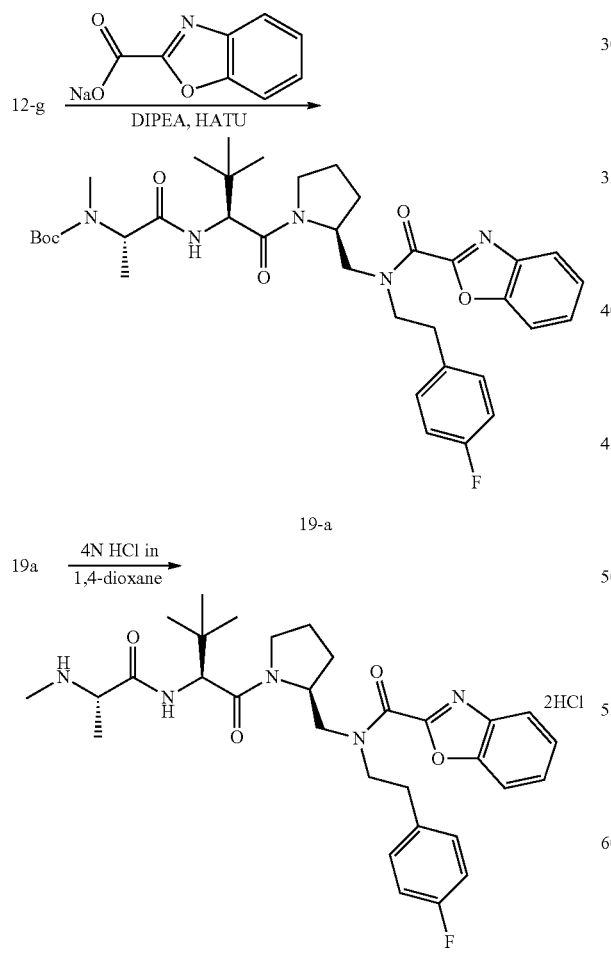

Scheme 19: Synthesis of compound 62

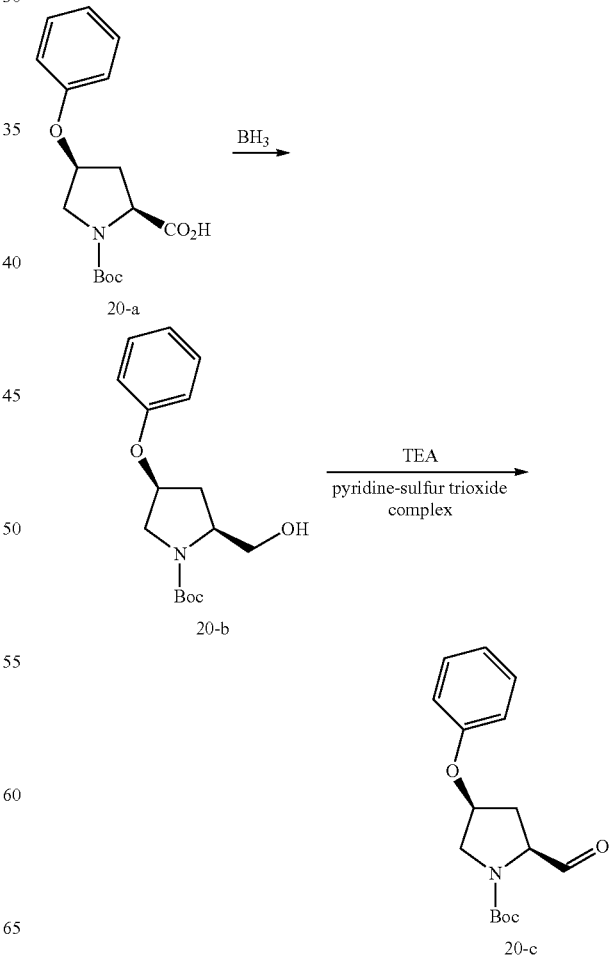

Scheme 20: Synthesis of compound 53

69
-continued
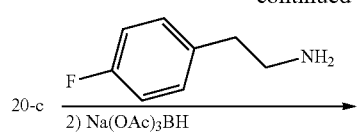
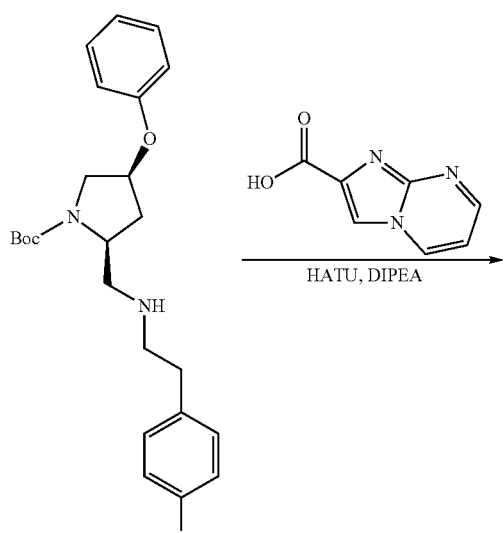
70
-continued
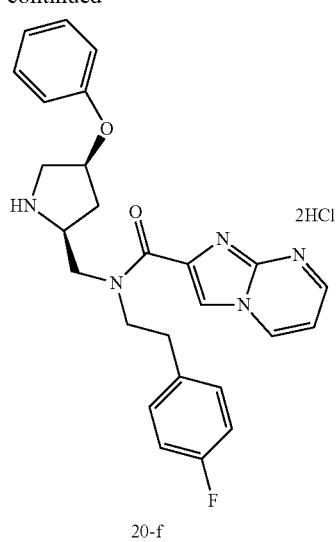
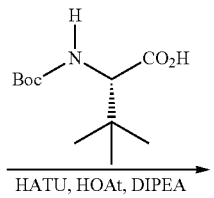
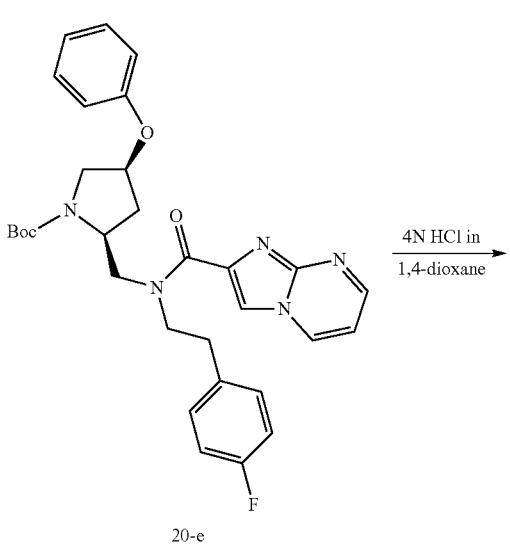

71
-continued

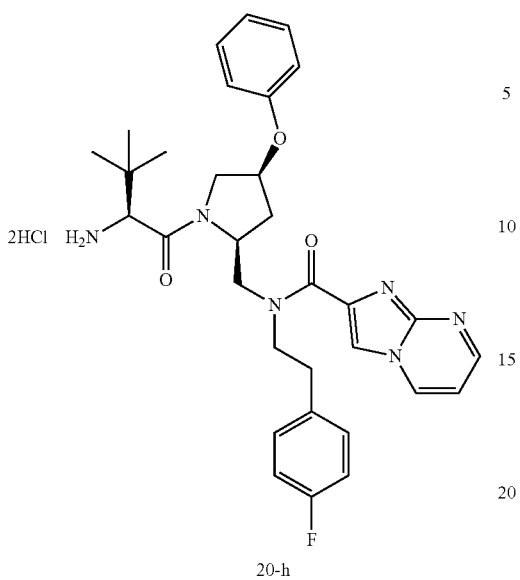
20-h

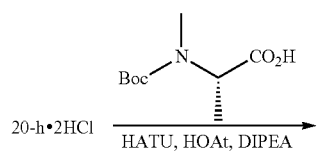

20-h•2HCl  $\xrightarrow{\text{HATU, HOAt, DIPEA}}$

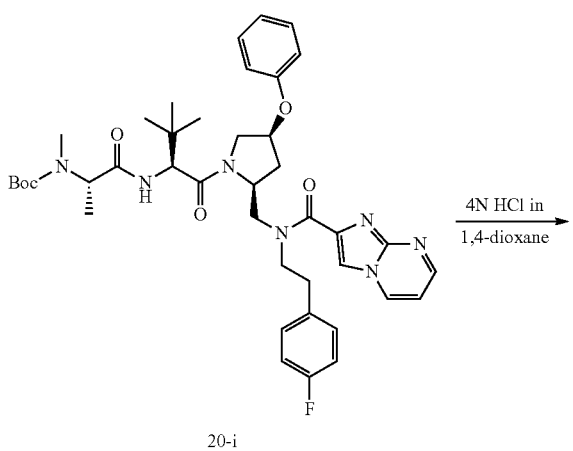
20-i $\xrightarrow{\text{4N HCl in 1,4-dioxane}}$

72
-continued

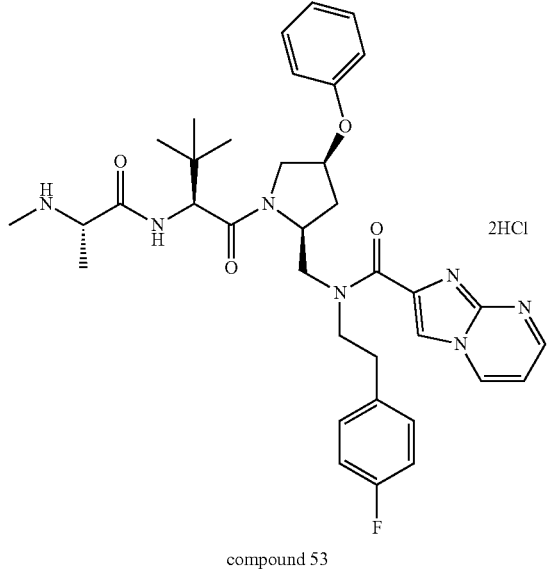
compound 53

Step 1:
To a solution of (2S,4S)-1-(tert-butoxycarbonyl)-4-phenoxypyrrolidine-2-carboxylic acid 20-a (1.40 g, 4.56 mmol) in THF cooled to 0° C. was added borane tetrahydrofuran complex (18.22 ml, 18.2 mmol), the reaction was stirred at 0° C. for 15 minutes and room temperature overnight. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo to provide intermediate 20-b as a colorless oil.

Step 2:
To a solution of intermediate 20-b (1.33 g, 4.53 mmol) in DMSO (5.24 mL, 73.9 mmol) and dichloromethane (10 mL) was added TEA (2.53 mL, 18.13 mmol) and pyridine-sulfur trioxide complex (1.44 g, 9.07 mmol), the reaction was then stirred at 0° C. for 30 minutes and room temperature for 30 minutes. Water and ethyl acetate were added; the organic layer was separated, washed with 10% aqueous citric acid, saturated aqueous NaHCO$_3$ and brine, dried over anhydrous MgSO$_4$, filtered and concentrated in vacuo to provide intermediate 20-c as colorless oil.

Step 3:
To a solution of intermediate 20-c (1.32 g, 4.53 mmol) in dichloromethane was added 2-(4-fluorophenyl)ethanamine (595 µL, 4.53 mmol). After stirring for 30 minutes sodium triacetoxyborohydride (1.21 g, 5.44 mmol) was added at 0° C. and the reaction mixture was then stirred at room temperature overnight. Water and ethyl acetate were added; the organic layer was separated, washed with 1N aqueous NaOH, water and brine, dried over MgSO$_4$, filtered and concentrated in vacuo to provide intermediate 20-d as colorless oil.

Step 4:
To a solution of intermediate 20-d (1.87 g, 4.51 mmol) in DMF, cooled to 0° C., were sequentially added imidazo[1,2-a]pyrimidine-2-carboxylic acid (1.21 g, 4.96 mmol), HATU (2.05 g, 5.41 mmol) and DIPEA (2.36 mL, 13.53 mmol) and the reaction mixture was then stirred at room temperature overnight. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 20-e as a white foam.

Step 5:

4N HCl in 1,4-dioxane (1.0 mL) was added to intermediate 20-e (800 mg, 1.43 mmol) and the solution was stirred at 0° C. for 1 hour. Volatiles were removed under reduced pressure and the residue was triturated with diethyl ether to provide intermediate 20-f.2HCl as a white solid. MS (m/z) M+1=460.4

Step 6:

To a solution of intermediate 20-f.2HCl (709 mg, 1.43 mmol) in DMF cooled to 0° C. were sequentially added Boc-tBu-gly-OH (397 mg, 1.71 mmol), HOAt (357 uL, 0.21 mmol), HATU (707 mg, 1.85 mmol) and DIPEA (1.0 mL, 5.72 mmol) and the reaction was then stirred at room temperature for 1 hour. Saturated aqueous ammonium chloride and ethyl acetate were added; the organic layer was separated, washed with saturated aqueous ammonium chloride, saturated aqueous NaHCO₃ and brine, dried over MgSO₄, filtered and concentrated in vacuo. Purification by silica gel chromatography provided the expected intermediate 20-g as white foam.

Step 7:

4N HCl in 1,4-dioxane (1.0 mL) was added to intermediate 20-g (651 mg, 0.96 mmol) and the solution was stirred for 1 hour at 0° C. Volatiles were removed under reduced pressure and the residue was triturated with diethyl ether to provide intermediate 20-h.2HCl as a white solid. MS (m/z) M+1=573.5

Step 8:

To a solution of intermediate 20-h.2HCl (300 mg, 0.49 mmol) in DMF cooled to 0° C. were sequentially added Boc-NMe-Ala-OH (140 mg, 0.69 mmol), HOAt (123 uL, 0.07 mmol), HATU (281 mg, 0.73 mmol), and DIPEA (344 uL, 1.97 mmol) and the reaction was then stirred at room temperature overnight. Saturated aqueous ammonium chloride and ethyl acetate were added; the organic layer was separated, washed with saturated aqueous ammonium chloride, saturated aqueous NaHCO₃ and brine, dried over MgSO₄, filtered and concentrated in vacuo. Purification by silica gel chromatography provided the expected intermediate 20-i as a white foam.

Step 9:

4N HCl in 1,4-dioxane (1.0 mL) was added to intermediate 20-i (348 mg, 0.45 mmol) and the solution was stirred for 1 hour at 0° C. Volatiles were removed under reduced pressure and the residue was triturated with diethyl ether to provide compound 53.2HCl as a white solid. MS (m/z) M+1=658.5

Example 17

The following example illustrates the preparation of compound 21-k, which can be used as an intermediate in the preparation of a compound of Formula 1 or salt thereof.

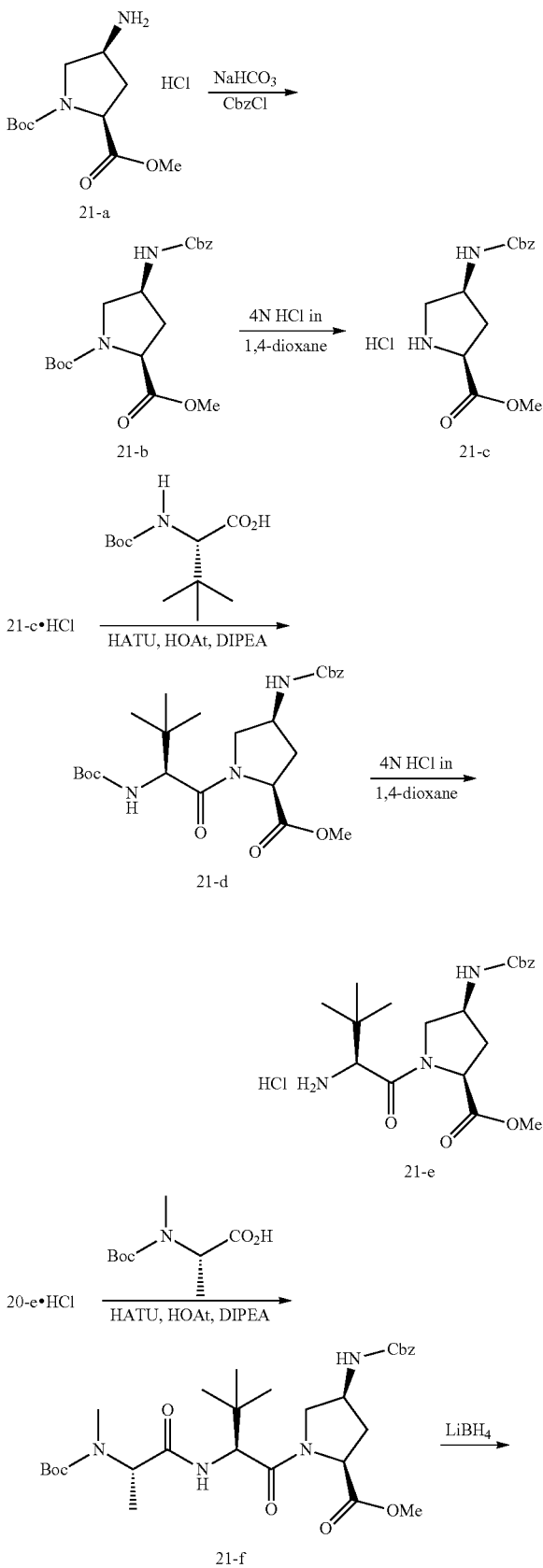

Scheme 21: Synthesis of Intermediate 21-k

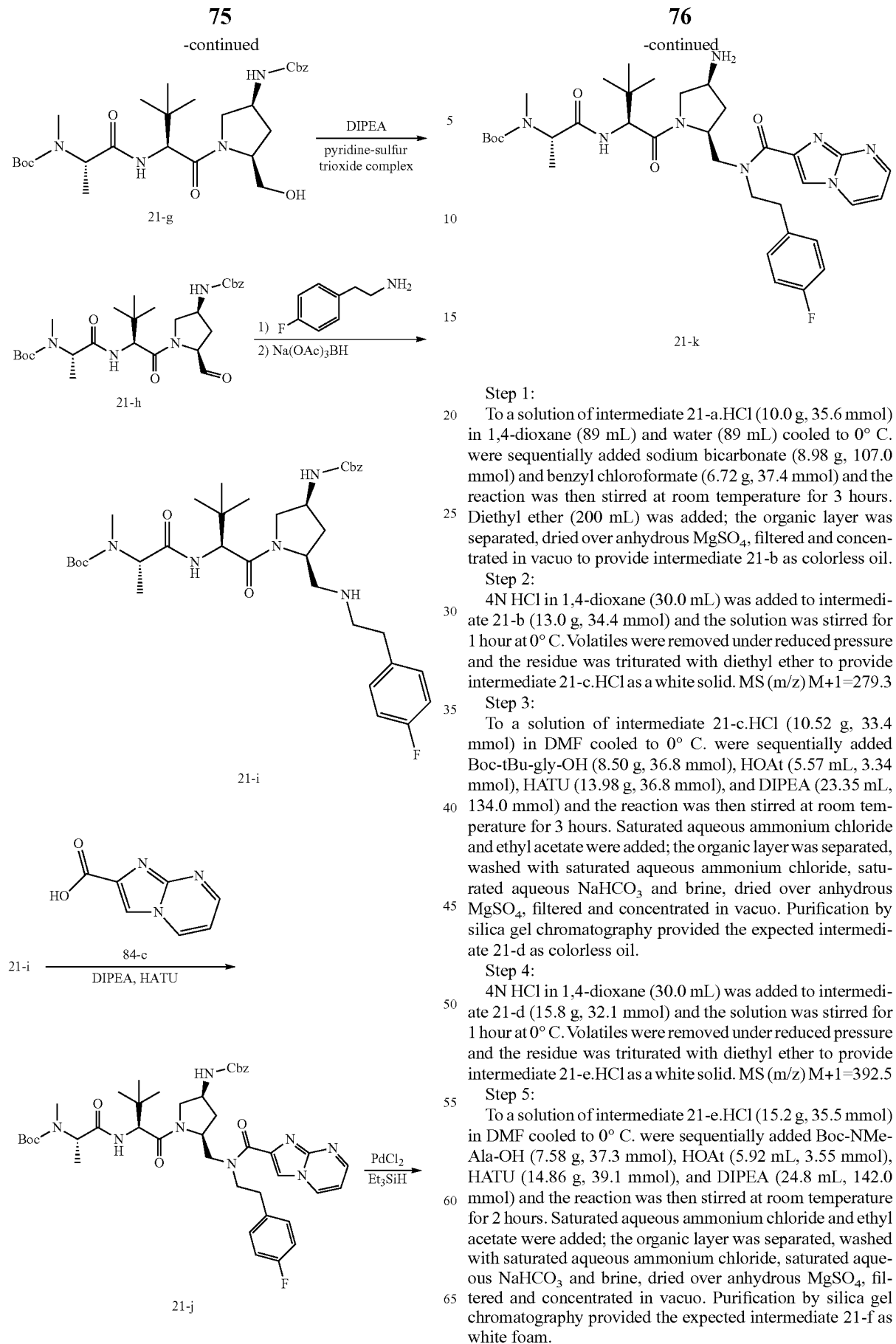

Step 1:
To a solution of intermediate 21-a.HCl (10.0 g, 35.6 mmol) in 1,4-dioxane (89 mL) and water (89 mL) cooled to 0° C. were sequentially added sodium bicarbonate (8.98 g, 107.0 mmol) and benzyl chloroformate (6.72 g, 37.4 mmol) and the reaction was then stirred at room temperature for 3 hours. Diethyl ether (200 mL) was added; the organic layer was separated, dried over anhydrous MgSO₄, filtered and concentrated in vacuo to provide intermediate 21-b as colorless oil.

Step 2:
4N HCl in 1,4-dioxane (30.0 mL) was added to intermediate 21-b (13.0 g, 34.4 mmol) and the solution was stirred for 1 hour at 0° C. Volatiles were removed under reduced pressure and the residue was triturated with diethyl ether to provide intermediate 21-c.HCl as a white solid. MS (m/z) M+1=279.3

Step 3:
To a solution of intermediate 21-c.HCl (10.52 g, 33.4 mmol) in DMF cooled to 0° C. were sequentially added Boc-tBu-gly-OH (8.50 g, 36.8 mmol), HOAt (5.57 mL, 3.34 mmol), HATU (13.98 g, 36.8 mmol), and DIPEA (23.35 mL, 134.0 mmol) and the reaction was then stirred at room temperature for 3 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided the expected intermediate 21-d as colorless oil.

Step 4:
4N HCl in 1,4-dioxane (30.0 mL) was added to intermediate 21-d (15.8 g, 32.1 mmol) and the solution was stirred for 1 hour at 0° C. Volatiles were removed under reduced pressure and the residue was triturated with diethyl ether to provide intermediate 21-e.HCl as a white solid. MS (m/z) M+1=392.5

Step 5:
To a solution of intermediate 21-e.HCl (15.2 g, 35.5 mmol) in DMF cooled to 0° C. were sequentially added Boc-NMe-Ala-OH (7.58 g, 37.3 mmol), HOAt (5.92 mL, 3.55 mmol), HATU (14.86 g, 39.1 mmol), and DIPEA (24.8 mL, 142.0 mmol) and the reaction was then stirred at room temperature for 2 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided the expected intermediate 21-f as white foam.

Step 6:
To a solution of intermediate 21-f (20.2 g, 35.0 mmol) in THF cooled to 0° C. was added lithium borohydride (1.60 g, 73.6 mmol) and the reaction was stirred at room temperature for 1 hour. Water and ethyl acetate were added; the organic layer was separated, washed with 10% aqueous citric acid, saturated aqueous NaHCO₃ and brine, dried over anhydrous MgSO₄, filtered and concentrated in vacuo. Purification by silica gel chromatography provided intermediate 21-g as a white foam.

Step 7:
To a solution of intermediate 21-g (10.1 g, 18.41 mmol) in DMSO (5.23 mL, 73.6 mmol) and dichloromethane (184 mL) cooled to 0° C. was added DIPEA (11.22 mL, 64.4 mmol) and pyridine sulfur trioxide complex (8.79 g, 55.2 mmol), the reaction was then stirred at 0° C. for 2 hours. Water and ethyl acetate were added; the organic layer was separated, washed with 10% aqueous citric acid, saturated aqueous NaHCO₃ and brine, dried over anhydrous MgSO₄, filtered and concentrated in vacuo to provide intermediate 21-h as white foam.

Step 8:
To a solution of intermediate 21-h (10.60 g, 19.39 mmol) in dichloromethane was added 2-(4-fluorophenyl)ethanamine (2.70 g, 19.39 mmol). After stirring at room temperature overnight sodium triacetoxyborohydride (4.93 g, 23.27 mmol) was added portion wise at 0° C. and the reaction mixture was then stirred at room temperature for 2 hours. Saturated aqueous NaHCO₃ was added; the organic layer was separated, washed with brine, dried over anhydrous MgSO₄, filtered and concentrated in vacuo to provide intermediate 21-i as white foam. MS (m/z) M+1=670.6

Step 9:
To a solution of intermediate 21-i (10.0 g, 14.93 mmol) and imidazo[1,2-a]pyrimidine-2-carboxylic acid, HBr salt (84-c) (3.64 g, 14.93 mmol) in DMF, cooled to 0° C., were sequentially added HATU (6.24 g, 16.42 mmol) and DIPEA (10.43 mL, 59.70 mmol) and the reaction mixture was stirred at room temperature for 2 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 21-j as a beige foam.

Step 10:
To a solution of intermediate 21-j (2.75 g, 3.37 mmol) in TEA (4.0 mL, 28.7 mmol) were sequentially added palladium (II) chloride (60 mg, 0.34 mmol) and triethylsilane (1.34 mL, 8.45 mmol). The reaction mixture was purged with H₂ and stirred at room temperature for 2 hours. The reaction was then filtered through celite and the filtrate was concentrated in vacuo to give intermediate 21-k as a beige solid. MS (m/z) M+1=681.7

Example 18

The following example illustrates the preparation of compound 55, which is a compound of Formula 1 or salt thereof.

Scheme 22: Synthesis of compound 55

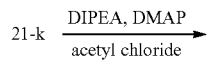

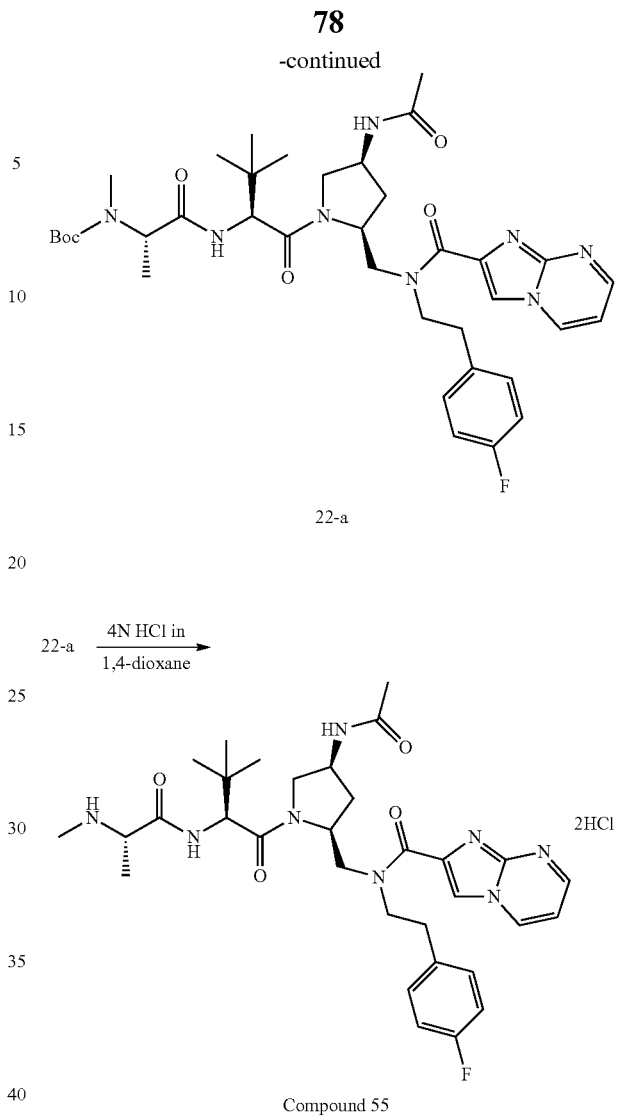

Step 1:
To a solution of intermediate 21-k (420 mg, 0.61 mmol) in dichloromethane (2.0 mL) cooled to 0° C. were sequentially added DIPEA (385 uL, 2.20 mmol), DMAP (4.50 mg, 0.03 mmol) and acetyl chloride (63 uL, 0.88 mmol) and the reaction was stirred at room temperature for 18 hours. Water and ethyl acetate were added; the organic layer was separated, washed with 10% aqueous citric acid, saturated aqueous NaHCO₃ and brine, dried over anhydrous MgSO₄, filtered and concentrated in vacuo to provide intermediate 22-a as white solid Step 2:
4N HCl in 1,4-dioxane (2.0 mL) was added to intermediate 22-a (230 mg, 0.32 mmol) and the solution was stirred for 1 hour at 0° C. Volatiles were removed under reduced pressure and the residue was triturated with diethyl ether to provide compound 55.2HCl as a white solid. MS (m/z) M+1=623.5

Example 19

The following example illustrates the preparation of compound 59, which is a compound of Formula 1 or salt thereof.

Scheme 23: Synthesis of compound 59

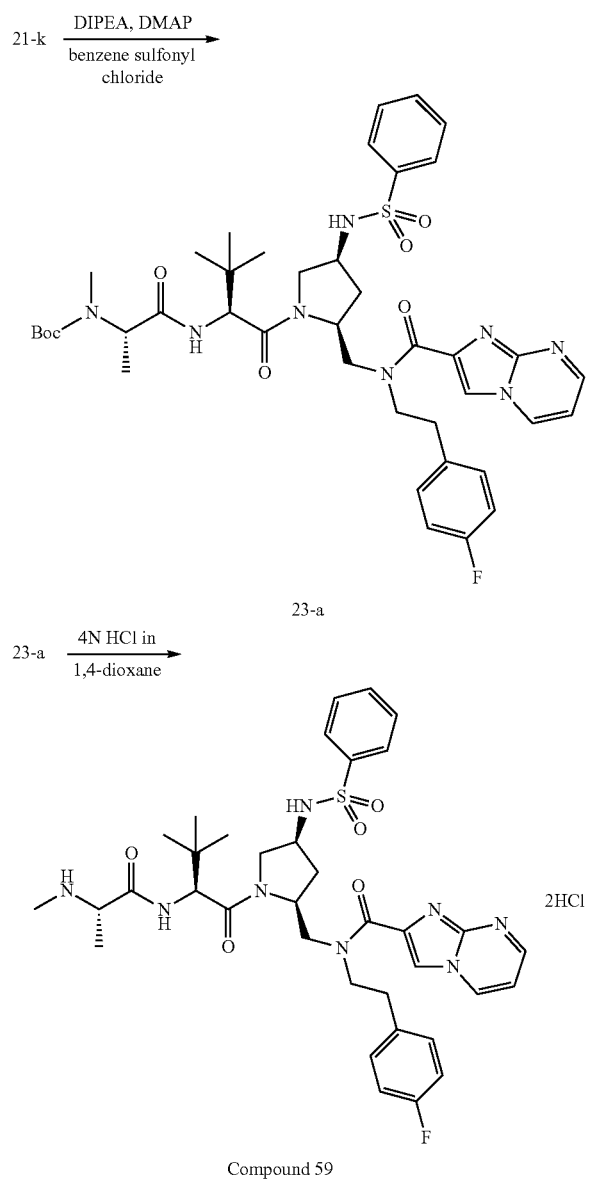

Compound 59

Example 20

The following example illustrates the preparation of compound 24-d, which can be used as an intermediate in the preparation of a compound of Formula 1 or salt thereof.

Scheme 24: Synthesis of Intermediate 24-d

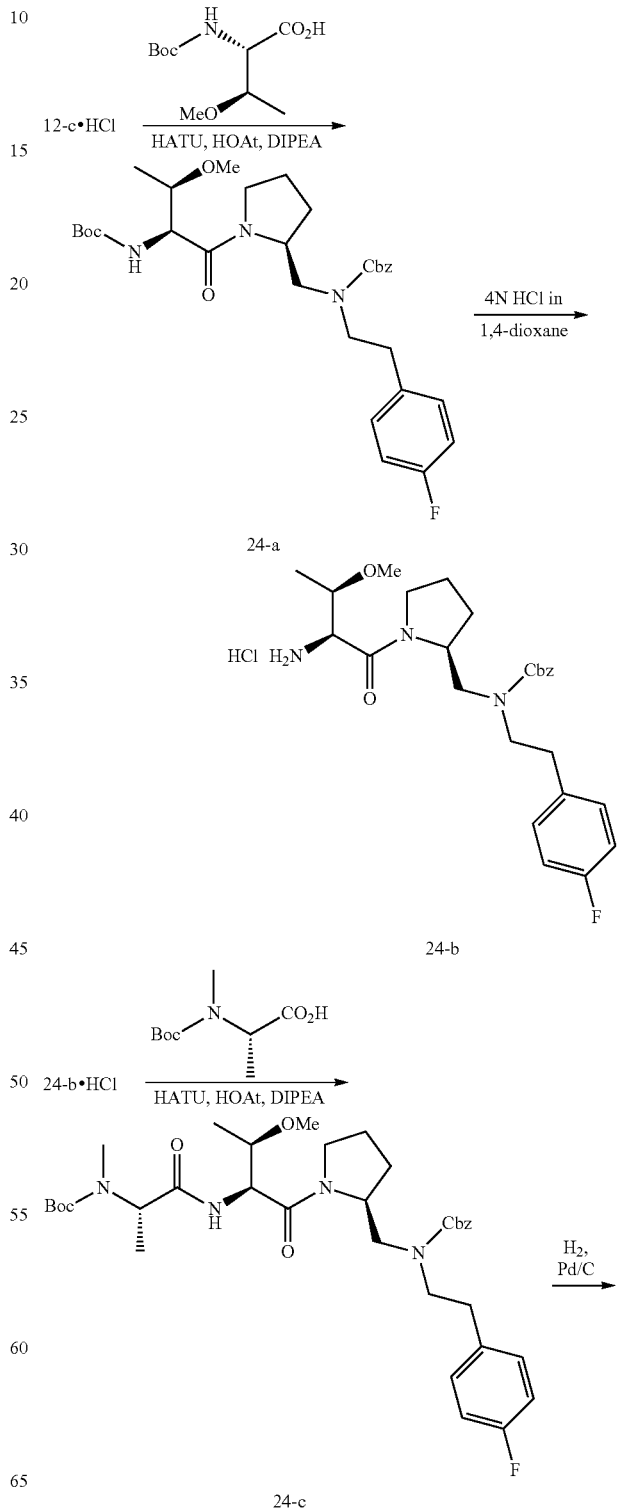

Step 1:

To a solution of intermediate 21-k (420 mg, 0.61 mmol) in pyridine (4.0 mL) cooled to 0° C. were sequentially added DIPEA (323 uL, 1.85 mmol), DMAP (3.8 mg, 0.03 mmol) and benzenesulfonyl chloride (79 uL, 0.61 mmol) and the reaction was stirred at room temperature overnight. Water and ethyl acetate were added; the organic layer was separated, washed with 10% aqueous citric acid, saturated aqueous NaHCO$_3$ and brine, dried over anhydrous MgSO$_4$, filtered and concentrated in vacuo to provide intermediate 23-a as a white solid.

Step 2:

4N HCl in 1,4-dioxane (2.0 mL) was added to intermediate 23-a (100 mg, 0.12 mmol) and the solution was stirred for 1 hour at 0° C. Volatiles were removed under reduced pressure and the residue was triturated with diethyl ether to provide compound 59.2HCl as a white solid. MS (m/z) M+1=721.5

-continued

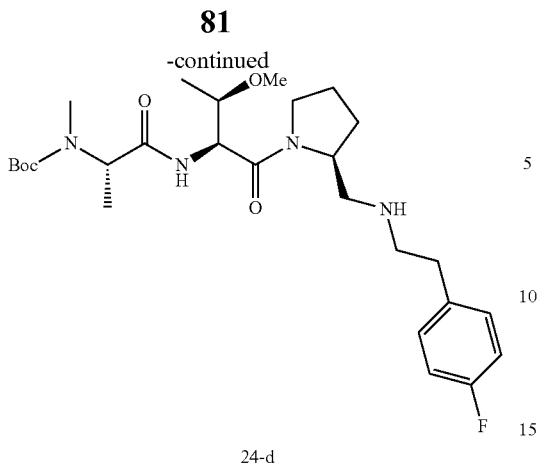

24-d

Step 1:

To a solution of intermediate 12-c.HCl (13.7 g, 34.9 mmol) in DMF cooled to −10° C. were sequentially added Boc-Thr (Me)-OH (8.1 g, 34.9 mmol), HATU (14.6 g, 38.4 mmol), HOAt (63.9 mL, 38.4 mmol) and DIPEA (24.4 mL, 139.0 mmol) and the reaction was then stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 24-a as white foam.

Step 2:

4N HCl in 1,4-dioxane (94.0 mL) was added to intermediate 24-a (10.8 g, 18.9 mmol) in ethyl acetate (10 mL) at 0° C. and the solution was stirred for 3 hours at 0° C. Volatiles were removed under reduced pressure and the residue was triturated with diethyl ether to provide intermediate 24-b.HCl as a white foam. MS (m/z) M+1=472.5

Step 3:

To a solution of intermediate 24-b.HCl (25.0 g, 49.2 mmol) in DMF cooled to 0° C. were sequentially added Boc-NMe-Ala-OH (12.0 g, 59.0 mmol), HATU (26.2 g, 68.9 mmol), HOAt (12.3 mL, 7.38 mmol) and DIPEA (34.3 mL, 197 mmol) and the reaction was then stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 24-c as white foam.

Step 4:

To a solution of intermediate 24-c (15.88 g, 23.67 mmol) in MeOH (118 mL) under N$_2$ was added 10% Pd/C (50% w/w water content) (3.53 g). The reaction mixture was purged with H$_2$ and stirred for 5 hours. The reaction was then filtered through celite and the filtrate was concentrated in vacuo to give intermediate 24-d as colorless oil. MS (m/z) M+1=537.5

Example 21

The following example illustrates the preparation of compound 58, which is a compound of Formula 1 or salt thereof.

Scheme 25: Synthesis of compound 58

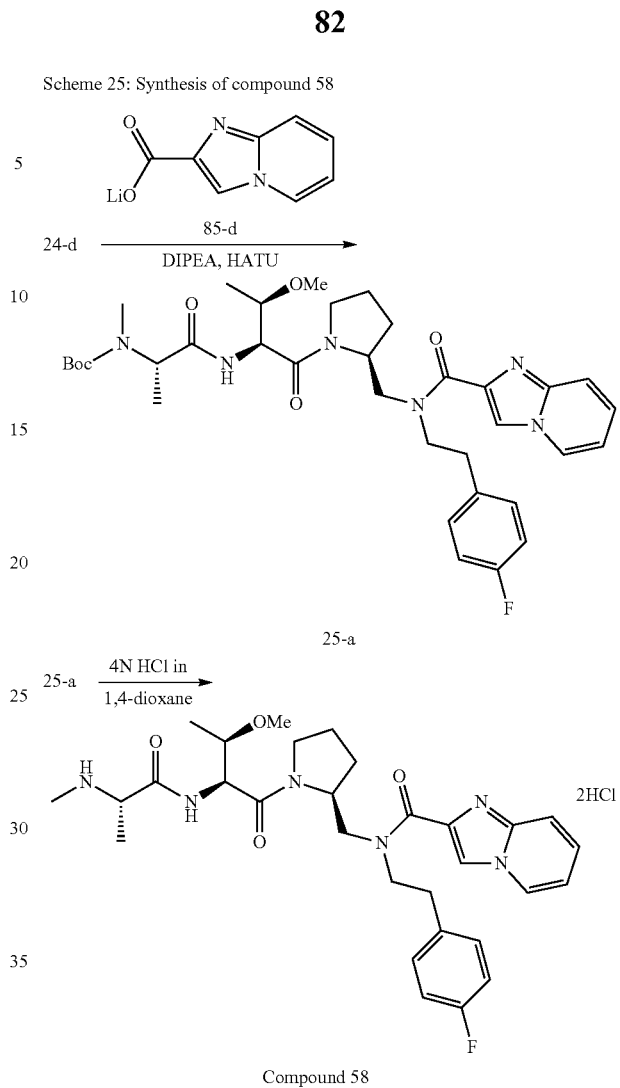

Compound 58

Step 1:

To a solution of intermediate 24-d (15.0 g, 28.7 mmol) in DMF, cooled to 0 PC, were sequentially added imidazo[1,2-a]pyridine-2-carboxylic acid, lithium salt (85-d) (5.79 g, 34.40 mmol), HATU (13.10 g, 34.40 mmol) and DIPEA (20.0 mL, 115.0 mmol) and the reaction mixture was stirred at 0° C. for 3 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 25-a as a white foam.

Step 2:

4N HCl in 1,4-dioxane (69.20 mL) was added to intermediate 25-a (12.30 g, 18.45 mmol) in ethyl acetate (9.20 mL) and the solution was stirred for 3 hours at 0° C. Diethyl ether was added, a precipitate formed and compound 58.2HCl was collected by filtration as a white solid. MS (m/z) M+1=567.5

Example 22

The following example illustrates the preparation of compound 72, which is a compound of Formula 1 or salt thereof.

Scheme 26: Synthesis of compound 72

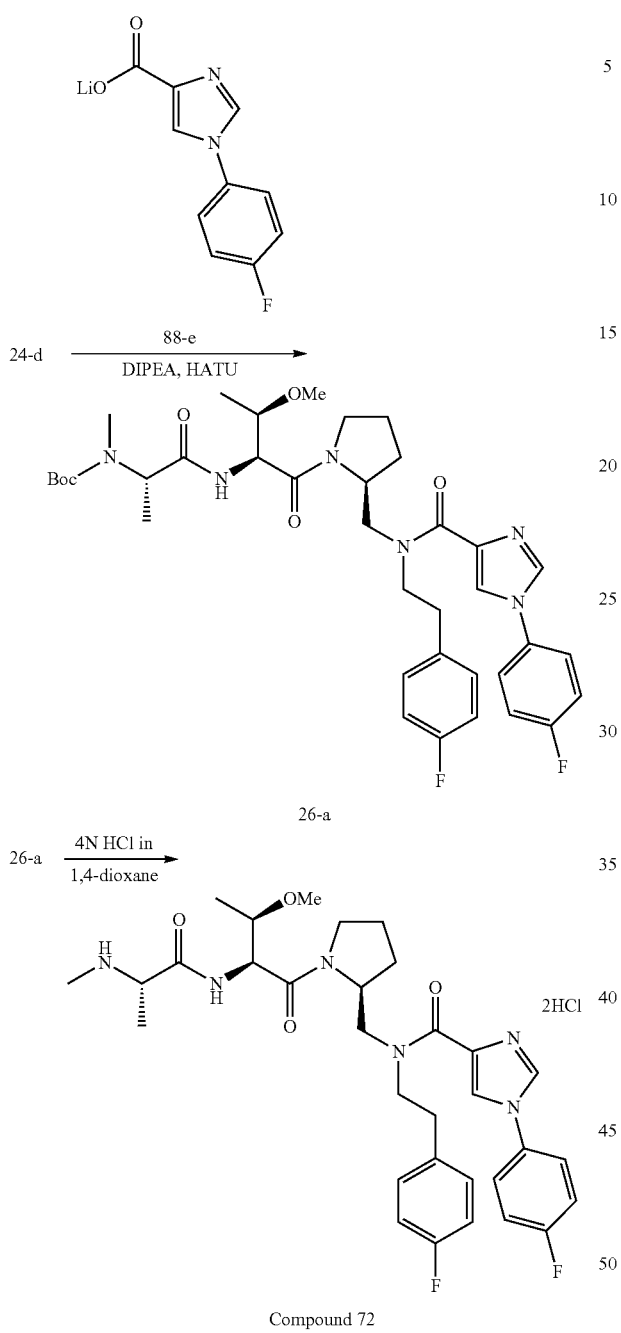

Compound 72

Step 1:
To a solution of intermediate 24-d (400 mg, 0.76 mmol) in DMF, cooled to 0° C., were sequentially added 1-(4-fluorophenyl)-1H-imidazole-4-carboxylic acid, lithium salt (88-e) (212 mg, 1.0 mmol), HATU (437 mg, 1.14 mmol) and DIPEA (400 uL, 2.29 mmol) and the reaction mixture was stirred at room temperature for 30 minutes. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 26-a as a white foam.

Step 2:
4N HCl in 1,4-dioxane (1.30 mL) was added to intermediate 26-a (385 mg, 0.54 mmol) in ethyl acetate (0.5 mL) and the solution was stirred for 2 hours at 0° C. Volatiles were removed under reduced pressure and the residue was triturated with diethyl ether to provide compound 72.2HCl as a white solid. MS (m/z) M+1=611.5

Example 23

The following example illustrates the preparation of compound 73, which is a compound of Formula 1 or salt thereof.

Scheme 27: Synthesis of compound 73

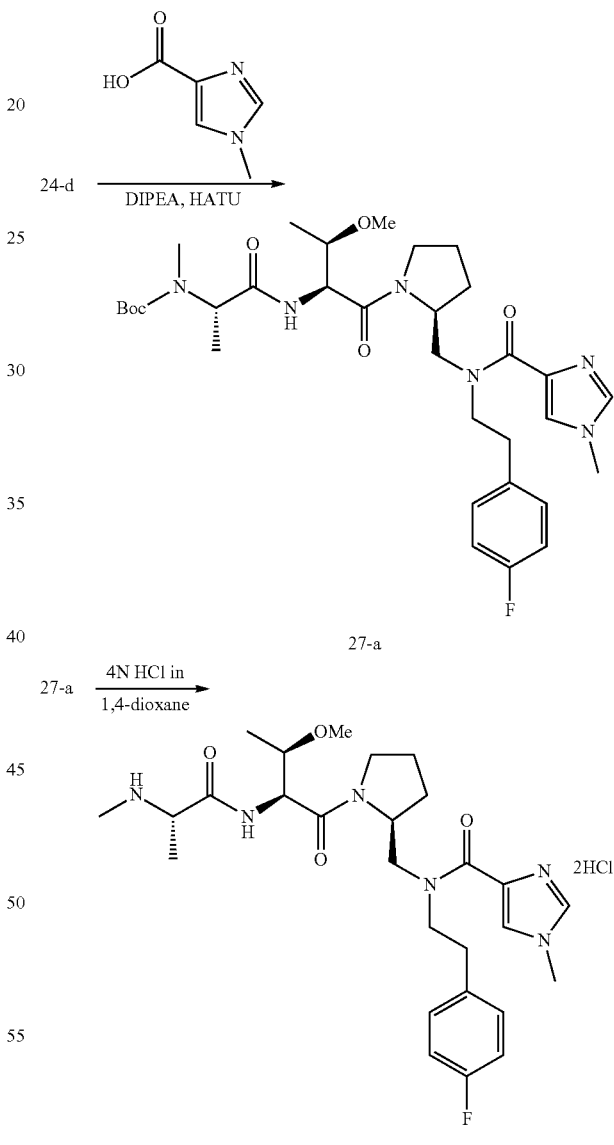

Compound 73

Step 1:
To a solution of intermediate 24-d (580 mg, 1.11 mmol) in DMF, cooled to 0° C., were sequentially added 1-methyl-1H-imidazole-4-carboxylic acid (168 mg, 1.33 mmol), HATU (591 mg, 1.55 mmol) and DIPEA (581 uL, 3.33 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 27-a as a white foam.

Step 2:

4N HCl in 1,4-dioxane (2.0 mL) was added to intermediate 27-a (510 mg, 0.81 mmol) in ethyl acetate (0.5 mL) and the solution was stirred for 3 hours at 0° C. Volatiles were removed under reduced pressure and the residue was triturated with diethyl ether to provide compound 73.2HCl as a white solid. MS (m/z) M+1=531.5

Example 24

The following example illustrates the preparation of compound 75, which is a compound of Formula 1 or salt thereof.

Scheme 28: Synthesis of compound 75

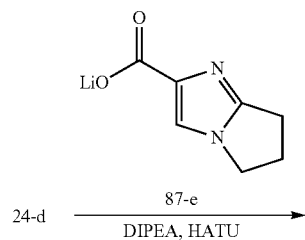

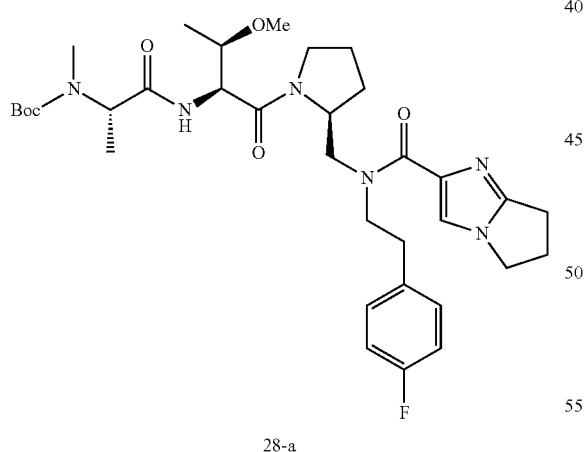

28-a 28-a $\xrightarrow{\text{4N HCl in 1,4-dioxane}}$

Compound 75

Step 1:

To a solution of intermediate 24-d (1.8 g, 3.44 mmol) in DMF, cooled to 0° C., were sequentially added 6,7-dihydro-5-H-pyrrolo[1,2-a]imidazole-2-carboxylic acid, lithium salt (87-e) (743 mg, 4.48 mmol), HATU (2.0 g, 5.51 mmol) and DIPEA (1.80 mL, 10.33 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 28-a as a white foam.

Step 2:

4N HCl in 1,4-dioxane (6.17 mL) was added to intermediate 28-a (1.62 g, 2.46 mmol) in ethyl acetate (1.0 mL) and the solution was stirred for 2 hours at 0° C. Diethyl ether was added, a precipitate formed and compound 75.2HCl was collected by filtration as a white solid. MS (m/z) M+1=557.4

Example 25

The following example illustrates the preparation of compound 74, which is a compound of Formula 1 or salt thereof.

Scheme 29: Synthesis of compound 74

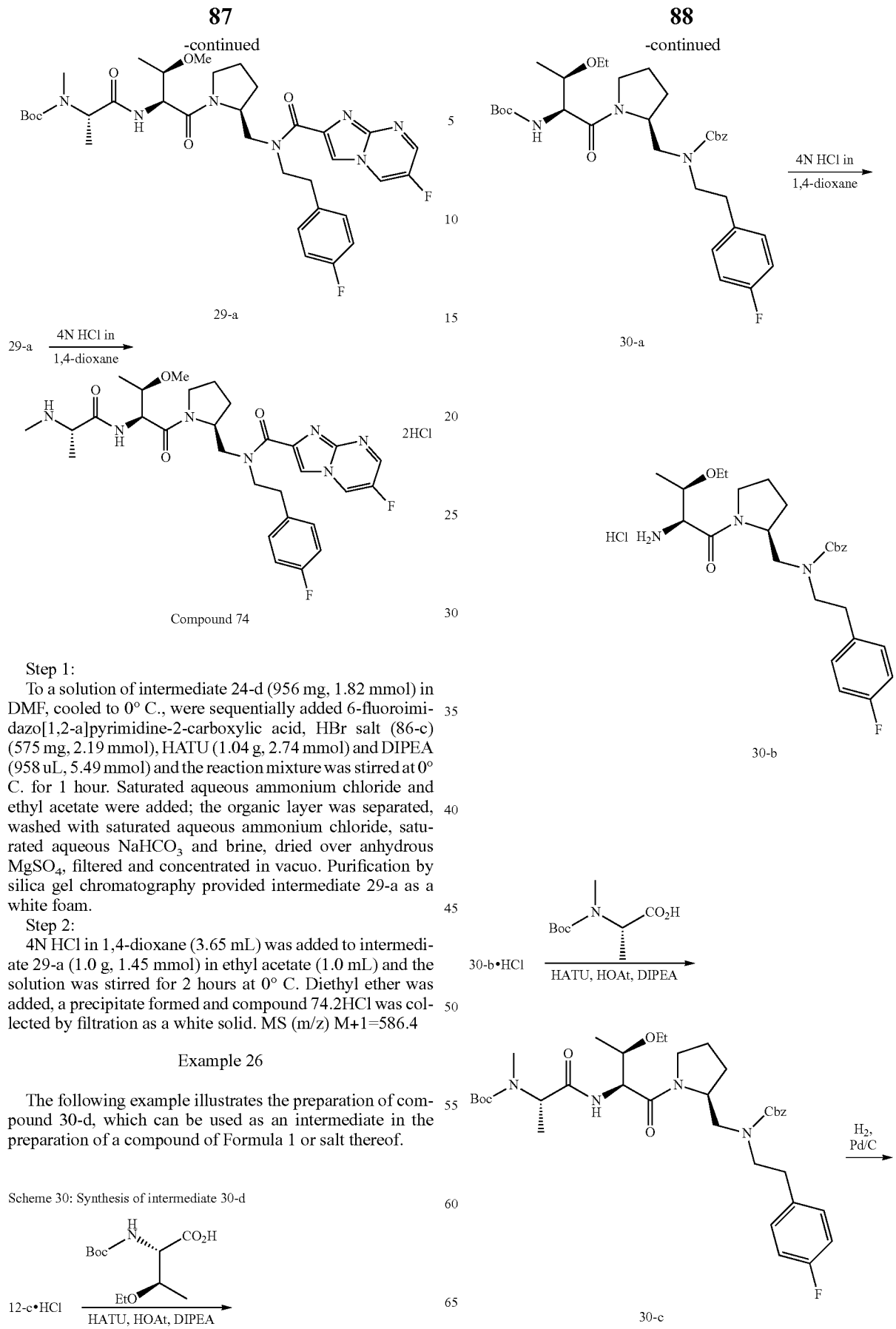

Step 1:
To a solution of intermediate 24-d (956 mg, 1.82 mmol) in DMF, cooled to 0° C., were sequentially added 6-fluoroimidazo[1,2-a]pyrimidine-2-carboxylic acid, HBr salt (86-c) (575 mg, 2.19 mmol), HATU (1.04 g, 2.74 mmol) and DIPEA (958 uL, 5.49 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous $NaHCO_3$ and brine, dried over anhydrous $MgSO_4$, filtered and concentrated in vacuo. Purification by silica gel chromatography provided intermediate 29-a as a white foam.

Step 2:
4N HCl in 1,4-dioxane (3.65 mL) was added to intermediate 29-a (1.0 g, 1.45 mmol) in ethyl acetate (1.0 mL) and the solution was stirred for 2 hours at 0° C. Diethyl ether was added, a precipitate formed and compound 74.2HCl was collected by filtration as a white solid. MS (m/z) M+1=586.4

Example 26

The following example illustrates the preparation of compound 30-d, which can be used as an intermediate in the preparation of a compound of Formula 1 or salt thereof.

Scheme 30: Synthesis of intermediate 30-d

-continued

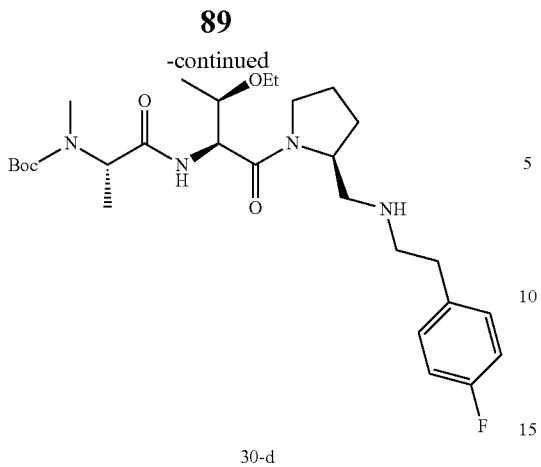

30-d

Step 1:

To a solution of intermediate 12-c.HCl (13.7 g, 34.9 mmol) in DMF cooled to −10° C. were sequentially added Boc-Thr(Et)-OH (8.1 g, 34.9 mmol), HATU (14.6 g, 38.4 mmol), HOAt (63.9 mL, 38.4 mmol) and DIPEA (24.4 mL, 139.0 mmol) and the reaction was then stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 30-a as white foam.

Step 2:

4N HCl in 1,4-dioxane (94.0 mL) was added to intermediate 30-a (10.8 g, 18.9 mmol) in ethyl acetate (10 mL) at 0° C. and the solution was stirred for 3 hours at 0° C. Volatiles were removed under reduced pressure and the residue was triturated with diethyl ether to provide intermediate 30-b.HCl as a white foam. MS (m/z) M+1=486.5

Step 3:

To a solution of intermediate 30-b.HCl (25.0 g, 49.2 mmol) in DMF cooled to 0° C. were sequentially added Boc-NMe-Ala-OH (12.0 g, 59.0 mmol), HATU (26.2 g, 68.9 mmol), HOAt (12.3 mL, 7.38 mmol) and DIPEA (34.3 mL, 197 mmol) and the reaction was then stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 30-c as a white foam.

Step 4:

To a solution of intermediate 30-c (15.88 g, 23.67 mmol) in MeOH (118 mL) under N$_2$ was added 10% Pd/C (50% w/w water content) (3.53 g). The reaction mixture was purged with H$_2$ and stirred for 1 hour. The reaction was then filtered through celite and the filtrate was concentrated in vacuo to provide intermediate 30-d as a colorless oil. MS (m/z) M+1=537.5

Example 27

The following example illustrates the preparation of compound 76, which is a compound of Formula 1 or salt thereof.

Scheme 31: Synthesis of compound 76

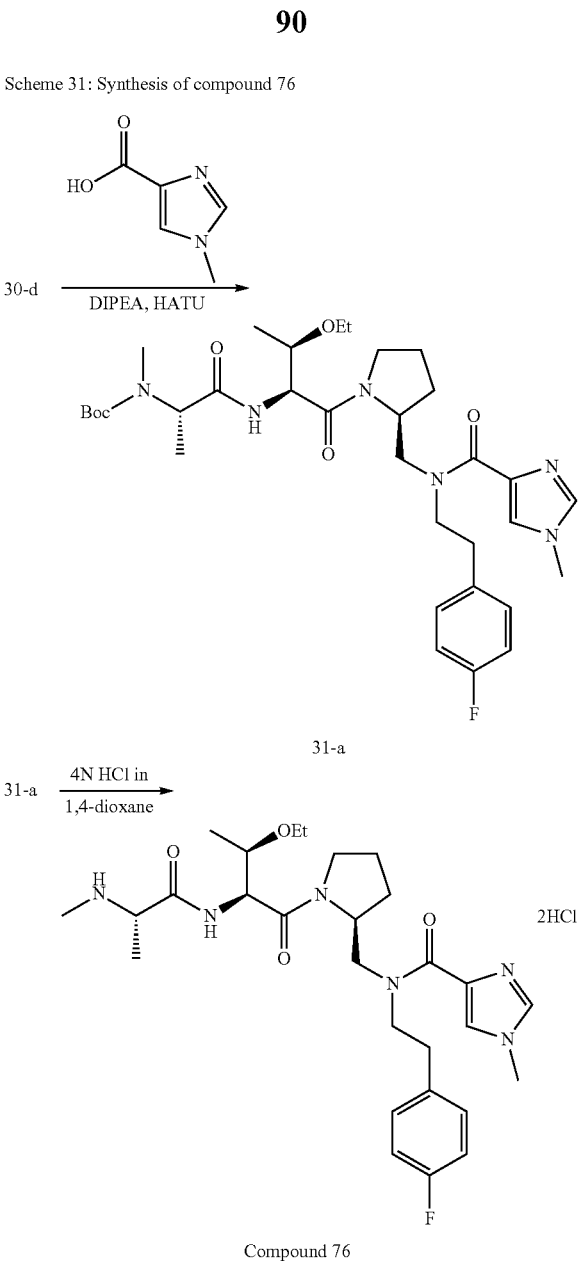

Compound 76

Step 1:

To a solution of intermediate 30-d (2.0 g, 3.73 mmol) in DMF, cooled to 0° C., were sequentially added 1-methyl-1H-imidazole-4-carboxylic acid (564 mg, 4.47 mmol), HATU (1.70 g, 4.47 mmol) and DIPEA (2.60 mL, 14.91 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 31-a as a white foam.

Step 2:

4N HCl in 1,4-dioxane (11.05 mL) was added to intermediate 31-a (1.90 g, 2.95 mmol) and the solution was stirred for 3 hours at 0° C. Volatiles were removed under reduced pressure and the residue was triturated with diethyl ether to provide compound 76.2HCl as a white solid. MS (m/z) M+1=545.5

Example 28

The following example illustrates the preparation of compound 78, which is a compound of Formula 1 or salt thereof.

Scheme 32: Synthesis of compound 78

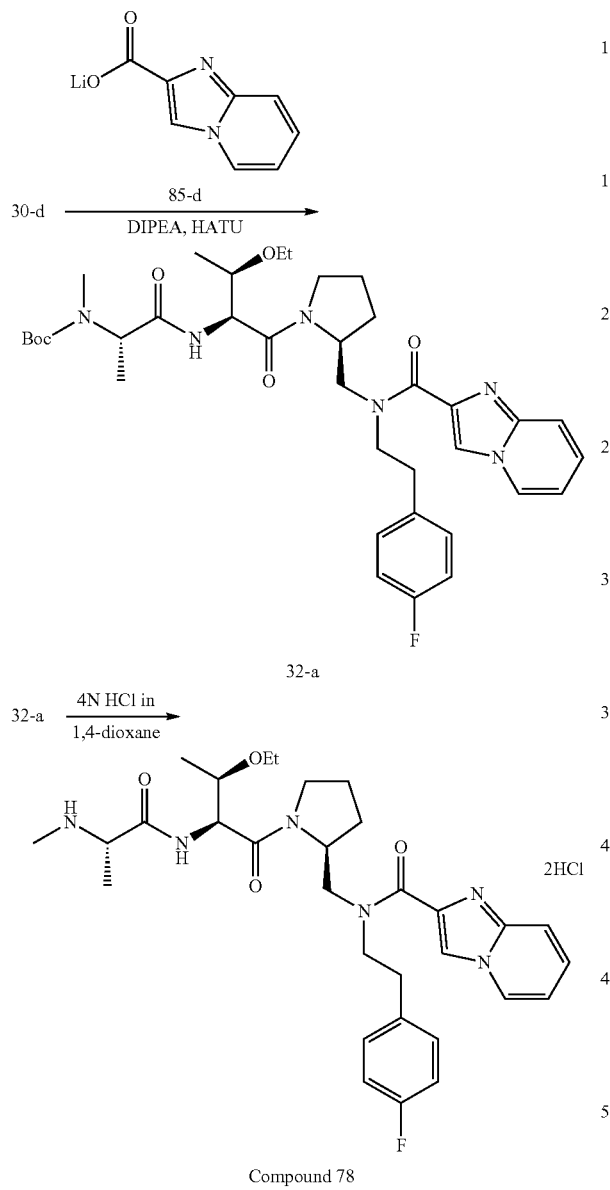

Compound 78

Step 1:

To a solution of intermediate 30-d (2.0 g, 3.73 mmol) in DMF, cooled to 0° C., were sequentially added imidazo[1,2-a]pyridine-2-carboxylic acid, lithium salt (85-d) (752 mg, 4.47 mmol), HATU (1.70 g, 4.47 mmol) and DIPEA (2.60 mL, 14.91 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 32-a as a white foam.

Step 2:

4N HCl in 1,4-dioxane (8.81 mL) was added to intermediate 32-a (1.60 g, 2.35 mmol) in ethyl acetate (0.783 mL) and the solution was stirred for 3 hours at 0° C. Volatiles were removed under reduced pressure and the residue was triturated with diethyl ether to provide compound 78.2HCl as a white solid. MS (m/z) M+1=581.4

Example 29

The following example illustrates the preparation of compound 79, which is a compound of Formula 1 or salt thereof.

Scheme 33: Synthesis of compound 79

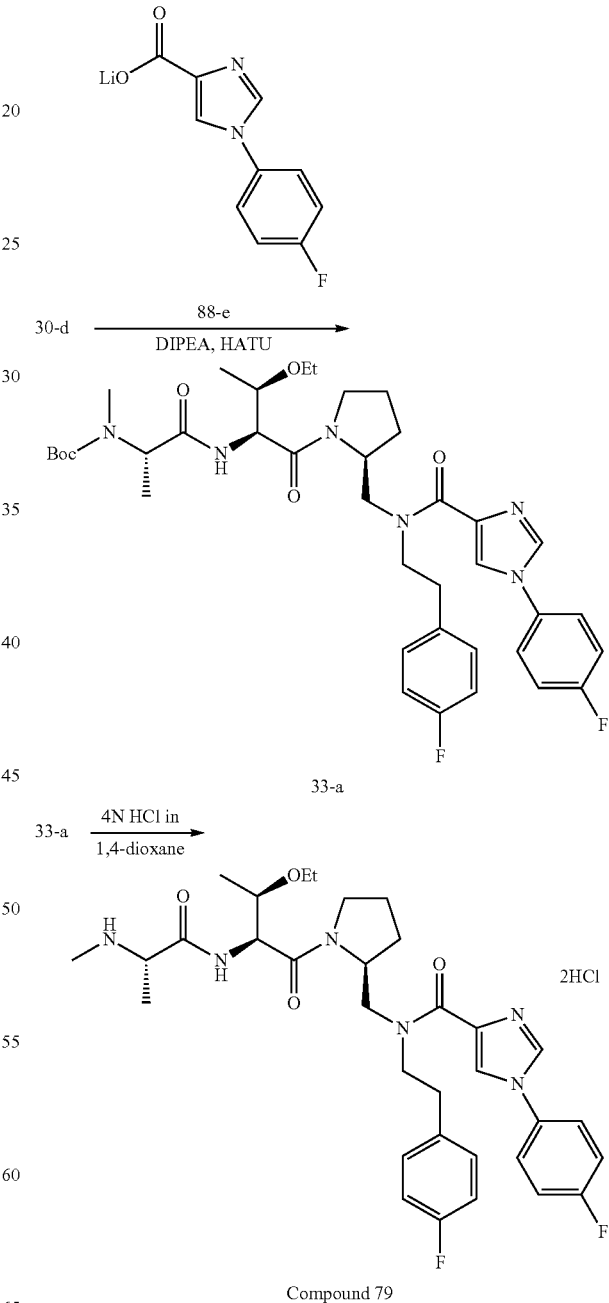

Compound 79

Step 1:

To a solution of intermediate 30-d (1.6 g, 2.98 mmol) in DMF, cooled to 0° C., were sequentially added 1-(4-fluorophenyl)-1H-imidazole-4-carboxylic acid, lithium salt (88-e) (632 mg, 2.98 mmol), HATU (1.36 g, 3.58 mmol) and DIPEA (2.10 L, 11.93 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 33-a as a white foam.

Step 2:

4N HCl in 1,4-dioxane (6.62 mL) was added to intermediate 33-a (1.28 g, 1.76 mmol) and the solution was stirred for 3 hours at 0° C. Volatiles were removed under reduced pressure and the residue was triturated with diethyl ether to provide compound 79.2HCl as a white solid. MS (m/z) M+1=625.5

Example 30

The following example illustrates the preparation of compound 80, which is a compound of Formula 1 or salt thereof.

Scheme 34: Synthesis of compound 80

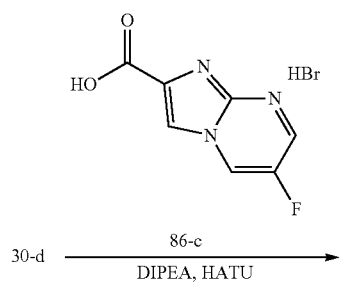

30-d $\xrightarrow[\text{DIPEA, HATU}]{\text{86-c}}$

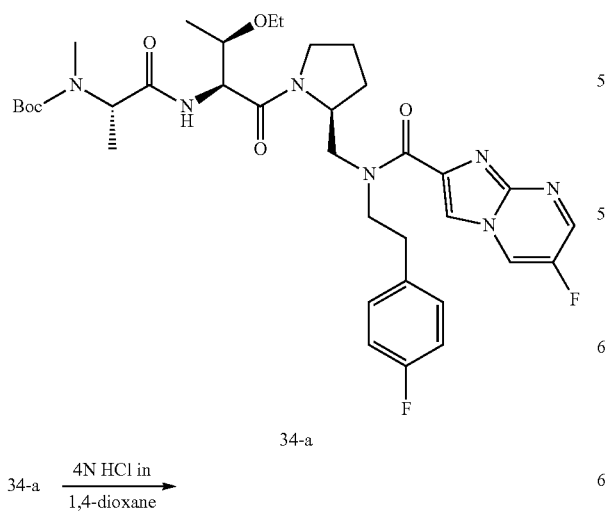

34-a $\xrightarrow[\text{1,4-dioxane}]{\text{4N HCl in}}$

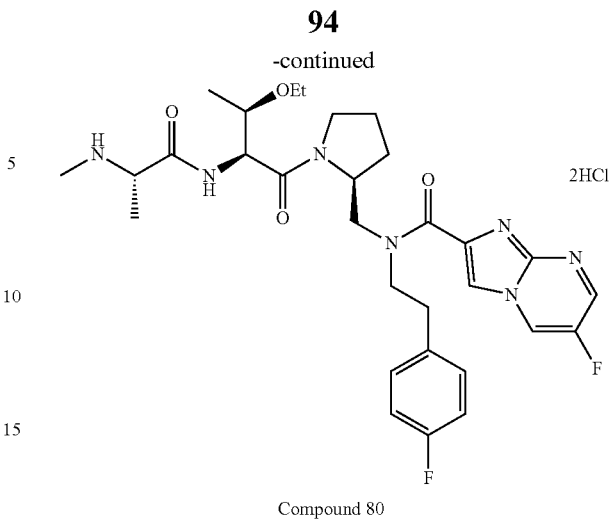

Compound 80

Step 1:

To a solution of intermediate 30-d (1.60 g, 2.98 mmol) in DMF, cooled to 0° C., were sequentially added 6-fluoroimidazo[1,2-a]pyrimidine-2-carboxylic acid, HBr salt (86-c) (937 mg, 3.58 mmol), HATU (1.36 g, 3.58 mmol) and DIPEA (2.07 mL, 11.93 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 34-a as a white foam.

Step 2:

4N HCl in 1,4-dioxane (7.93 mL) was added to intermediate 34-a (1.48 g, 2.11 mmol) and the solution was stirred for 3 hours at 0° C. Diethyl ether was added, a precipitate formed and compound 80.2HCl was collected by filtration as a white solid. MS (m/z) M+1=600.5

Example 31

The following example illustrates the preparation of compound 81, which is a compound of Formula 1 or salt thereof.

Scheme 35: Synthesis of compound 81

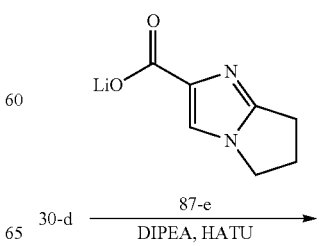

30-d $\xrightarrow[\text{DIPEA, HATU}]{\text{87-e}}$

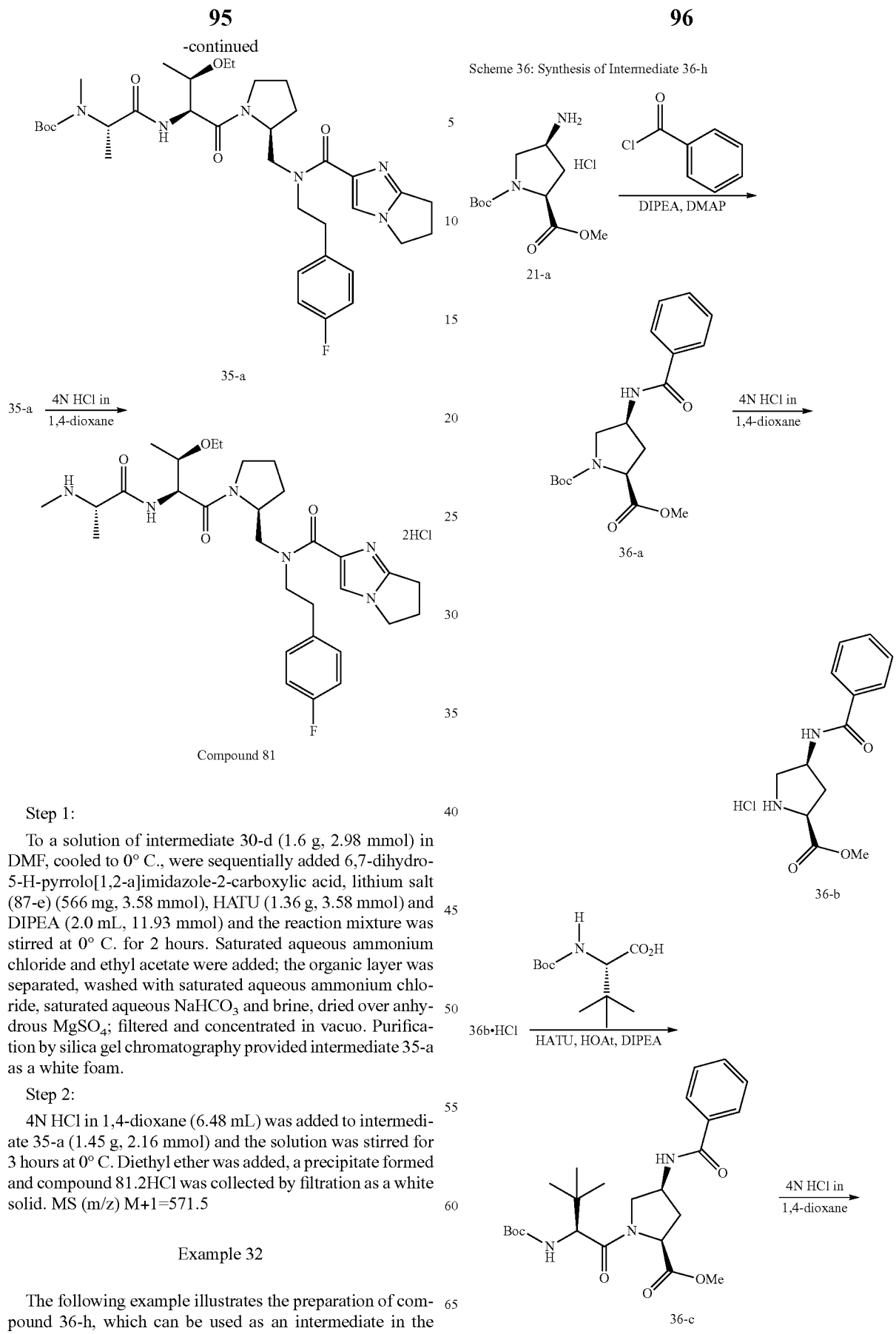

Step 1:

To a solution of intermediate 30-d (1.6 g, 2.98 mmol) in DMF, cooled to 0° C., were sequentially added 6,7-dihydro-5-H-pyrrolo[1,2-a]imidazole-2-carboxylic acid, lithium salt (87-e) (566 mg, 3.58 mmol), HATU (1.36 g, 3.58 mmol) and DIPEA (2.0 mL, 11.93 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄; filtered and concentrated in vacuo. Purification by silica gel chromatography provided intermediate 35-a as a white foam.

Step 2:

4N HCl in 1,4-dioxane (6.48 mL) was added to intermediate 35-a (1.45 g, 2.16 mmol) and the solution was stirred for 3 hours at 0° C. Diethyl ether was added, a precipitate formed and compound 81.2HCl was collected by filtration as a white solid. MS (m/z) M+1=571.5

Example 32

The following example illustrates the preparation of compound 36-h, which can be used as an intermediate in the preparation of a compound of Formula 1 or salt thereof.

-continued

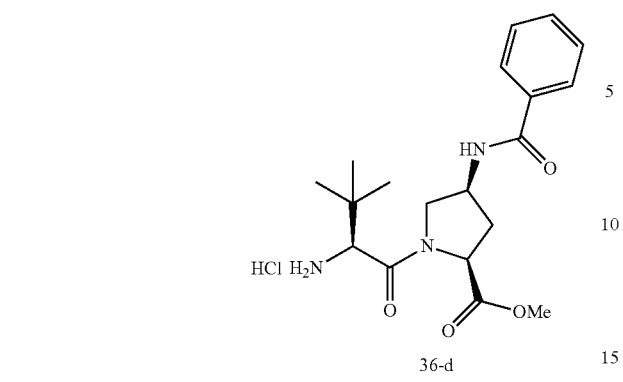

36-d

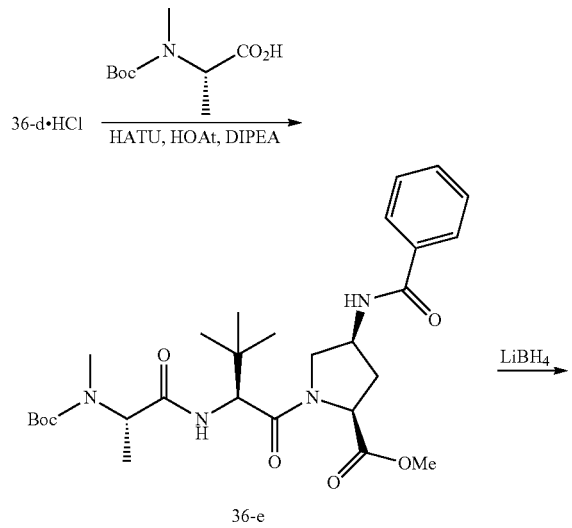

36-d·HCl $\xrightarrow{\text{HATU, HOAt, DIPEA}}$

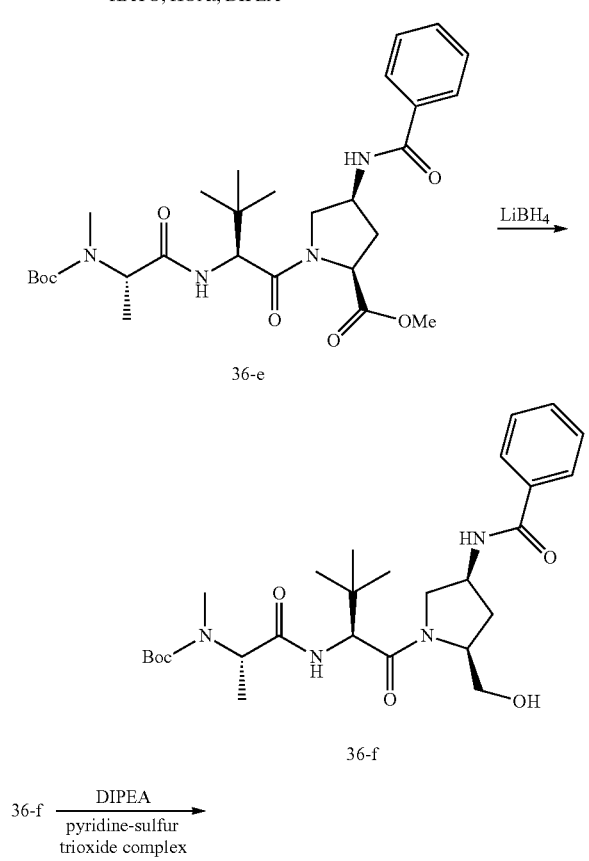

36-e 36-f 36-f $\xrightarrow[\text{pyridine-sulfur trioxide complex}]{\text{DIPEA}}$

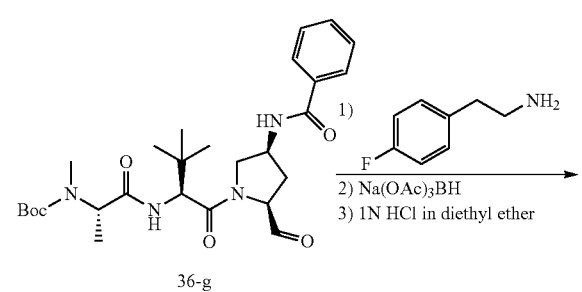

36-g

-continued

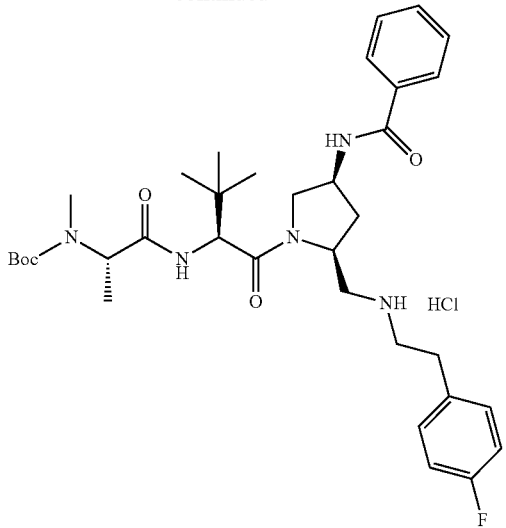

36-h

Step 1:

To a solution of intermediate 21-a.HCl (15.0 g, 53.4 mmol) in dichloromethane cooled to 0° C. were sequentially added DIPEA (37.3 mL, 214.0 mmol), DMAP (326 mg, 2.67 mmol) and benzoyl chloride (6.82 mL, 58.8 mmol) and the reaction was then stirred at room temperature overnight. Water and ethyl acetate were added, the organic layer was separated, washed with 10% aqueous citric acid, saturated aqueous NaHCO$_3$ and brine, dried over MgSO$_4$, filtered and concentrated in vacuo. Purification by silica gel chromatography provided the expected intermediate 36-a as white solid.

Step 2:

4N HCl in 1,4-dioxane (141.0 mL) was added to intermediate 36-a (19.6 g, 56.3 mmol) and the solution was stirred for 1 hour at 0° C. Volatiles were removed under reduced pressure and the residue was triturated with diethyl ether to provide intermediate 36-b.HCl as a white solid. MS (m/z) M+1=249.2

Step 3:

To a solution of intermediate 36-b.HCl (14.7 g, 51.6 mmol) in DMF cooled to 0° C. were sequentially added Boc-tBu-Gly-OH (13.13 g, 56.8 mmol), HOAt (8.60 mL, 5.16 mmol), HATU (21.59 g, 56.8 mmol), and DIPEA (36.1 mL, 207.0 mmol) and the reaction was then stirred at room temperature for 3 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 36-c as colorless oil.

Step 4:

4N HCl in 1,4-dioxane (130.0 mL) was added to intermediate 36-c (24.0 g, 52.0 mmol) and the solution was stirred for 1 hour at 0° C. Volatiles were removed under reduced pressure and the residue was triturated with diethyl ether to provide intermediate 36-d.HCl as a white solid. MS (m/z) M+1=362.2

Step 5:

To a solution of intermediate 36-d.HCl (10.73 g, 52.8 mmol) in DMF cooled to 0° C. were sequentially added Boc-NMe-Ala-OH (10.73 g, 52.8 mmol), HOAt (8.80 mL, 5.28 mmol), HATU (22.07 g, 58.1 mmol), and DIPEA (36.9 mL, 211.0 mmol) and the reaction was then stirred at room temperature for 3 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 36-e as white foam.

Step 6:

To a solution of intermediate 36-e (29.0 g, 53.0 mmol) in THF cooled to 0° C. was added lithium borohydride (2.42 g, 111.0 mmol) and the reaction was stirred at room temperature for 1 hour. Water and ethyl acetate were added; the organic layer was separated, washed with 10% aqueous citric acid, saturated aqueous NaHCO$_3$ and brine, dried over anhydrous MgSO$_4$, filtered and concentrated in vacuo. Purification by silica gel chromatography provided intermediate 36-f as a white foam.

Step 7:

To a solution of intermediate 36-f (25.8 g, 49.7 mmol) in DMSO (14.13 mL, 199.0 mmol) and dichloromethane (200 mL) cooled to 0° C. was added DIPEA (30.3 mL, 174.0 mmol) and pyridine sulfur trioxide complex (23.75 g, 149.0 mmol), the reaction was then stirred at 0° C. for 1 hour. Water and ethyl acetate were added; the organic layer was separated, washed with 10% aqueous citric acid, saturated aqueous NaHCO$_3$ and brine, dried over anhydrous MgSO$_4$, filtered and concentrated in vacuo to provide intermediate 36-g as white foam.

Step 8:

To a solution of intermediate 36-g (25.7 g, 49.7 mmol) in dichloromethane was added 2-(4-fluorophenyl)ethanamine (6.21 mL, 47.4 mmol). After stirring at room temperature overnight, sodium triacetoxyborohydride (21.14 g, 95.0 mmol) was added portion wise at 0° C. and the reaction mixture was then stirred at room temperature for 2 hours. Saturated aqueous NaHCO$_3$ was added; the organic layer was separated, washed with brine, dried over anhydrous MgSO$_4$, filtered and concentrated in vacuo to provide intermediate 36-h as white foam. To a solution of intermediate 36-h (27.4 g, 42.8 mmol) in diethyl ether (500 mL) was added 1N HCl in diethyl ether (52.1 mL, 52.1 mmol), a precipitate formed and intermediate 36-h.HCl was collected by filtration as a white solid. MS (m/z) M+1=640.6

Example 33

The following example illustrates the preparation of compound 49, which is a compound of Formula 1 or salt thereof.

Scheme 37: Synthesis of compound 49

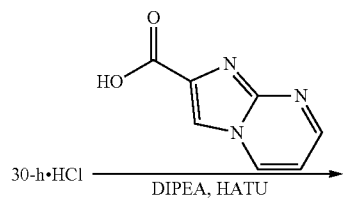

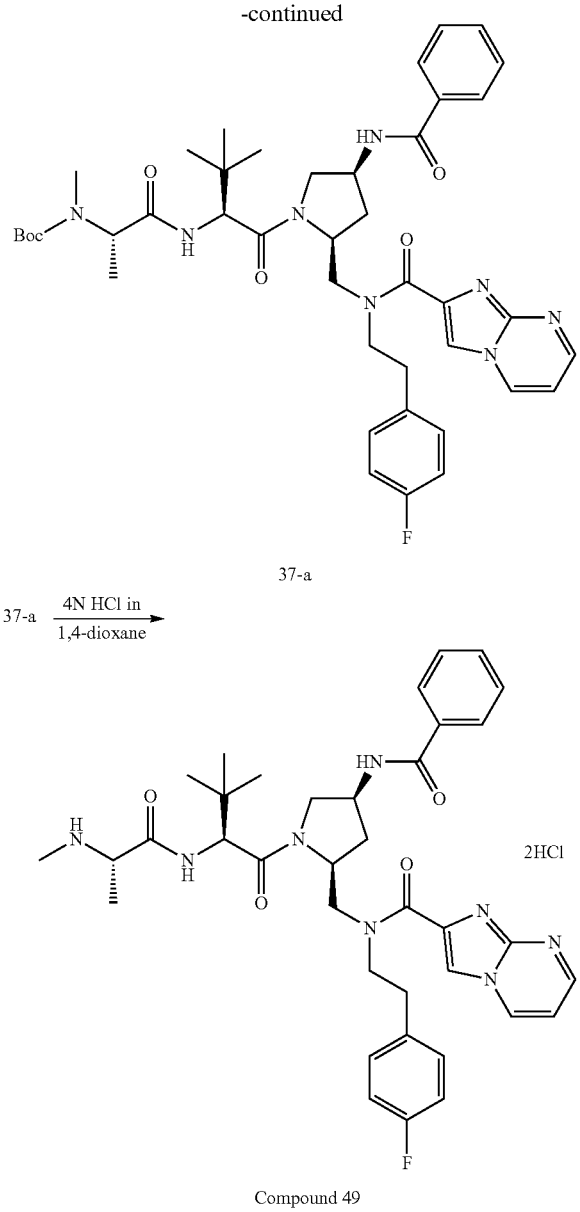

Compound 49

Step 1:

To a solution of intermediate 36-h.HCl (2.0 g, 2.96 mmol) in DMF, cooled to 0° C., were sequentially added imidazo[1,2-a]pyrimidine-2-carboxylic acid (507 mg, 3.11 mmol), HATU (1.23 g, 3.25 mmol) and DIPEA (2.06 mL, 11.83 mmol) and the reaction mixture was stirred at room temperature for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 37-a as a white foam.

Step 2:

4N HCl in 1,4-dioxane (3.19 mL) was added to intermediate 37-a (1.0 g, 1.27 mmol) and the solution was stirred for 1 hour at 0° C. Volatiles were removed under reduced pressure and the residue was triturated with diethyl ether to provide compound 49.2HCl as a white solid. MS (m/z) M+1=685.5

Example 34

The following example illustrates the preparation of compound 69, which is a compound of Formula 1 or salt thereof.

Scheme 38: Synthesis of compound 69

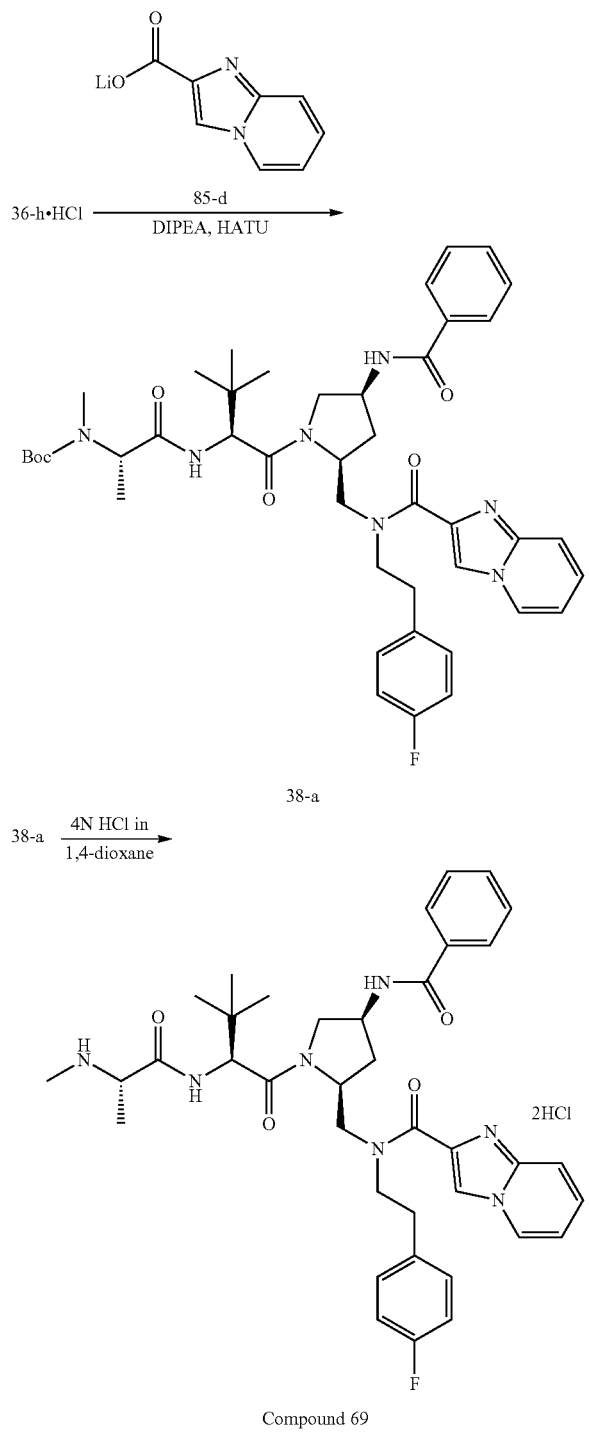

Compound 69

Step 1:

To a solution of intermediate 36-h.HCl (2.0 g, 2.96 mmol) in DMF, cooled to 0° C., were sequentially added imidazo[1,2-a]pyridine-2-carboxylic acid, lithium salt (85-d) (525 mg, 3.11 mmol), HATU (1.23 g, 3.25 mmol) and DIPEA (2.06 mL, 11.83 mmol) and the reaction mixture was stirred at room temperature for 3 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 38-a as a white foam.

Step 2:

4N HCl in 1,4-dioxane (3.19 mL) was added to intermediate 38-a (1.24 g, 1.58 mmol) and the solution was stirred for 1 hour at 0° C. Volatiles were removed under reduced pressure and the residue was triturated with diethyl ether to provide compound 69.2HCl as a white solid. MS (m/z) M+1=684.4

Example 35

The following example illustrates the preparation of compound 86, which is a compound of Formula 1 or salt thereof.

Scheme 39: Synthesis of compound 86

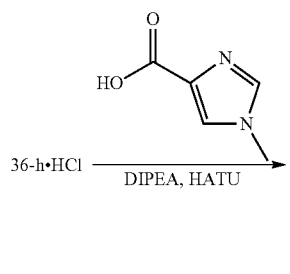

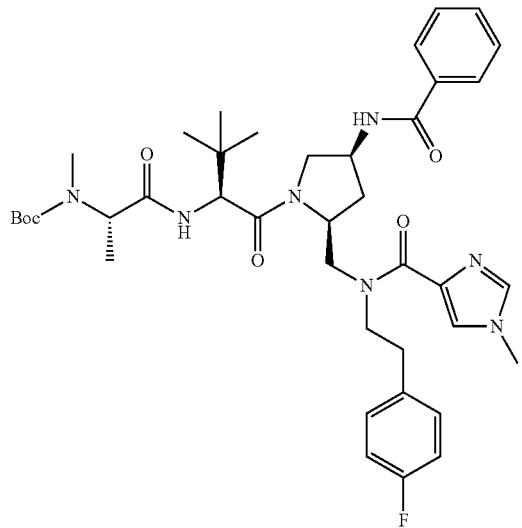

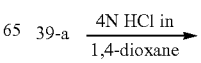

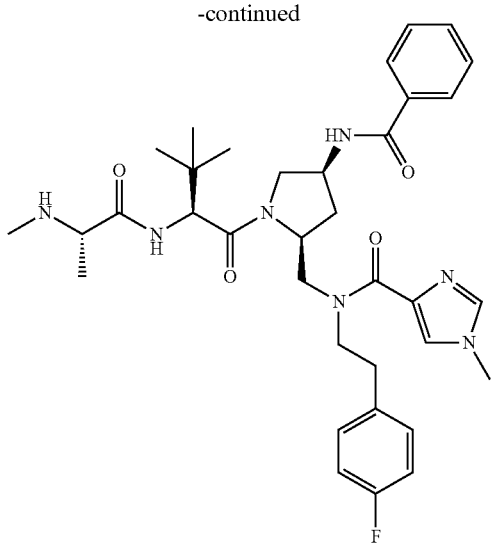

Compound 86

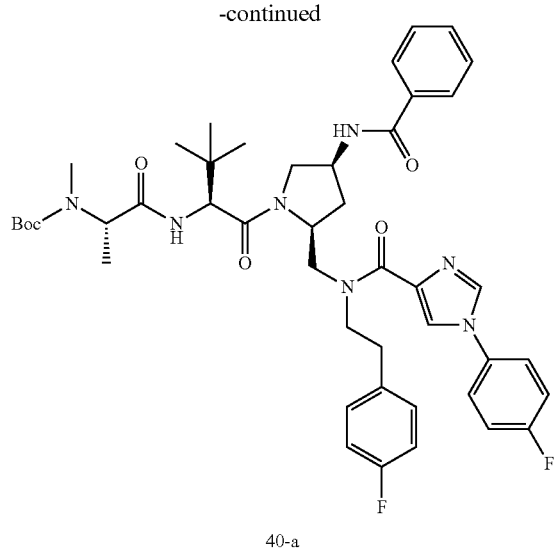

40-a $$\text{40-a} \xrightarrow{\text{4N HCl in 1,4-dioxane}}$$

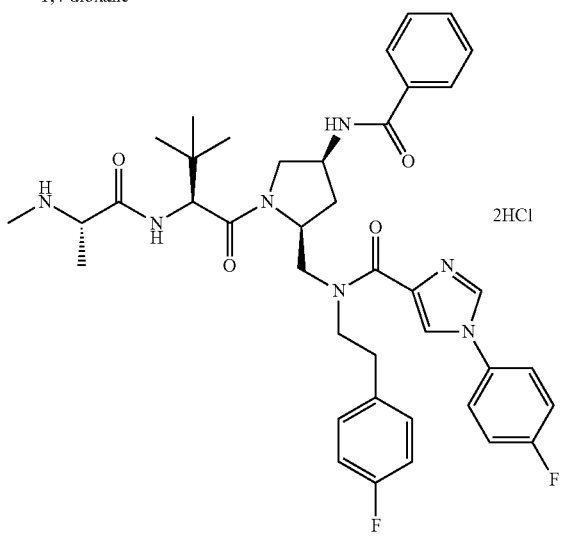

Compound 87

Step 1:

To a solution of intermediate 36-h.HCl (2.0 g, 2.96 mmol) in DMF, cooled to 0° C., were sequentially added 1-methyl-1H-imidazole-4-carboxylic acid (448 mg, 3.55 mmol), HATU (1.23 g, 3.25 mmol) and DIPEA (2.06 mL, 11.83 mmol) and the reaction mixture was stirred at room temperature for 3 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 39-a as a white foam.

Step 2:

4N HCl in 1,4-dioxane (4.68 mL) was added to intermediate 39-a (1.40 g, 1.87 mmol) and the solution was stirred for 1 hour at 0° C. Volatiles were removed under reduced pressure and the residue was triturated with diethyl ether to provide compound 86.2HCl as a white solid. MS (m/z) M+1=648.5

Example 36

The following example illustrates the preparation of compound 87, which is a compound of Formula 1 or salt thereof.

Scheme 40: Synthesis of compound 87

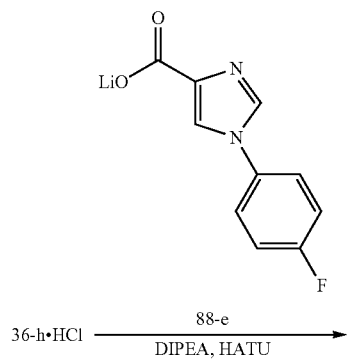

$$\text{36-h·HCl} \xrightarrow[\text{DIPEA, HATU}]{\text{88-e}}$$

Step 1:

To a solution of intermediate 36-h.HCl (2.0 g, 2.96 mmol) in DMF, cooled to 0° C., were sequentially added 1-(4-fluorophenyl)-1H-imidazole-4-carboxylic acid, lithium salt (88-e) (662 mg, 3.11 mmol), HATU (1.23 g, 3.25 mmol) and DIPEA (2.06 mL, 11.83 mmol) and the reaction mixture was stirred at room temperature for 3 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 40-a as a white foam.

Step 2:

4N HCl in 1,4-dioxane (5.92 mL) was added to intermediate 40-a (1.40 g, 1.87 mmol) and the solution was stirred for 1 hour at 0° C. Volatiles were removed under reduced pressure and the residue was triturated with diethyl ether to provide compound 87.2HCl as a white solid. MS (m/z) M+1=728.5

Example 37

The following example illustrates the preparation of compound 89, which is a compound of Formula 1 or salt thereof.

Scheme 41: Synthesis of compound 89

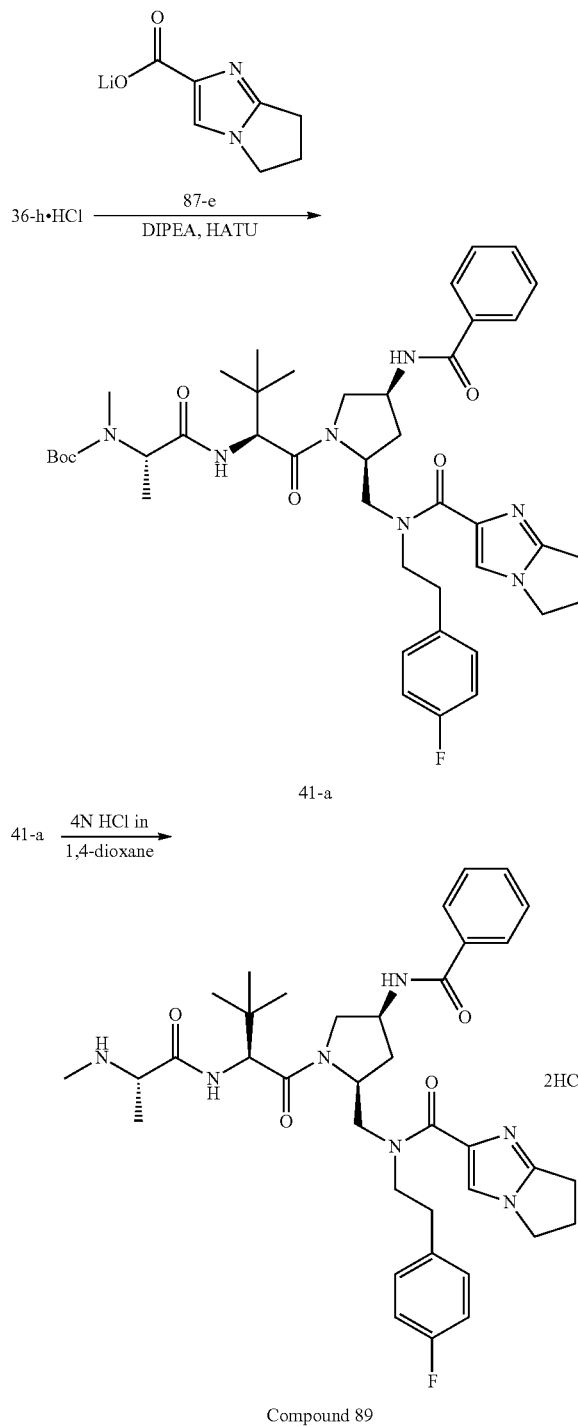

Compound 89

Step 1:

To a solution of intermediate 36-h.HCl (2.0 g, 2.96 mmol) in DMF, cooled to 0° C., were sequentially added 6,7-dihydro-5-H-pyrrolo[1,2-a]imidazole-2-carboxylic acid, lithium salt (87-e) (589 mg, 3.55 mmol), HATU (1.23 g, 3.25 mmol) and DIPEA (2.06 mL, 11.83 mmol) and the reaction mixture was stirred at room temperature for 3 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 41-a as a white foam.

Step 2:

4N HCl in 1,4-dioxane (3.29 mL) was added to intermediate 41-a (1.02 g, 1.32 mmol) and the solution was stirred for 1 hour at 0° C. Volatiles were removed under reduced pressure and the residue was triturated with diethyl ether to provide compound 89.2HCl as a white solid. MS (m/z) M+1=674.5

Example 38

The following example illustrates the preparation of compound 42-h, which can be used as an intermediate in the preparation of a compound of Formula 1 or salt thereof.

Scheme 42: Synthesis of Intermediate 42-h

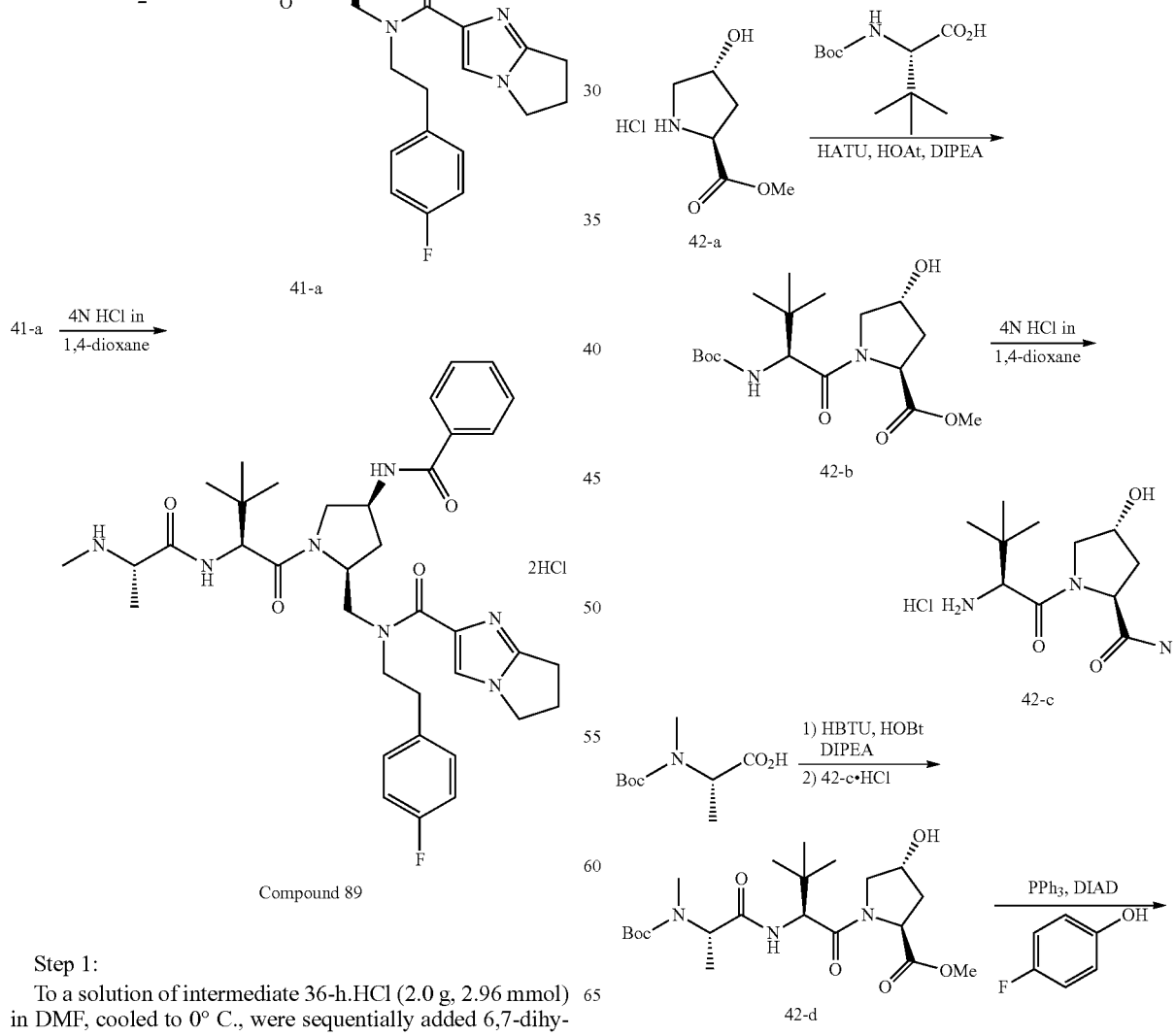

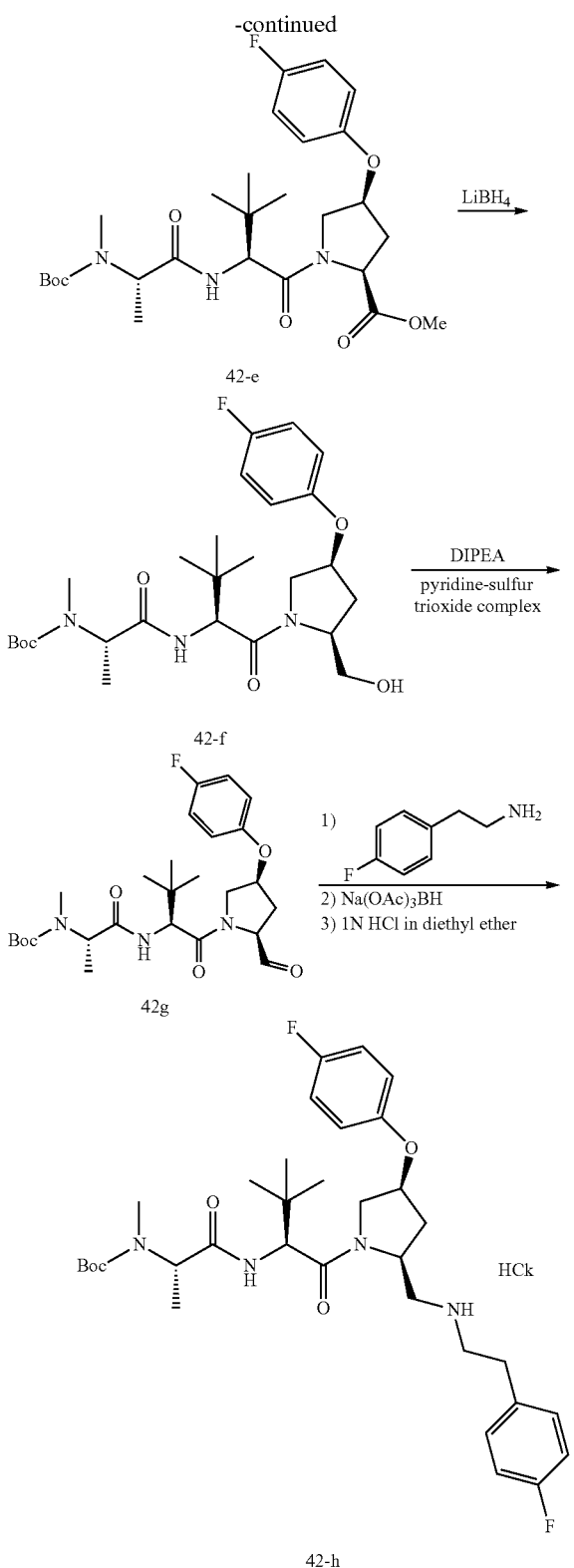

the reaction was then stirred at room temperature for 3 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 42-b as a beige solid.

Step 2:

4N HCl in 1,4-dioxane (80 mL) was added to intermediate 42-b (7.89 g, 22.0 mmol) and the solution was stirred for 3 hours at 0° C. Volatiles were removed under reduced pressure and the residue was triturated with diethyl ether to provide intermediate 42-c.HCl as a white foam. MS (m/z) M+1=259.1

Step 3:

To a solution of Boc-NMe-Ala-OH (7.16 g, 35.2 mmol) in DMF cooled to 0° C. were sequentially added HOBt (5.73 g, 37.4 mmol), HBTU (14.19 g, 37.4 mmol), and DIPEA (19.23 mL, 40.0 mmol). After stirring for 10 minutes, intermediate 42-c (6.49 g, 25.1 mmol) was added and the reaction was then stirred at room temperature overnight. Water and ethyl acetate were added; the organic layer was separated, washed with 10% aqueous citric acid, saturated aqueous NaHCO$_3$ and brine, dried over anhydrous MgSO$_4$, filtered and concentrated in vacuo. Purification by silica gel chromatography provided the expected intermediate 42-d as a white solid.

Step 4:

To a solution of intermediate 42-d (2.32 g, 5.23 mmol), 4-fluorophenol (704 mg, 6.28 mmol) and triphenylphosphine (1.92 g, 7.32 mmol) in THF was added DIAD (1.42 mL, 7.32 mmol) dropwise and the reaction was then stirred at room temperature for 2 days. Diethyl ether and hexane were added, a precipitate formed and triphenyl phosphine oxide was removed by filtration. Volatiles were removed under reduced pressure and the residue was purified by silica gel chromatography to provide the expected intermediate 42-e as a colorless oil.

Step 5:

To a solution of intermediate 42-e (4.6 g, 8.56 mmol) in THF cooled to 0° C. was added lithium borohydride (559 mg, 25.7 mmol) and the reaction was stirred at room temperature for 3 hours. Water and ethyl acetate were added; the organic layer was separated, washed with 10% citric acid, saturated aqueous NaHCO$_3$ and brine, dried over anhydrous MgSO$_4$, filtered and concentrated in vacuo. Purification by silica gel chromatography provided intermediate 42-f as colorless oil.

Step 6:

To a solution of intermediate 42-f (4.2 g, 8.24 mmol) in DMSO (2.33 mL, 33.0 mmol) and dichloromethane (80 mL) cooled to 0° C. was added DIPEA (5.04 mL, 28.8 mmol) and pyridine sulfur trioxide complex (3.94 g, 24.72 mmol), the reaction was then stirred at 0° C. for 1 hour. Water and ethyl acetate were added; the organic layer was separated, washed with 10% citric acid, saturated aqueous NaHCO$_3$ and brine, dried over anhydrous MgSO$_4$, filtered and concentrated in vacuo to provide intermediate 42-g as beige solid.

Step 7:

To a solution of intermediate 42-g (3.8 g, 7.49 mmol) in dichloromethane was added 2-(4-fluorophenyl)ethanamine (935 uL, 7.13 mmol). After stirring at room temperature overnight, sodium triacetoxyborohydride (3.18 g, 14.26 mmol) was added portion wise at 0° C. and the reaction mixture was then stirred at room temperature for 2 hours. Saturated aqueous NaHCO$_3$ was added; the organic layer was separated, washed with brine, dried over MgSO$_4$, filtered and concentrated in vacuo to provide intermediate 42-g as yellow Step 1:

To a solution of (2S,4R)-methyl 4-hydroxypyrrolidine-2-carboxylate, HCl salt 42-a (4.0 g, 22.02 mmol) in DMF cooled to 0° C. were sequentially added Boc-tBu-Gly-OH (6.11 g, 26.4 mmol), HOAt (5.51 mL, 3.30 mmol), HATU (10.89 g, 28.6 mmol), and DIPEA (15.39 mL, 88.0 mmol) and oil. To a solution of intermediate 42-g in diethyl ether (100 mL) was added 1N HCl in diethyl ether (7.84 mL, 7.84 mmol), a precipitate formed and intermediate 42-h.HCl was collected by filtration as beige solid. MS (m/z) M+1=631.5

Example 39

The following example illustrates the preparation of compound 82, which is a compound of Formula 1 or salt thereof.

Scheme 43: Synthesis of compound 82

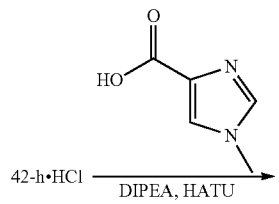

42-h•HCl $\xrightarrow{\text{DIPEA, HATU}}$

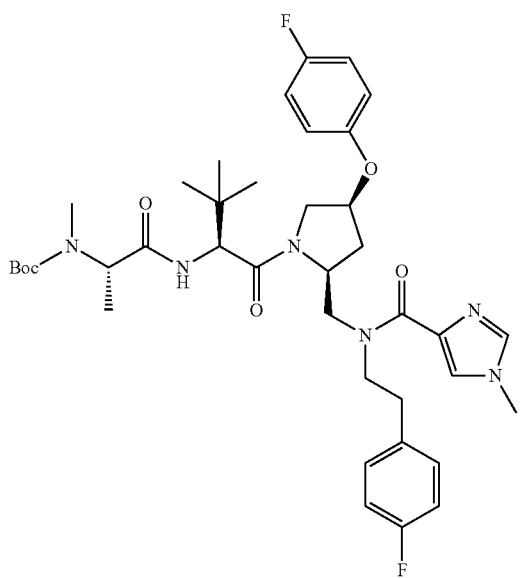

43-a 43-a $\xrightarrow[\text{1,4-dioxane}]{\text{4N HCl in}}$

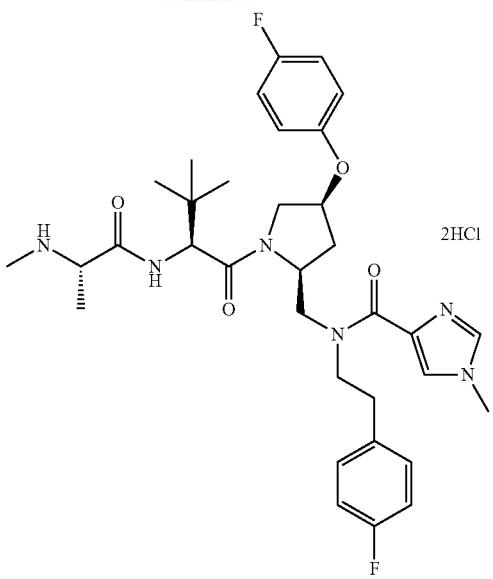

Compound 82

Step 1:

To a solution of intermediate 42-h.HCl (1.50 g, 2.24 mmol) in DMF, cooled to 0° C., were sequentially added 1-methyl-1H-imidazole-4-carboxylic acid (397 mg, 3.15 mmol), HATU (1.19 g, 3.15 mmol) and DIPEA (1.57 mL, 8.99 mmol) and the reaction mixture was stirred at room temperature for 2 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 43-a as a white foam.

Step 2:

4N HCl in 1,4-dioxane (4.50 mL) was added to intermediate 43-a (1.10 g, 1.48 mmol) and the solution was stirred for 2 hour at 0° C. Volatiles were removed under reduced pressure and the residue was triturated with diethyl ether to provide compound 82.2HCl as a white solid. MS (m/z) M+1=639.5

Example 40

The following example illustrates the preparation of compound 83, which is a compound of Formula 1 or salt thereof.

Scheme 44: Synthesis of compound 83

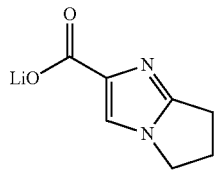

42-h•HCl $\xrightarrow[\text{DIPEA, HATU}]{\text{87-e}}$

-continued

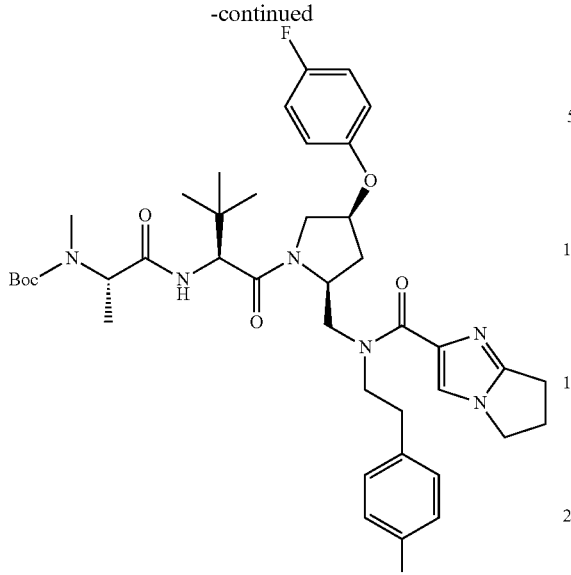

44-a 44-a →(4N HCl in 1,4-dioxane)→

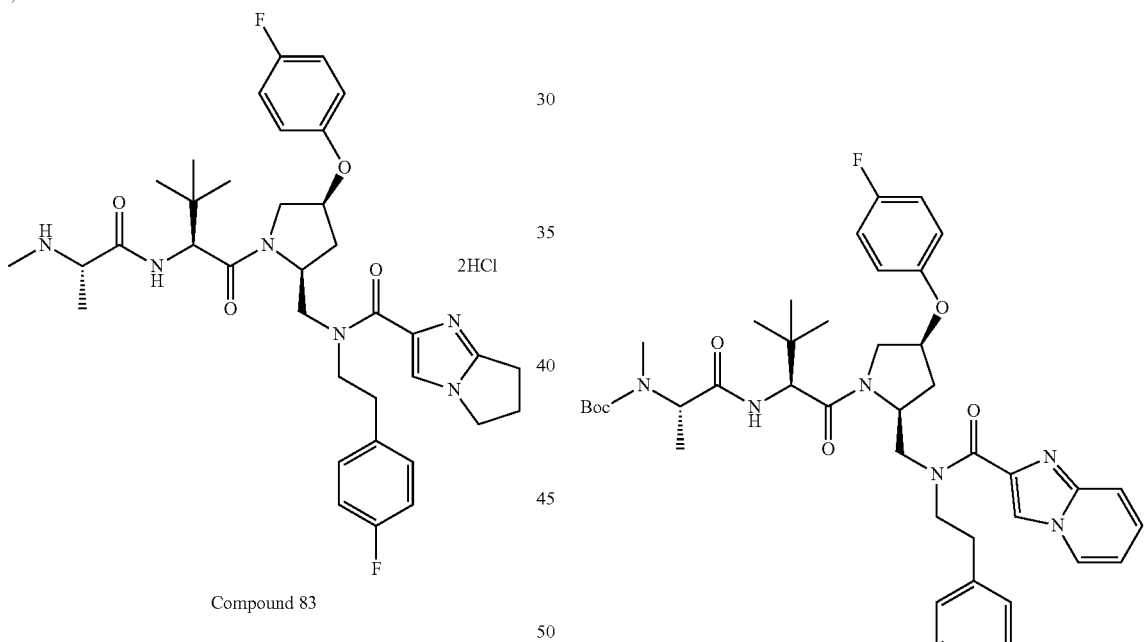

Compound 83

Step 1:
To a solution of intermediate 42-h.HCl (1.40 g, 2.01 mmol) in DMF, cooled to 0° C., were sequentially added 6,7-dihydro-5-H-pyrrolo[1,2-a]imidazole-2-carboxylic acid, lithium salt (87-e) (447 mg, 2.94 mmol), HATU (1.12 g, 2.94 mmol) and DIPEA (1.46 mL, 8.39 mmol) and the reaction mixture was stirred at room temperature for 2 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 44-a as a white foam.

Step 2:
4N HCl in 1,4-dioxane (6.69 mL) was added to intermediate 44-a (1.02 g, 1.33 mmol) and the solution was stirred for 2 hours at 0° C. Volatiles were removed under reduced pressure and the residue was triturated with diethyl ether to provide compound 83.2HCl as a white solid. MS (m/z) M+1=665.5

Example 41

The following example illustrates the preparation of compound 84, which is a compound of Formula 1 or salt thereof.

Scheme 45: Synthesis of compound 84

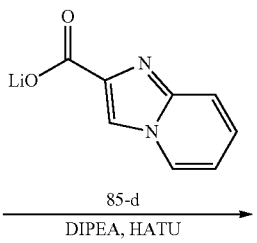

42-h•HCl →(85-d / DIPEA, HATU)→

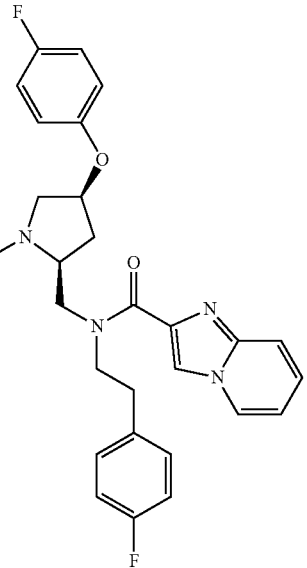

45-a 45-a →(4N HCl in 1,4-dioxane)→

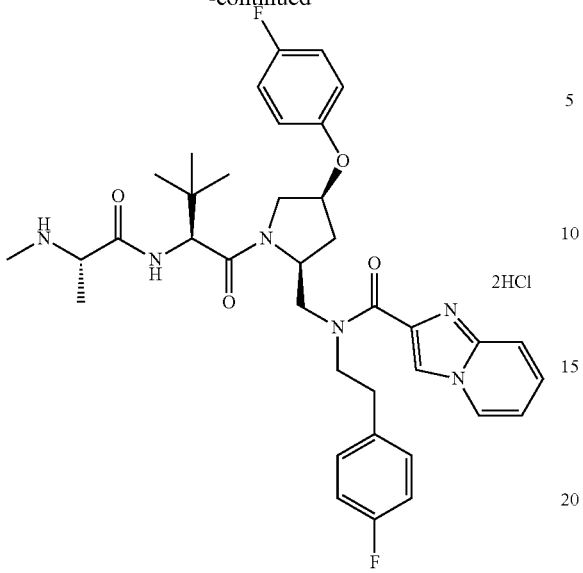

Compound 84

Step 1:

To a solution of intermediate 42-h.HCl (2.0 g, 2.96 mmol) in DMF, cooled to 0° C., were sequentially added imidazo[1,2-a]pyridine-2-carboxylic acid, lithium salt (85-d) (494 mg, 2.94 mmol), HATU (1.11 g, 2.94 mmol) and DIPEA (1.46 mL, 8.39 mmol) and the reaction mixture was stirred at room temperature for 3 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 45-a as a white foam.

Step 2:

4N HCl in 1,4-dioxane (5.97 mL) was added to intermediate 45-a (926 mg, 1.19 mmol) and the solution was stirred for 2 hours at 0° C. Volatiles were removed under reduced pressure and the residue was triturated with diethyl ether to provide compound 84.2HCl as a white solid. MS (m/z) M+1=675.5

Example 42

The following example illustrates the preparation of compound 10, which is a compound of Formula 1 or salt thereof.

Scheme 46: Synthesis of compound 10

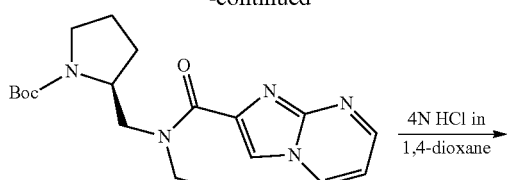

46-a

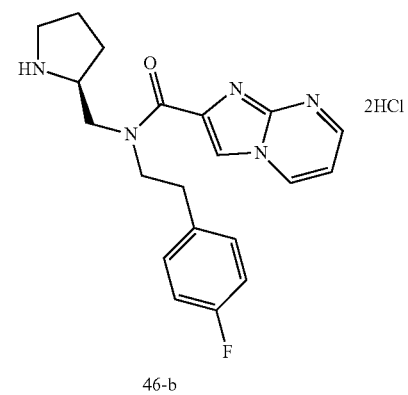

46-b

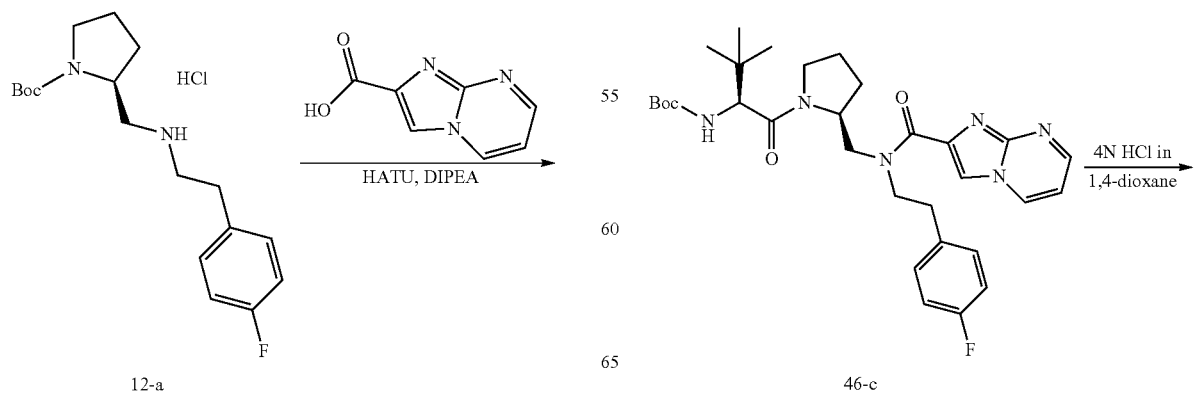

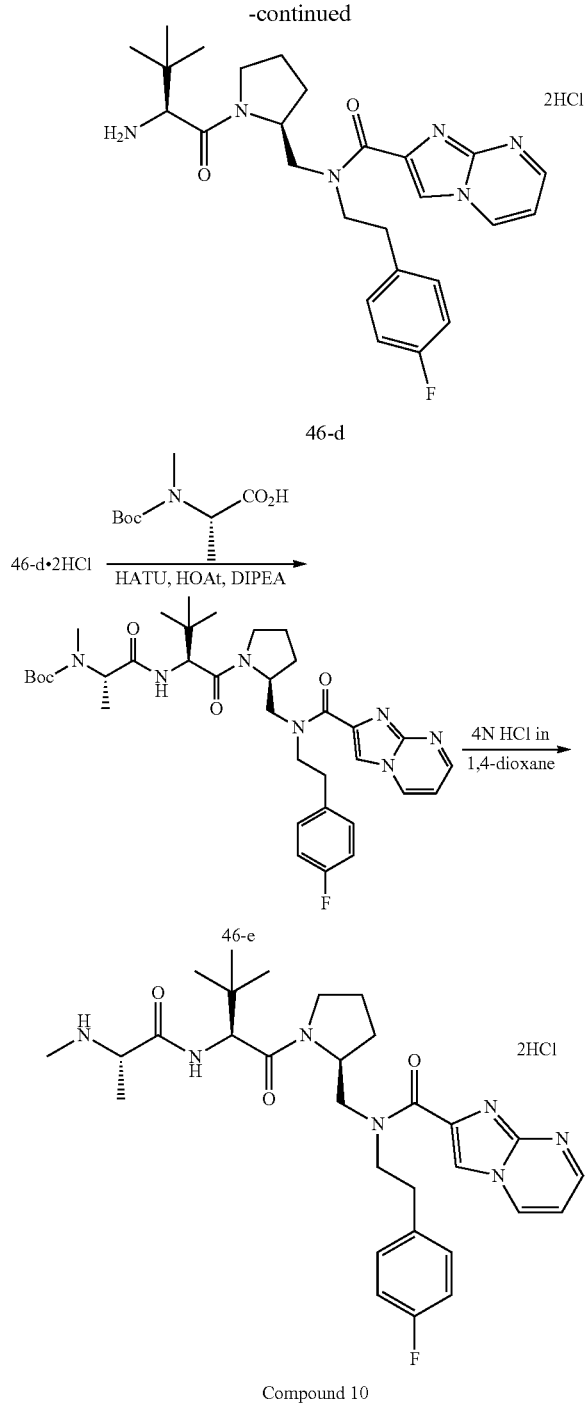

46-d 46-e

Compound 10

Step 1:
To a solution of intermediate 12-a.HCl (25.0 g, 69.7 mmol) in DMF cooled to 0° C. were sequentially added imidazo[1,2-a]pyrimidine-2-carboxylic acid (13.64 g, 84.0 mmol), HATU (34.4 g, 91.0 mmol) and DIPEA (48.5 mL, 279.0 mmol) dropwise over a period of 45 minutes and the reaction was then stirred at 0° C. for 30 minutes. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 46-a as a beige foam.

Step 2:
4N HCl in 1,4-dioxane (171 mL) was added to intermediate 46-a (32.0 g, 68.4 mmol) and the solution was stirred for 1 hour at 0° C. Diethyl ether was added and intermediate 46-b.2HCl was collected by filtration as a white solid. MS (m/z) M+1=368.3

Step 3:
To a solution of intermediate 46-b.2HCl (25.0 g, 56.8 mmol) in DMF cooled to 0° C. were sequentially added Boc-tBu-gly-OH (14.44 g, 62.5 mmol), HATU (28.1 g, 73.8 mmol), HOAt (14.19 mL, 8.52 mmol) and DIPEA (39.6 mL, 227.0 mmol) dropwise over a period of 30 minutes and the reaction was then stirred at 0° C. for 45 minutes. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 46-c as white foam.

Step 4:
4N HCl in 1,4-dioxane (62.4 mL) was added to intermediate 46-c (14.5 g, 24.97 mmol) and the solution was stirred for 2 hours at 0° C. Diethyl ether was added and intermediate 46-d.2HCl was collected by filtration as a white solid. MS (m/z) M+1=481.5

Step 5:
To a solution of intermediate 46-d.2HCl (13.8 g, 26.7 mmol) in DMF cooled to 0° C. were sequentially added Boc-NMe-Ala-OH (5.97 g, 29.4 mmol), HATU (13.19 g, 34.7 mmol), HOAt (6.67 mL, 4.0 mmol) and DIPEA (18.6 mL, 107.0 mmol) dropwise over a period of 30 minutes and the reaction was then stirred at 0° C. for 30 minutes. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 46-e as white foam.

Step 6:
4N HCl in 1,4-dioxane (58.2 mL) was added to intermediate 46-e (15.5 g, 23.28 mmol) in ethyl acetate (5 mL) and the solution was stirred for 1.5 hours at 0° C. Diethyl ether was added and compound 10.2HCl was collected by filtration as a white solid. MS (m/z) M+1=566.5

Example 43

The following example illustrates the preparation of compound 47-d, which can be used as an intermediate in the preparation of a compound of Formula 1 or salt thereof.

Scheme 47: Synthesis of intermediate 47-d

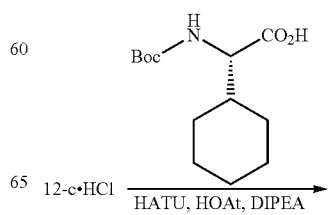

12-c•HCl $\xrightarrow{\text{HATU, HOAt, DIPEA}}$

-continued

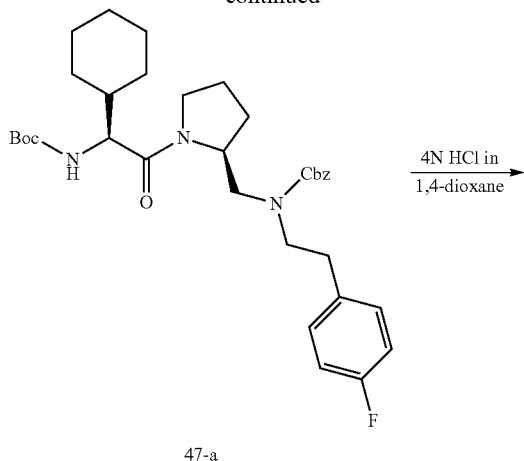

47-a

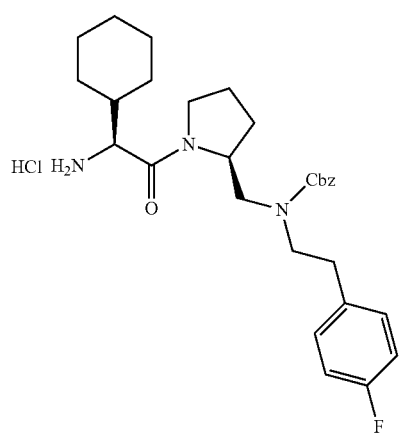

47-b

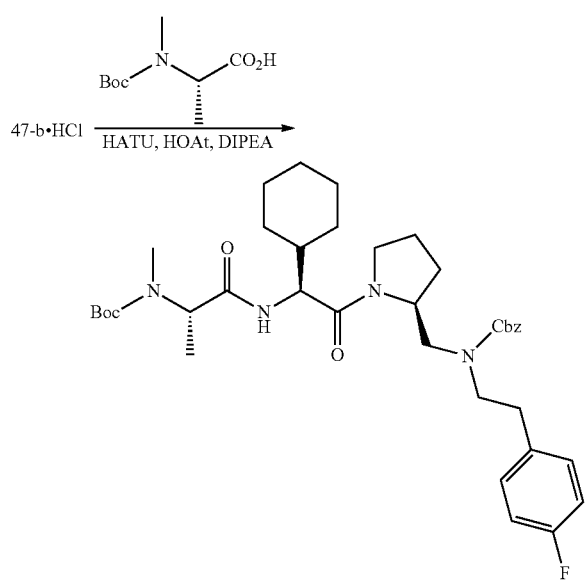

47-c 47-c $\xrightarrow{H_2, Pd/C}$

-continued

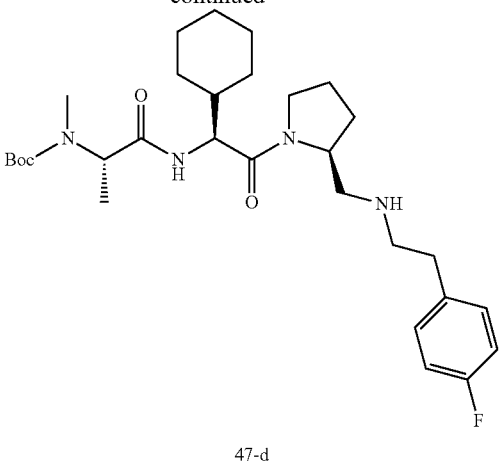

47-d

Step 1:

To a solution of intermediate 12-c.HCl (29.57 g, 75.0 mmol) in DMF cooled to 0° C. were sequentially added Boc-Chg-OH (22.27 g, 87.0 mmol), HATU (42.9 g, 113.0 mmol), HOAt (18.82 mL, 11.29 mmol) and DIPEA (41.4 mL, 226.0 mmol) over a period of 30 minutes and the reaction was then stirred at room temperature for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 47-a as a white foam.

Step 2:

4N HCl in 1,4-dioxane (188 mL) was added to intermediate 47-a (44.7 g, 75.0 mmol) in ethyl acetate (10 mL) at 0° C. and the solution was stirred for 4 hours at 0° C. Volatiles were removed under reduced pressure and the residue was triturated with diethyl ether to provide intermediate 47-b.HCl as a white foam. MS (m/z) M+1=596.4

Step 3:

To a solution of intermediate 47-b.HCl (25.8 g, 48.50 mmol) in DMF cooled to 0° C. were sequentially added Boc-NMe-Ala-OH (11.33 g, 55.8 mmol), HATU (25.8 g, 67.9 mmol), HOAt (8.08 mL, 4.85 mmol) and DIPEA (33.8 mL, 194.0 mmol) dropwise over a period of 30 minutes and the reaction was then stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided the expected intermediate 47-c as a white foam.

Step 4:

To a solution of intermediate 47-c (23.7 g, 34.8 mmol) in MeOH (100 mL) under N$_2$ was added 10% Pd/C (50% w/w water content) (7.4 g). The reaction mixture was purged with H$_2$ and stirred for 2 hours. The reaction was then filtered through celite and the filtrate was concentrated in vacuo to provide intermediate 47-d as a white foam. MS (m/z) M+1=547.4

Example 44

The following example illustrates the preparation of compound 20, which is a compound of Formula 1 or salt thereof.

Scheme 48: Synthesis of compound 20

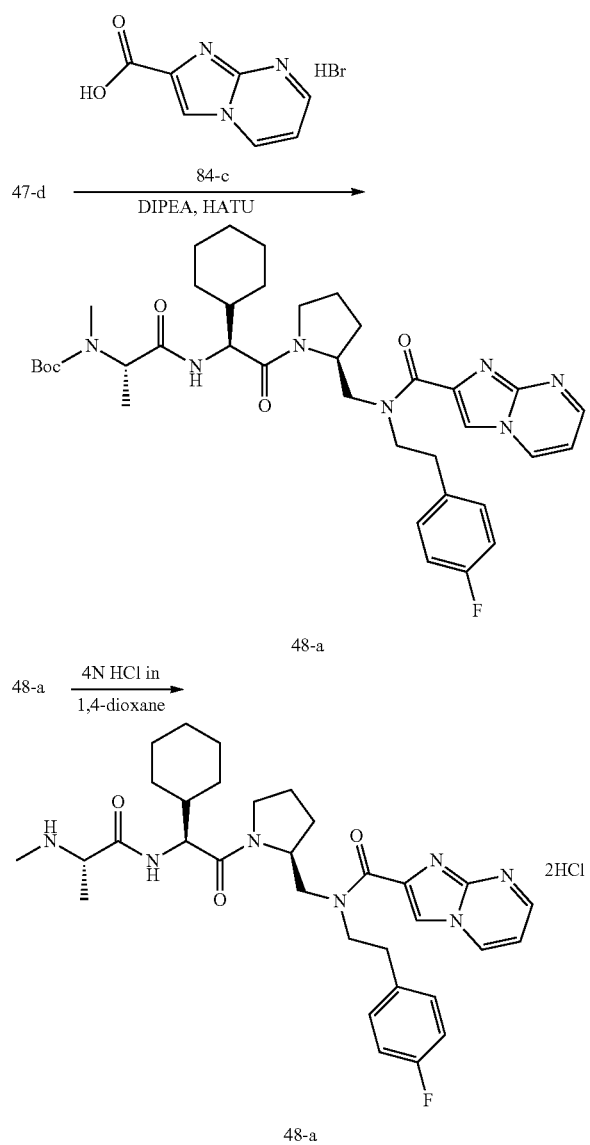

48-a

Example 45

The following example illustrates the preparation of compound 103, which is a compound of Formula 1 or salt thereof.

Scheme 49: Synthesis of compound 103

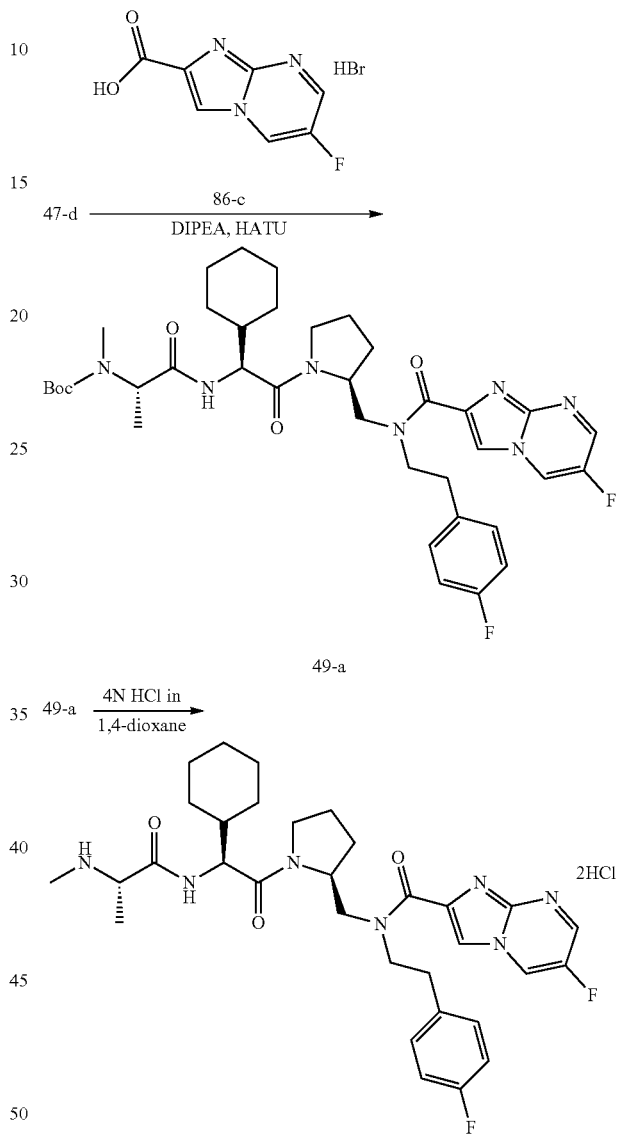

Compound 103

Step 1:

To a solution of intermediate 47-d (17.9 g, 32.7 mmol) in DMF cooled to 0° C. were sequentially added imidazo[1,2-a]pyrimidine-2-carboxylic acid, HBr salt (84-c) (9.59 g, 39.3 mmol), HATU (18.67 g, 49.1 mmol) and DIPEA (17.11 mL, 98.0 mmol) over a period of 30 minutes and the reaction mixture was stirred at 0° C. for 1 hour. Saturated aqueous ammonium chloride and ethyl acetate were added; the organic layer was separated, washed with saturated aqueous NaHCO₃ and brine, dried over anhydrous MgSO₄, filtered and concentrated in vacuo. Purification by silica gel chromatography provided intermediate 48-a as white foam.

Step 2:

4N HCl in 1,4-dioxane (44.5 mL) was added to intermediate 48-a (12.32 g, 17.81 mmol) in ethyl acetate (10 mL) at 0° C. and the solution was stirred for 4 hours at 0° C. Volatiles were removed under reduced pressure and the residue was triturated with diethyl ether to provide compound 20.2HCl as a white solid. MS (m/z) M+1=592.4

Step 1:

To a solution of intermediate 47-d (500 mg, 0.91 mmol) in DMF, cooled to 0° C., were sequentially added 6-fluoroimidazo[1,2-a]pyrimidine-2-carboxylic acid, HBr salt (86-c) (276 mg, 1.05 mmol), HATU (522 mg, 1.37 mmol) and DIPEA (478 uL, 2.74 mmol) and the reaction mixture was stirred at 0° for 1 hour. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 49-a as a white foam.

Step 2:

4N HCl in 1,4-dioxane (882 uL) was added to intermediate 49-a (250 mg, 0.35 mmol) in ethyl acetate (500 uL) and the solution was stirred for 2 hours at 0° C. Volatiles were removed under reduced pressure and the residue was triturated with diethyl ether to provide compound 103.2HCl as a white solid. MS (m/z) M+1=610.3

Example 46

The following example illustrates the preparation of compound 18, which is a compound of Formula 1 or salt thereof.

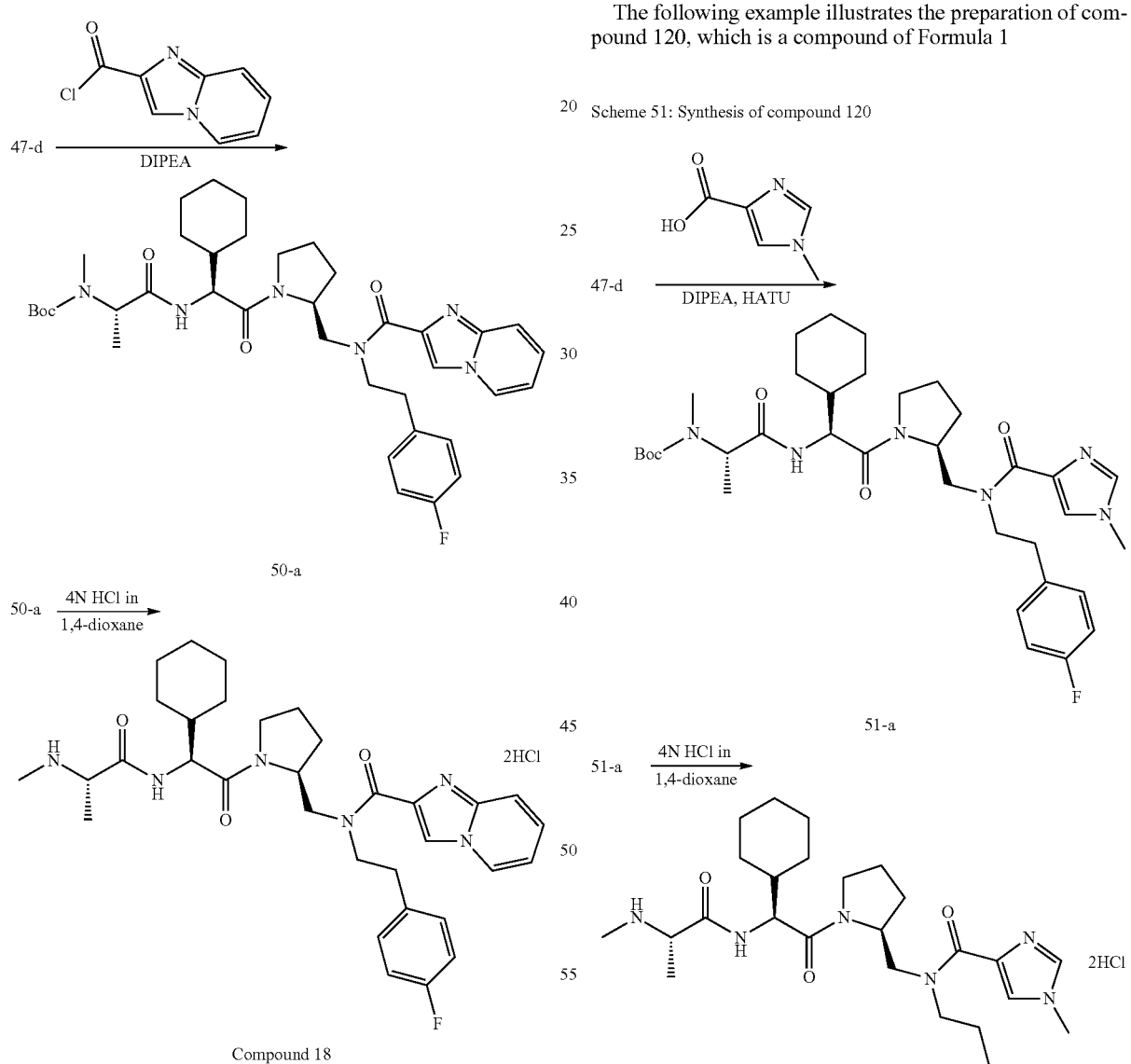

Compound 18

Step 1:

To a solution of intermediate 47-d (303 mg, 0.55 mmol) in DMF, cooled to 0° C., were sequentially added DIPEA (483 uL, 2.77 mmol) and imidazo[1,2-a]pyrimidine-2-carbonyl chloride (250 mg, 1.38 mmol) and the reaction mixture was stirred at room temperature for 30 minutes. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 50-a as a white foam.

Step 2:

4N HCl in 1,4-dioxane (1.85 mL) was added to intermediate 50-a (366 mg, 0.53 mmol) in methanol (200 uL) and the solution was stirred for 2 hours at 0° C. Volatiles were removed under reduced pressure and the residue was triturated with diethyl ether to provide compound 18.2HCl as white solid. MS (m/z) M+1=591.4

Example 47

The following example illustrates the preparation of compound 120, which is a compound of Formula 1

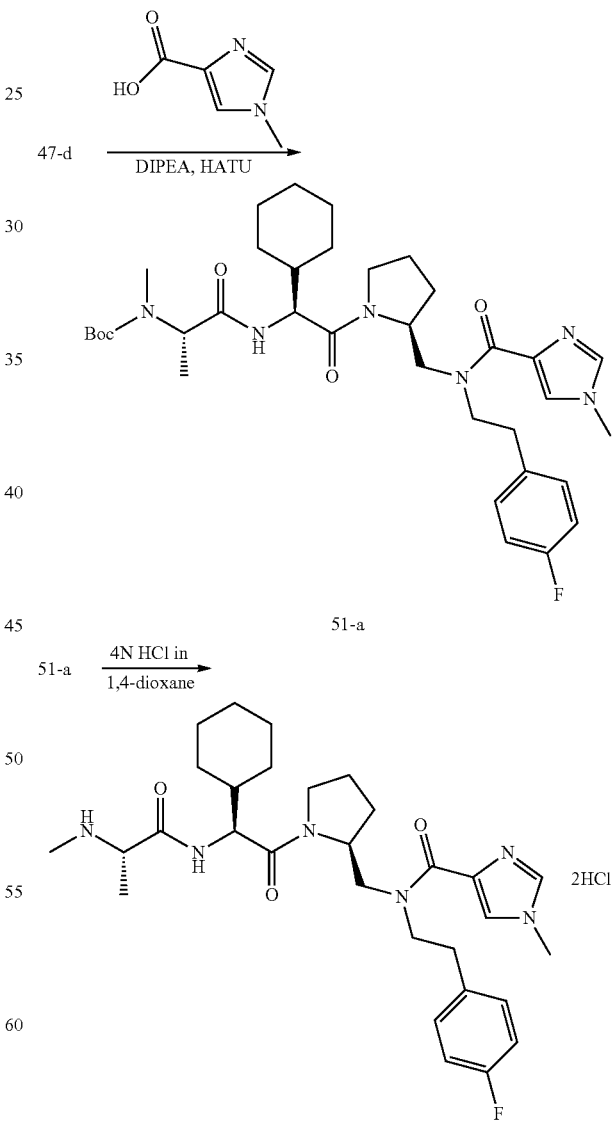

Compound 120

Step 1:

To a solution of intermediate 47-d (500 mg, 0.91 mmol) in DMF, cooled to 0° C., were sequentially added 1-methyl-1H-imidazole-4-carboxylic acid (138 mg, 1.09 mmol), HATU (522 mg, 1.37 mmol) and DIPEA (478 uL, 2.74 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 51-a as a white foam.

Step 2:

4N HCl in 1,4-dioxane (918 uL) was added to intermediate 51-a (240 mg, 0.37 mmol) in ethyl acetate (500 uL) and the solution was stirred for 2 hours at 0° C. Volatiles were removed under reduced pressure and the residue was triturated with diethyl ether to provide compound 120.2HCl as a white solid. MS (m/z) M+1=555.3

Example 48

The following example illustrates the preparation of compound 113, which is a compound of Formula 1

Scheme 52: Synthesis of compound 113

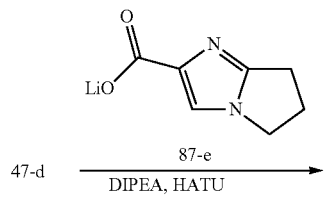

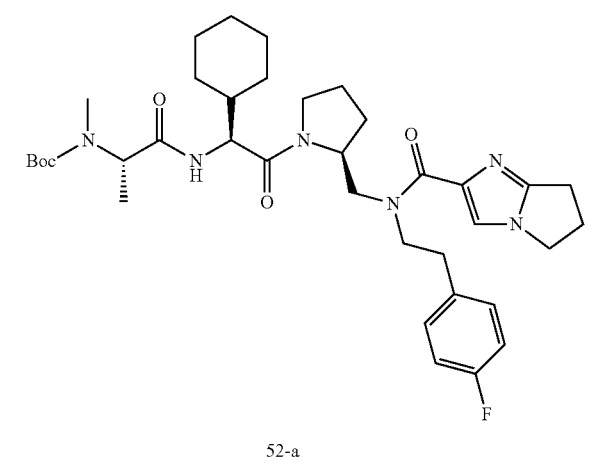

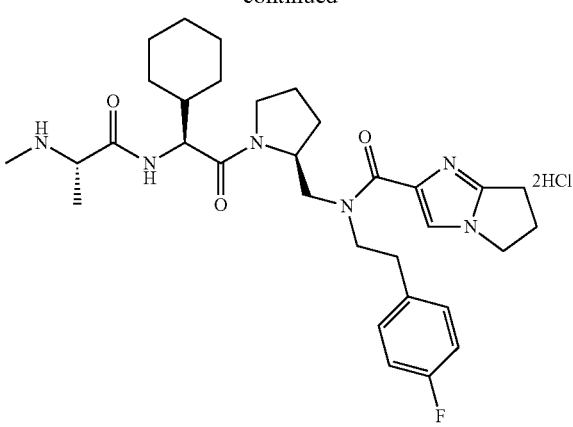

Compound 113

Step 1:

To a solution of intermediate 47-d (500 mg, 0.91 mmol) in DMF, cooled to 0° C., were sequentially added 6,7-dihydro-5-H-pyrrolo[1,2-a]imidazole-2-carboxylic acid, lithium salt (87-e) (152 mg, 915 mmol), HATU (522 g, 1.37 mmol) and DIPEA (478 uL, 2.74 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 52-a as a white foam.

Step 2:

4N HCl in 1,4-dioxane (1.37 mL) was added to intermediate 52-a (373 mg, 0.54 mmol) in ethyl acetate (500 uL) and the solution was stirred for 2 hours at 0° C. Diethyl ether was added, a precipitate formed and compound 113.2HCl was collected by filtration as a white solid. MS (m/z) M+1=581.3

Example 49

The following example illustrates the preparation of compound 104, which is a compound of Formula 1

Scheme 53: Synthesis of compound 104

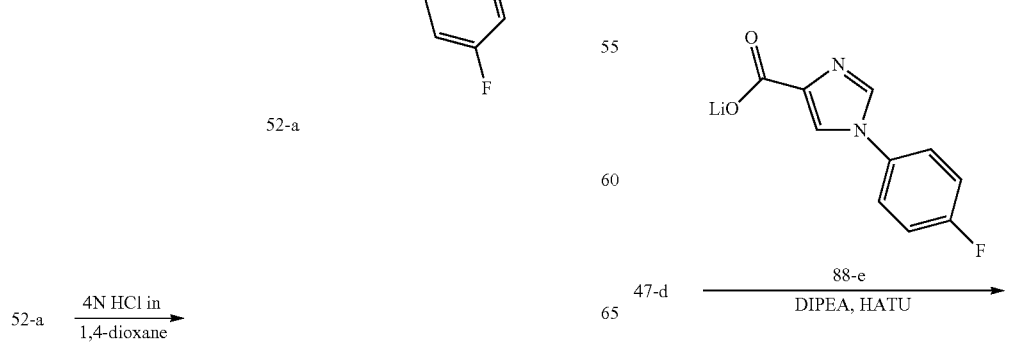

-continued

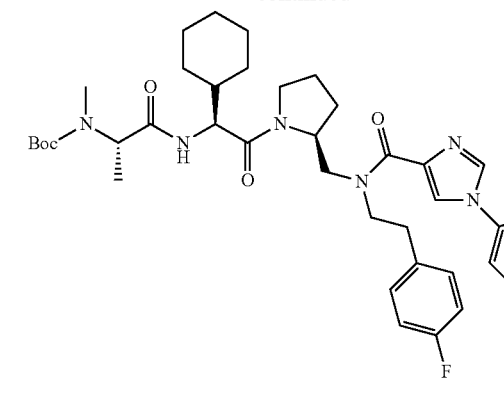

53-a 53-a → (4N HCl in 1,4-dioxane) →

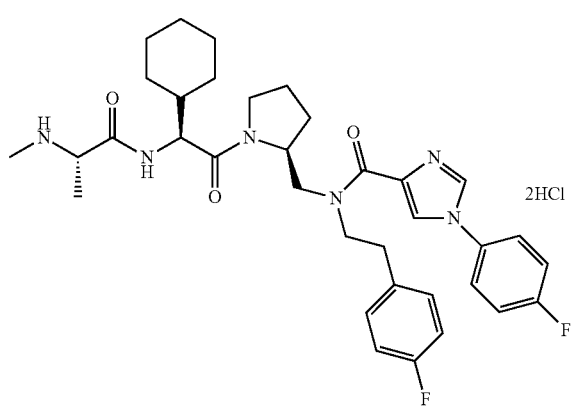

Compound 104

Step 1:

To a solution of intermediate 47-d (500 mg, 0.91 mmol) in DMF, cooled to 0° C., were sequentially added 1-(4-fluorophenyl)-1H-imidazole-4-carboxylic acid, lithium salt (88-e) (224 mg, 1.05 mmol), HATU (522 mg, 1.37 mmol) and DIPEA (478 uL, 2.74 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 53-a as a white foam.

Step 2:

4N HCl in 1,4-dioxane (886 uL) was added to intermediate 53-a (260 mg, 0.35 mmol) in ethyl acetate (0.5 mL) and the solution was stirred for 2 hours at 0° C. Volatiles were removed under reduced pressure and the residue was triturated with diethyl ether to provide compound 104.2HCl as a white solid. MS (m/z) M+1=635.3

Example 50

The following example illustrates the preparation of compound 91, which is a compound of Formula 1

Scheme 54: Synthesis of compound 91

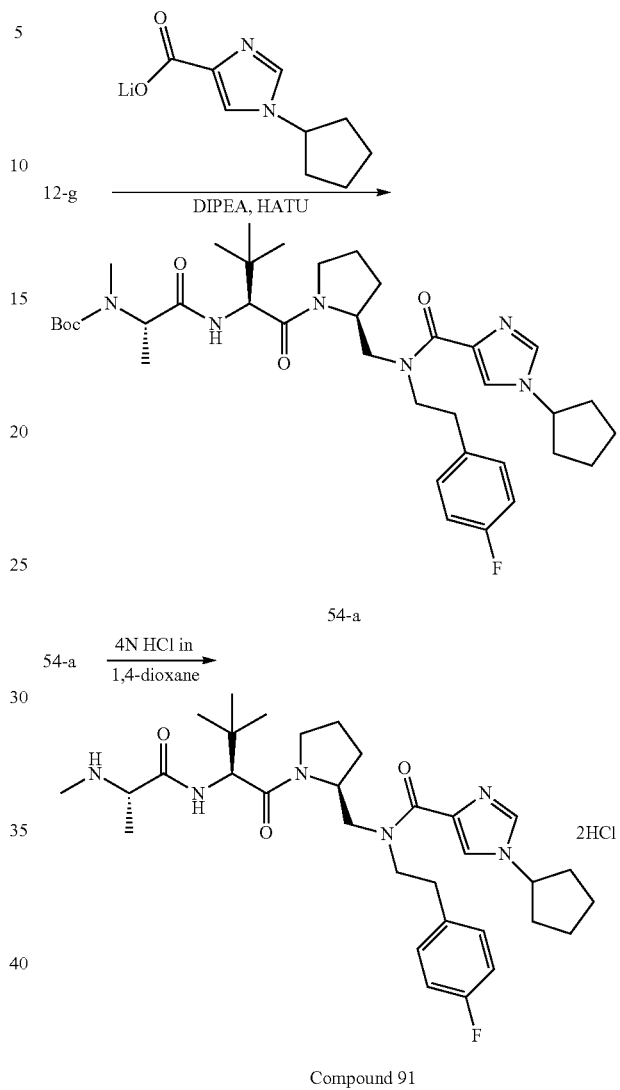

Step 1:

To a solution of intermediate 12-g (1.50 g, 2.88 mmol) in DMF, cooled to 0° C., were sequentially added 1-cyclopentyl-1H-imidazole-4-carboxylic acid, lithium salt (831 mg, 4.47 mmol), HATU (1.31 g, 3.46 mmol) and DIPEA (2.0 mL, 11.52 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 54-a as a white foam.

Step 2:

4N HCl in 1,4-dioxane (8.79 mL) was added to intermediate 54-a (1.20 g, 1.75 mmol) in ethyl acetate (500 uL) and the solution was stirred for 1.5 hour at 0° C. Volatiles were removed under reduced pressure and the residue was triturated with diethyl ether to provide compound 91.2HCl as a white solid. MS (m/z) M+1=583.5

Example 51

The following example illustrates the preparation of compound 93, which is a compound of Formula 1

Scheme 55: Synthesis of compound 93

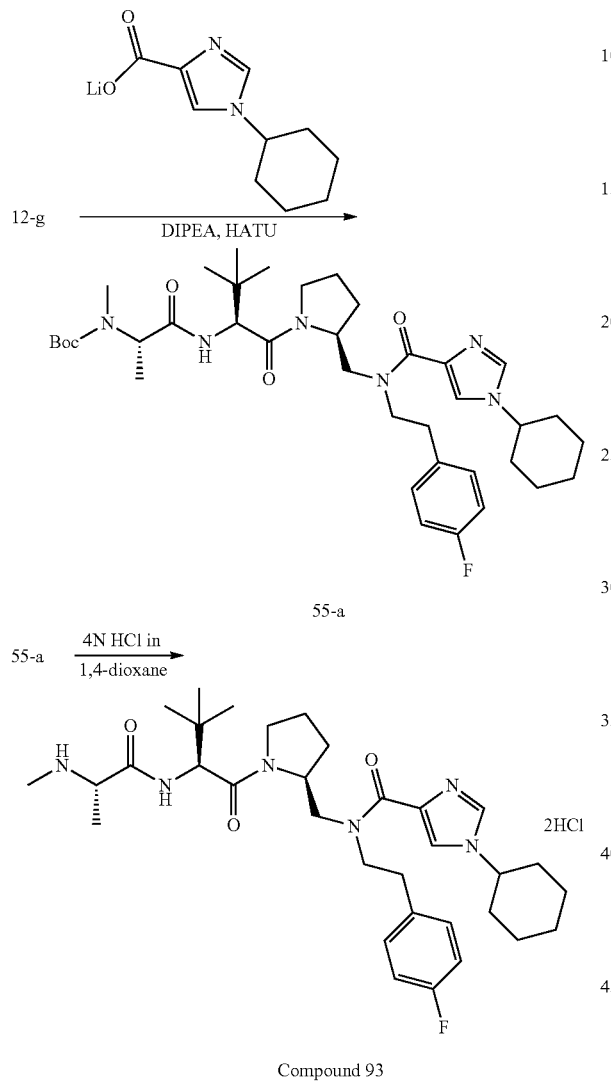

Compound 93

Step 1:
To a solution of intermediate 12-g (1.40 g, 2.69 mmol) in DMF, cooled to 0° C., were sequentially added 1-cyclohexyl-1H-imidazole-4-carboxylic acid (783 mg, 4.03 mmol), HATU (1.23 g, 3.23 mmol) and DIPEA (1.87 mL, 10.76 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 55-a as a white foam.

Step 2:
4N HCl in 1,4-dioxane (5.17 mL) was added to intermediate 55-a (960 mg, 1.37 mmol) in ethyl acetate (1.0 mL) and the solution was stirred for 1.5 hours at 0° C. Volatiles were removed under reduced pressure and the residue was triturated with diethyl ether to provide compound 93.2HCl as a white solid. MS (m/z) M+1=597.4

Example 52

The following example illustrates the preparation of compound 94, which is a compound of Formula 1

Scheme 56: Synthesis of compound 94

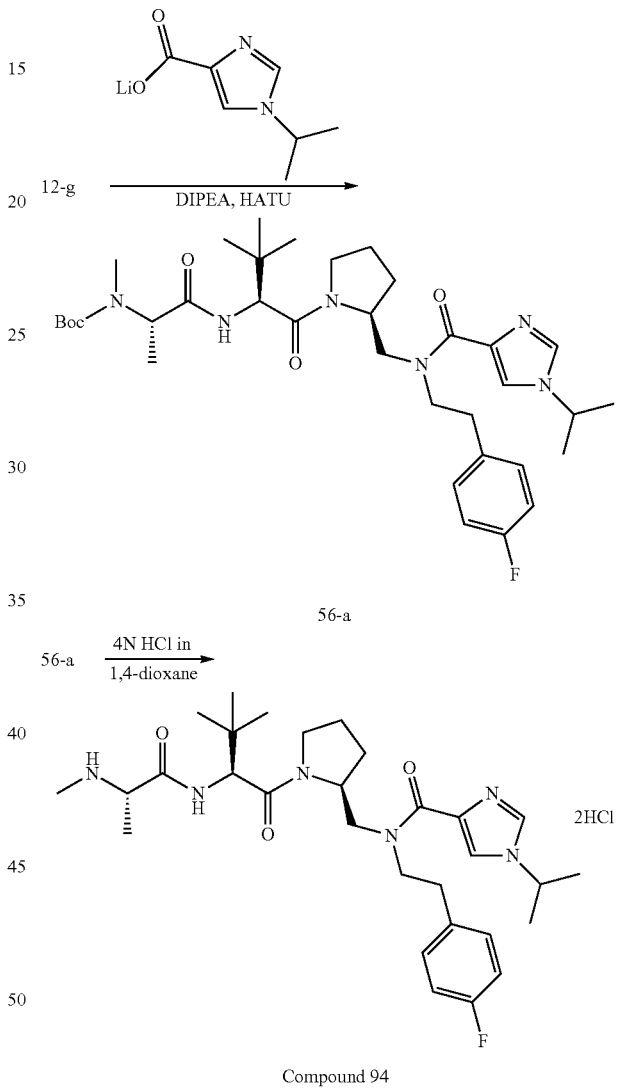

Compound 94

Step 1:
To a solution of intermediate 12-g (1.60 g, 3.07 mmol) in DMF, cooled to 0° C., were sequentially added 1-isopropyl-1H-imidazole-4-carboxylic acid, lithium salt (734 mg, 4.76 mmol), HATU (1.40 g, 3.69 mmol) and DIPEA (2.14 mL, 12.29 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 56-a as a white foam.

Step 2:

4N HCl in 1,4-dioxane (4.14 mL) was added to intermediate 56-a (850 mg, 1.10 mmol) in ethyl acetate (1.0 mL) and the solution was stirred for 2 hours at 0° C. Volatiles were removed under reduced pressure and the residue was triturated with diethyl ether to provide compound 94.2HCl as a white solid. MS (m/z) M+1=557.4

Example 53

The following example illustrates the preparation of compound 95, which is a compound of Formula 1

Scheme 57: Synthesis of compound 95

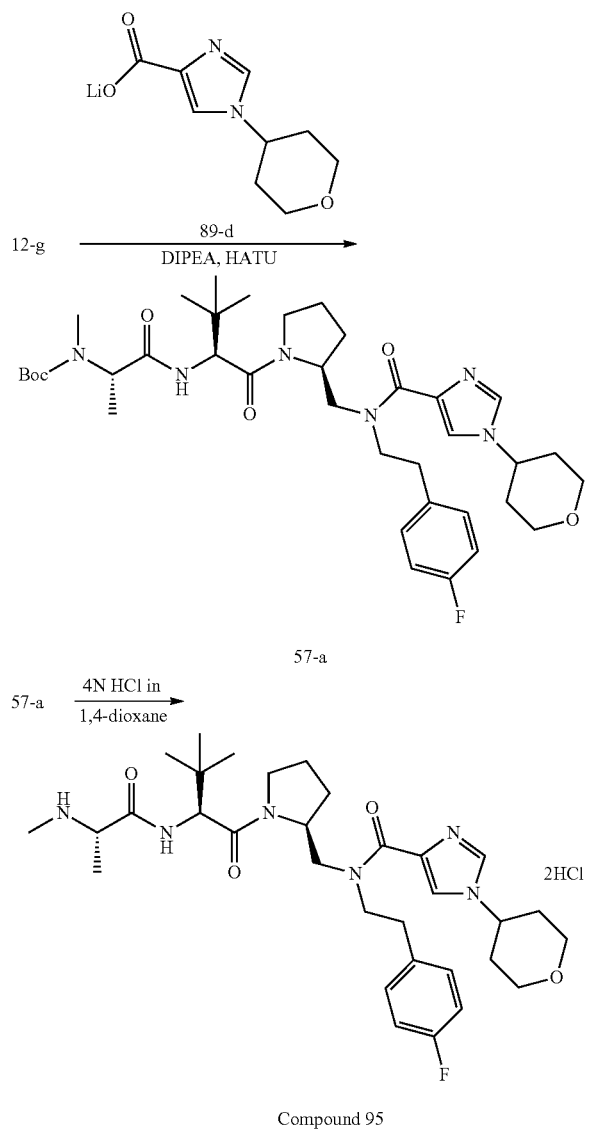

Compound 95 chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 57-a as a white foam.

Step 2:

4N HCl in 1,4-dioxane (4.43 mL) was added to intermediate 57-a (960 mg, 1.18 mmol) in ethyl acetate (1.0 mL) and the solution was stirred for 2 hours at 0° C. Volatiles were removed under reduced pressure and the residue was triturated with diethyl ether to provide compound 95.2HCl as a white solid. MS (m/z) M+1=599.4

Example 54

The following example illustrates the preparation of compound 61, which is a compound of Formula 1

Scheme 58: Synthesis of compound 61

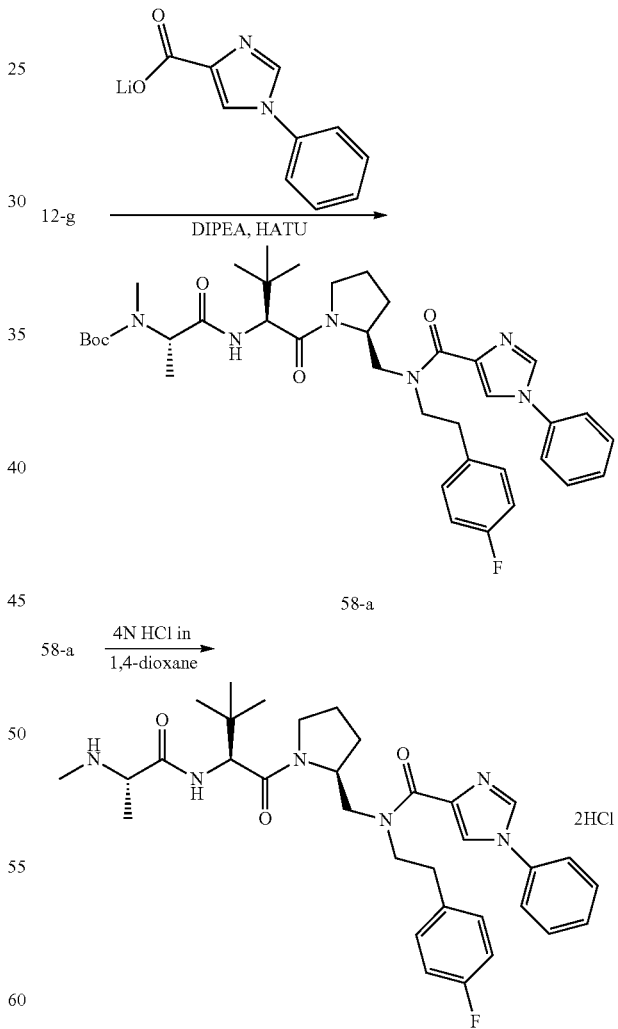

Compound 61

Step 1:

To a solution of intermediate 12-g (1.30 g, 2.49 mmol) in DMF, cooled to 0° C., were sequentially added 1-(tetrahydro-2H-pyran-4-yl)-1H-imidazole-4-carboxylic acid, lithium salt (89-d) (656 mg, 3.25 mmol), HATU (1.23 g, 3.25 mmol) and DIPEA (1.74 mL, 10.0 mmol) and the reaction mixture was stirred at 0° C. for 2 hours. Saturated aqueous ammonium Step 1:

To a solution of intermediate 12-g (350 mg, 0.67 mmol) in DMF, cooled to 0° C., were sequentially added 1-phenyl-1H- imidazole-4-carboxylic acid, lithium salt (190 mg, 1.0 mmol), HATU (435 mg, 1.14 mmol) and DIPEA (468 uL, 2.69 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 58-a as a white foam.

Step 2:

4N HCl in 1,4-dioxane (1.25 mL) was added to intermediate 58-a (345 mg, 0.50 mmol) in methanol (500 uL) and the solution was stirred for 2 hours at 0° C. Volatiles were removed under reduced pressure and the residue was triturated with diethyl ether to provide compound 61.2HCl as a white solid. MS (m/z) M+1=591.5

Example 55

The following example illustrates the preparation of compound 122, which is a compound of Formula 1

Scheme 59: Synthesis of compound 122

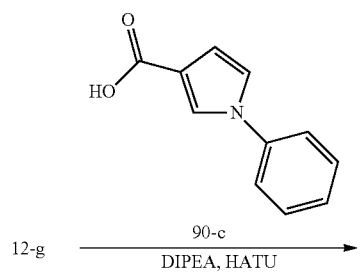

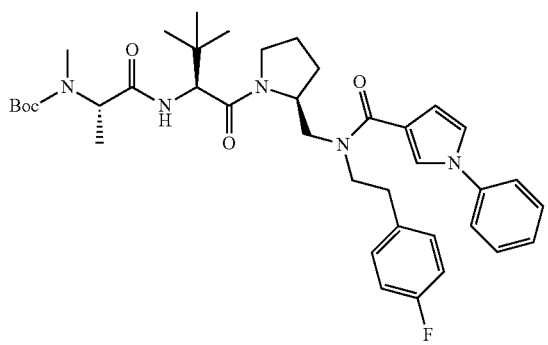

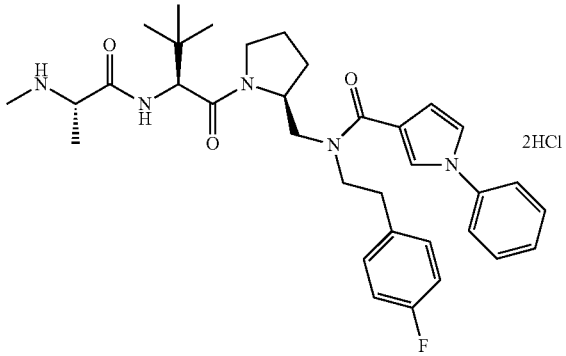

Compound 122

Step 1:

To a solution of intermediate 12-g (213 mg, 0.41 mmol) in DMF, cooled to 0° C., were sequentially added 1-phenyl-1H-pyrrole-3-carboxylic acid (90-c) (100 mg, 0.53 mmol), HATU (203 mg, 0.53 mmol) and DIPEA (286 uL, 1.64 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 59-a as a white foam.

Step 2:

4N HCl in 1,4-dioxane (1.22 mL) was added to intermediate 59-a (244 mg, 0.32 mmol) in ethyl acetate (325 uL) and the solution was stirred for 2 hours at 0° C. Volatiles were removed under reduced pressure and the residue was triturated with diethyl ether to provide compound 122.2HCl as a white solid. MS (m/z) M+1=590.2

Example 56

The following example illustrates the preparation of compound 109, which is a compound of Formula 1

Scheme 60: Synthesis of compound 109

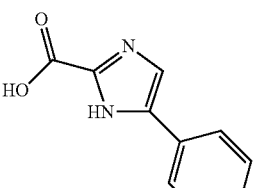

-continued

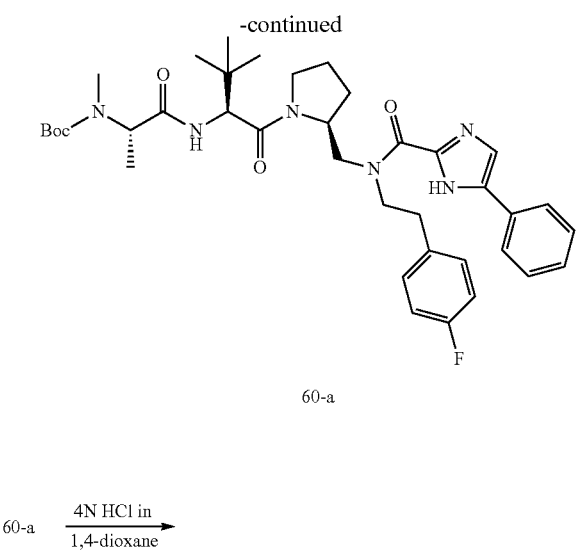

60-a 60-a →[4N HCl in 1,4-dioxane]

Compound 109

Step 1:

To a solution of intermediate 12-g (229 mg, 0.44 mmol) in DMF, cooled to 0° C., were sequentially added 5-phenyl-1H-imidazole-2-carboxylic acid (195 mg, 0.87 mmol), HATU (220 mg, 0.57 mmol) and DIPEA (310 uL, 1.78 mmol) and the reaction mixture was stirred at 0° C. for 1 hour. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 60-a as a white foam.

Step 2:

4N HCl in 1,4-dioxane (2.22 mL) was added to intermediate 60-a (307 mg, 0.44 mmol) in ethyl acetate (445 uL) and the solution was stirred for 2 hours at 0° C. Volatiles were removed under reduced pressure and the residue was triturated with diethyl ether to provide compound 109.2HCl as a white solid. MS (m/z) M+1=591.2

Example 57

The following example illustrates the preparation of compound 90, which is a compound of Formula 1

Scheme 61: Synthesis of compound 90

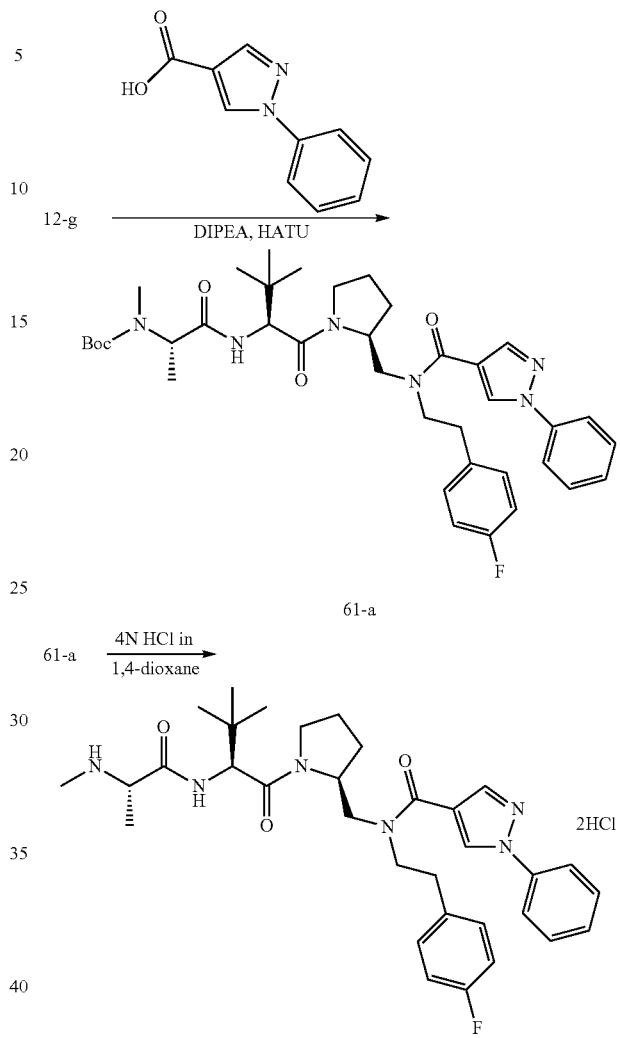

Compound 90

Step 1:

To a solution of intermediate 12-g (598 mg, 0.44 mmol) in DMF, cooled to 0° C., were sequentially added 1-phenyl-1H-pyrazole-4-carboxylic acid (217 mg, 1.15 mmol), HATU (526 mg, 1.38 mmol) and DIPEA (803 uL, 4.61 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 61-a as a white foam.

Step 2:

4N HCl in 1,4-dioxane (3.13 mL) was added to intermediate 61-a (577 mg, 0.83 mmol) in ethyl acetate (500 uL) and the solution was stirred for 2 hours at 0° C. Volatiles were removed under reduced pressure and the residue was triturated with diethyl ether to provide compound 90.2HCl as a white solid. MS (m/z) M+1=591.4

Example 58

The following example illustrates the preparation of compound 88, which is a compound of Formula 1

Scheme 62: Synthesis of compound 88

Scheme 63: Synthesis of compound 117

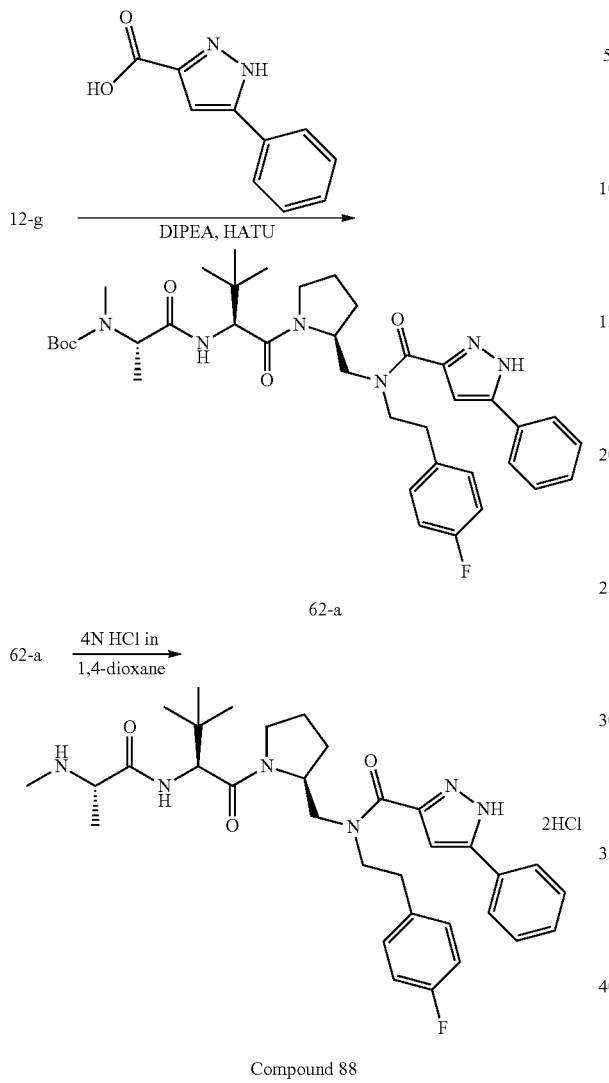

Compound 88

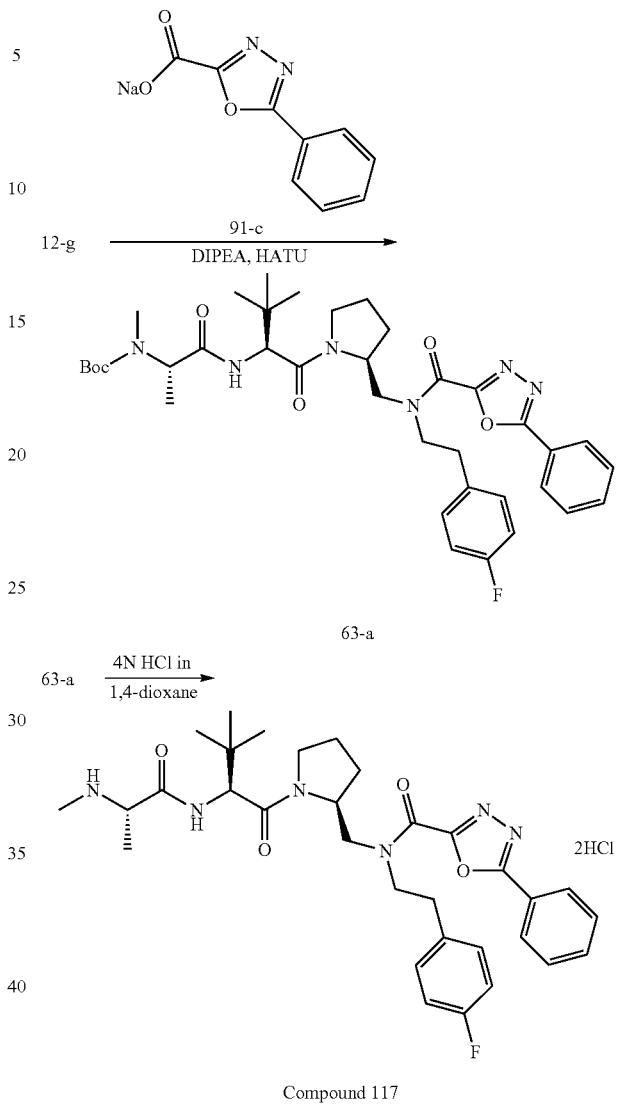

Compound 117

Step 1:

To a solution of intermediate 12-g (1.2 g, 2.30 mmol) in DMF, cooled to 0° C., were sequentially added 5-phenyl-1H-pyrazole-3-carboxylic acid (455 mg, 2.42 mmol), HATU (1.0 g, 2.77 mmol) and DIPEA (1.60 mL, 9.22 mmol) and the reaction mixture was stirred at 0° C. for 2 hours. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 62-a as a white solid.

Step 2:

4N HCl in 1,4-dioxane (6.15 mL) was added to intermediate 62-a (850 mg, 1.23 mmol) in ethyl acetate (500 uL) and the solution was stirred for 1.5 hour at 0° C. Volatiles were removed under reduced pressure and the residue was triturated with diethyl ether to provide compound 88.2HCl as a white solid. MS (m/z) M+1=591.4

Example 59

The following example illustrates the preparation of compound 117, which is a compound of Formula 1

Step 1:

To a solution of intermediate 12-g (1.0 g, 1.92 mmol) in DMF, cooled to 0° C., were sequentially added 5-phenyl-1,3,4-oxadiazole-2-carboxylic acid sodium salt (91-c) (1.36 g, 6.41 mmol), HATU (2.19 g, 5.76 mmol) and DIPEA (1.34 mL, 7.68 mmol) and the reaction mixture was stirred at room temperature overnight. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 63-a as a white solid.

Step 2:

4N HCl in 1,4-dioxane (10.0 mL) was added to intermediate 63-a (453 mg, 0.65 mmol) and the solution was stirred for 3 hours at 0° C. Volatiles were removed under reduced pressure and the residue was triturated with diethyl ether to provide compound 117.2HCl as a white solid. MS (m/z) M+1=593.2

Example 60

The following example illustrates the preparation of compound 115, which is a compound of Formula 1

Scheme 64: Synthesis of compound 115

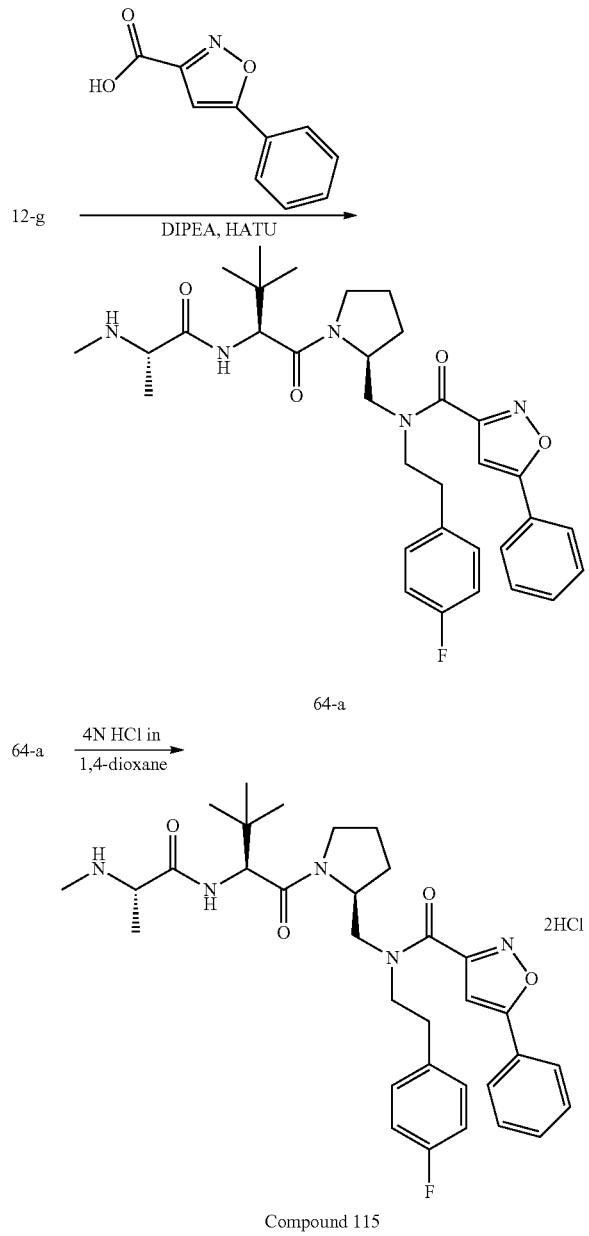

Compound 115

Step 1:

To a solution of intermediate 12-g (847 g, 1.62 mmol) in DMF, cooled to 0° C., were sequentially added 5-phenylisoxazole-3-carboxylic acid (431 mg, 2.27 mmol), HATU (1.05 g, 2.77 mmol) and DIPEA (1.13 mL, 6.51 mmol) and the reaction mixture was stirred at room temperature overnight. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 64-a as a white foam.

Step 2:

4N HCl in 1,4-dioxane (5.0 mL) was added to intermediate 64-a (356 mg, 0.51 mmol) and the solution was stirred for 2 hours at 0° C. Diethyl ether was added, a precipitate formed and compound 115.2HCl was collected by filtration as a white solid. MS (m/z) M+1=592.1

Example 61

The following example illustrates the preparation of compound 65-i, which can be used as an intermediate in the preparation of a compound of Formula 1 or salt thereof.

Scheme 65: Synthesis of intermediate 65-i

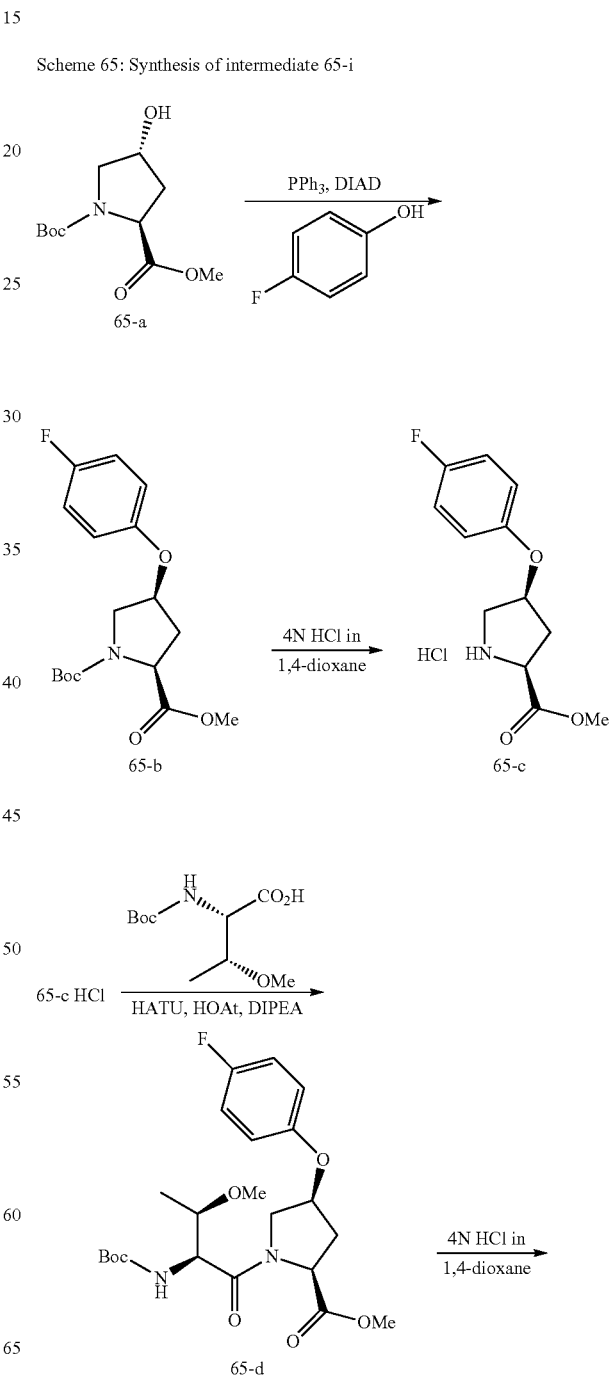

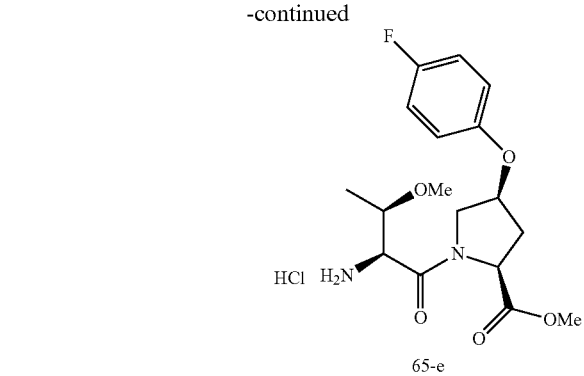

65-e

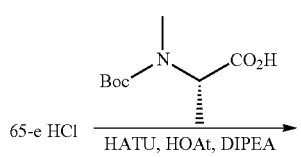

65-e HCl →(HATU, HOAt, DIPEA)

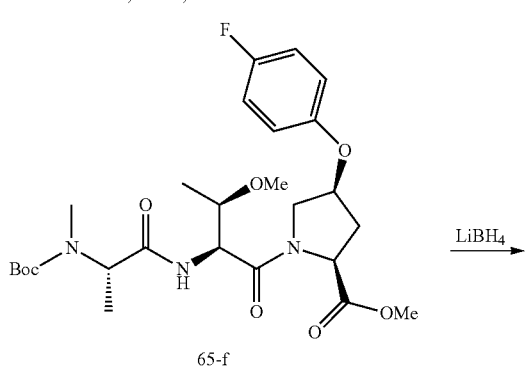

65-f

→ LiBH₄

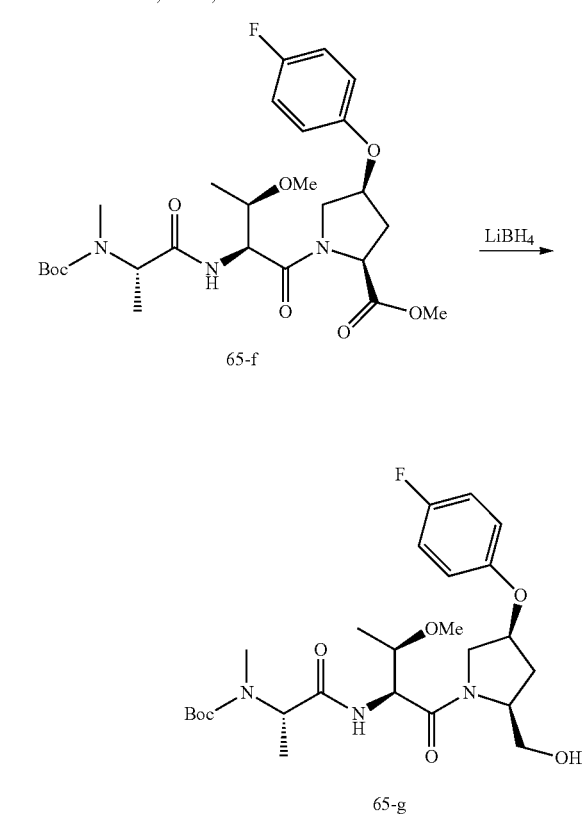

65-g 65-g →(DIPEA, pyridine-sulfur trioxide complex)

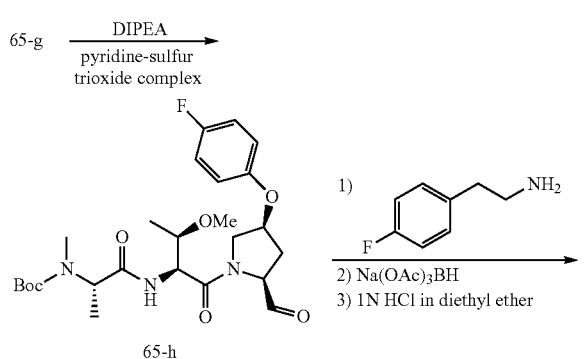

65-h 1) 4-F-C₆H₄-CH₂CH₂-NH₂
2) Na(OAc)₃BH
3) 1 N HCl in diethyl ether

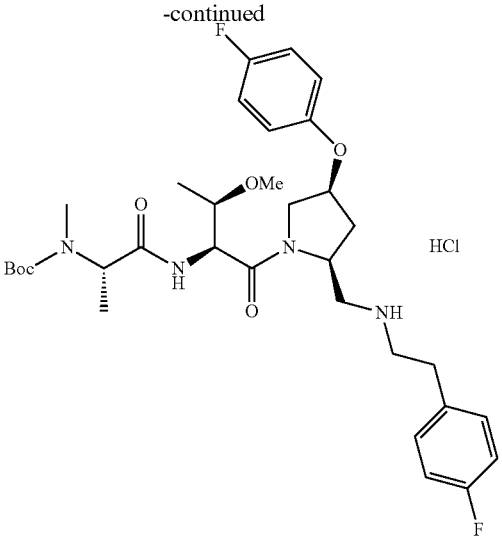

65-i

Step 1:

To a solution of (2S,4R)-1-Boc-2-methyl-4-hydroxypyrrolidine-2-carboxylate (18.0 g, 73.4 mmol), 4-fluorophenol (9.05 g, 81.0 mmol) and triphenylphosphine (21.17 g, 81.0 mmol) in THF was added DIAD (17.07 g, 84.0 mmol) in THF (20 mL) dropwise and the reaction was then stirred at room temperature for 2 days. Diethyl ether and hexane were added, a precipitate formed and triphenyl phosphine oxide was removed by filtration. Volatiles were removed under reduced pressure and the residue was purified by silica gel chromatography to provide the expected intermediate 65-b as yellow solid.

Step 2:

4N HCl in 1,4-dioxane (78 mL, 312 mmol) was added to intermediate 65-b (21.2 g, 62.5 mmol) and the solution was stirred for 1 hour at 0° C. and then 30 minutes at room temperature. Diethyl ether was added, a precipitate formed and intermediate 65-c.HCl was collected by filtration as a white solid. MS (m/z) M+1=240.0

Step 3:

To a solution of intermediate 65-c.HCl (14.2 g, 51.5 mmol) in DMF cooled to 0° C. were sequentially added Boc-Thr(Me)-OH (13.22 g, 56.7 mmol), HATU (21.54 g, 56.7 mmol), HOAt (8.58 mL, 5.15 mmol) and DIPEA (36.0 mL, 206 mmol) and the reaction was then stirred at room temperature for 3 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided the expected intermediate 65-d as white foam.

Step 4:

4N HCl in 1,4-dioxane (63.3 mL) was added to intermediate 65-d (23.0 g, 50.6 mmol) and the solution was stirred for 1 hour at 0° C. and then 30 minutes at room temperature. Diethyl ether was added, a precipitate formed and intermediate 65-e.HCl was collected by filtration as a white solid. MS (m/z) M+1=355.2

Step 5:

To a solution of intermediate 65-e.HCl (16.2 g, 41.4 mmol) in DMF cooled to 0° C. were sequentially added Boc-NMe-Ala-OH (9.27 g, 45.6 mmol), HATU (1734 g, 45.6 mmol), HOAt (6.91 mL, 4.14 mmol) and DIPEA (29.0 mL, 166.0 mmol) and the reaction was then stirred at room temperature for 3 hours. Saturated aqueous ammonium chloride and ethyl acetate were added; the organic layer was separated, washed with saturated aqueous ammonium chloride, saturated aqueous NaHCO$_3$ and brine, dried over MgSO$_4$, filtered and concentrated in vacuo. Purification by silica gel chromatography provided the expected intermediate 65-f as a white foam.

Step 6:

To a solution of intermediate 65-f (23.0 g, 42.6 mmol) in THF cooled to 0° C. was added lithium borohydride (1.95 g, 90.0 mmol) and the reaction was stirred at room temperature overnight. Water and ethyl acetate were added; the organic layer was separated, washed with 10% aqueous citric acid, saturated aqueous NaHCO$_3$ and brine, dried over anhydrous MgSO$_4$, filtered and concentrated in vacuo. Purification by silica gel chromatography provided intermediate 65-g as white foam.

Step 7:

To a solution of intermediate 65-g (8.7 g, 17.01 mmol) in DMSO (4.83 mL, 68.0 mmol) and dichloromethane (150 mL) cooled to 0° C. was added DIPEA (10.40 mL, 59.5 mmol) and pyridine sulfur trioxide complex (8.12 g, 51.0 mmol), the reaction was then stirred at room temperature overnight. Water and ethyl acetate were added; the organic layer was separated, washed with 10% citric acid, saturated aqueous NaHCO$_3$ and brine, dried over anhydrous MgSO$_4$, filtered and concentrated in vacuo to provide intermediate 65-h as white foam.

Step 8:

To a solution of intermediate 65-h (8.0 g, 15.70 mmol) in dichloromethane was added 2-(4-fluorophenyl)ethanamine (1.87 mL, 14.3 mmol). After stirring at room temperature for 2 hours, sodium triacetoxyborohydride (6.37 g, 28.5 mmol) was added portion wise and the reaction mixture was then stirred at room temperature for 2 hours. Saturated aqueous NaHCO$_3$ was added; the organic layer was separated, washed with brine, dried over anhydrous MgSO$_4$, filtered and concentrated in vacuo to provide intermediate 65-i as a yellow oil. To a solution of intermediate 65-i in diethyl ether (100 mL) was added 1N HCl in diethyl ether (15.7 mL), a precipitate formed and intermediate 65-i.HCl was collected by filtration as beige solid. MS (m/z) M+1=633.4

Example 62

The following example illustrates the preparation of compound 100, which is a compound of Formula 1

Scheme 66: Synthesis of compound 100

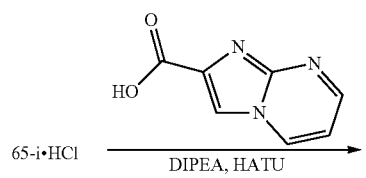

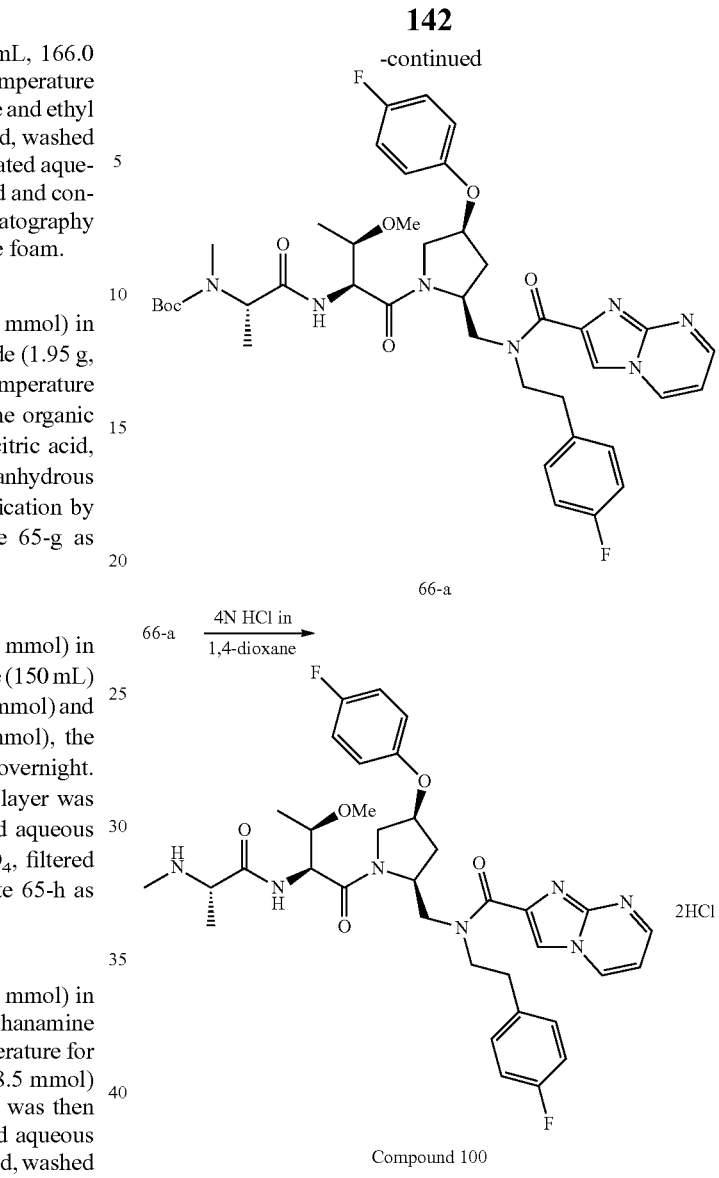

Step 1:

To a solution of intermediate 65-i.HCl (1.5 g, 2.24 mmol) in DMF cooled to 0° C. were sequentially added imidazo[1,2-a]pyrimidine-2-carboxylic acid (464 mg, 2.84 mmol), HATU (992 mg, 2.61 mmol) and DIPEA (1.65 mL, 9.48 mmol) and the reaction mixture was stirred at room temperature overnight. Saturated aqueous ammonium chloride and ethyl acetate were added; the organic layer was separated, washed with saturated aqueous NaHCO$_3$ and brine, dried over anhydrous MgSO$_4$, filtered and concentrated in vacuo. Purification by silica gel chromatography provided intermediate 66-a as white foam.

Step 2:

4N HCl in 1,4-dioxane (2.0 mL) was added to intermediate 66-a (760 mg, 0.97 mmol) at 0° C. and the solution was stirred for 1 hour at 0° C. and then 30 minutes at room temperature. Ethyl acetate was added, a precipitate formed and compound 100.2HCl was collected by filtration as a white solid. MS (m/z) M+1=678.5

Example 63

The following example illustrates the preparation of compound 102, which is a compound of Formula 1

143

Scheme 67: Synthesis of compound 102

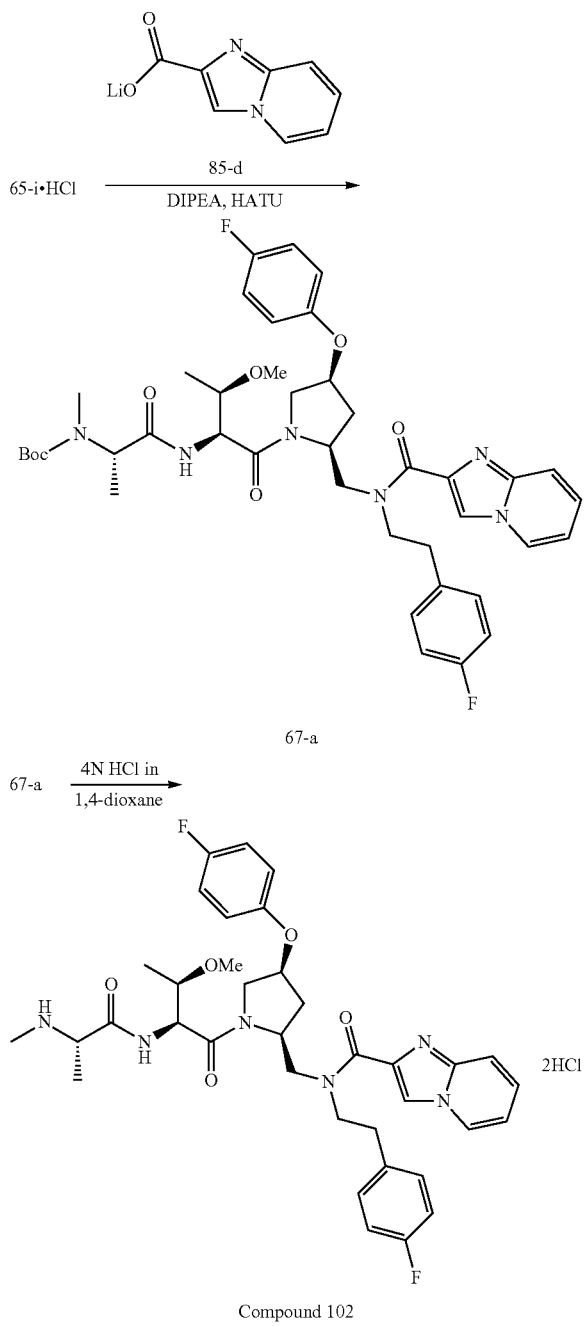

Compound 102

Step 1:
To a solution of intermediate 65-i.HCl (2.0 g, 2.98 mmol) in DMF cooled to 0° C. were sequentially added imidazo[1,2-a]pyridine-2-carboxylic acid lithium salt (85-d) (641 mg, 3.79 mmol), HATU (1.32 g, 3.48 mmol) and DIPEA (2.20 mL, 12.64 mmol) and the reaction mixture was stirred at room temperature overnight. Saturated aqueous ammonium chloride and ethyl acetate were added; the organic layer was separated, washed with saturated aqueous $NaHCO_3$ and brine, dried over anhydrous $MgSO_4$, filtered and concentrated in vacuo. Purification by silica gel chromatography provided intermediate 67-a as white foam.

144

Step 2:
4N HCl in 1,4-dioxane (3.0 mL) was added to intermediate 67-a (900 mg, 1.16 mmol) at 0° C. and the solution was stirred for 1 hour at 0° C. and then 30 minutes at room temperature. Ethyl acetate was added, a precipitate formed and compound 102.2HCl was collected by filtration as a white solid. MS (m/z) M+1=677.5

Example 64

The following example illustrates the preparation of compound 99, which is a compound of Formula 1

Scheme 68: Synthesis of compound 99

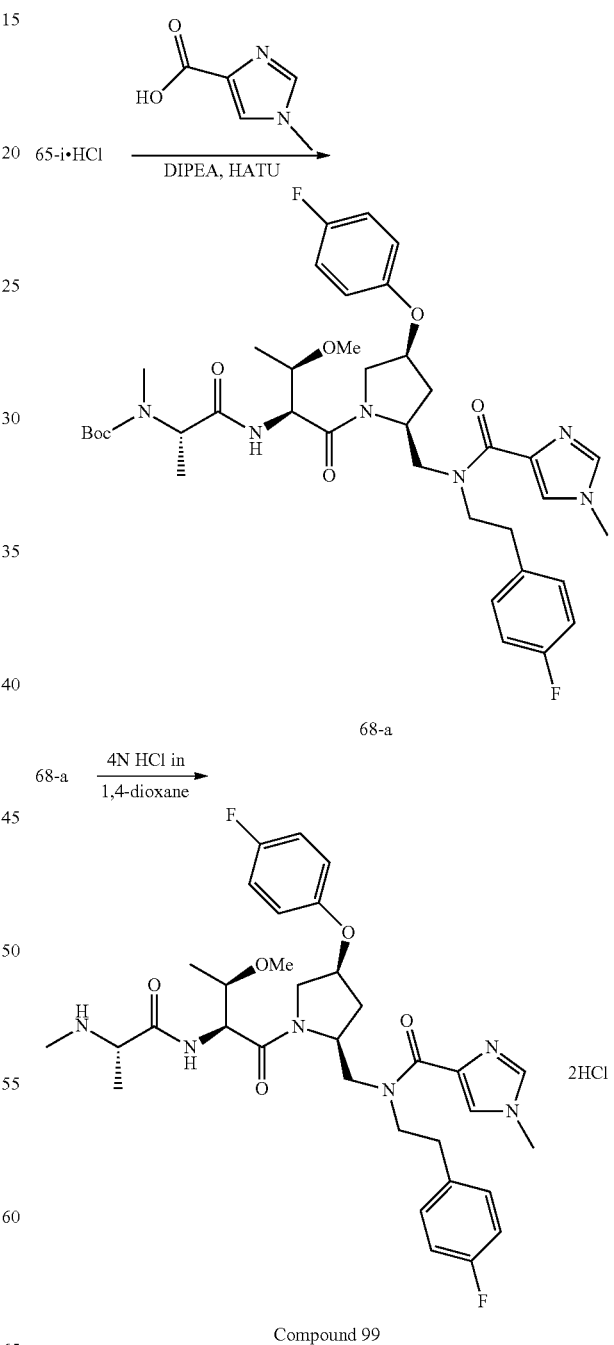

Compound 99

145

Step 1:

To a solution of intermediate 65-i.HCl (2.0 g, 2.98 mmol) in DMF, cooled to 0° C., were sequentially added 1-methyl-1H-imidazole-4-carboxylic acid (478 mg, 3.79 mmol), HATU (1.32 g, 3.48 mmol) and DIPEA (2.20 mL, 12.64 mmol) and the reaction mixture was stirred at 0° C. for 1 hour and room temperature overnight. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 68-a as a white foam.

Step 2:

4N HCl in 1,4-dioxane (3.0 mL) was added to intermediate 68-a (900 mg, 1.16 mmol) at 0° C. and the solution was stirred for 1 hour at 0° C. and then 30 minutes at room temperature. Ethyl acetate was added, a precipitate formed and compound 99.2HCl was collected by filtration as a white solid. MS (m/z) M+1=641.4

Example 65

The following example illustrates the preparation of compound 114, which is a compound of Formula 1

Scheme 69: Synthesis of compound 114

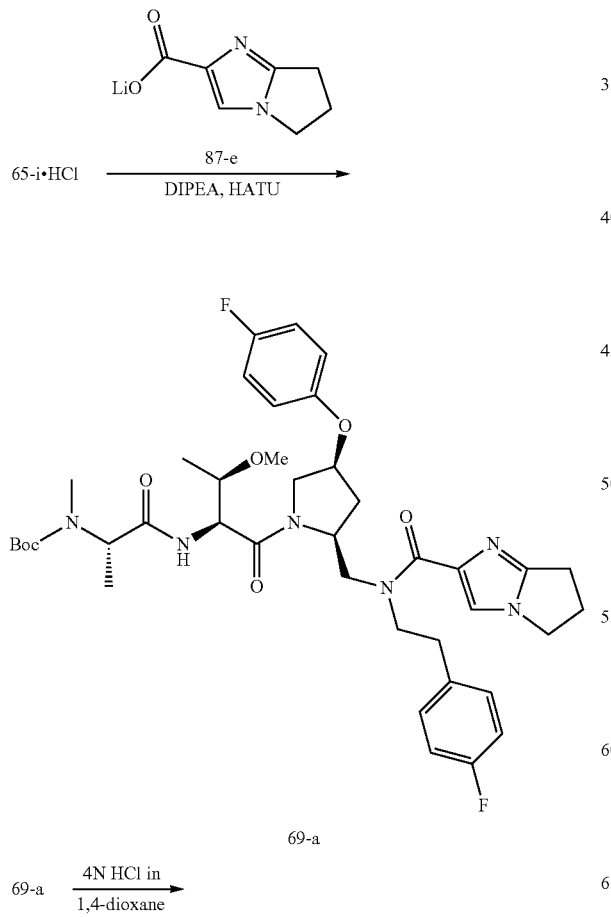

69-a

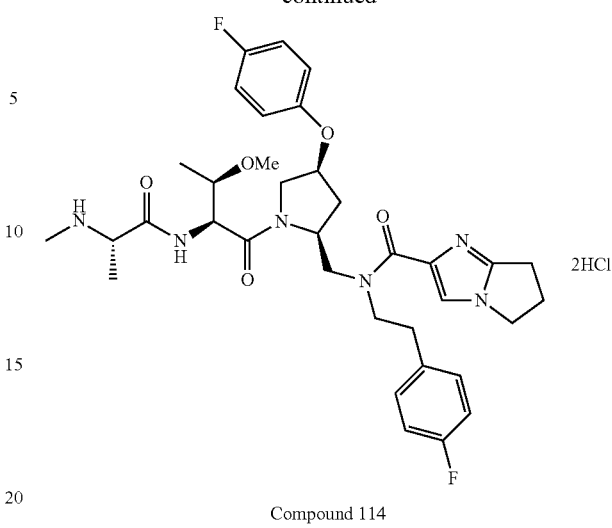

Compound 114

Step 1:

To a solution of intermediate 65-i.HCl (600 mg, 0.90 mmol) in DMF, cooled to 0° C., were sequentially added 6,7-dihydro-5-H-pyrrolo[1,2-a]imidazole-2-carboxylic acid, lithium salt (87-e) (236 mg, 1.42 mmol), HATU (397 mg, 1.04 mmol) and DIPEA (662 uL, 3.79 mmol) and the reaction mixture was stirred at 0° C. for 1 hour and room temperature for 2 hours. Saturated aqueous ammonium chloride and ethyl acetate were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 69-a as a white foam.

Step 2:

4N HCl in 1,4-dioxane (750 uL) was added to intermediate 69-a (230 mg, 0.30 mmol) at 0° C. and the solution was stirred for 1 hour at 0° C. and then 30 minutes at room temperature. Ethyl acetate was added, a precipitate formed and compound 114.2HCl was collected by filtration as a white solid. MS (m/z) M+1=667.1

Example 66

The following example illustrates the preparation of compound 107, which is a compound of Formula 1

Scheme 70: Synthesis of compound 107

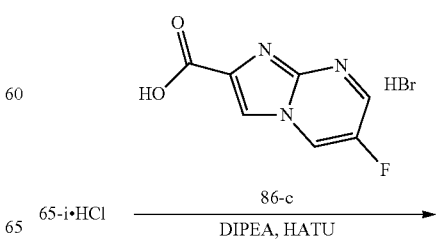

147

-continued

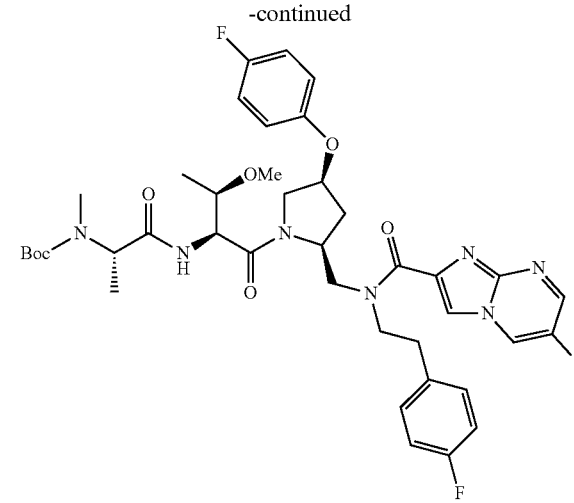

70-a 70-a →[4N HCl in 1,4-dioxane]

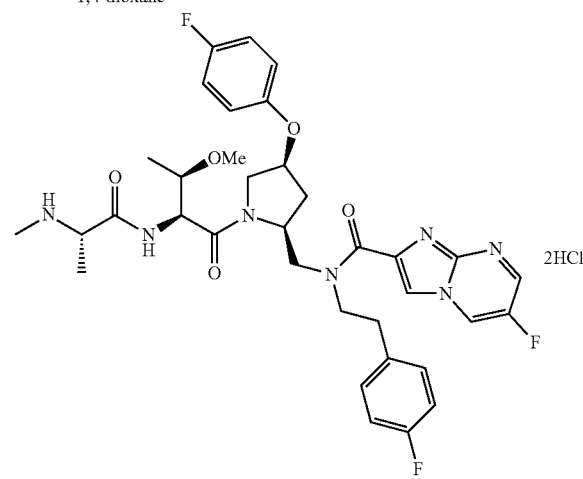

Compound 107

Step 1:
To a solution of intermediate 65-i.HCl (600 mg, 0.87 mmol) in DMF, cooled to 0° C., were sequentially added 6-fluoroimidazo[1,2-a]pyrimidine-2-carboxylic acid, HBr salt (86-c) (298 mg, 1.13 mmol), HATU (397 mg, 1.04 mmol) and DIPEA (662 uL, 3.79 mmol) and the reaction mixture was stirred at 0° C. for 1 hour and room temperature overnight. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 70-a as a white foam.

Step 2:
4N HCl in 1,4-dioxane (1.41 mL) was added to intermediate 70-a (450 mg, 0.56 mmol) at 0° C. and the solution was stirred for 1 hour at 0° C. Ethyl acetate was added, a precipitate formed and compound 107.2HCl was collected by filtration as a white solid. MS (m/z) M+1=696.3

Example 67

The following example illustrates the preparation of compound 108, which is a compound of Formula 1

148

Scheme 71: Synthesis of compound 108

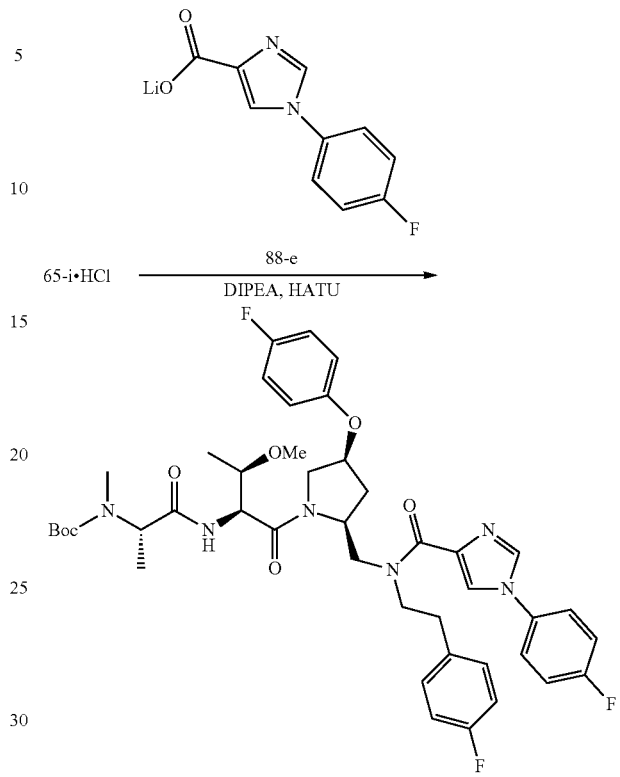

65-i•HCl →[88-e / DIPEA, HATU]

71-a 71-a →[4N HCl in 1,4-dioxane]

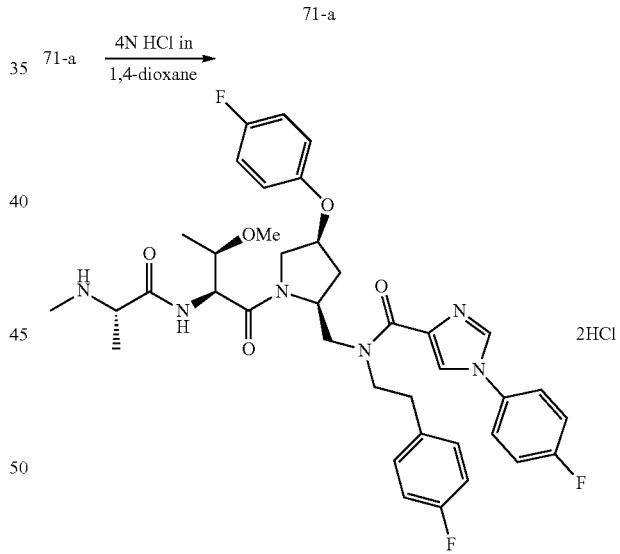

Compound 108

Step 1:
To a solution of intermediate 65-i.HCl (600 mg, 0.87 mmol) in DMF, cooled to 0° C., were sequentially added 1-(4-fluorophenyl)-1H-imidazole-4-carboxylic acid, lithium salt (88-e) (303 mg, 1.42 mmol), HATU (397 mg, 1.04 mmol) and DIPEA (662 uL, 3.79 mmol) and the reaction mixture was stirred at 0° C. for 1 hour and room temperature overnight. Saturated aqueous ammonium chloride and ethyl acetate were added; the organic layer was separated, washed with saturated aqueous ammonium chloride, saturated aqueous NaHCO$_3$ and brine, dried over anhydrous MgSO$_4$, filtered and concentrated in vacuo. Purification by silica gel chromatography provided intermediate 71-a as a white foam.

Step 2:

4N HCl in 1,4-dioxane (670 uL) was added to intermediate 71-a (220 mg, 0.26 mmol) at 0° C. and the solution was stirred for 1 hour at 0° C. Ethyl acetate was added, a precipitate formed and compound 108.2HCl was collected by filtration as a white solid. MS (m/z) M+1=721.1

Example 68

The following example illustrates the preparation of compound 72-d, which can be used as an intermediate in the preparation of a compound of Formula 1 or salt thereof.

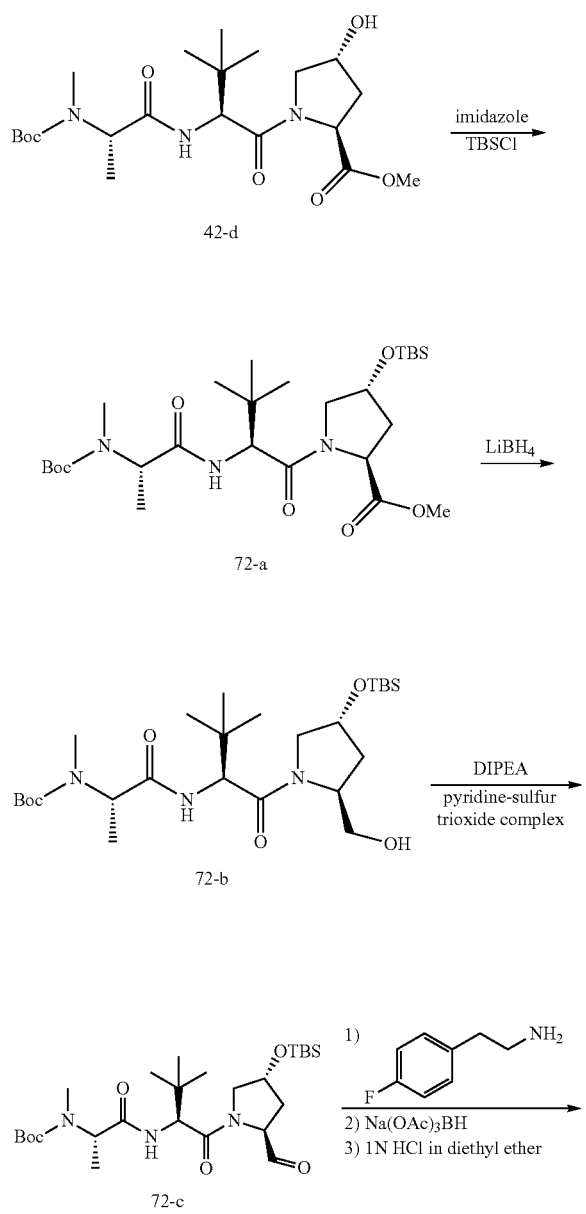

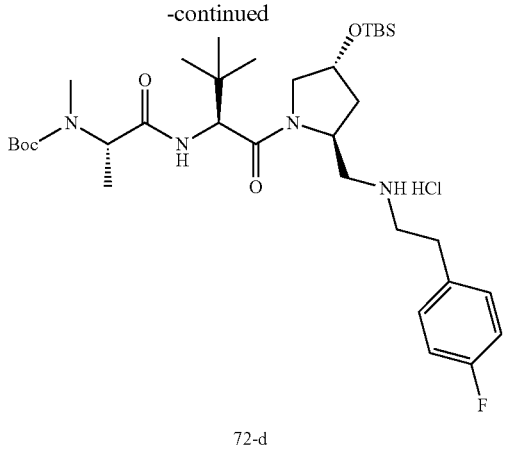

72-d

Step 1:

To a solution of intermediate 42-d (18.0 g, 40.6 mmol) in DMF cooled to 0° C. were sequentially added imidazole (3.32 g, 48.7 mmol), DMAP (496 mg, 4.06 mmol) and tert-butyl-chlorodimethylsilane (6.73 mL, 44.6 mmol) and the reaction mixture was stirred at room temperature overnight. Water and ethyl acetate were added; the organic layer was separated, washed with saturated aqueous NaHCO$_3$ and brine, dried over anhydrous MgSO$_4$, filtered and concentrated in vacuo. Purification by silica gel chromatography provided intermediate 72-a as a colorless oil.

Step 2:

To a solution of intermediate 72-a (6.0 g, 10.76 mmol) in THF cooled to 0° C. was added lithium borohydride (1.17 g, 53.8 mmol) and the reaction was stirred at room temperature overnight. Saturated aqueous ammonium chloride and ethyl acetate were added; the organic layer was separated, washed with 10% aqueous citric acid, saturated aqueous NaHCO$_3$ and brine, dried over anhydrous MgSO$_4$, filtered and concentrated in vacuo. Purification by silica gel chromatography provided intermediate 72-b as a white foam.

Step 3:

To a solution of intermediate 72-b (5.6 g, 10.57 mmol) in DMSO (3.0 mL, 42.3 mmol) and dichloromethane (80 mL) cooled to 0° C. was added TEA (5.89 mL, 42.3 mmol) and pyridine sulfur trioxide complex (5.05 g, 31.7 mmol), the reaction was then stirred at 0° C. for 30 minutes and room temperature for 1 hour. Saturated aqueous ammonium chloride and ethyl acetate were added; the organic layer was separated, washed with 10% aqueous citric acid, saturated aqueous NaHCO$_3$ and brine, dried over anhydrous MgSO$_4$, filtered and concentrated in vacuo to provide intermediate 72-c as white foam.

Step 4:

To a solution of intermediate 72-c (3.0 g, 5.68 mmol) in dichloromethane was added 2-(4-fluorophenyl)ethanamine (746 uL, 5.68 mmol). After stirring at room temperature overnight, the reaction was cooled to −5° C., sodium triacetoxyborohydride (2.54 g, 11.37 mmol) was added portion wise and the reaction mixture was then stirred at room temperature for 2 hours. Saturated aqueous NaHCO$_3$ was added; the organic layer was separated, washed with brine, dried over MgSO$_4$, filtered and concentrated in vacuo to provide intermediate 72-d as yellow foam. To a solution of intermediate 72-d in diethyl ether (100 mL) was added 1N HCl in diethyl ether (5.68 mL), a precipitate formed and intermediate 72-d.HCl was collected by filtration as beige solid. MS (m/z) M+1=651.6

Example 69

The following example illustrates the preparation of compound 73-b, which can be used as an intermediate in the preparation of a compound of Formula 1 or salt thereof.

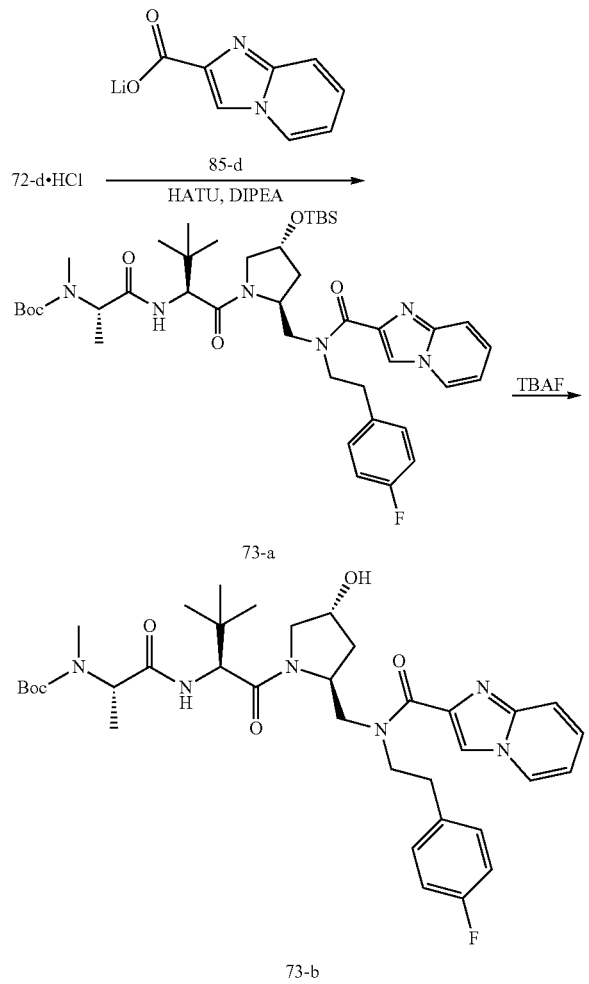

Step 1:
To a solution of intermediate 72-d.HCl (7.02 g, 10.78 mmol) in DMF cooled to 0° C. were sequentially added imidazo[1,2-a]pyridine-2-carboxylic acid, lithium salt (85-d) (3.08 g, 18.33 mmol), HATU (6.97 g, 18.33 mmol) and DIPEA (7.53 mL, 43.1 mmol) and the reaction mixture was stirred at room temperature overnight. Saturated aqueous ammonium chloride and ethyl acetate were added; the organic layer was separated, washed with saturated aqueous NaHCO₃ and brine, dried over anhydrous MgSO₄, filtered and concentrated in vacuo. Purification by silica gel chromatography provided intermediate 73-a as white foam.

Step 2:
To a solution of intermediate 73-a (6.14 g, 7.72 mmol) in THF cooled to 0° C. was added 1.0 M solution of TBAF in THF (10.04 mL, 10.04 mmol) and the reaction mixture was stirred at room temperature for 2 hours. Water and ethyl acetate were added; the organic layer was separated, washed with brine, dried over anhydrous MgSO₄, filtered and concentrated in vacuo. Purification by silica gel chromatography provided intermediate 73-b as a white foam.

Example 70

The following example illustrates the preparation of compound 111, which is a compound of Formula 1

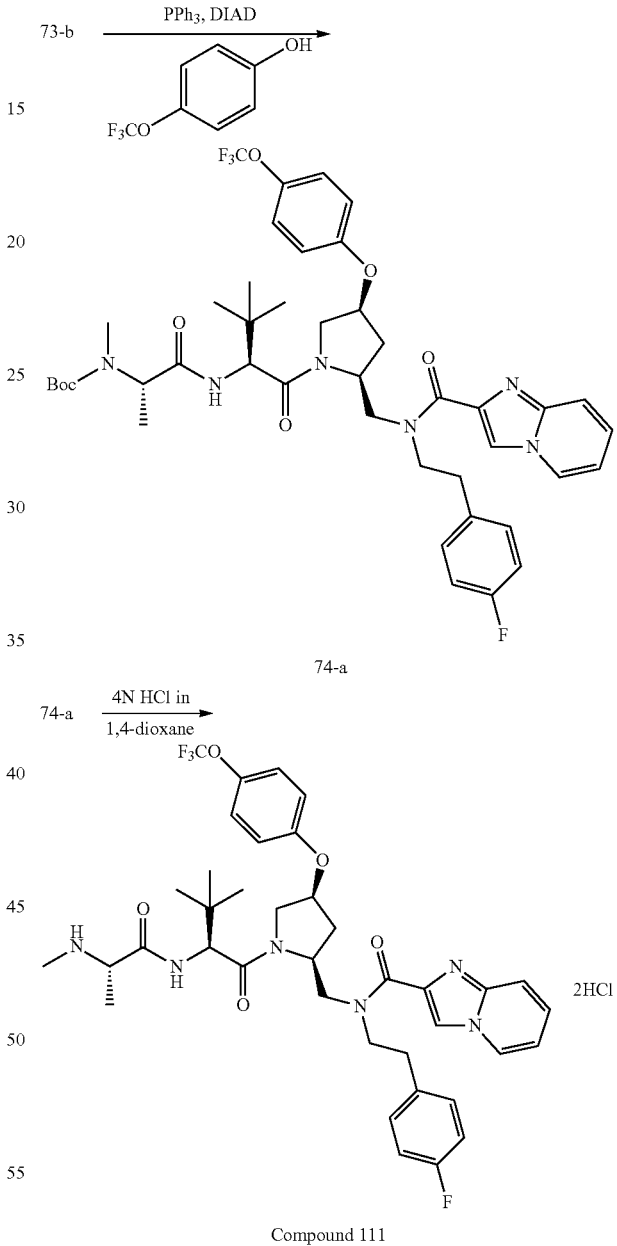

Step 1:
To a solution of intermediate 73-b (1.95 g, 2.86 mmol), 4-(trifluoromethoxy)phenol (561 mg, 3.15 mmol) and triphenylphosphine (901 mg, 3.44 mmol) in THF was added DIAD (724 uL, 3.72 mmol) dropwise and the reaction was then stirred at room temperature for 2 days. Diethyl ether and hexane were added, a precipitate formed and triphenyl phosphine oxide was removed by filtration. Volatiles were removed under reduced pressure and the residue was purified by silica gel chromatography to provide the expected intermediate 74-a as colorless oil.

Step 2:

4N HCl in 1,4-dioxane (6.85 mL) was added to intermediate 74-a (921 mg, 1.09 mmol) in ethyl acetate (500 uL) and the solution was stirred for 2 hours at 0° C. Diethyl ether was added, a precipitate formed and compound 111.2HCl was collected by filtration as a white solid. MS (m/z) M+1=741.3

Example 71

The following example illustrates the preparation of compound 106, which is a compound of Formula 1

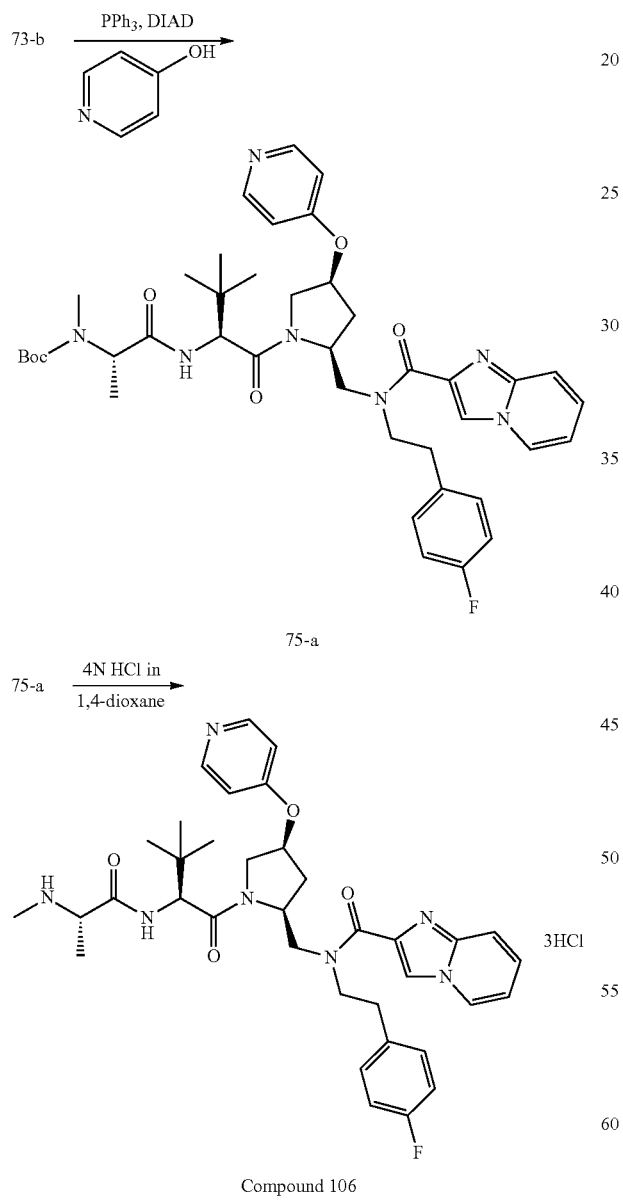

Compound 106

Step 1:

To a solution of intermediate 73-b (2.30 g, 3.38 mmol), pyridine-4-ol (353 mg, 3.72 mmol) and triphenylphosphine (1.06 g, 4.05 mmol) in THF was added DIAD (854 uL, 4.39 mmol) dropwise and the reaction was then stirred at room temperature for 2 days. Diethyl ether and hexane were added, a precipitate formed and triphenyl phosphine oxide was removed by filtration. Volatiles were removed under reduced pressure and the residue was purified by silica gel chromatography to provide the expected intermediate 75-a as colorless oil.

Step 2:

4N HCl in 1,4-dioxane (9.24 mL) was added to intermediate 75-a (1.12 g, 1.47 mmol) in ethyl acetate (500 uL) and the solution was stirred for 2 hours at 0° C. Diethyl ether was added, a precipitate formed and compound 106.3HCl was collected by filtration as a white solid. MS (m/z) M+1=658.1

Example 72

The following example illustrates the preparation of compound 105, which is a compound of Formula 1

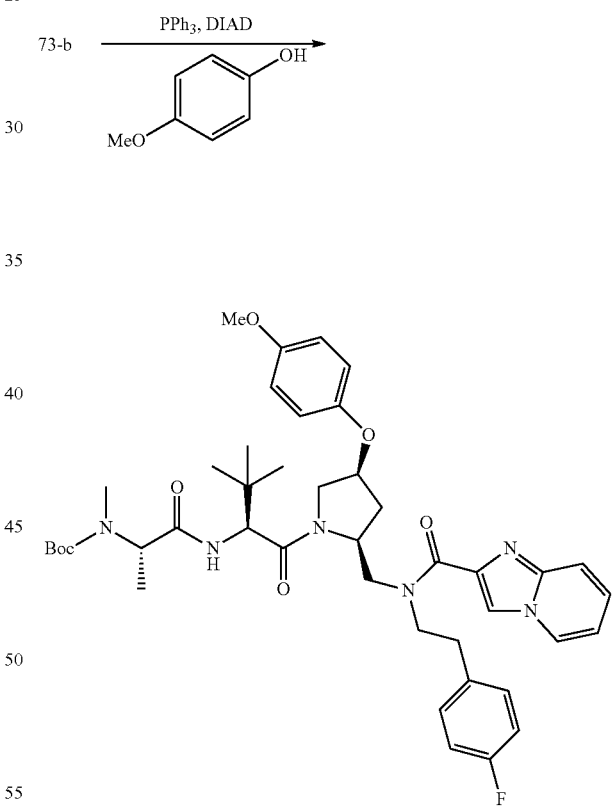

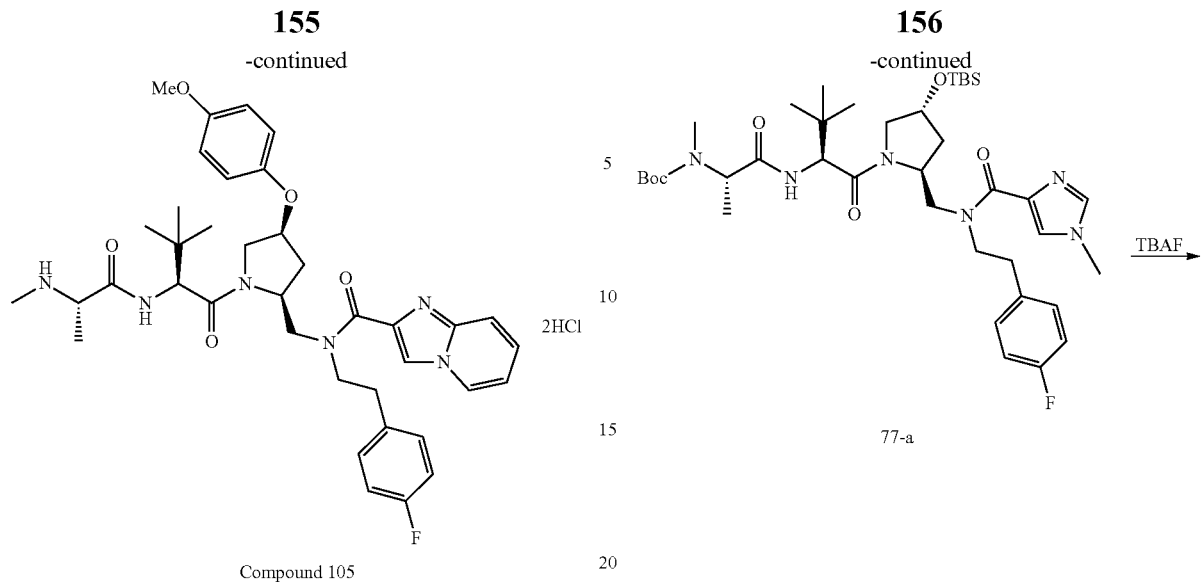

Compound 105

Step 1:

To a solution of intermediate 73-b (1.79 g, 2.63 mmol), 4-methoxyphenol (359 mg, 2.89 mmol) and triphenylphosphine (828 mg, 3.16 mmol) in THF was added DIAD (665 uL, 3.42 mmol) dropwise and the reaction was then stirred at room temperature for 2 days. Diethyl ether and hexane were added, a precipitate formed and triphenyl phosphine oxide was removed by filtration. Volatiles were removed under reduced pressure and the residue was purified by silica gel chromatography to provide the expected intermediate 76-a as a colorless oil.

Step 2:

4N HCl in 1,4-dioxane (4.05 mL) was added to intermediate 76-a (510 mg, 0.64 mmol) in ethyl acetate (500 uL) and the solution was stirred for 2 hours at 0° C. Diethyl ether was added, a precipitate formed and compound 105.2HCl was collected by filtration as a white solid. MS (m/z) M+1=687.1

Example 73

The following example illustrates the preparation of compound 77-b, which can be used as an intermediate in the preparation of a compound of Formula 1 or salt thereof Scheme 77: Synthesis of intermediate 77-b

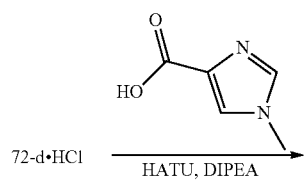

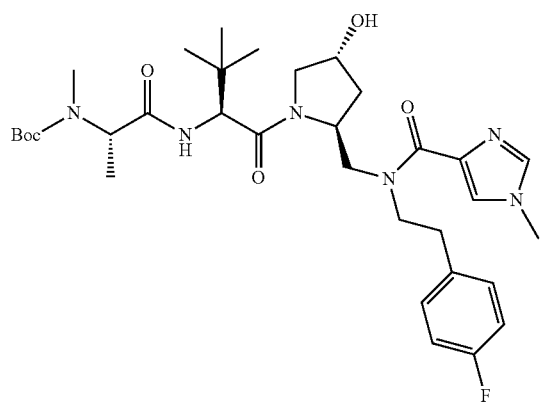

Step 1:

To a solution of intermediate 72-d.HCl (3.0 g, 4.61 mmol) in DMF cooled to 0° C. were sequentially added 1-N-methylimidazole carboxylic acid (988 mg, 7.83 mmol), HATU (2.98 g, 7.83 mmol) and DIPEA (3.22 mL, 18.43 mmol) and the reaction mixture was stirred at room temperature overnight. Saturated aqueous ammonium chloride and ethyl acetate were added; the organic layer was separated, washed with saturated aqueous NaHCO₃ and brine, dried over anhydrous MgSO₄, filtered and concentrated in vacuo. Purification by silica gel chromatography provided intermediate 77-a as white foam.

Step 2:

To a solution of intermediate 77-a (570 mg, 0.75 mmol) in THF cooled to 0° C. was added 1.0 M solution of TBAF in THF (970 uL, 0.97 mmol) and the reaction mixture was stirred at room temperature for 2 hours. Water and ethyl acetate were added; the organic layer was separated, washed with brine, dried over anhydrous MgSO₄, filtered and concentrated in vacuo. Purification by silica gel chromatography provided intermediate 77-b as white foam.

Example 74

The following example illustrates the preparation of compound 97, which is a compound of Formula 1

Scheme 78: Synthesis of compound 97

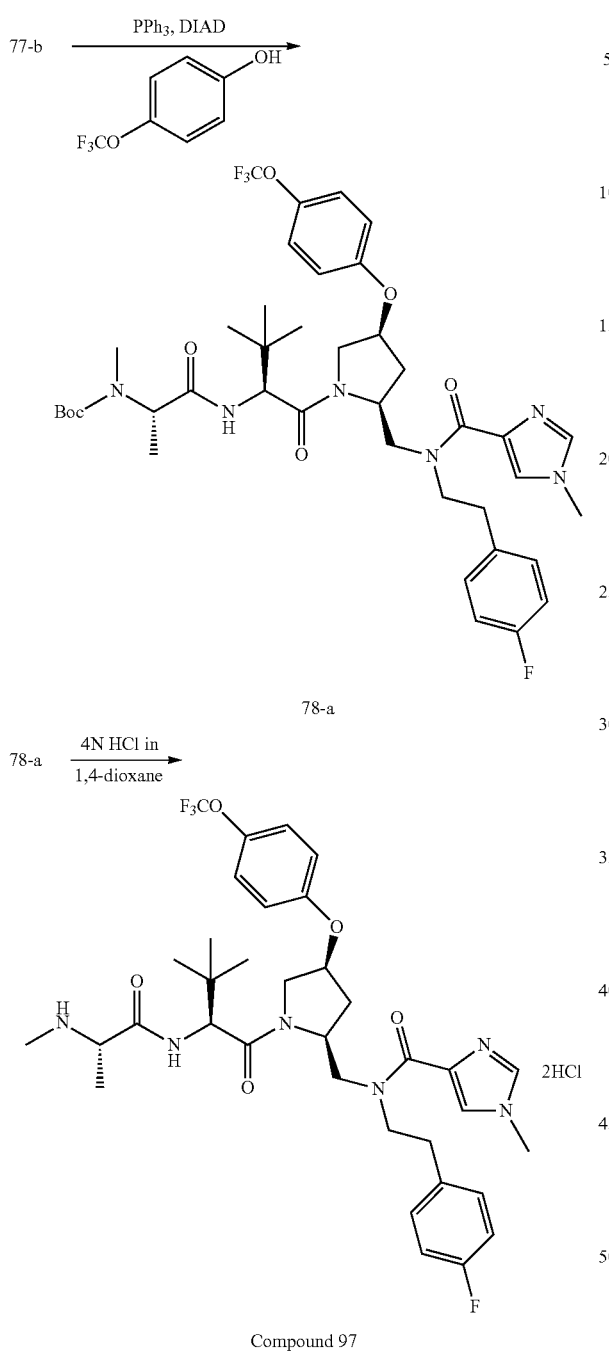

Step 2:

4N HCl in 1,4-dioxane (6.0 mL) was added to intermediate 78-a (450 mg, 0.56 mmol) in ethyl acetate (500 uL) and the solution was stirred for 2 hours at 0° C. Diethyl ether was added, a precipitate formed and compound 97.2HCl was collected by filtration as a white solid. MS (m/z) M+1=705.4

Example 75

The following example illustrates the preparation of compound 96, which is a compound of Formula 1

Scheme 79: Synthesis of compound 96

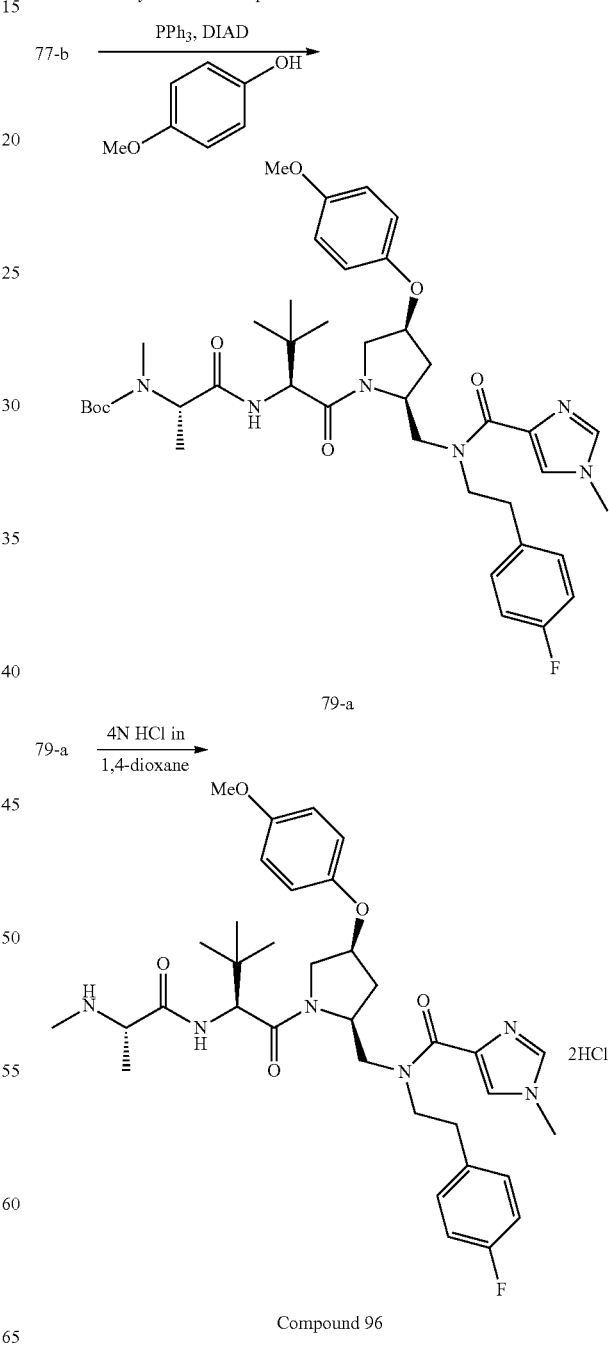

Step 1:

To a solution of intermediate 77-b (700 mg, 1.08 mmol), 4-(trifluoromethoxy)phenol (445 mg, 2.49 mmol) and triphenylphosphine (712 mg, 2.71 mmol) in THF was added DIAD (549 uL, 2.82 mmol) and the reaction was then stirred at room temperature for 2 days. Diethyl ether and hexane were added, a precipitate formed and triphenyl phosphine oxide was removed by filtration. Volatiles were removed under reduced pressure and the residue was purified by silica gel chromatography to provide the expected intermediate 78-a as colorless oil.

Step 1:

To a solution of intermediate 77-b (484 mg, 0.75 mmol), 4-methoxyphenol (214 mg, 1.72 mmol) and triphenylphosphine (492 mg, 1.87 mmol) in THF was added DIAD (379 uL, 195 mmol) and the reaction was then stirred at room temperature for 2 days. Diethyl ether and hexane were added, a precipitate formed and triphenyl phosphine oxide was removed by filtration. Volatiles were removed under reduced pressure and the residue was purified by silica gel chromatography to provide the expected intermediate 79-a as beige solid.

Step 2:

4N HCl in 1,4-dioxane (2.80 mL) was added to intermediate 79-a (420 mg, 0.56 mmol) in ethyl acetate (500 uL) and the solution was stirred for 2 hours at 0° C. Diethyl ether was added, a precipitate formed and compound 96.2HCl was collected by filtration as a white solid. MS (m/z) M+1=651.4

Example 76

The following example illustrates the preparation of compound 123, which is a compound of Formula 1

Scheme 80: Synthesis of compound 123

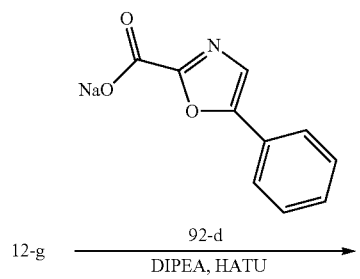

12-g  →  92-d / DIPEA, HATU

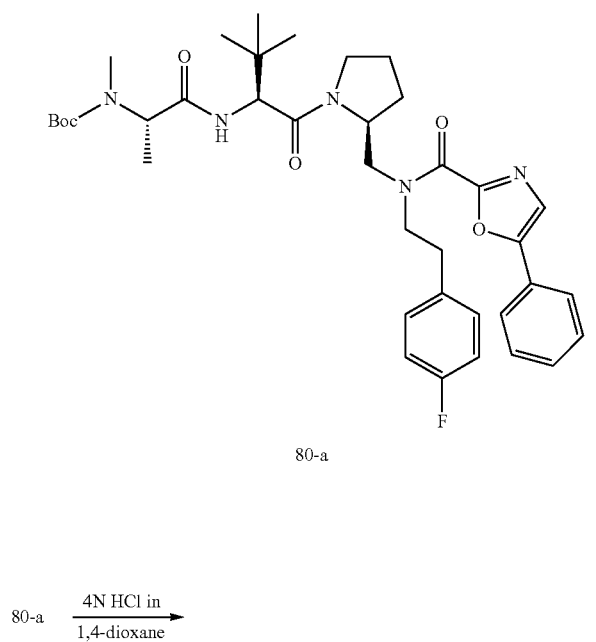

80-a 80-a  →  4N HCl in 1,4-dioxane

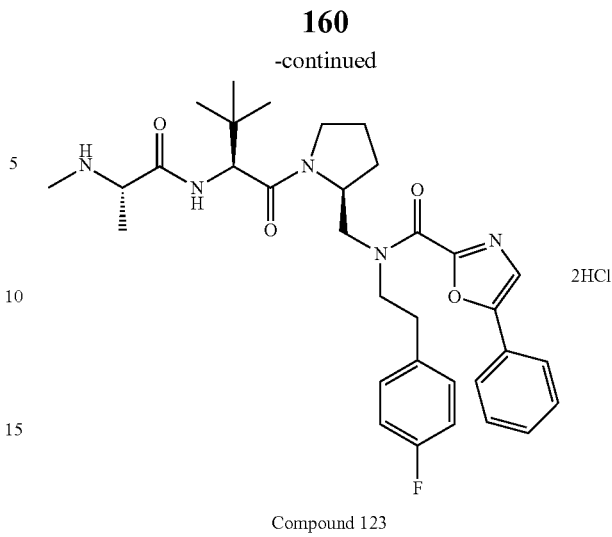

Compound 123

Step 1:

To a solution of intermediate 12-g (0.478 g, 0.919 mmol) in DMF at 0° C. were sequentially added 5-phenyloxazole-2-carboxylic acid, sodium salt (92-d) (0.194 g, 0.919 mmol), HATU (1.05 g, 2.76 mmol) and DIPEA (0.642 mL, 3.68 mmol) and the reaction mixture was stirred at room temperature overnight. Ethyl acetate and saturated aqueous ammonium chloride were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 80-a as a white solid.

Step 2:

4N HCl in 1,4-dioxane (5 mL, 20.0 mmol) was added to intermediate 80-a (390 mg, 0.564 mmol) at 0° C. and the solution was stirred for 3 hours at 0° C. Diethyl ether was added, a precipitate was formed and compound 123.2HCl was collected by filtration as a white solid. MS m/z M+1=592.2

Example 77

The following example illustrates the preparation of compound 125, which is a compound of Formula 1

Scheme 81: Synthesis of compound 125

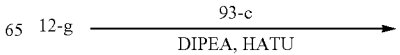

12-g  →  93-c / DIPEA, HATU

-continued

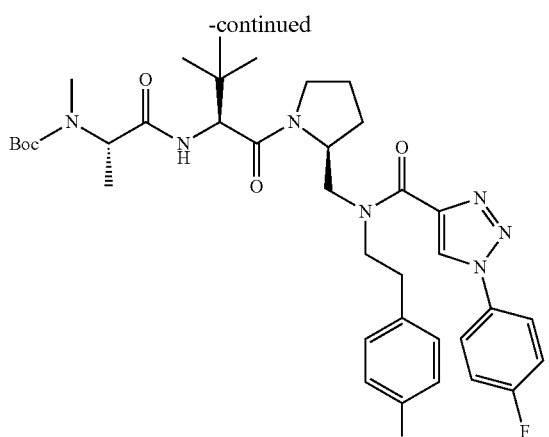

81-a 81-a →(4N HCl in 1,4-dioxane)

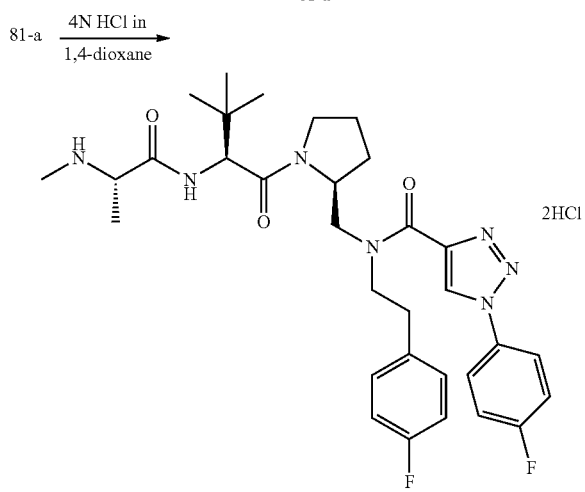

Compound 125

Step 1:

To a solution of intermediate 12-g (316 mg, 0.608 mmol) in DMF at 0° C. were sequentially added 1-(4-fluorophenyl)-1H-1,2,3-triazole-4-carboxylic acid, sodium salt (93-c) (0.2 g, 0.790 mmol), HATU (0.347 g, 0.912 mmol) and DIPEA (0.423 mL, 2.431 mmol) and the reaction mixture was stirred at room temperature overnight. Ethyl acetate and saturated aqueous ammonium chloride were added; the organic layer was separated, washed with saturated aqueous ammonium chloride, saturated aqueous NaHCO₃ and brine, dried over anhydrous MgSO₄, filtered and concentrated in vacuo. Purification by silica gel chromatography provided intermediate 81-a as a white solid.

Step 2:

4N HCl in 1,4-dioxane (1.5 mL, 6.06 mmol) was added to a solution of intermediate 81-a (0.43 g, 0.606 mmol) in ethyl acetate (1.2 mL) and the solution was stirred for 2 hours at 0° C. Volatiles were removed under reduced pressure and the residue was triturated with diethyl ether to provide compound 125.2HCl as an off-white solid. MS m/z M+1=610.1

Example 78

The following example illustrates the preparation of compound 119, which is a compound of Formula 1

Scheme 82: Synthesis of compound 119

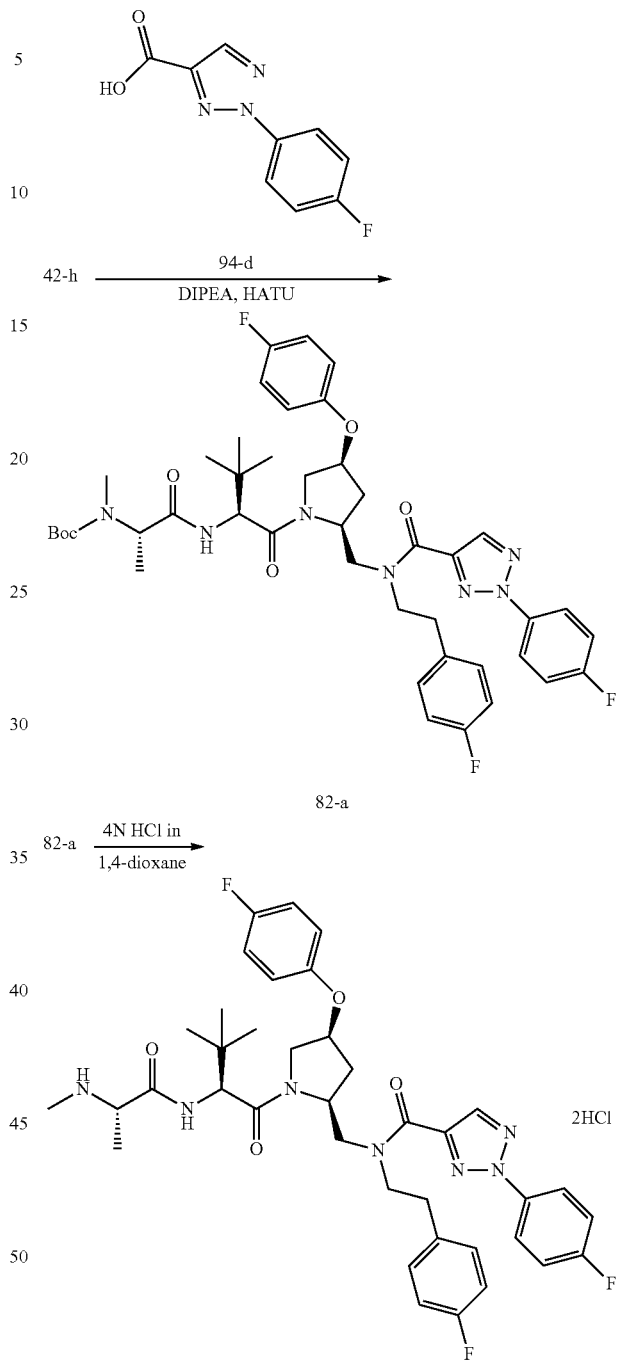

Step 1:

To a solution of intermediate 42-h (250 mg, 0.396 mmol) in DMF at 0° C. were sequentially added 2-(4-fluorophenyl)-2H-1,2,3-triazole-4-carboxylic acid (94-d) (130 mg, 0.630 mmol), HATU (271 mg, 0.713 mmol) and DIPEA (207 uL, 1.189 mmol). The reaction mixture was stirred for 3 hours at 0° C. and at room temperature overnight. Ethyl acetate and saturated aqueous ammonium chloride were added; the organic layers were separated. The aqueous phase was extracted with ethyl acetate; the combined organic extracts were washed with saturated aqueous ammonium chloride, saturated aqueous NaHCO$_3$ and brine, dried over anhydrous MgSO$_4$, filtered and concentrated in vacuo. Purification by silica gel chromatography provided intermediate 82-a as a white solid.

Step 2:

4N HCl in 1,4-dioxane (924 uL, 3.70 mmol) was added to intermediate 82-a (303 mg, 0.370 mmol) and the solution was stirred for 1 hour at 0° C. Volatiles were removed under reduced pressure and the residue was triturated with diethyl ether to provide compound 119.2HCl as a white solid. MS m/z M+1=720.1

Example 79

The following example illustrates the preparation of compound 126, which is a compound of Formula 1

Scheme 83: Synthesis of compound 126

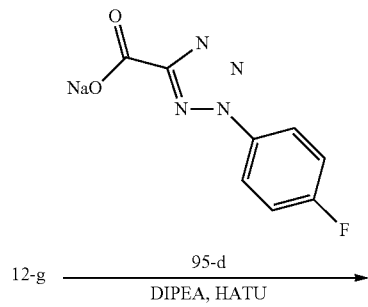

12-g $\xrightarrow{\text{95-d}}_{\text{DIPEA, HATU}}$

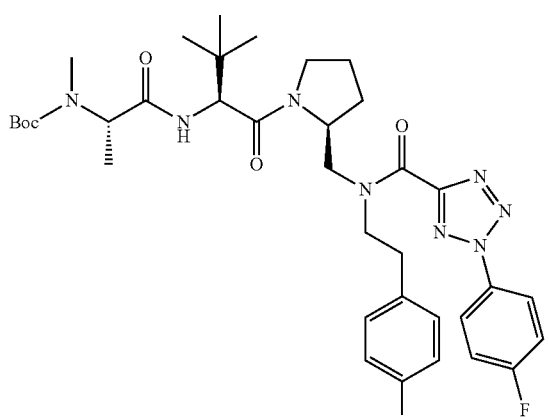

83-a

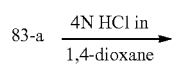

83-a $\xrightarrow{\text{4N HCl in}}_{\text{1,4-dioxane}}$

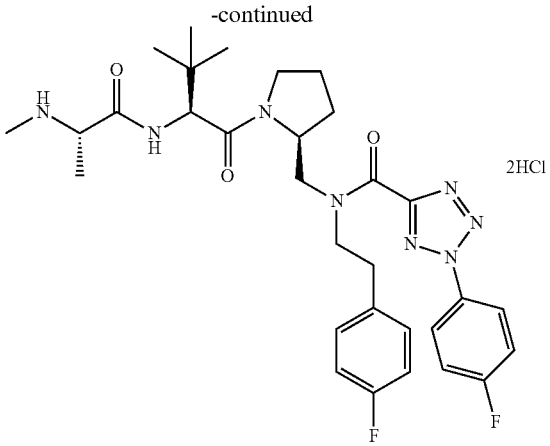

Compound 126

Step 1:

To a solution of intermediate 12-g (300 mg, 0.576 mmol) in DMF at 0° C. were sequentially added 2-(4-fluorophenyl)-2H-tetrazole-5-carboxylic acid, sodium salt (95-d) (190 mg, 0.749 mmol), HATU (329 mg, 0.864 mmol) and DIPEA (400 uL, 2.305 mmol). The reaction mixture was stirred at 0° C. for 1 hour. Ethyl acetate and saturated aqueous ammonium chloride were added; the organic layers were separated. The aqueous phase was extracted with ethyl acetate; the combined organic extracts were washed with saturated aqueous ammonium chloride, saturated aqueous NaHCO$_3$ and brine, dried over anhydrous MgSO$_4$, filtered and concentrated in vacuo to give intermediate 83-a.

Step 2:

4N HCl in 1,4-dioxane (1.76 mL, 7.03 mmol) was added to a solution of intermediate 83-a (303 mg, 0.370 mmol) and the solution was stirred at 0° C. for 2 hours. Volatiles were removed under reduced pressure. Purification by reverse phase chromatography provided compound 126.2HCl as a white solid. MS m/z M+1=611.1

Example 80

The following example illustrates the preparation of imidazo[1,2-a]pyrimidine-2-carboxylic acid, HBr salt (84-c)

Scheme 84: Synthesis of 84-c

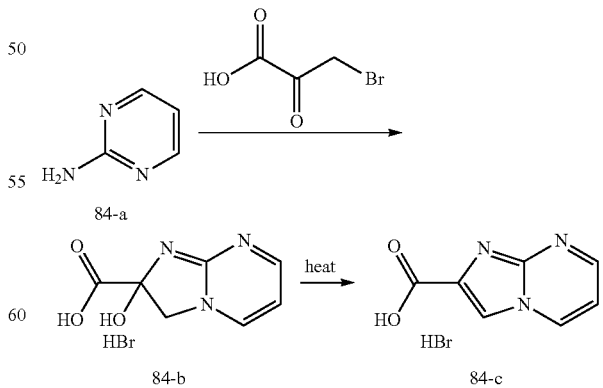

Step 1:

To a solution of 2-aminopyrimidine 84-a (50.00 g, 526 mmol) in DMF (375 mL) cooled to 0° C. was added 3-bromo- 2-oxopropanoic acid (88.00 g, 526 mmol). The reaction was stirred at 0° C. for 2 hours and then warmed to room temperature over 2 hours and stirred for 18 hours. Acetonitrile (650 mL) was added; precipitate formed and was collected by filtration. The precipitate was rinsed with acetonitrile and diethyl ether and dried in vacuo to obtain intermediate 84-b.HBr as a white solid. MS m/z M+1=182.0

Step 2:

To a suspension of intermediate 84-b.HBr (98.80 g, 377 mmol) in THF (600 mL) was added N,N-dimethylacetamide (48 mL). The reaction was stirred at 80° C. for 48 hours, cooled to room temperature and poured into acetonitrile (700 mL). A precipitate was formed and collected by filtration, rinsed with acetonitrile and diethyl ether and dried in vacuo to give imidazo[1,2-a]pyrimidine-2-carboxylic acid, HBr salt (84-c) as a beige solid. MS m/z M+1=164.2

Example 81

The following example illustrates the preparation of imidazo[1,2-a]pyridine-2-carboxylic acid, lithium salt (85-d)

Scheme 85: Synthesis of 85-d

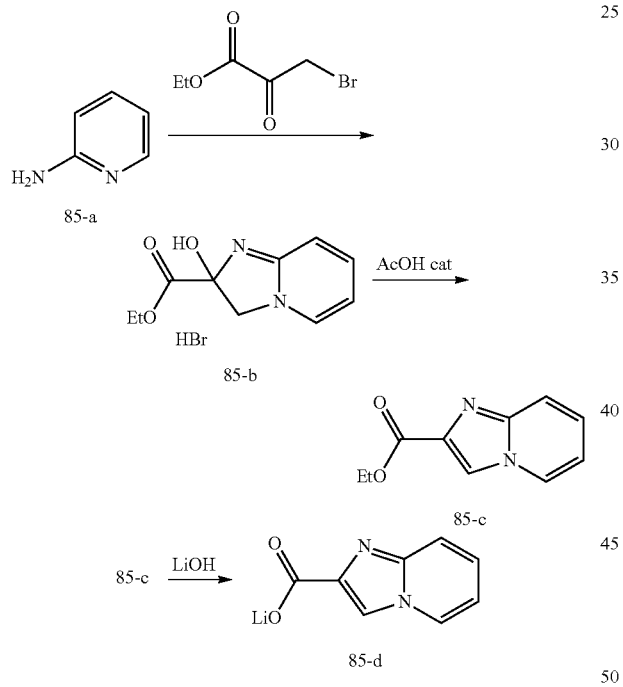

Step 1:

To a solution of 2-aminopyridine 85-a (20.00 g, 213 mmol) in THF (417 mL) was added ethyl bromopyruvate (30.0 mL, 215 mmol). The reaction mixture was stirred at room temperature for 18 hours. A precipitate formed and was collected by filtration and rinsed with THF to provide intermediate 85-b.HBr as a yellow solid.

Step 2:

To a suspension of intermediate 85-b.HBr in ethanol (550 mL) was added AcOH (5 mL) and the mixture was heated at reflux for 3 hours to give a clear solution. The solution was concentrated in vacuo, precipitate was formed and triturated with diethyl ether; intermediate 85-c.HBr was collected by filtration as a beige solid, dissolved in water (0.5 L) and basified to pH 8 by using NaOH pellets. This solution was extracted with ethyl acetate four times; the combined organic layers were washed with brine, dried over anhydrous MgSO$_4$, filtered and concentrated in vacuo to provide intermediate 85-c as an off-white solid.

Step 3:

To a solution of intermediate 85-c (26.40 g, 0.139 mmol) in ethanol (140 mL) was added 2M aqueous LiOH (70 mL, 140 mmol) and the reaction was stirred at room temperature for 5 hours. The reaction mixture was cooled to 0° C., precipitate was formed, collected by filtration and rinsed with diethyl ether to obtain imidazo[1,2-a]pyridine-2-carboxylic acid, lithium salt (85-d) as a white solid. $^1$H NMR (200 MHz, CD$_3$OD), δ ppm 8.41 (d, J=6.6 Hz, 1H), 8.11 (s, 1H), 7.53 (d, J=9.2 Hz, 1H), 7.29 (dd, J=8.0 Hz, J=7.3 Hz, 1H), 6.90 (dd, J=6.7 Hz, J=6.7 1H)

Example 82

The following example illustrates the preparation of 6-fluoroimidazo[1,2-a]pyrimidine-2-carboxylic acid, HBr salt (86-c)

Scheme 86: Synthesis of 86-c

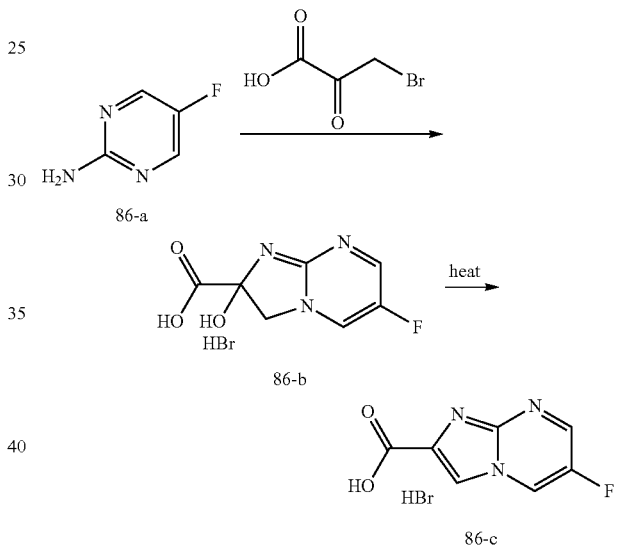

Step 1:

To a solution of 5-fluoropyrimidin-2-amine 86-a (3.17 g, 28.0 mmol) in DMF (14 mL) at 0° C. was added bromopyruvic acid (7.73 g, 53.4 mmol). The reaction mixture was stirred for 2 hours at 0° C. and then for 2 days at room temperature. The reaction was diluted with acetone; precipitate formed and intermediate 86-b.HBr was collected by filtration as a beige solid.

Step 2:

A suspension of intermediate 86-b.HBr (8.40 g, 30.0 mmol) in THF (100 mL) and AcOH (10 mL) was stirred at 70° C. for 72 hours. THF was added and the precipitate was collected by filtration, rinsed with THF and diethyl ether and dried in vacuo to provide 6-fluoroimidazo[1,2-a]pyrimidine-2-carboxylic acid, HBr salt (86-c) as a pale beige solid. MS m/z M+1=182.0

Example 83

The following example illustrates the preparation of 6,7-dihydro-5H-pyrrolo[1,2-a]imidazole-2-carboxylic acid, lithium salt (87-e)

Scheme 87: Synthesis of 87-e

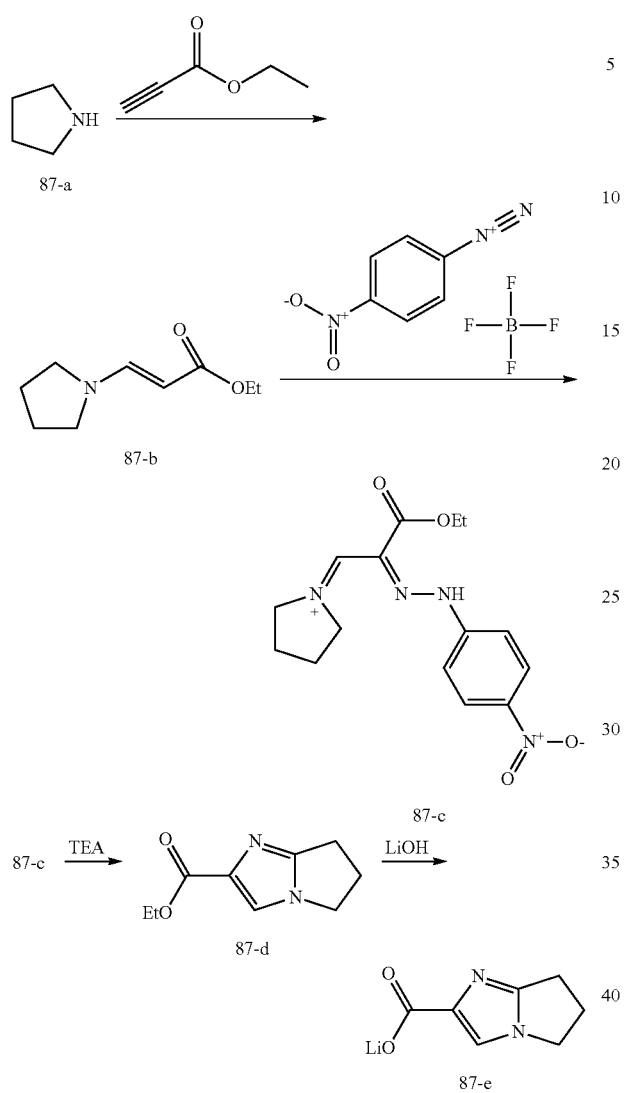

Example 84

The following example illustrates the preparation of 1-(4-fluorophenyl)-1H-imidazole-4-carboxylic acid, lithium salt (88-e)

Scheme 88: Synthesis of 88-e

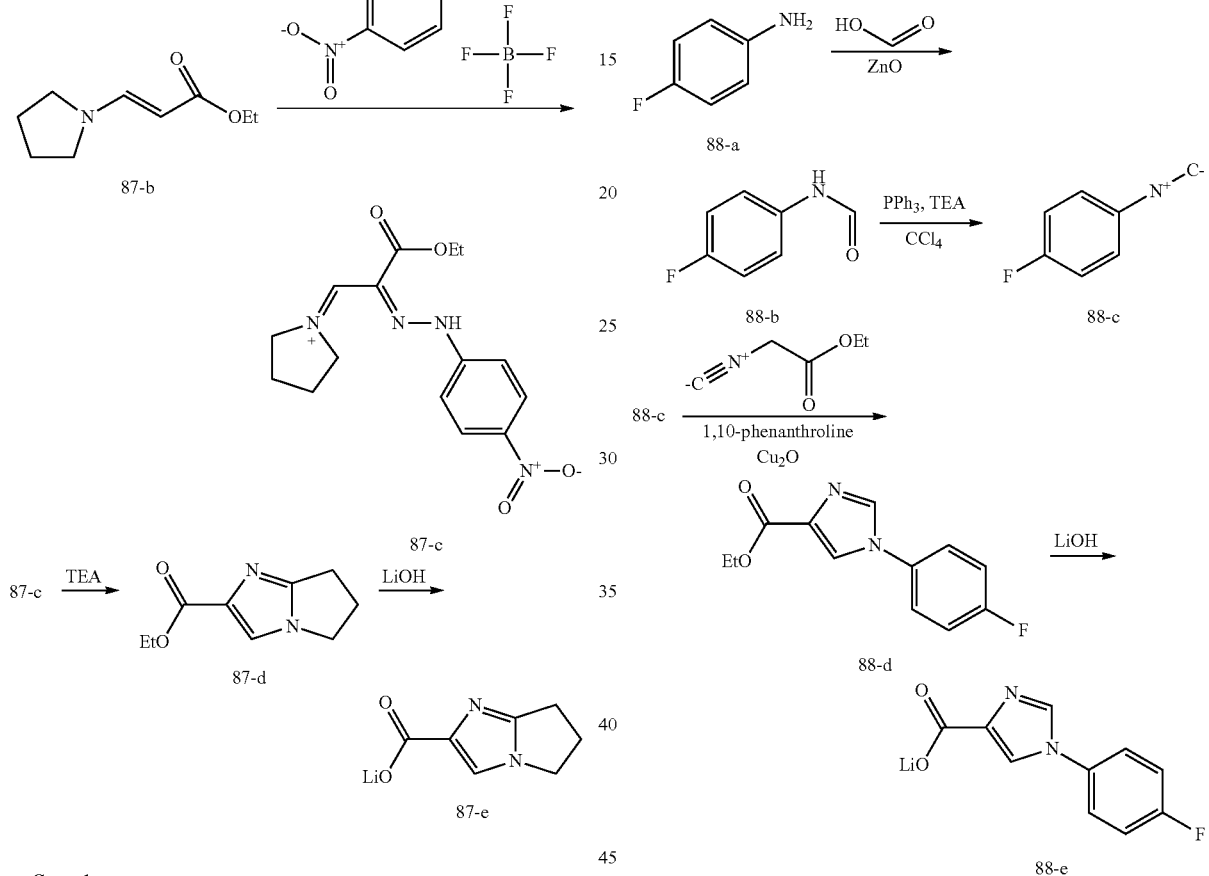

hours and concentrated in vacuo to obtain 6,7-dihydro-5H-pyrrolo[1,2-a]imidazole-2-carboxylic acid, lithium salt (87-e) as a pale beige solid. MS m/z M+1=153.0

Step 1
To a solution of intermediate 87-a (5.00 g, 70.3 mmol) in THF was added ethyl propiolate (6.90 g, 70.3 mmol) at 10° C. The reaction mixture was stirred for 1 hour at room temperature and concentrated in vacuo to provide intermediate 87-b as a yellow oil.

Step 2:
To a solution of intermediate 87-b (11.90 g, 70.3 mmol) in acetonitrile (1400 mL) was added 4-nitrobenzenediazonium tetrafluoroborate (16.66 g, 70.3 mmol) and the reaction was stirred for 1 hour at room temperature to provide a solution of intermediate 87-c.

Step 3:
To a solution of intermediate 87-c was added TEA (19.0 mL, 141 mmol) and the reaction mixture was heated at reflux for 2 hours, cooled to room temperature and concentrated in vacuo. Purification by silica gel chromatography provided intermediate 87-d as a brown solid. MS m/z M+Na=202.9

Step 4:
To a solution of intermediate 87-d (5.36 g, 29.7 mmol) in THF was added 2N aqueous LiOH (32.7 mL, 65.4 mmol). The reaction mixture was stirred at room temperature for 48

Step 1:
To a solution of zinc oxide (7.32 g, 90 mmol) in formic acid (20.7 mL, 540 mmol) at 0° C. was added 4-fluoroaniline 88-a (20.00 g, 180 mmol). The reaction mixture was stirred at 70° C. for 1 hour, cooled to room temperature, diluted with ethyl acetate and filtered over a pad of Celite. The filtrate was washed with water, 10% aqueous $Na_2CO_3$ and brine, dried over anhydrous $MgSO_4$, filtered and concentrated in vacuo to give intermediate 88-b as a beige solid. MS m/z M+1=140.0

Step 2:
To a solution of intermediate 88-b (8.35 g, 60.0 mmol) in dichloromethane (111 mL) were sequentially added triphenylphosphine (17.79 g, 67.8 mmol), TEA (8.32 mL, 60.0 mmol) and carbon tetrachloride (6.21 mL, 64.2 mmol). After stirring for 72 hours at room temperature, the reaction mixture was cooled to 0° C. A precipitate was formed, collected by filtration and discarded. The filtrate was concentrated and suspended in cold diethyl ether. An insoluble residue was collected by filtration and discarded. The filtrate was concentrated in vacuo to provide intermediate 88-c as a brown oil.

Step 3:

To a suspension of copper oxide (1.20 g, 8.40 mmol) and 1,10-phenanthroline (3.03 g, 16.80 mmol) in THF (400 mL) purged with nitrogen were sequentially added intermediate 88-c (7.27 g, 60.0 mmol) and ethyl isocyanoacetate (9.2 mL, 84 mmol). After stirring at 70° C. for 18 hours the reaction mixture was cooled to room temperature and filtered over a pad of Celite. The filtrate was concentrated in vacuo. Purification by silica gel chromatography provided intermediate 88-d as a light yellow solid. MS m/z M+1=235.0

Step 4:

To a solution of intermediate 88-d (10.47 g, 44.7 mmol) in THF was added 2N aqueous LiOH (24.6 mL, 49.2 mmol). After stirring at room temperature overnight, the reaction mixture was concentrated in vacuo. The resulting residue was diluted with water and extracted with dichloromethane. The organic fractions were discarded and the aqueous layer was concentrated in vacuo to provide 1-(4-fluorophenyl)-1H-imidazole-4-carboxylic acid, lithium salt (88-e) as a light yellow solid. MS m/z M+1=207

Example 85

The following example illustrates the preparation of 1-(tetrahydro-2H-pyran-4-yl)-1H-imidazole-4-carboxylic acid, lithium salt (89-d)

Scheme 89: Synthesis of 89-d

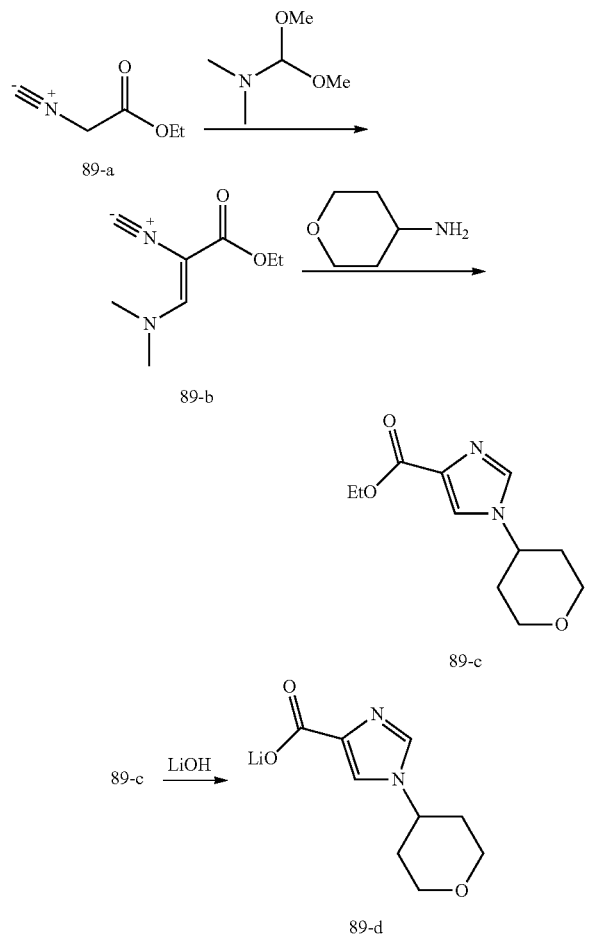

Step 1:

To a solution of ethyl 2-isocyanoacetate 89-a (5 g, 44.2 mmol) in anhydrous ethanol (50 mL) at 0° C. was added 1,1-dimethoxy-N,N-dimethylmethanamine (10.53 g, 88 mmol). After stirring at room temperature overnight, the reaction mixture was concentrated in vacuo. Purification by chromatography on neutral aluminum provided intermediate 89-b as a yellow oil.

Step 2:

To a seal-tube were added intermediate 89-b (1.00 g, 5.95 mmol) and tetrahydro-2H-pyran-4-amine (1.80 g, 17.84 mmol). The tube was filled with nitrogen, sealed and heated at 70° C. for 2 hours. After cooling to room temperature, the reaction mixture was purified by silica gel chromatography to provide intermediate 89-c as a beige solid.

Step 3:

To a solution of intermediate 89-c (0.72 g, 3.22 mmol) in a 3:1 methanol/water mixture was added LiOH (0.116 g, 4.83 mmol). After stirring at room temperature for 18 hours, the reaction mixture was concentrated in vacuo to give 1-(tetrahydro-2H-pyran-4-yl)-1H-imidazole-4-carboxylic acid, lithium salt (89-d) as a white foam. MS m/z M+1=197.0

Example 86

The following example illustrates the preparation of 1-phenyl-1H-pyrrole-3-carboxylic acid, lithium salt (90-c)

Scheme 90: Synthesis of 90-c

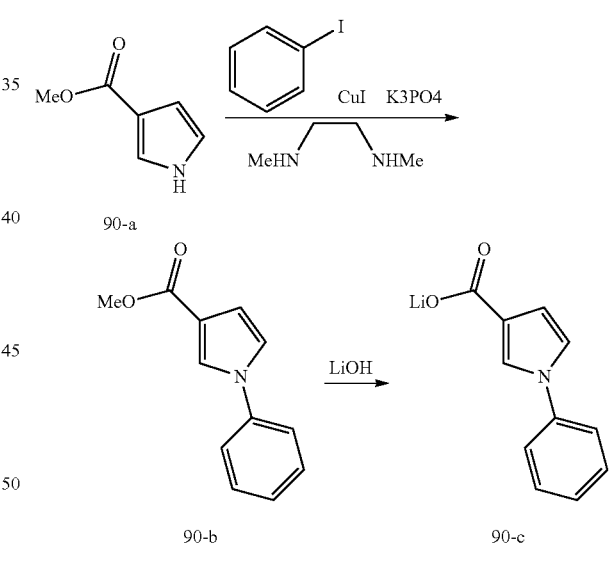

Step 1:

To a dried seal-tube were added methyl 1H-pyrrole-3-carboxylate 90-a (150 mg, 1.199 mmol), copper(I) iodide (11.4 mg, 0.060 mmol), $K_3PO_4$ (534 mg, 2.52 mmol), iodobenzene (160 uL, 1.439 mmol) and toluene (1.2 mL). Nitrogen was bubbled through the mixture for 5 min followed by addition of $N^1,N^2$-dimethylethane-1,2-diamine (21 mg, 0.240 mmol). The tube was sealed and the reaction was stirred overnight at 100° C. It was then diluted with ethyl acetate and filtered over a pad of Celite. The filtrate was washed with saturated aqueous ammonium chloride and brine, dried over anhydrous $MgSO_4$, filtered and concentrated in vacuo to give intermediate 90-b. MS m/z M+1=202.2

Step 2:

To a solution of intermediate 90-b (241 mg, 1.198 mmol) in a 2:1 THF/water mixture was added LiOH (92 mg, 3.832 mmol). The reaction mixture was heated at 50° C. overnight and concentrated in vacuo. The residue was dissolved in water, extracted with dichloromethane and diethyl ether and the organic extracts were discarded. The aqueous phase was acidified to pH 2 using 37% aqueous HCl and extracted twice with dichloromethane. The combined organic extracts were dried over anhydrous MgSO$_4$ and concentrated in vacuo to give 1-phenyl-1H-pyrrole-3-carboxylic acid, lithium salt (90-c) as a white solid. MS m/z M+Na=210.2

Example 87

The following example illustrates the preparation of 5-phenyl-1,3,4-oxadiazole-2-carboxylic acid, sodium salt (91-c)

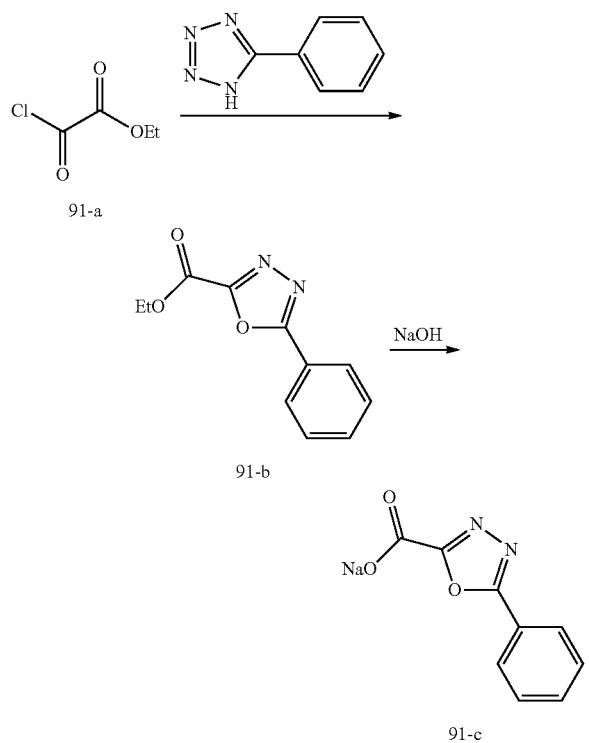

Step 1:

To a solution of ethyl 2-chloro-2-oxoacetate 91-a (5.61 g, 41.1 mmol) in toluene was added 5-phenyl-1H-tetrazole (6.00 g, 41.1 mmol). After stirring at reflux for 2 hours, the reaction mixture was diluted with ethyl acetate and water. The organic layer was washed twice with 1N aqueous HCl, water and brine, dried over anhydrous MgSO$_4$, filtered and concentrated in vacuo. Purification by silica gel chromatography provided intermediate 91-b as a yellow solid. MS m/z M+1=219.1

Step 2:

To a solution of intermediate 91-b (1.40 g, 6.42 mmol) in THF was added 1N aqueous NaOH (6.7 mL, 6.74 mmol) at 0° C. The reaction mixture was stirred at room temperature for 2 hours and concentrated in vacuo to provide 5-phenyl-1,3,4-oxadiazole-2-carboxylic acid, sodium salt (91-c) as a white solid. MS m/z M+1=191.1

Example 88

The following example illustrates the preparation of 5-phenyloxazole-2-carboxylic acid, sodium salt (92-d)

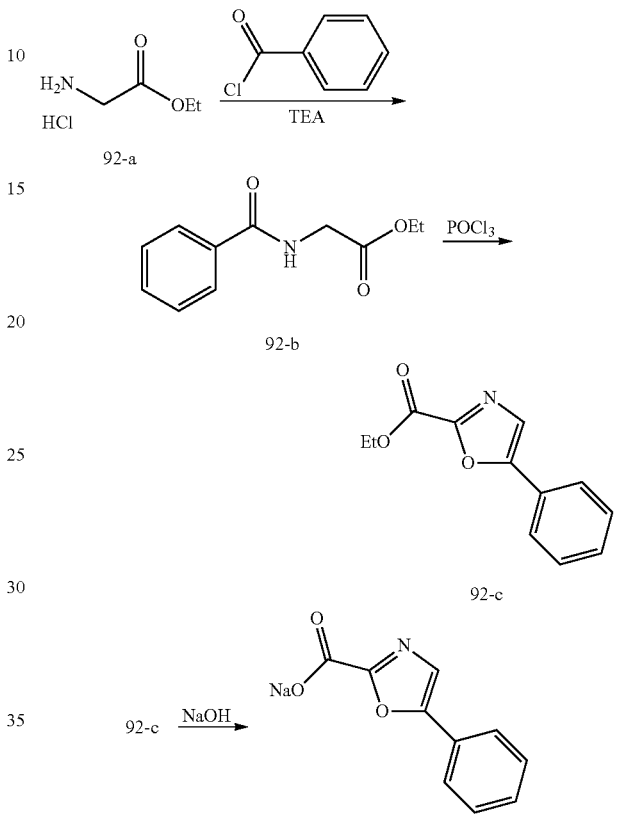

Step 1:

To a solution of glycine ethyl ester hydrochloride 92-a (4.64 g, 33.2 mmol) in dichloromethane at 0° C. were sequentially added benzoyl chloride (3.22 mL, 27.7 mmol) and TEA (11.49 mL, 83 mmol). The reaction mixture was stirred at 0° C. for 2 hours and at room temperature overnight. Ethyl acetate and water were added; the organic layer was separated, washed with 1N aqueous HCl twice, followed by water and brine wash, dried over anhydrous MgSO$_4$, filtered and concentrated in vacuo to give intermediate 92-b as an oil.

Step 2:

To a solution of intermediate 92-b (1.10 g, 4.68 mmol) in toluene (5.0 mL) was added phosphorus oxychloride (2.18 mL, 23.38 mmol). The reaction mixture was heated at reflux overnight and cooled to room temperature. Ethyl acetate and saturated aqueous NaHCO$_3$ were added; the organic layer was separated, washed with saturated aqueous NaHCO$_3$, water and brine, dried over anhydrous MgSO$_4$, filtered and concentrated in vacuo. Purification by silica gel chromatography provided intermediate 92-c as a white solid. MS m/z M+1=218.1

Step 2:

To a solution of intermediate 92-c (200 mg, 0.921 mmol) in THF was added 1 N aqueous NaOH (1.1 mL, 1.105 mmol) at 0° C. After stirring at room temperature for 3 hours, the reaction mixture was concentrated in vacuo to give 5-phenyloxazole-2-carboxylic acid, sodium salt (92-d) as a white solid. MS m/z M+1=190.2

Example 89

The following example illustrates the preparation of 1-(4-fluorophenyl)-1H-1,2,3-triazole-4-carboxylic acid, sodium salt (93-c)

Scheme 93: Synthesis of 93-c

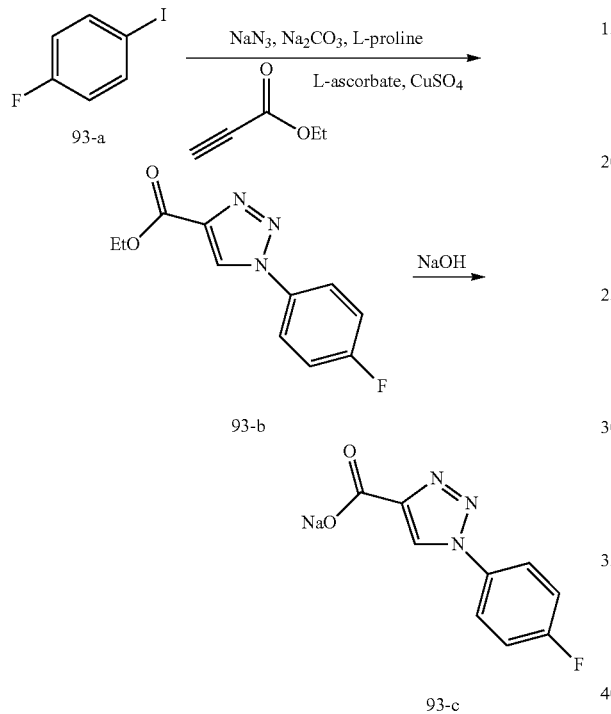

Step 1:

To a solution of 1-fluoro-4-iodobenzene 93-a (0.926 g, 4.17 mmol) in DMSO (4.0 mL) and water (0.44 mL) were sequentially added sodium azide (0.325 g, 5.01 mmol), sodium carbonate (0.088 g, 0.833 mmol), L-proline (0.096 g, 0.833 mmol), ethyl propiolate (0.409 g, 4.17 mmol), sodium L-ascorbate (0.207 g, 1.043 mmol) and copper(II) sulfate (0.052 g, 0.208 mmol). The reaction mixture was stirred at 65° C. for 18 hours and cooled to room temperature. Aqueous ammonia (1 mL), ethyl acetate (25 mL) and water (20 mL) were added. The phases were separated and the aqueous phase was extracted with ethyl acetate. The combined organic extracts were washed with brine, dried over anhydrous MgSO$_4$, filtered and concentrated in vacuo. Purification by reverse phase chromatography provided intermediate 93-b. MS m/z M+1=236.1

Step 2:

To a solution of intermediate 93-b (200 mg, 0.850 mmol) in THF was added 2N aqueous NaOH (0.425 mL, 0.850 mmol). After stirring at room temperature for 18 hours, the reaction mixture was concentrated in vacuo to provide 1-(4-fluorophenyl)-1H-1,2,3-triazole-4-carboxylic acid, sodium salt (93-c) as a yellow solid. MS m/z M+Na=230.0

Example 90

The following example illustrates the preparation of 2-(4-fluorophenyl)-2H-1,2,3-triazole-4-carboxylic acid, sodium salt (94-d)

Scheme 94: Synthesis of 94-d

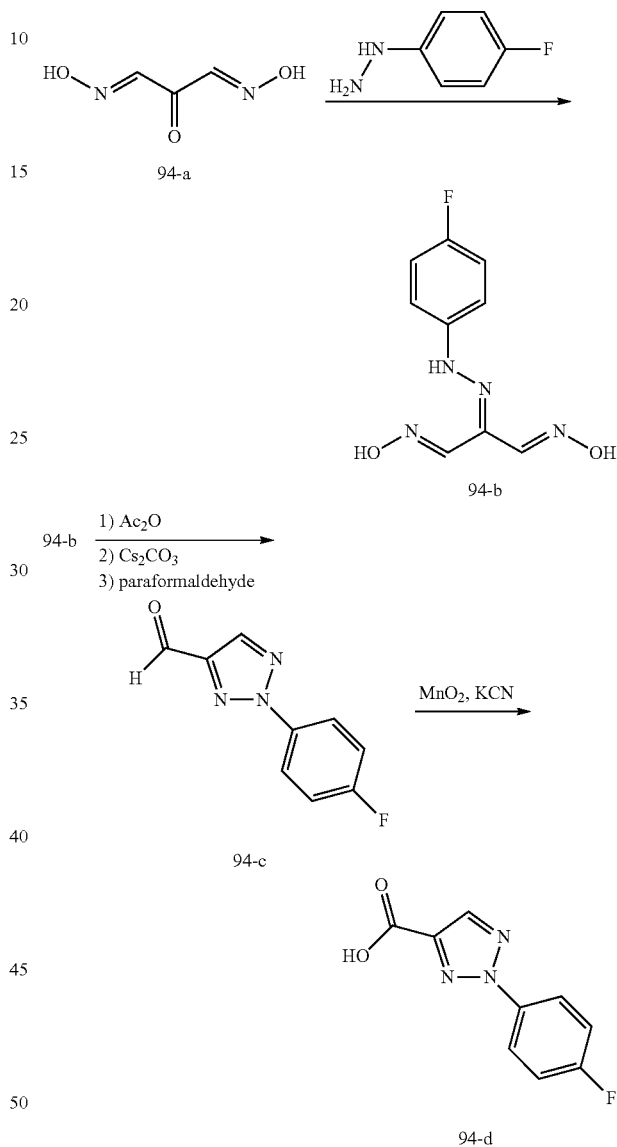

Step 1:

To a solution of 94-a (1.75 g, 15.08 mmol) in ethanol (16 mL) was added 4-fluorophenylhydrazine (1.90 g, 15.08 mmol) and the reaction was stirred at 70° C. for 30 minutes. Water (16 mL) was added, the reaction mixture was heated to 85° C., concentrated by one third and cooled in an ice bath. A yellow precipitate formed and was collected by filtration. The precipitate was dissolved in a 25% ethanol/toluene mixture (40 mL). The flask was equipped with a condenser and a Dean-Stark trap and the reaction mixture was heated at reflux until all ethanol was collected in the Dean-Stark trap. The mixture was cooled to room temperature; precipitate formed and intermediate 94-b was collected by filtration as a brown solid.

Step 2:

A solution of intermediate 94-b (1.64 g, 7.32 mmol) in acetic anhydride (13.8 mL, 146 mmol) was stirred at room temperature for 30 minutes. The reaction was diluted with water (60 mL), stirred for 30 min and the resulting precipitate was collected by filtration. The solid was partitioned between ethyl acetate and water. The layers were separated; the organic layer was dried over anhydrous MgSO₄, filtered and concentrated in vacuo. The residue was dissolved in THF and cesium carbonate (2.62 g, 8.05 mmol) was added. The mixture was stirred at room temperature for 30 minutes and filtered. The filtrate was concentrated in vacuo; the residue was dissolved in diethyl ether and washed with water, dried over anhydrous MgSO₄, filtered and concentrated in vacuo. The resulting solid was dissolved in 2M aqueous HCl (50 mL), paraformaldehyde (0.433 g, 14.41 mmol) was added and the reaction mixture was heated at reflux for 2 hours. Upon cooling to room temperature, the mixture was extracted with diethyl ether. The organic layer was separated and washed with water, dried over anhydrous MgSO₄, filtered and concentrated in vacuo. Purification by silica gel chromatography provided intermediate 94-c as a pale yellow solid.

Step 3:

To a solution of intermediate 94-c (300 mg, 1.569 mmol) in methanol (15 mL) at 0° C. were added potassium cyanide (171 mg, 2.62 mmol) and manganese (IV) oxide (1078 mg, 12.40 mmol). The reaction mixture was stirred at room temperature for 18 hours, filtered over a pad of Celite and the cake was rinsed with methanol. The filtrate was concentrated in vacuo. Purification by silica gel chromatography provided 2-(4-fluorophenyl)-2H-1,2,3-triazole-4-carboxylic acid, sodium salt (94-d) as a pale yellow solid. MS m/z M+1=244.2

Example 91

The following example illustrates the preparation of 2-(4-fluorophenyl)-2H-tetrazole-5-carboxylic acid, sodium salt (95-e)

Scheme 95: synthesis of 95-e

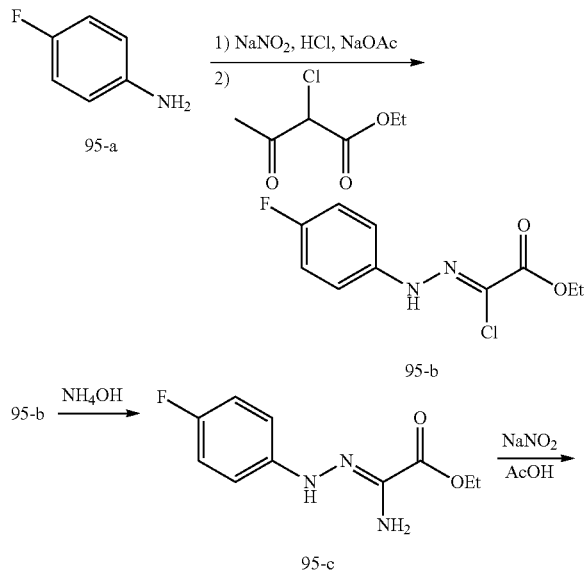

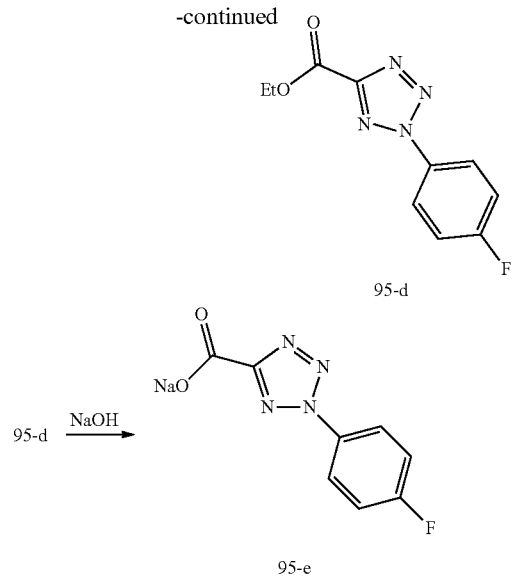

Step 1:

To a solution of 4-fluoroaniline 95-a (2.00 g, 18.00 mmol) in ethanol (5.7 mL) and water (2.0 mL) was added 37% aqueous HCl (3.7 mL, 45.0 mmol) and the reaction mixture was cooled to −5° C. To the mixture was added 5N aqueous sodium nitrite (3.96 mL, 19.80 mmol) drop-wise followed by an addition of 6N aqueous sodium acetate (9.0 mL, 54.0 mmol). The reaction mixture was stirred for 10 minutes at 0° C. then ethyl 2-chloro-3-oxobutanoate (2.96 g, 18.00 mmol) was added and stirring continued overnight at 27° C. THF (20 mL) was added and the reaction mixture was warmed up to 40° C. and transferred to a separation funnel. The aqueous layer was separated and discarded. The organic layer contained intermediate 95-b as a THF solution. MS m/z M+Na=267.1

Step 2:

To a solution of intermediate 95-b (4.40 g, 18 mmol) in THF was added 25% aqueous NH₄OH (16 mL, 108 mmol) at 0° C. The reaction mixture was stirred at room temperature for 3 hours and transferred to a separation funnel. The aqueous layer was separated and discarded. The organic layer was concentrated and the residue was triturated with diethyl ether/hexanes mixture; precipitate was formed and intermediate 95-c was collected as a red-brick solid.

Step 3:

To a solution of intermediate 95-c (1.36 g, 6.04 mmol) in THF (27 mL) was added acetic acid (1.1 mL, 18.12 mmol) and the reaction mixture was warmed up to 85° C. To the reaction was added 2.6N aqueous sodium nitrite (2.8 mL, 7.25 mmol), the mixture was stirred at 85° C. for 4 hours and concentrated in vacuo. The residue was dissolved in ethyl acetate and washed with saturated aqueous NaHCO₃, the layers were separated and the aqueous phase was extracted with ethyl acetate. The combined organic layers were washed with brine, dried over anhydrous MgSO₄, filtered and concentrated in vacuo. Purification by silica gel flash chromatography provided intermediate 95-d as a yellow solid. MS m/z M+Na=258.9

Step 4:

To a solution of intermediate 95-d (840 mg, 3.56 mmol) in THF was added 2N aqueous NaOH (1.78 mL, 3.56 mmol). The reaction mixture was stirred at 50° C. for 18 hours and concentrated in vacuo to provide 2-(4-fluorophenyl)-2H-tetrazole-5-carboxylic acid, sodium salt (95-e) as a yellow solid. MS m/z M+1=209.1

Compounds prepared according to the above procedures, or minor modifications thereof, are illustrated in table 1. Minor modifications to the procedures above and use of the appropriate starting materials as needed to arrive at the compounds of table 1 will be apparent to one skilled to the art.

TABLE 1

| Cmpd # | Structure | MS |
|---|---|---|
| 1 | 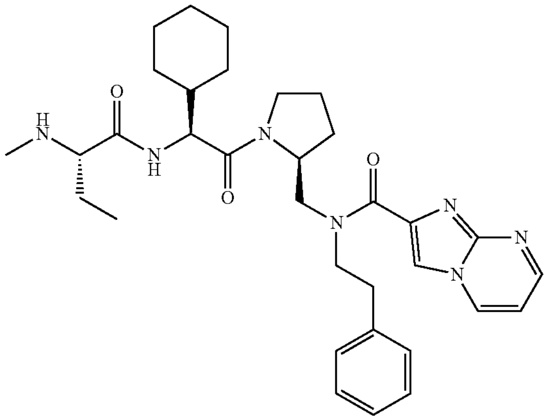 [SMILES: CC[C@H](NC)C(=O)N[C@H](C(=O)N1CCC[C@H]1CN(CCc1ccccc1)C(=O)c1cn2cccnc2n1)C1CCCCC1] | M + 1 = 588.5 |
| 2 | 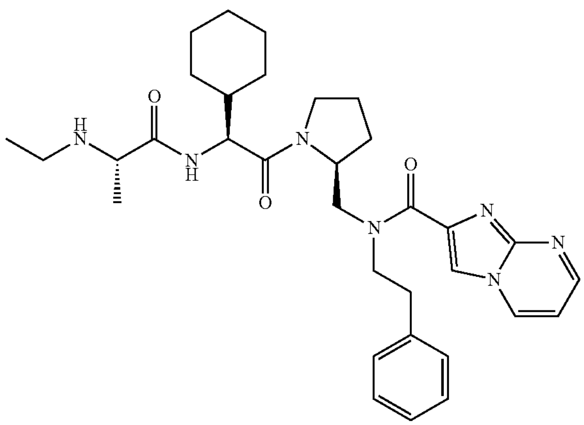 [SMILES: CCN[C@@H](C)C(=O)N[C@H](C(=O)N1CCC[C@H]1CN(CCc1ccccc1)C(=O)c1cn2cccnc2n1)C1CCCCC1] | M + 1 = 588.4 |
| 3 | 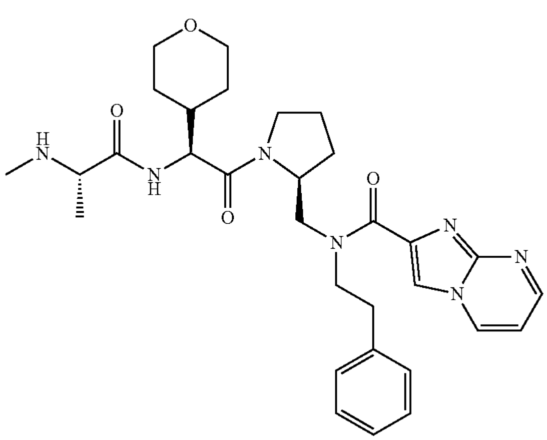 [SMILES: CN[C@@H](C)C(=O)N[C@H](C(=O)N1CCC[C@H]1CN(CCc1ccccc1)C(=O)c1cn2cccnc2n1)C1CCOCC1] | M + 1 = 576.4 |

TABLE 1-continued
| Cmpd # | Structure | MS |
|---|---|---|
| 4 | 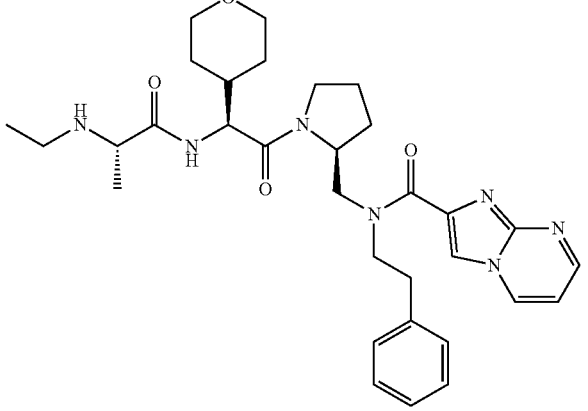 | M + 1 = 590.4 |
| 5 | 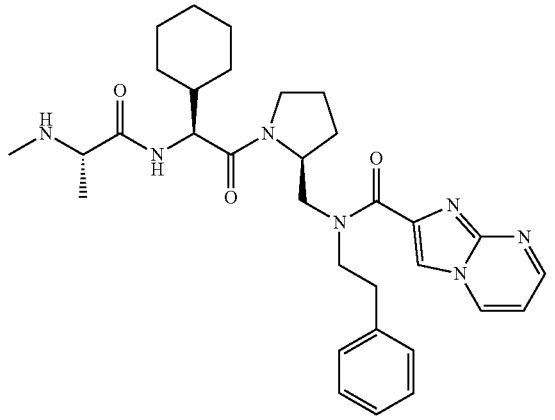 | M + 1 = 574.4 |
| 6 | 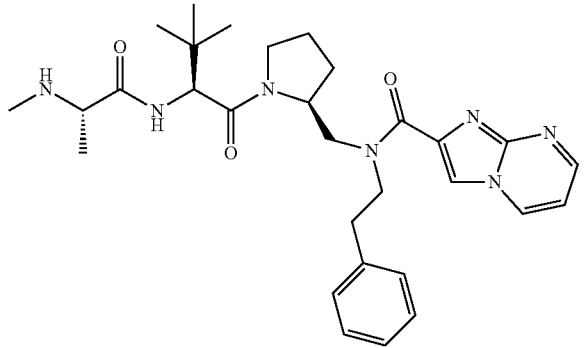 [SMILES: CN[C@@H](C)C(=O)N[C@H](C(=O)N1CCC[C@H]1CN(CCc1ccccc1)C(=O)c1cn2cccnc2n1)C(C)(C)C] | M + 1 = 548.4 |
| 7 | 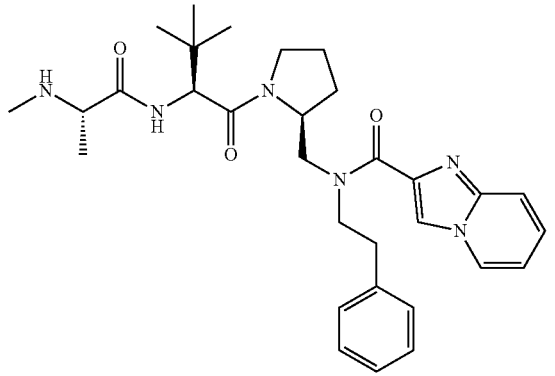 [SMILES: CN[C@@H](C)C(=O)N[C@H](C(=O)N1CCC[C@H]1CN(CCc1ccccc1)C(=O)c1cn2ccccc2n1)C(C)(C)C] | M + 1 = 547.5 |

TABLE 1-continued
| Cmpd # | Structure | MS |
|---|---|---|
| 8 | 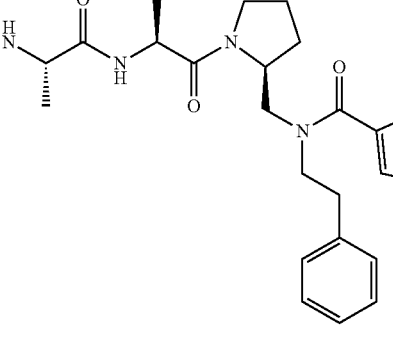 | M + 1 = 546.5 |
| 9 | 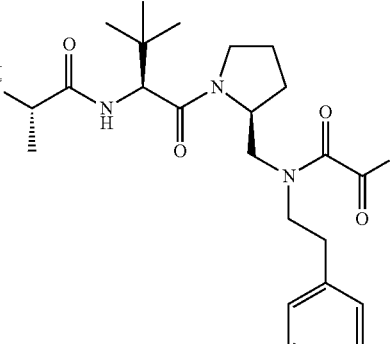 | M + 1 = 550.1 |
| 10 | 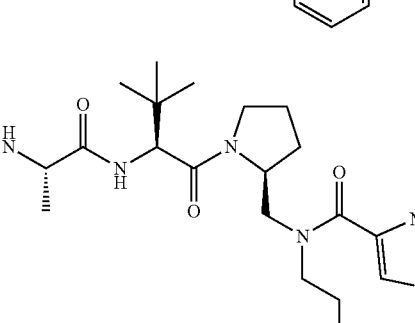 | M + 1 = 566.4 |
| 11 | 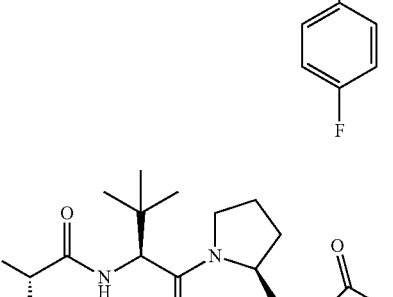 | M + 1 = 566.4 |

TABLE 1-continued

| Cmpd # | Structure | MS |
|---|---|---|
| 12 | 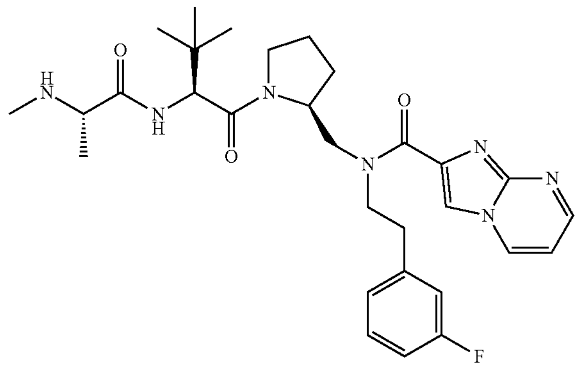 [SMILES: CN[C@@H](C)C(=O)N[C@H](C(=O)N1CCC[C@H]1CN(CCc1cccc(F)c1)C(=O)c1cn2cccnc2n1)C(C)(C)C] | M + 1 = 566.4 |
| 13 | 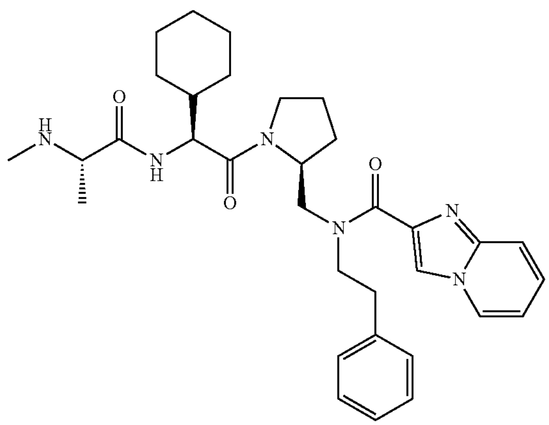 [SMILES: CN[C@@H](C)C(=O)N[C@H](C(=O)N1CCC[C@H]1CN(CCc1ccccc1)C(=O)c1cn2ccccc2n1)C1CCCCC1] | M + 1 = 573.5 |
| 14 | 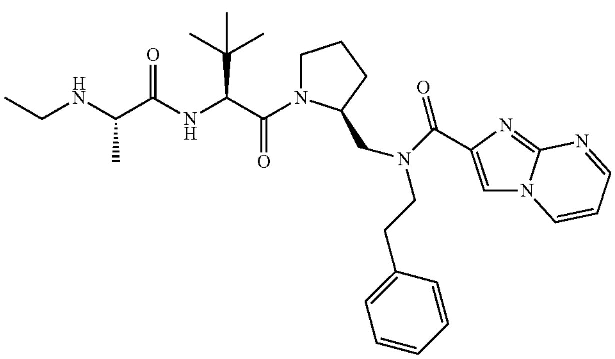 [SMILES: CCN[C@@H](C)C(=O)N[C@H](C(=O)N1CCC[C@H]1CN(CCc1ccccc1)C(=O)c1cn2cccnc2n1)C(C)(C)C] | M + 1 = 562.4 |
| 15 | 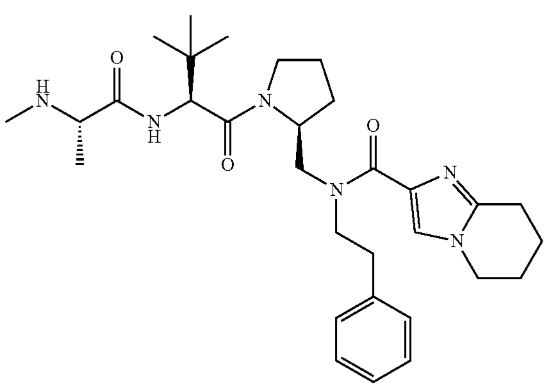 [SMILES: CN[C@@H](C)C(=O)N[C@H](C(=O)N1CCC[C@H]1CN(CCc1ccccc1)C(=O)c1cn2c(n1)CCCC2)C(C)(C)C] | M + 1 = 551.5 |

TABLE 1-continued

| Cmpd # | Structure | MS |
|---|---|---|
| 16 | 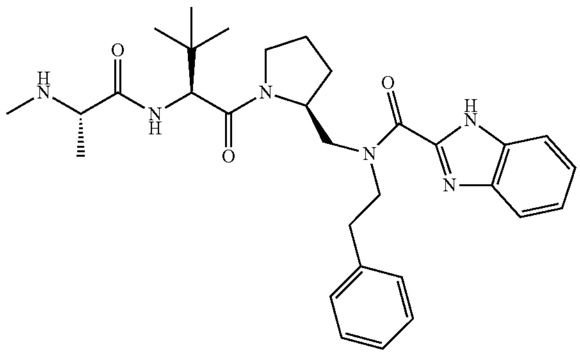 [SMILES: CN[C@@H](C)C(=O)N[C@H](C(=O)N1CCC[C@H]1CN(CCc1ccccc1)C(=O)c1nc2ccccc2[nH]1)C(C)(C)C] | M + 1 = 547.4 |
| 17 | 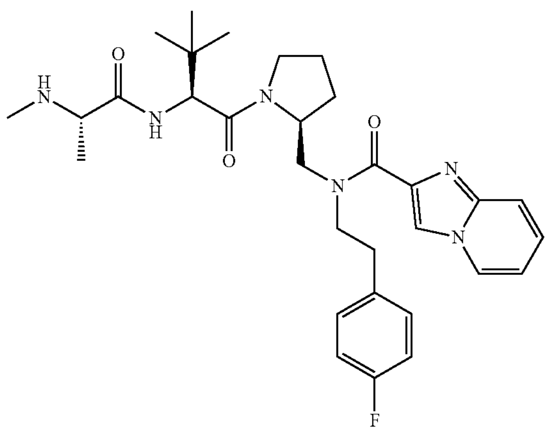 | M + 1 = 565.4 |
| 18 | 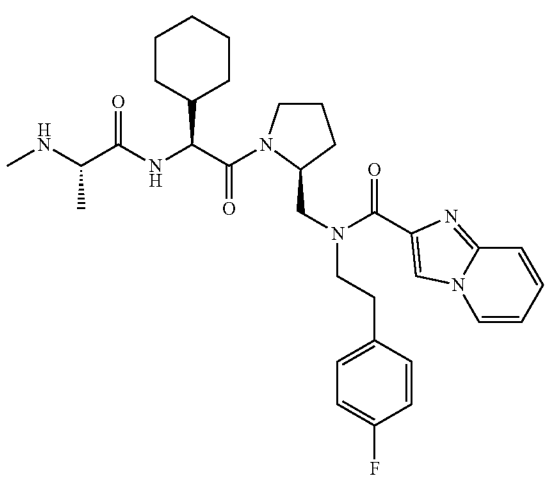 [SMILES: CN[C@@H](C)C(=O)N[C@H](C(=O)N1CCC[C@H]1CN(CCc1ccc(F)cc1)C(=O)c1cn2ccccc2n1)C1CCCCC1] | M + 1 = 591.4 |

TABLE 1-continued

| Cmpd # | Structure | MS |
|---|---|---|
| 19 | 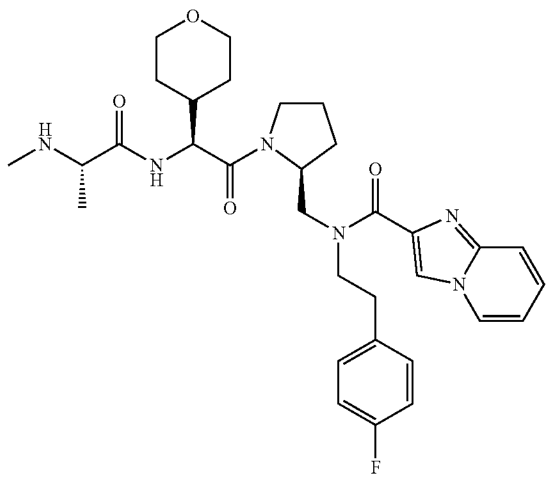 [SMILES: CN[C@@H](C)C(=O)N[C@H](C(=O)N1CCC[C@H]1CN(CCc1ccc(F)cc1)C(=O)c1cn2ccccc2n1)C1CCOCC1] | M + 1 = 593.4 |
| 20 | 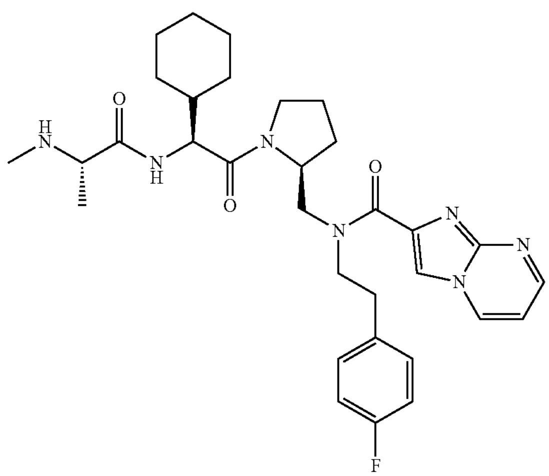 | M + 1 = 592.4 |
| 21 | 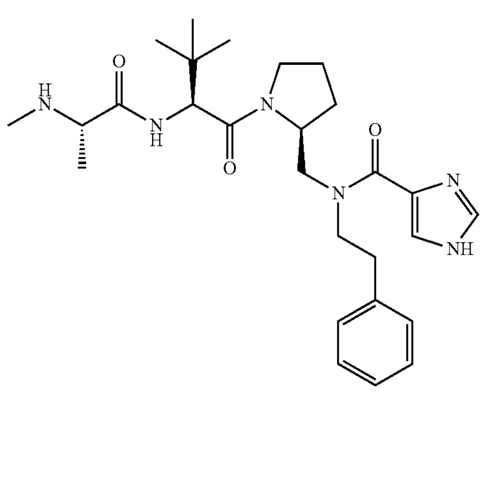 [SMILES: CN[C@@H](C)C(=O)N[C@H](C(=O)N1CCC[C@H]1CN(CCc1ccccc1)C(=O)c1c[nH]cn1)C(C)(C)C] | M + 1 = 497.2 |

TABLE 1-continued

| Cmpd # | Structure | MS |
|---|---|---|
| 22 | 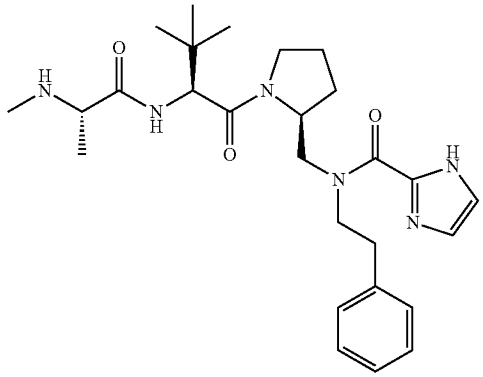 | M + 1 = 497.2 |
| 23 | 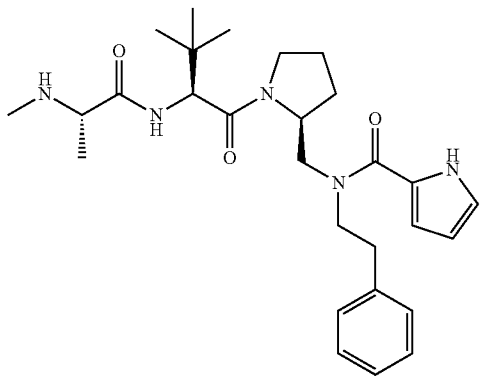 | M + 1 = 496.4 |
| 24 | 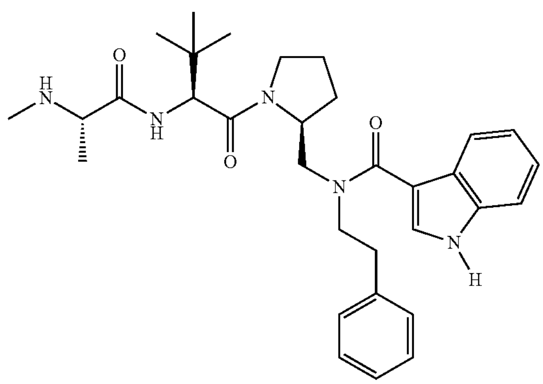 [SMILES: CN[C@@H](C)C(=O)N[C@H](C(=O)N1CCC[C@H]1CN(CCc1ccccc1)C(=O)c1c[nH]c2ccccc12)C(C)(C)C] | M + 1 = 546.2 |
| 25 | 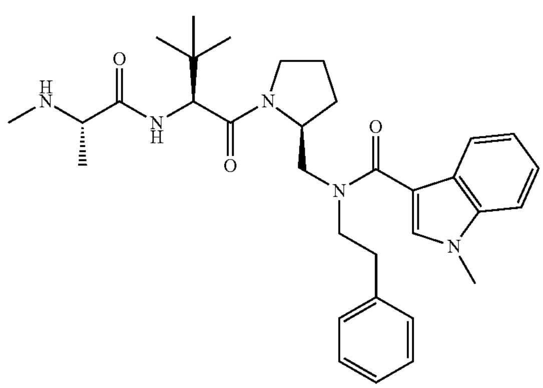 | M + 1 = 560.4 |

TABLE 1-continued

| Cmpd # | Structure | MS |
|---|---|---|
| 26 | 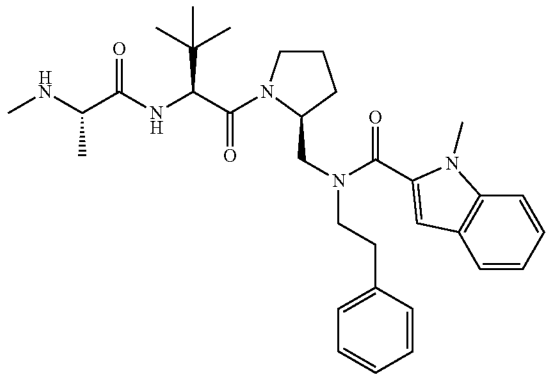 [SMILES: CN[C@@H](C)C(=O)N[C@H](C(=O)N1CCC[C@H]1CN(CCc1ccccc1)C(=O)c1cc2ccccc2n1C)C(C)(C)C] | M + 1 = 560.4 |
| 27 | 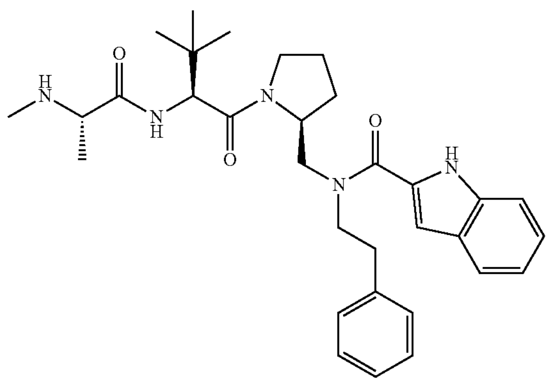 [SMILES: CN[C@@H](C)C(=O)N[C@H](C(=O)N1CCC[C@H]1CN(CCc1ccccc1)C(=O)c1cc2ccccc2[nH]1)C(C)(C)C] | M + 1 = 546.2 |
| 28 | 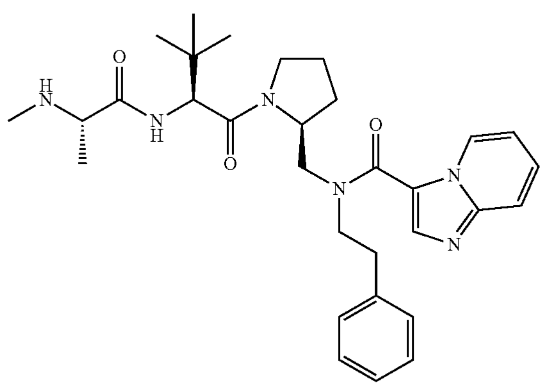 [SMILES: CN[C@@H](C)C(=O)N[C@H](C(=O)N1CCC[C@H]1CN(CCc1ccccc1)C(=O)c1cnc2ccccn12)C(C)(C)C] | M + 1 = 548.5 |
| 29 | 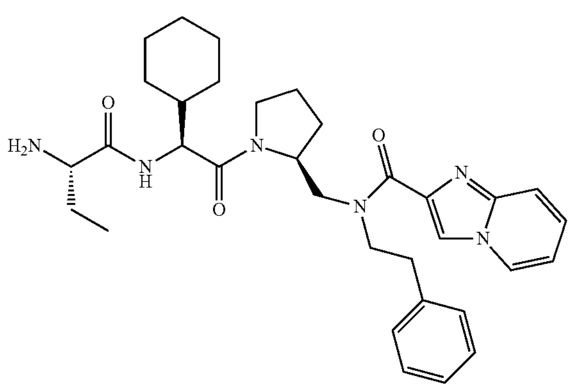 [SMILES: CC[C@H](N)C(=O)N[C@H](C(=O)N1CCC[C@H]1CN(CCc1ccccc1)C(=O)c1cn2ccccc2n1)C1CCCCC1] | M + 1 = 573.4 |

TABLE 1-continued

| Cmpd # | Structure | MS |
|---|---|---|
| 30 | 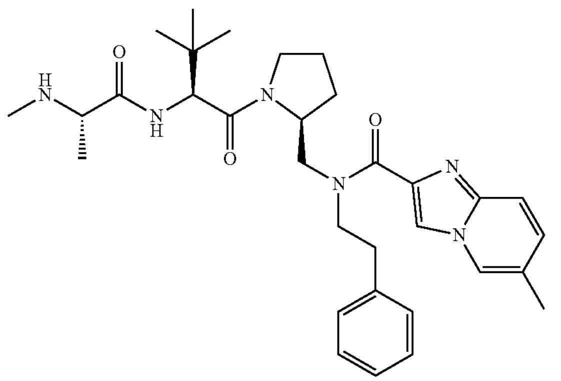 | M + 1 = 561.4 |
| 31 | 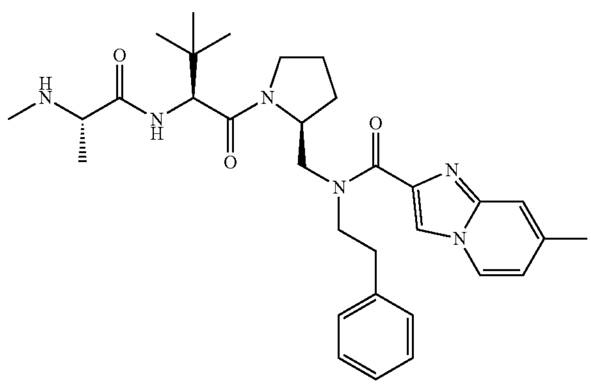 | M + 1 = 561.4 |
| 32 | 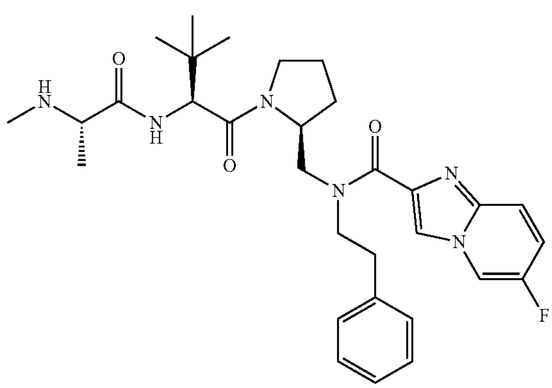 [SMILES: CN[C@@H](C)C(=O)N[C@H](C(=O)N1CCC[C@H]1CN(CCc1ccccc1)C(=O)c1cn2cc(F)ccc2n1)C(C)(C)C] | M + 1 = 565.4 |
| 33 | 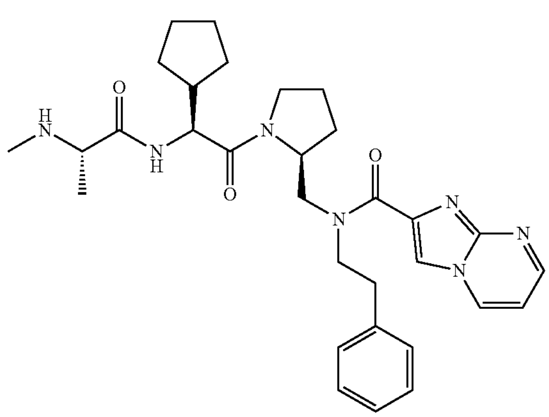 [SMILES: CN[C@@H](C)C(=O)N[C@H](C(=O)N1CCC[C@H]1CN(CCc1ccccc1)C(=O)c1cn2cccnc2n1)C1CCCC1] | M + 1 = 560.4 |

TABLE 1-continued

| Cmpd # | Structure | MS |
|---|---|---|
| 34 | 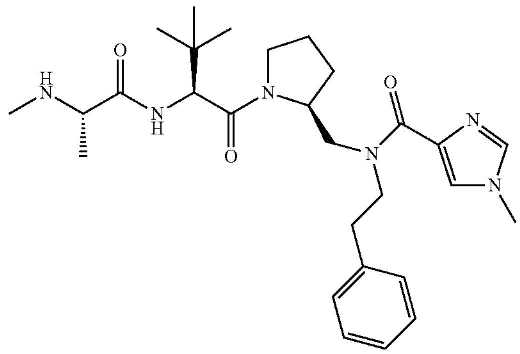 | M + 1 = 511.4 |
| 35 | 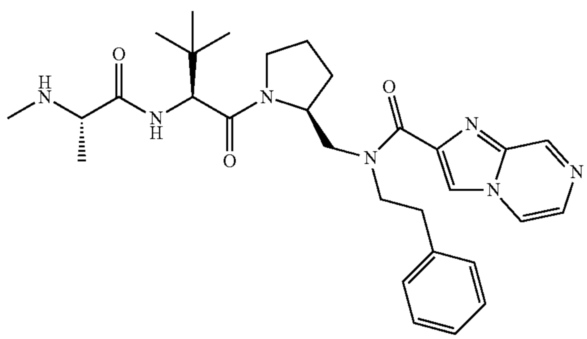 [SMILES: CN[C@@H](C)C(=O)N[C@H](C(=O)N1CCC[C@H]1CN(CCc1ccccc1)C(=O)c1cn2ccncc2n1)C(C)(C)C] | M + 1 = 548.5 |
| 36 | 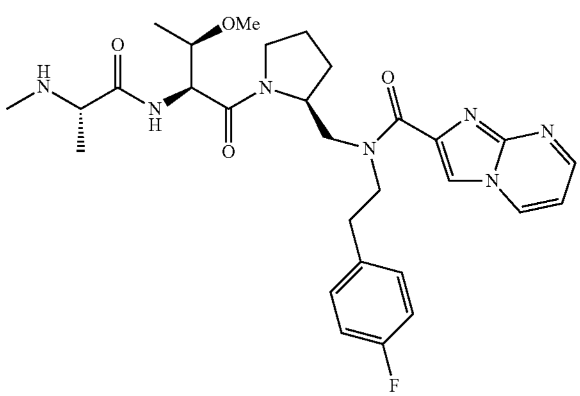 [SMILES: CN[C@@H](C)C(=O)N[C@H](C(=O)N1CCC[C@H]1CN(CCc1ccc(F)cc1)C(=O)c1cn2cccnc2n1)[C@@H](C)OC] | M + 1 = 568.5 |
| 37 | 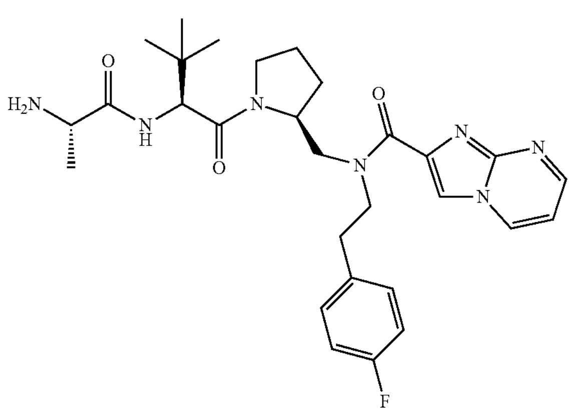 [SMILES: C[C@H](N)C(=O)N[C@H](C(=O)N1CCC[C@H]1CN(CCc1ccc(F)cc1)C(=O)c1cn2cccnc2n1)C(C)(C)C] | M + 1 = 552.5 |

TABLE 1-continued

| Cmpd # | Structure | MS |
|---|---|---|
| 38 | 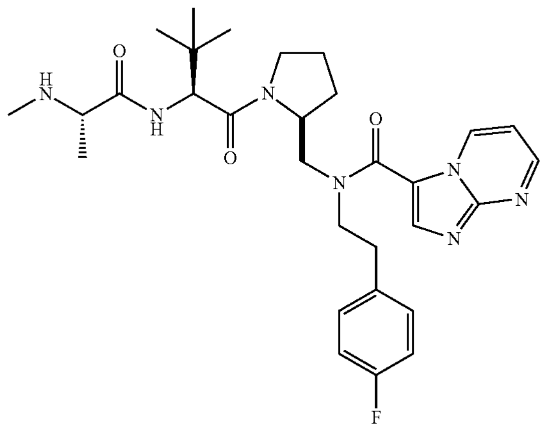 [SMILES: CN[C@@H](C)C(=O)N[C@H](C(=O)N1CCC[C@H]1CN(CCc1ccc(F)cc1)C(=O)c1cnc2ncccn12)C(C)(C)C] | M + 1 = 566.5 |
| 39 | 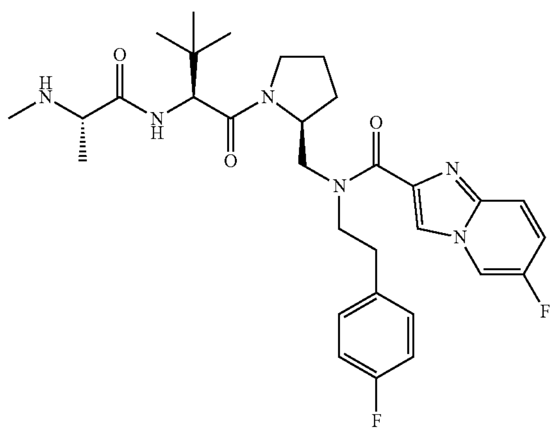 [SMILES: CN[C@@H](C)C(=O)N[C@H](C(=O)N1CCC[C@H]1CN(CCc1ccc(F)cc1)C(=O)c1cn2cc(F)ccc2n1)C(C)(C)C] | M + 1 = 583.4 |
| 40 | 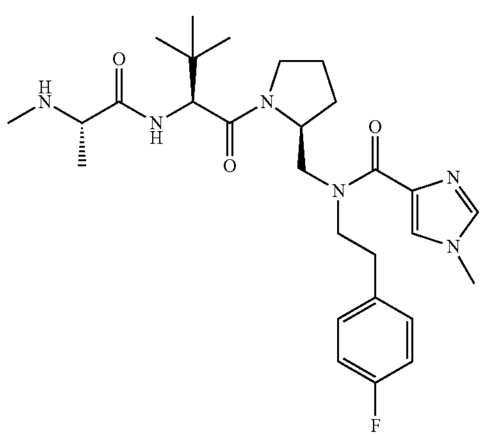 [SMILES: CN[C@@H](C)C(=O)N[C@H](C(=O)N1CCC[C@H]1CN(CCc1ccc(F)cc1)C(=O)c1cn(C)cn1)C(C)(C)C] | M + 1 = 529.5 |

TABLE 1-continued

| Cmpd # | Structure | MS |
|---|---|---|
| 41 | 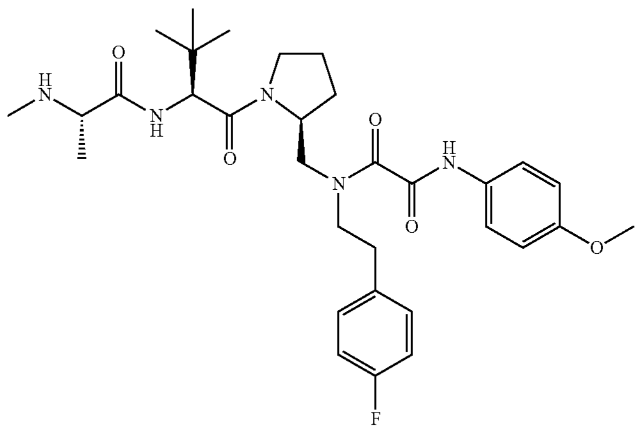 | M + 1 = 598.5 |
| 42 | 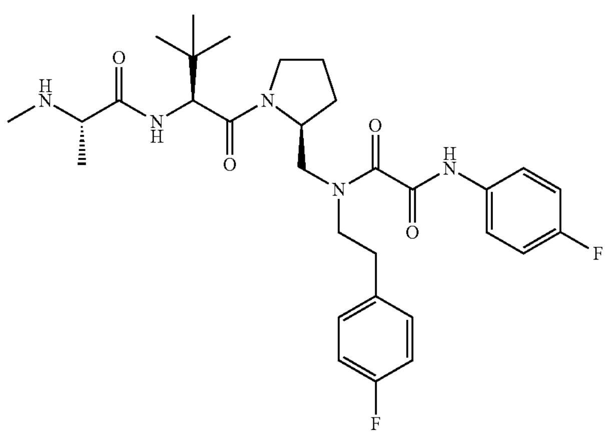 [SMILES: CN[C@@H](C)C(=O)N[C@H](C(=O)N1CCC[C@H]1CN(CCc1ccc(F)cc1)C(=O)C(=O)Nc1ccc(F)cc1)C(C)(C)C] | M + 1 = 586.5 |
| 43 | 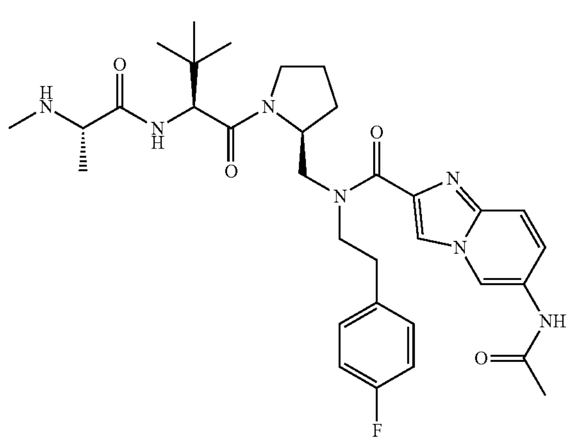 [SMILES: CN[C@@H](C)C(=O)N[C@H](C(=O)N1CCC[C@H]1CN(CCc1ccc(F)cc1)C(=O)c1cn2cc(NC(C)=O)ccc2n1)C(C)(C)C] | M + 1 = 622.6 |

TABLE 1-continued

| Cmpd # | Structure | MS |
|---|---|---|
| 44 | 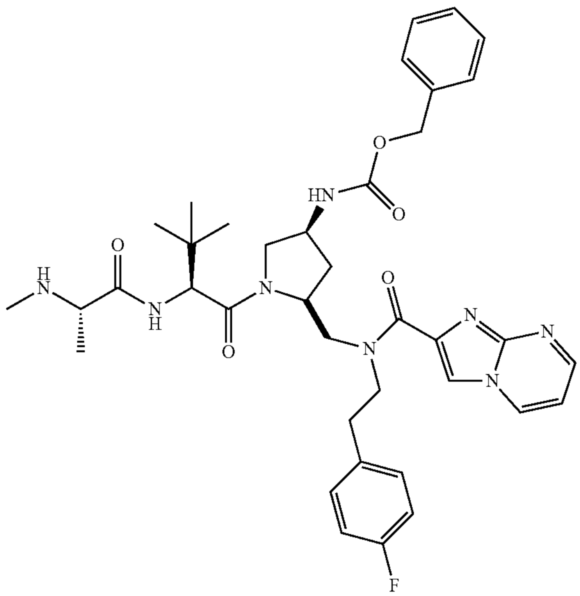 [SMILES: CN[C@@H](C)C(=O)N[C@H](C(=O)N1C[C@@H](NC(=O)OCc2ccccc2)C[C@H]1CN(CCc1ccc(F)cc1)C(=O)c1cn2cccnc2n1)C(C)(C)C] | M + 1 = 715.5 |
| 45 | 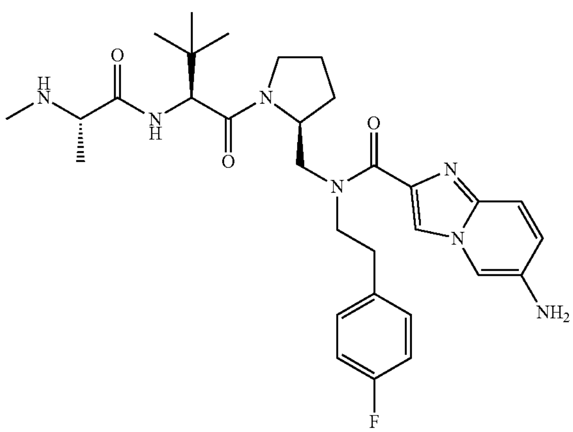 [SMILES: CN[C@@H](C)C(=O)N[C@H](C(=O)N1CCC[C@H]1CN(CCc1ccc(F)cc1)C(=O)c1cn2cc(N)ccc2n1)C(C)(C)C] | M + 1 = 580.5 |
| 46 | 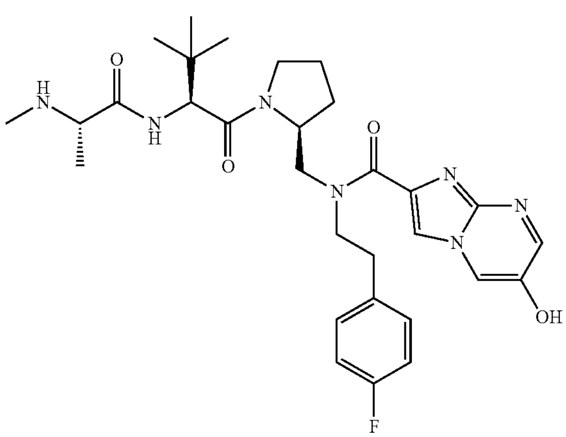 [SMILES: CN[C@@H](C)C(=O)N[C@H](C(=O)N1CCC[C@H]1CN(CCc1ccc(F)cc1)C(=O)c1cn2cc(O)cnc2n1)C(C)(C)C] | M + 1 = 582.5 |

TABLE 1-continued

| Cmpd # | Structure | MS |
|---|---|---|
| 47 | 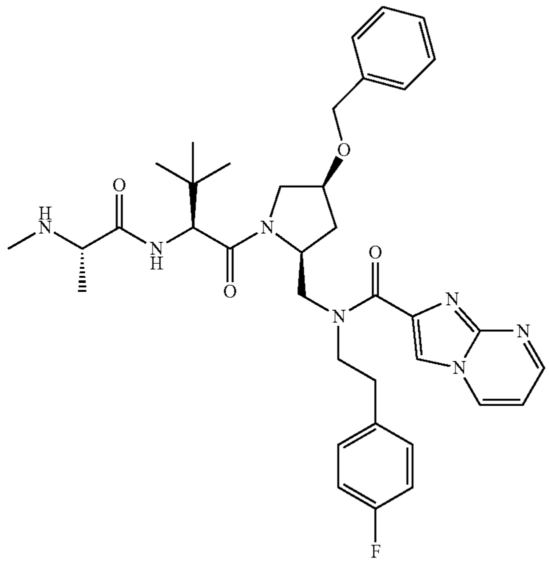 [SMILES: CN[C@@H](C)C(=O)N[C@H](C(=O)N1C[C@@H](OCc2ccccc2)C[C@H]1CN(CCc1ccc(F)cc1)C(=O)c1cn2cccnc2n1)C(C)(C)C] | M + 1 = 672.5 |
| 48 | 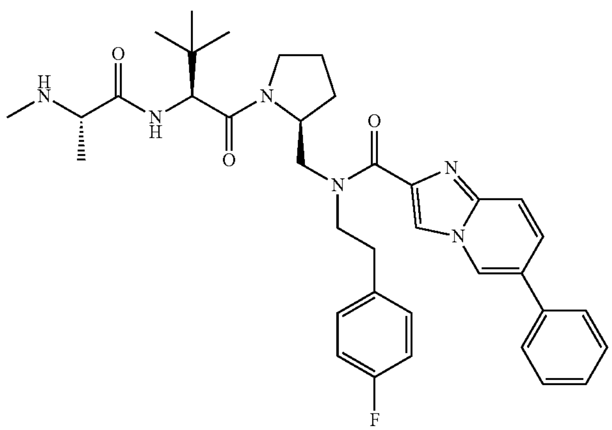 [SMILES: CN[C@@H](C)C(=O)N[C@H](C(=O)N1CCC[C@H]1CN(CCc1ccc(F)cc1)C(=O)c1cn2cc(-c3ccccc3)ccc2n1)C(C)(C)C] | M + 1 = 641.5 |
| 49 | 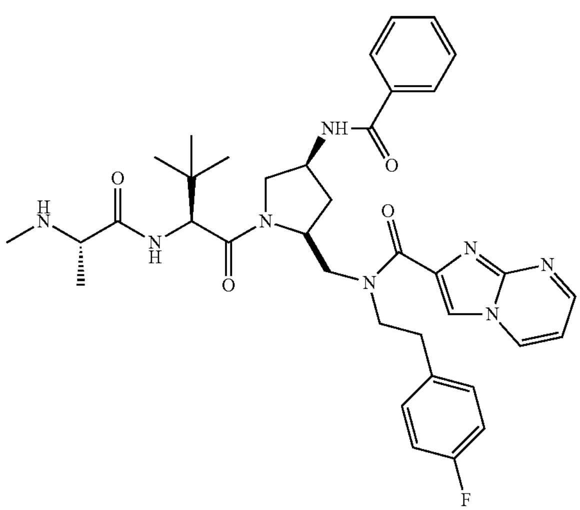 [SMILES: CN[C@@H](C)C(=O)N[C@H](C(=O)N1C[C@@H](NC(=O)c2ccccc2)C[C@H]1CN(CCc1ccc(F)cc1)C(=O)c1cn2cccnc2n1)C(C)(C)C] | M + 1 = 685.5 |

TABLE 1-continued

| Cmpd # | Structure | MS |
|---|---|---|
| 50 | 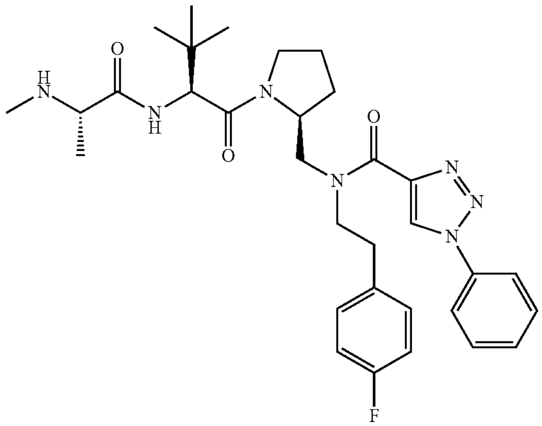 [SMILES: CN[C@@H](C)C(=O)N[C@H](C(=O)N1CCC[C@H]1CN(CCc1ccc(F)cc1)C(=O)c1cn(-c2ccccc2)nn1)C(C)(C)C] | M + 1 = 592.5 |
| 51 | 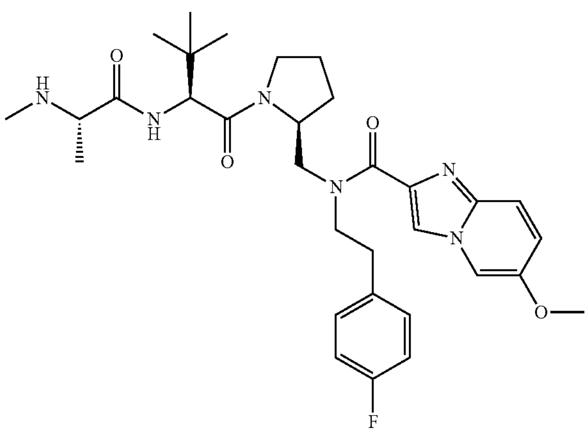 | M + 1 = 595.5 |
| 52 | 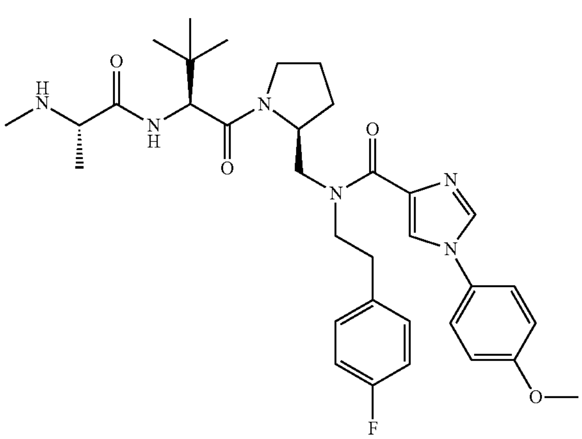 | M + 1 = 621.5 |

TABLE 1-continued

| Cmpd # | Structure | MS |
|---|---|---|
| 53 | 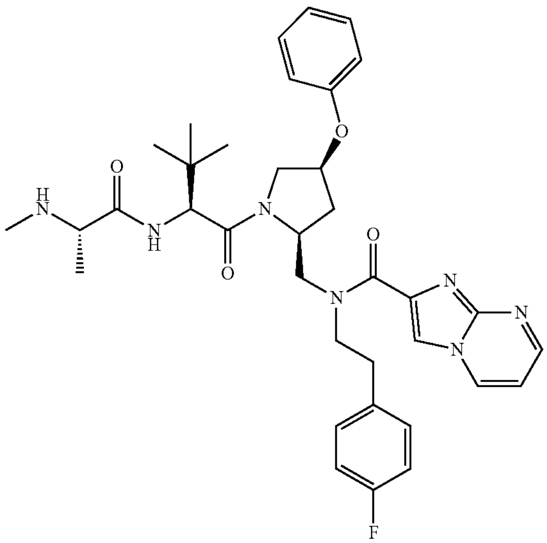 [SMILES: CN[C@@H](C)C(=O)N[C@H](C(=O)N1C[C@@H](Oc2ccccc2)C[C@H]1CN(CCc1ccc(F)cc1)C(=O)c1cn2cccnc2n1)C(C)(C)C] | M + 1 = 658.5 |
| 54 | 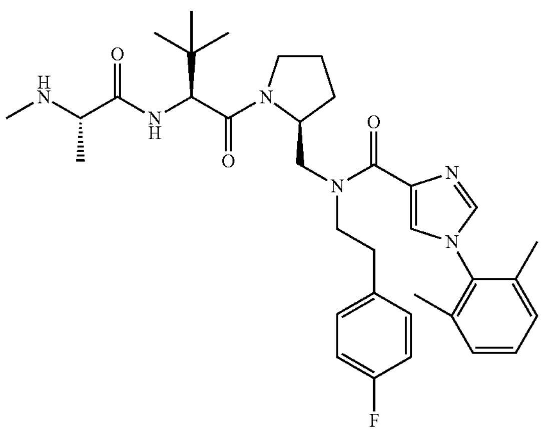 | M + 1 = 619.6 |
| 55 | 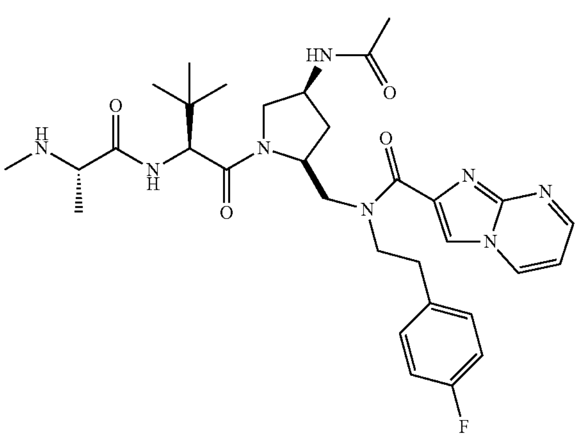 [SMILES: CN[C@@H](C)C(=O)N[C@H](C(=O)N1C[C@@H](NC(C)=O)C[C@H]1CN(CCc1ccc(F)cc1)C(=O)c1cn2cccnc2n1)C(C)(C)C] | M + 1 = 623.5 |

TABLE 1-continued

| Cmpd # | Structure | MS |
|---|---|---|
| 56 | 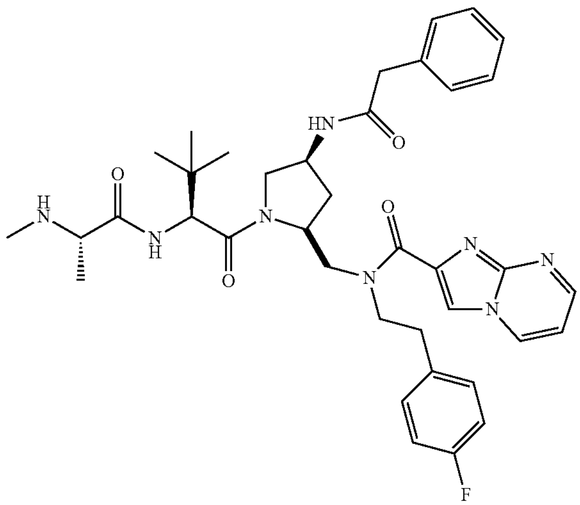 [SMILES: CN[C@@H](C)C(=O)N[C@H](C(=O)N1C[C@@H](NC(=O)Cc2ccccc2)C[C@H]1CN(CCc1ccc(F)cc1)C(=O)c1cn2cccnc2n1)C(C)(C)C] | M + 1 = 699.5 |
| 57 | 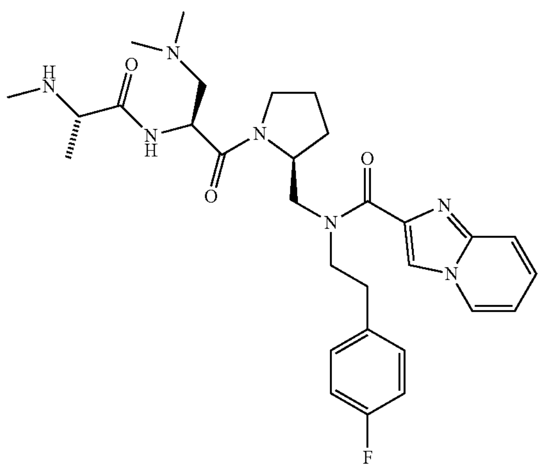 [SMILES: CN[C@@H](C)C(=O)N[C@@H](CN(C)C)C(=O)N1CCC[C@H]1CN(CCc1ccc(F)cc1)C(=O)c1cn2ccccc2n1] | M + 1 = 566.6 |
| 58 | 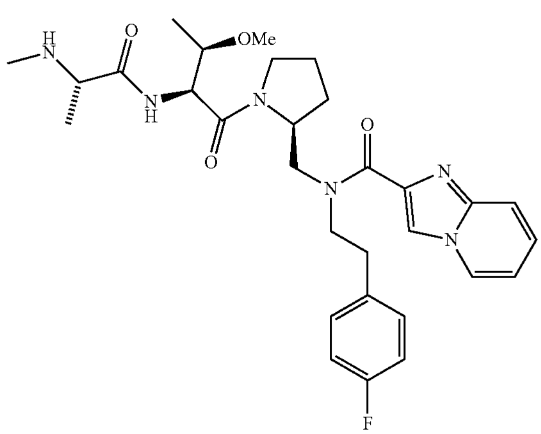 [SMILES: CN[C@@H](C)C(=O)N[C@H](C(=O)N1CCC[C@H]1CN(CCc1ccc(F)cc1)C(=O)c1cn2ccccc2n1)[C@@H](C)OC] | M + 1 = 567.5 |

TABLE 1-continued

| Cmpd # | Structure | MS |
|---|---|---|
| 59 | 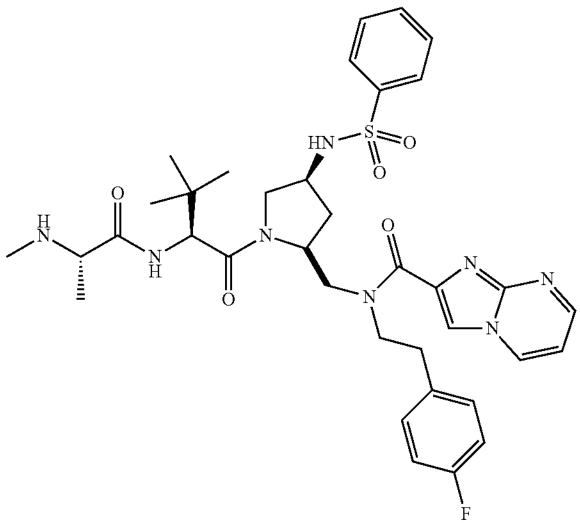 [SMILES: CN[C@@H](C)C(=O)N[C@H](C(=O)N1C[C@@H](NS(=O)(=O)c2ccccc2)C[C@H]1CN(CCc1ccc(F)cc1)C(=O)c1cn2cccnc2n1)C(C)(C)C] | M + 1 = 721.5 |
| 60 | 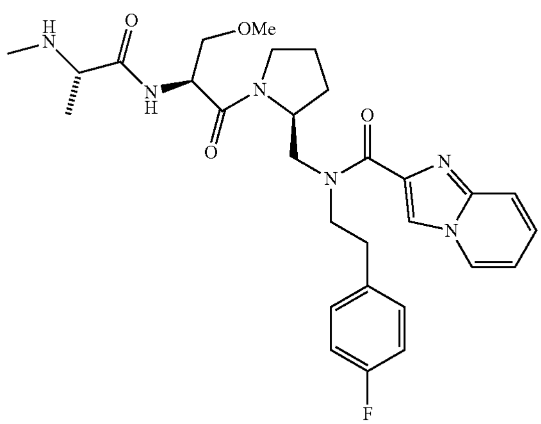 [SMILES: CN[C@@H](C)C(=O)N[C@@H](COC)C(=O)N1CCC[C@H]1CN(CCc1ccc(F)cc1)C(=O)c1cn2ccccc2n1] | M + 1 = 553.5 |
| 61 | 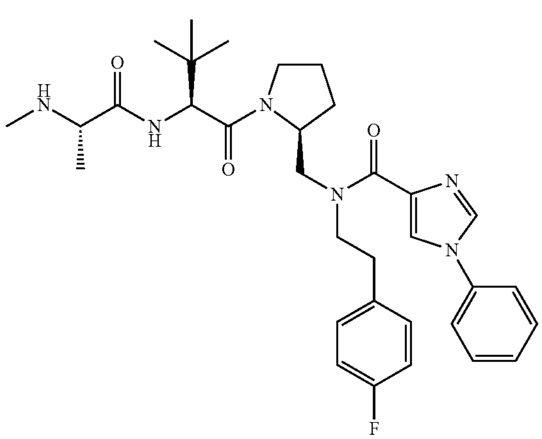 [SMILES: CN[C@@H](C)C(=O)N[C@H](C(=O)N1CCC[C@H]1CN(CCc1ccc(F)cc1)C(=O)c1cn(-c2ccccc2)cn1)C(C)(C)C] | M + 1 = 591.5 |

TABLE 1-continued
| Cmpd # | Structure | MS |
|---|---|---|
| 62 | 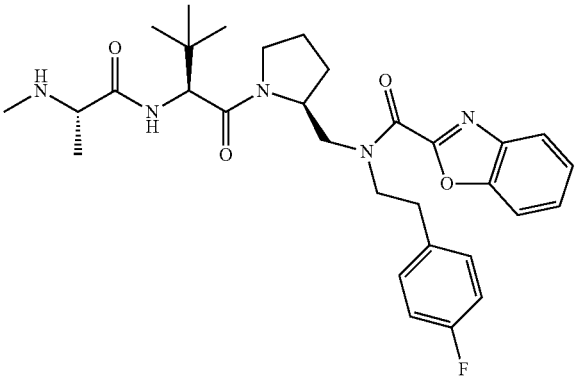 [SMILES: CN[C@@H](C)C(=O)N[C@H](C(=O)N1CCC[C@H]1CN(CCc1ccc(F)cc1)C(=O)c1nc2ccccc2o1)C(C)(C)C] | M + 1 = 566.5 |
| 63 | 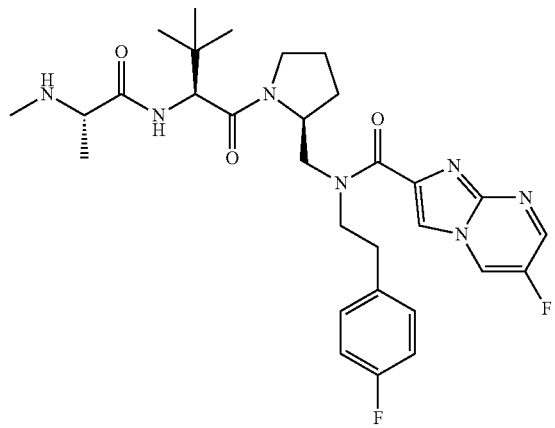 | M + 1 = 584.5 |
| 64 | 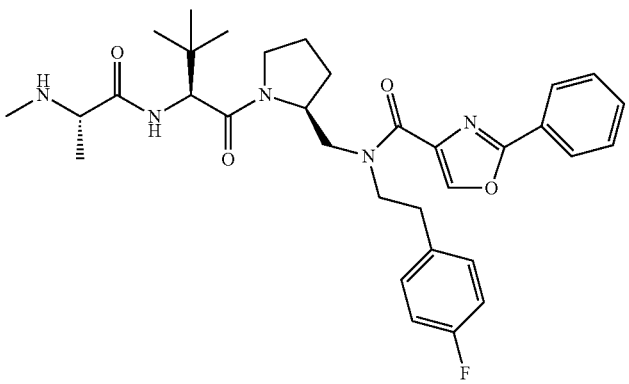 [SMILES: CN[C@@H](C)C(=O)N[C@H](C(=O)N1CCC[C@H]1CN(CCc1ccc(F)cc1)C(=O)c1coc(-c2ccccc2)n1)C(C)(C)C] | M + 1 = 592.5 |

TABLE 1-continued
| Cmpd # | Structure | MS |
|---|---|---|
| 65 | 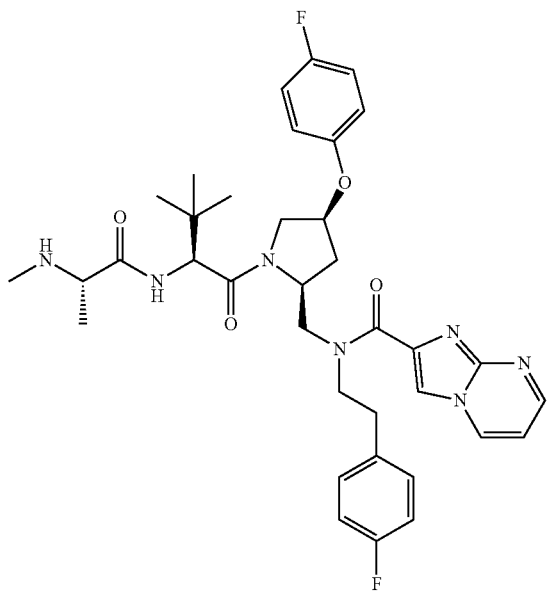 | M + 1 = 676.6 |
| 66 | 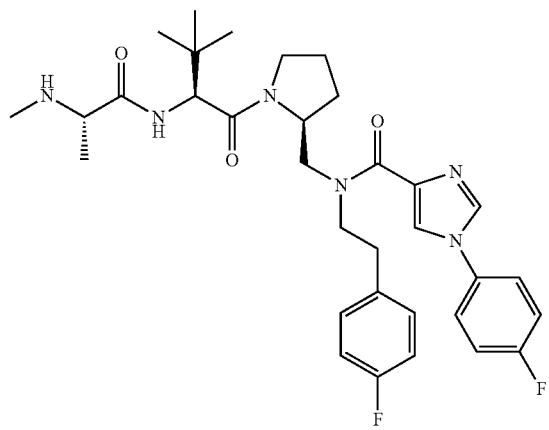 [SMILES: CN[C@@H](C)C(=O)N[C@H](C(=O)N1CCC[C@H]1CN(CCc1ccc(F)cc1)C(=O)c1cn(-c2ccc(F)cc2)cn1)C(C)(C)C] | M + 1 = 609.5 |
| 67 | 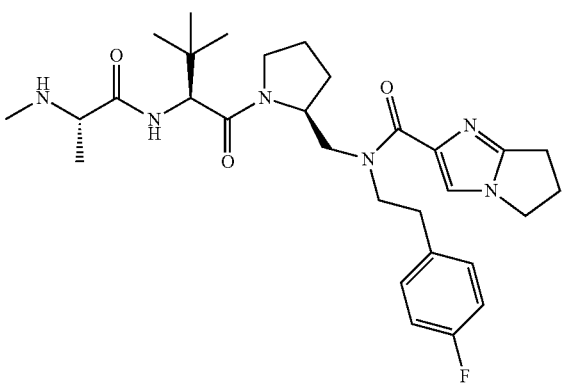 [SMILES: CN[C@@H](C)C(=O)N[C@H](C(=O)N1CCC[C@H]1CN(CCc1ccc(F)cc1)C(=O)c1cn2c(n1)CCC2)C(C)(C)C] | M + 1 = 555.6 |

TABLE 1-continued
| Cmpd # | Structure | MS |
|---|---|---|
| 68 | 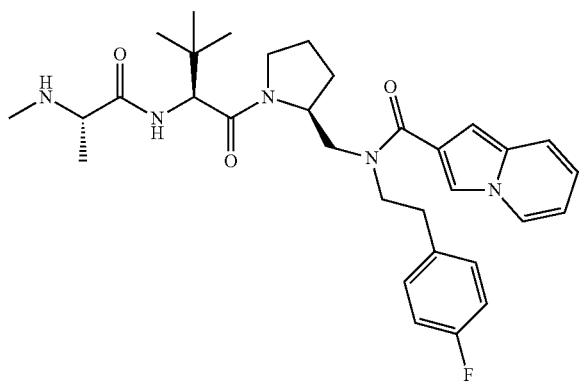 [SMILES: CN[C@@H](C)C(=O)N[C@H](C(=O)N1CCC[C@H]1CN(CCc1ccc(F)cc1)C(=O)c1cc2ccccn2c1)C(C)(C)C] | M + 1 = 564.5 |
| 69 | 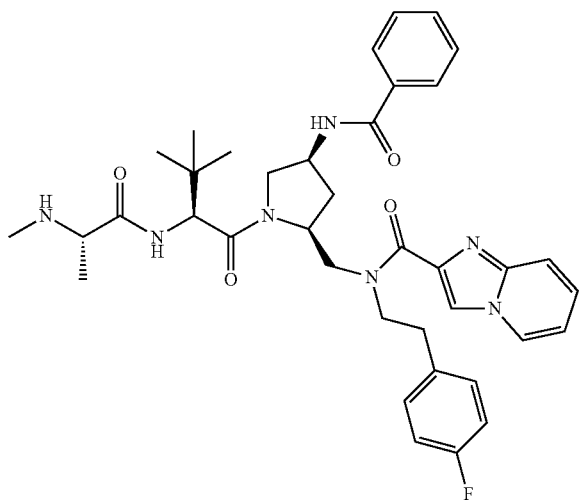 [SMILES: CN[C@@H](C)C(=O)N[C@H](C(=O)N1C[C@@H](NC(=O)c2ccccc2)C[C@H]1CN(CCc1ccc(F)cc1)C(=O)c1cn2ccccc2n1)C(C)(C)C] | M + 1 = 684.5 |
| 70 | 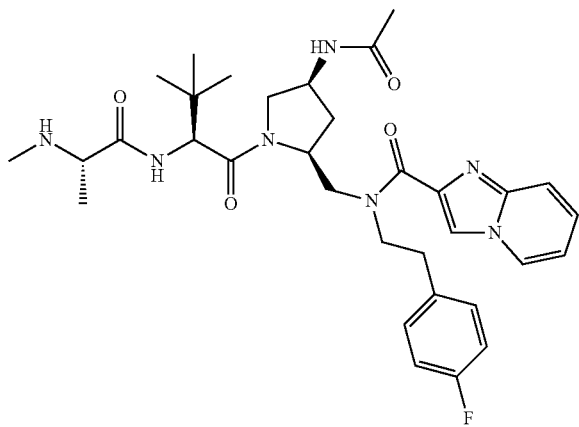 [SMILES: CN[C@@H](C)C(=O)N[C@H](C(=O)N1C[C@@H](NC(C)=O)C[C@H]1CN(CCc1ccc(F)cc1)C(=O)c1cn2ccccc2n1)C(C)(C)C] | M + 1 = 622.5 |

TABLE 1-continued

| Cmpd # | Structure | MS |
|---|---|---|
| 71 | 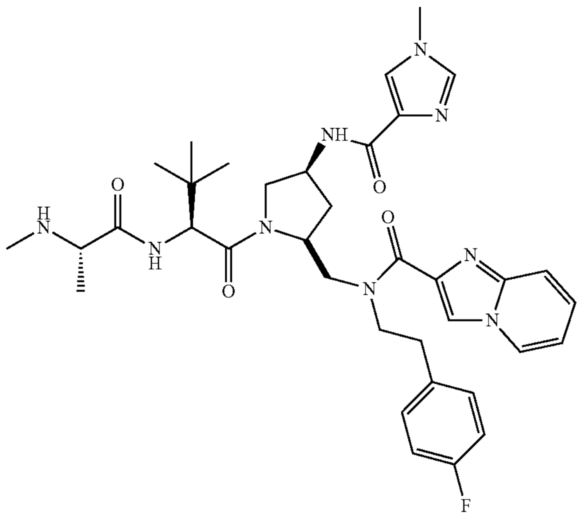 | M + 1 = 668.5 |
| 72 | 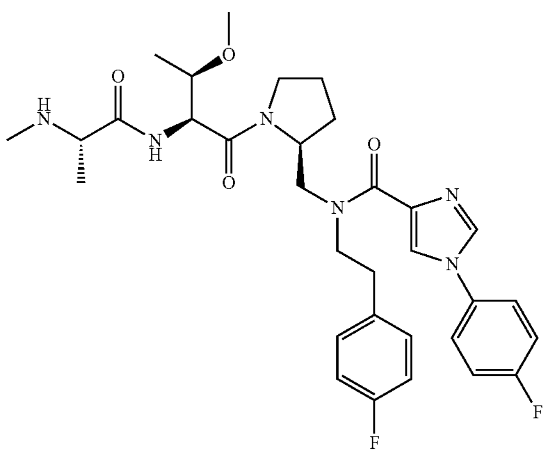 [SMILES: CN[C@@H](C)C(=O)N[C@H](C(=O)N1CCC[C@H]1CN(CCc1ccc(F)cc1)C(=O)c1cn(-c2ccc(F)cc2)cn1)[C@@H](C)OC] | M + 1 = 611.5 |
| 73 | 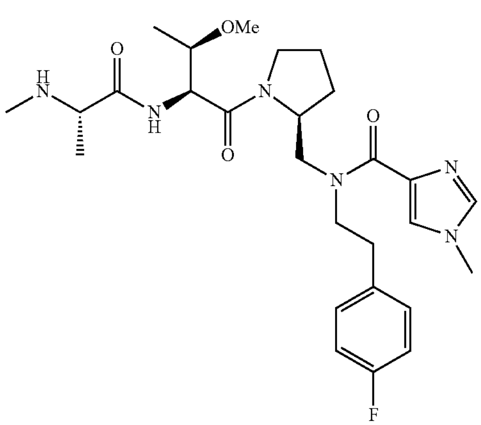 | M + 1 = 531.5 |

TABLE 1-continued
| Cmpd # | Structure | MS |
|---|---|---|
| 74 | 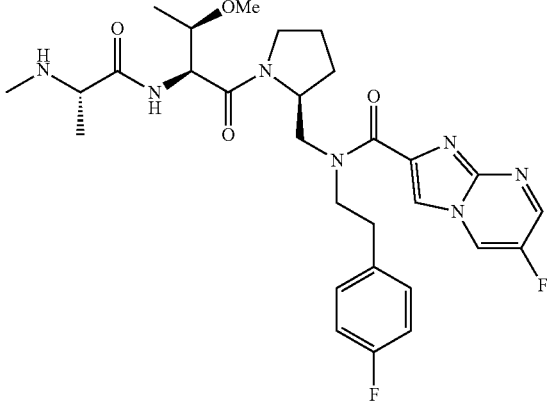 | M + 1 = 586.4 |
| 75 | 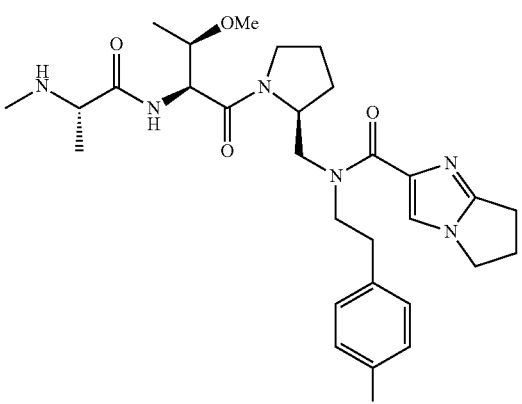 | M + 1 = 557.5 |
| 76 | 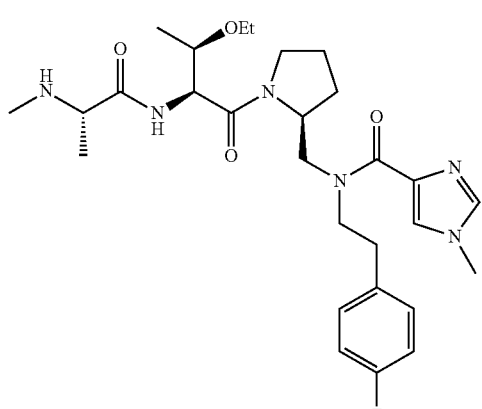 | M + 1 = 545.5 |

TABLE 1-continued
| Cmpd # | Structure | MS |
|---|---|---|
| 77 | 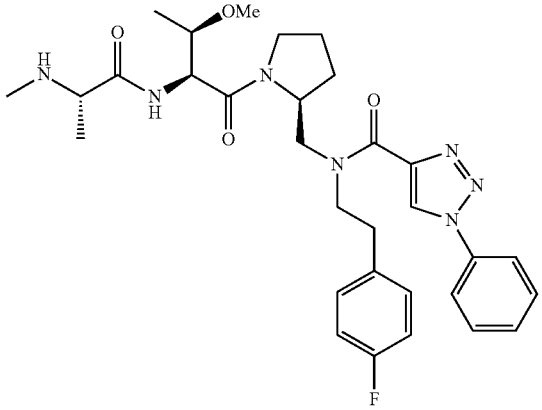 [SMILES: CN[C@@H](C)C(=O)N[C@H](C(=O)N1CCC[C@H]1CN(CCc1ccc(F)cc1)C(=O)c1cn(-c2ccccc2)nn1)[C@@H](C)OC] | M + 1 = 594.4 |
| 78 | 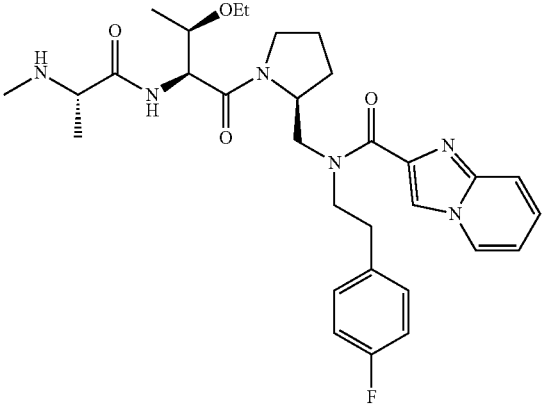 [SMILES: CCO[C@H](C)[C@H](NC(=O)[C@H](C)NC)C(=O)N1CCC[C@H]1CN(CCc1ccc(F)cc1)C(=O)c1cn2ccccc2n1] | M + 1 = 581.4 |
| 79 | 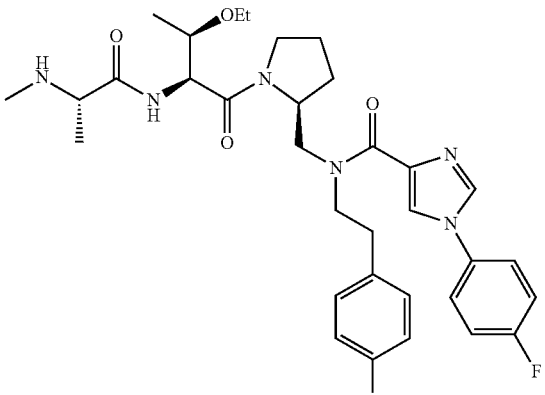 | M + 1 = 625.5 |

TABLE 1-continued
| Cmpd # | Structure | MS |
|---|---|---|
| 80 | 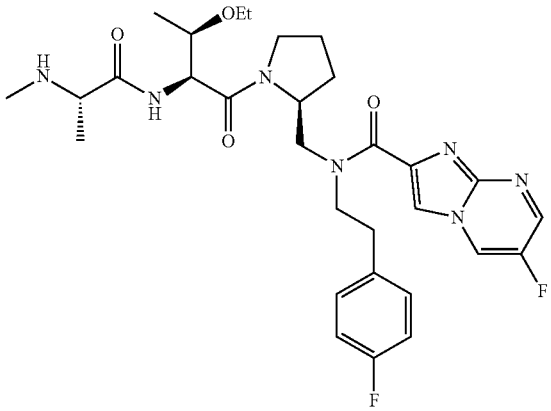 [SMILES: CCO[C@H](C)[C@H](NC(=O)[C@H](C)NC)C(=O)N1CCC[C@H]1CN(CCc1ccc(F)cc1)C(=O)c1cn2cc(F)cnc2n1] | M + 1 = 600.5 |
| 81 | 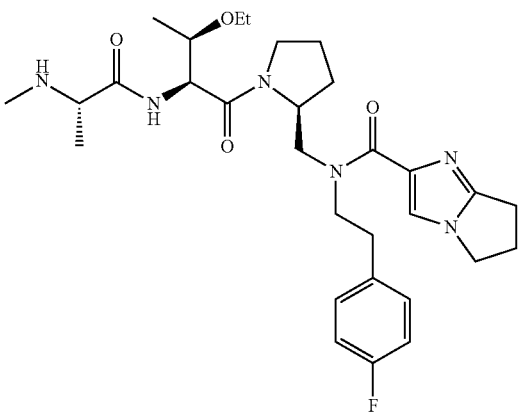 [SMILES: CCO[C@H](C)[C@H](NC(=O)[C@H](C)NC)C(=O)N1CCC[C@H]1CN(CCc1ccc(F)cc1)C(=O)c1cn2c(n1)CCC2] | M + 1 = 571.5 |
| 82 | 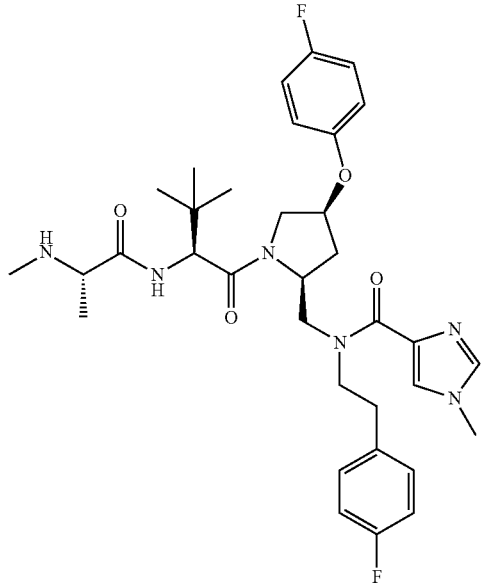 [SMILES: CN[C@@H](C)C(=O)N[C@H](C(=O)N1C[C@@H](Oc2ccc(F)cc2)C[C@H]1CN(CCc1ccc(F)cc1)C(=O)c1cn(C)cn1)C(C)(C)C] | M + 1 = 639.5 |

TABLE 1-continued
| Cmpd # | Structure | MS |
|---|---|---|
| 83 | 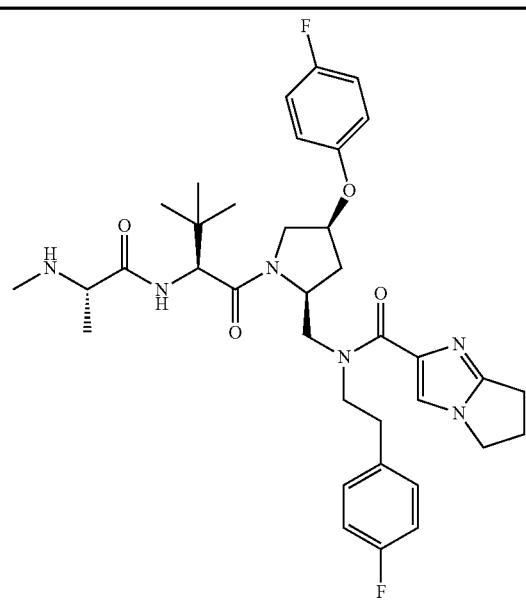 | M + 1 = 665.5 |
| 84 | 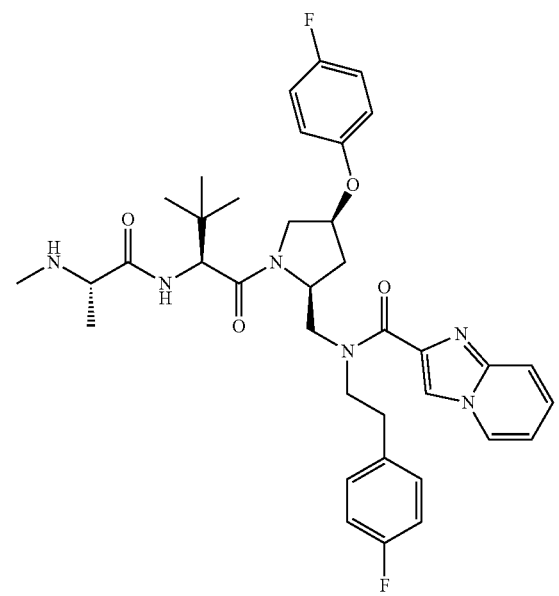 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2ccccc2n1)C(C)(C)C] | M + 1 = 675.5 |
| 85 | 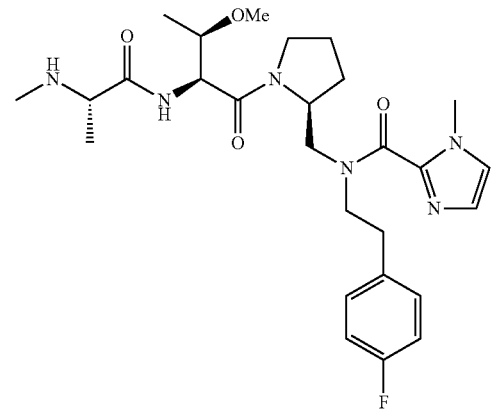 [SMILES: CN[C@@H](C)C(=O)N[C@H](C(=O)N1CCC[C@H]1CN(CCc1ccc(F)cc1)C(=O)c1nccn1C)[C@@H](C)OC] | M + 1 = 531.5 |

TABLE 1-continued

| Cmpd # | Structure | MS |
|---|---|---|
| 86 | 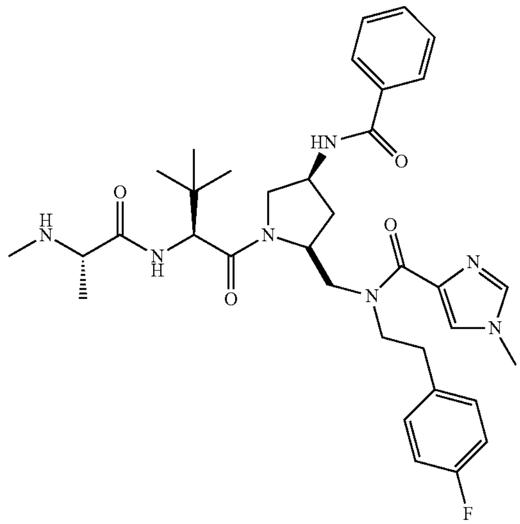 | M + 1 = 648.5 |
| 87 | 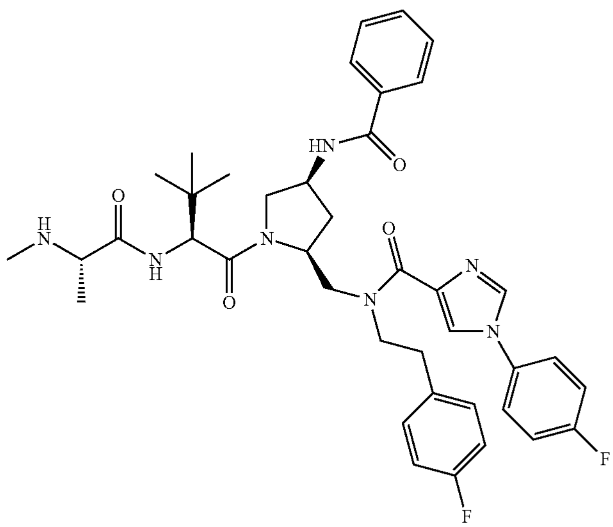 [SMILES: CN[C@@H](C)C(=O)N[C@H](C(=O)N1C[C@@H](NC(=O)c2ccccc2)C[C@H]1CN(CCc1ccc(F)cc1)C(=O)c1cn(-c2ccc(F)cc2)cn1)C(C)(C)C] | M + 1 = 728.5 |
| 88 | 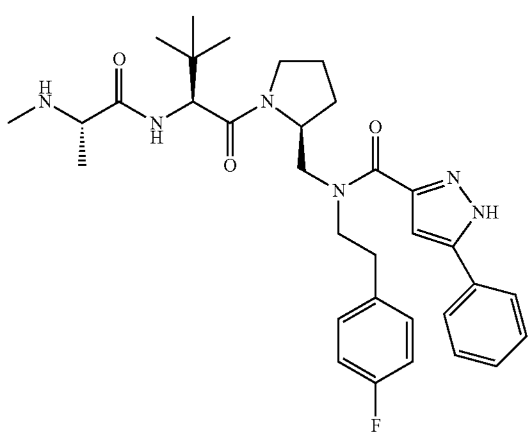 | M + 1 = 591.4 |

TABLE 1-continued

| Cmpd # | Structure | MS |
|---|---|---|
| 89 | 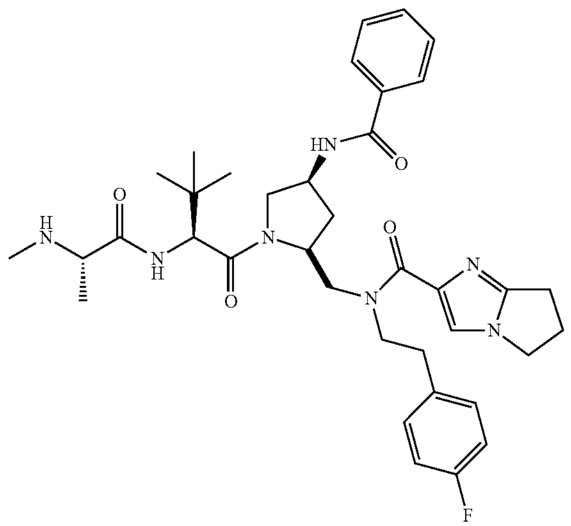 [SMILES: CN[C@@H](C)C(=O)N[C@H](C(=O)N1C[C@@H](NC(=O)c2ccccc2)C[C@H]1CN(CCc1ccc(F)cc1)C(=O)c1cn2c(n1)CCC2)C(C)(C)C] | M + 1 = 674.5 |
| 90 | 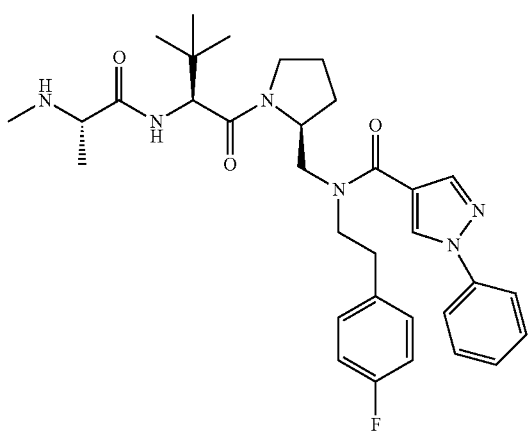 [SMILES: CN[C@@H](C)C(=O)N[C@H](C(=O)N1CCC[C@H]1CN(CCc1ccc(F)cc1)C(=O)c1cnn(-c2ccccc2)c1)C(C)(C)C] | M + 1 = 591.4 |
| 91 | 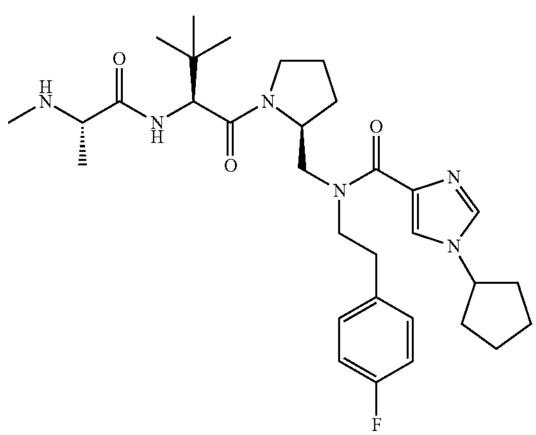 [SMILES: CN[C@@H](C)C(=O)N[C@H](C(=O)N1CCC[C@H]1CN(CCc1ccc(F)cc1)C(=O)c1cn(C2CCCC2)cn1)C(C)(C)C] | M + 1 = 583.5 |

TABLE 1-continued

| Cmpd # | Structure | MS |
|---|---|---|
| 92 | 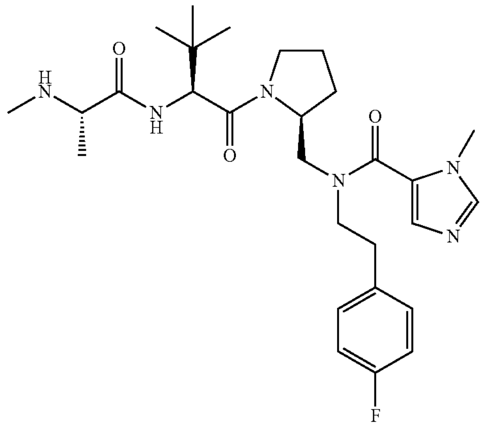 [SMILES: CN[C@@H](C)C(=O)N[C@H](C(=O)N1CCC[C@H]1CN(CCc1ccc(F)cc1)C(=O)c1cncn1C)C(C)(C)C] | M + 1 = 529.4 |
| 93 | 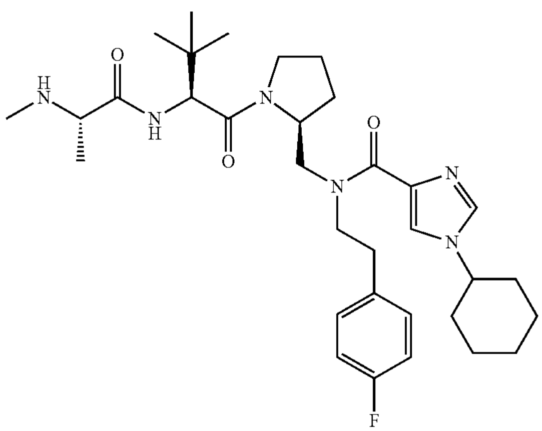 | M + 1 = 597.4 |
| 94 | 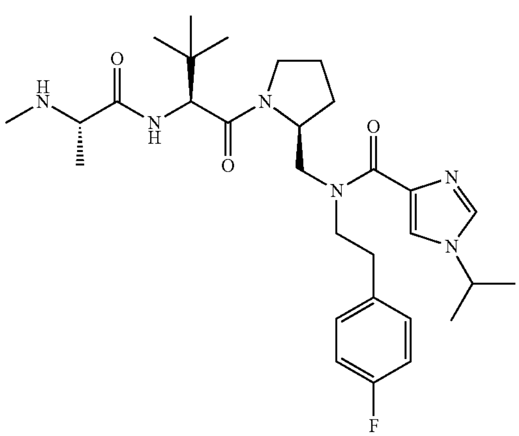 [SMILES: CN[C@@H](C)C(=O)N[C@H](C(=O)N1CCC[C@H]1CN(CCc1ccc(F)cc1)C(=O)c1cn(C(C)C)cn1)C(C)(C)C] | M + 1 = 557.4 |

TABLE 1-continued
| Cmpd # | Structure | MS |
|---|---|---|
| 95 | 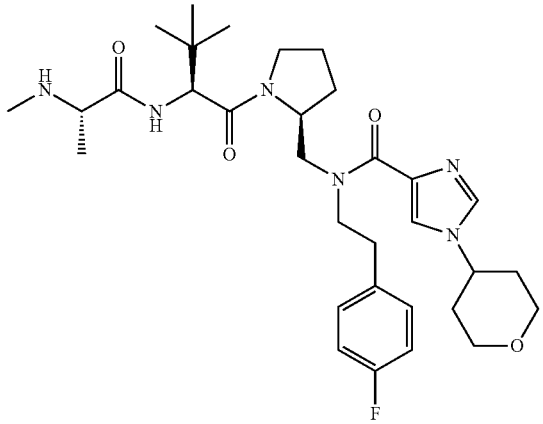 | M + 1 = 599.4 |
| 96 | 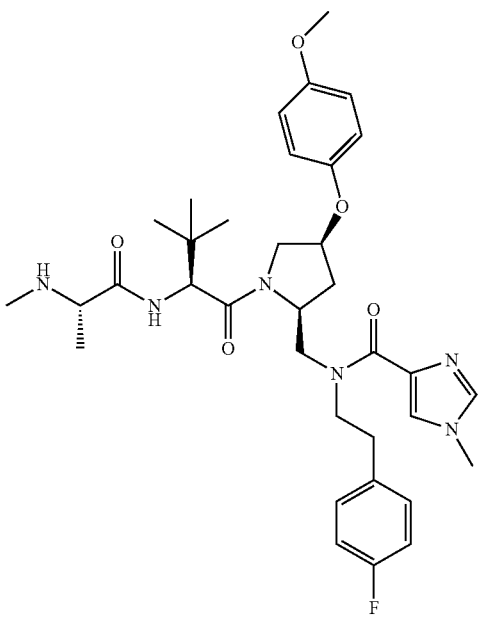 [SMILES: CN[C@@H](C)C(=O)N[C@H](C(=O)N1C[C@@H](Oc2ccc(OC)cc2)C[C@H]1CN(CCc1ccc(F)cc1)C(=O)c1cn(C)cn1)C(C)(C)C] | M + 1 = 651.4 |

US 9,284,350 B2
237 238
TABLE 1-continued
| Cmpd # | Structure | MS |
|---|---|---|
| 97 | 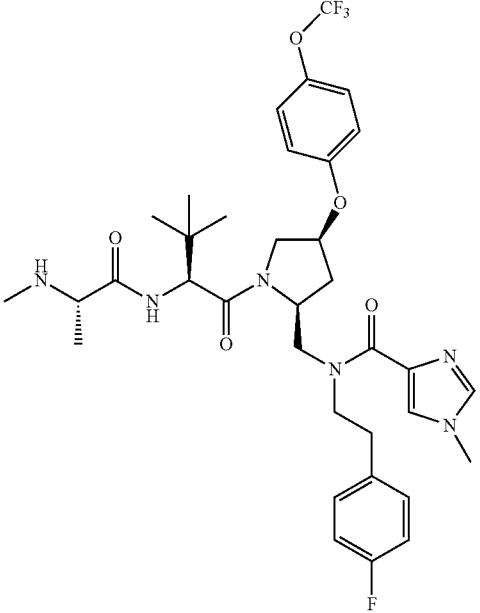 [SMILES: CN[C@@H](C)C(=O)N[C@H](C(=O)N1C[C@@H](Oc2ccc(OC(F)(F)F)cc2)C[C@H]1CN(CCc1ccc(F)cc1)C(=O)c1cn(C)cn1)C(C)(C)C] | M + 1 = 705.4 |
| 98 | 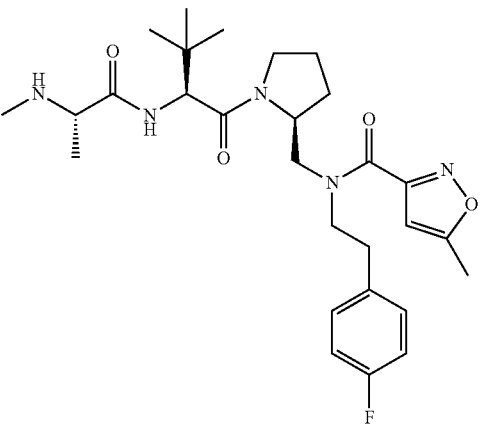 [SMILES: CN[C@@H](C)C(=O)N[C@H](C(=O)N1CCC[C@H]1CN(CCc1ccc(F)cc1)C(=O)c1cc(C)on1)C(C)(C)C] | M + 1 = 530.3 |
| 99 | 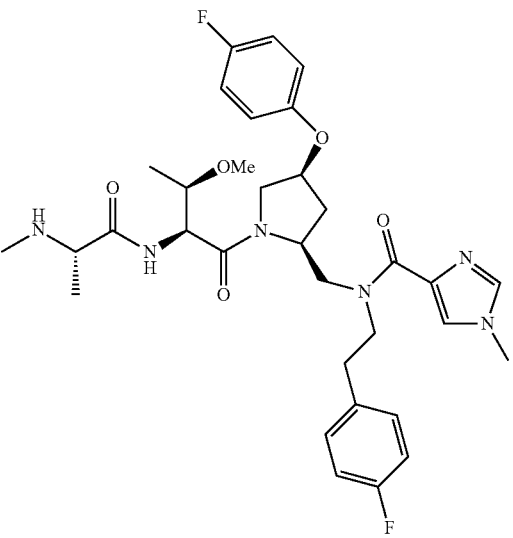 | M + 1 = 641.4 |

| Cmpd # | Structure | MS |
|---|---|---|
| 100 | 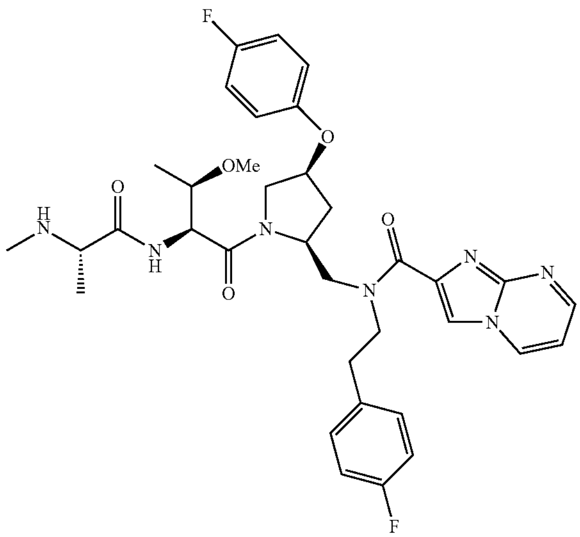 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2cccnc2n1)[C@@H](C)OC] | M + 1 = 678.5 |
| 101 | 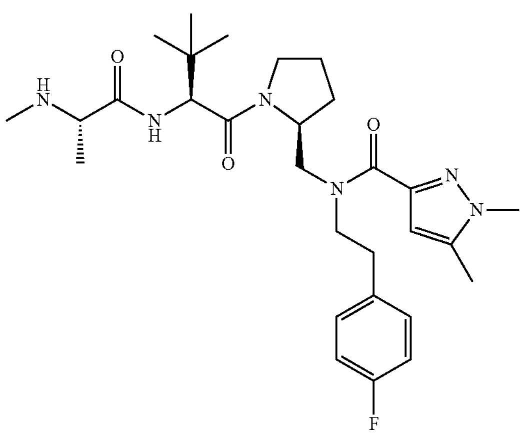 | M + 1 = 543.4 |
| 102 | 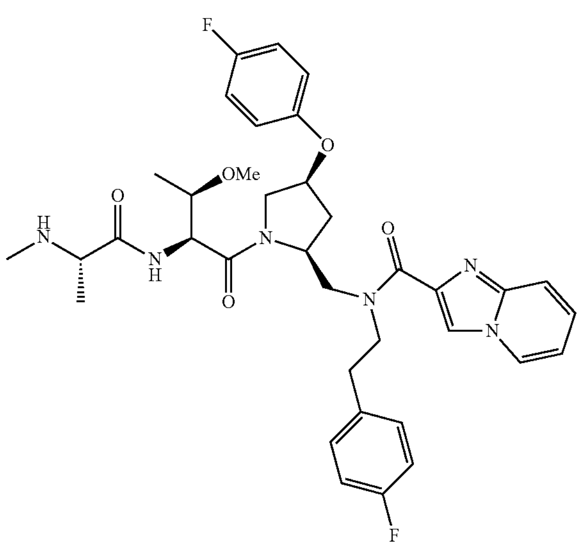 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2ccccc2n1)[C@@H](C)OC] | M + 1 = 677.5 |

TABLE 1-continued
| Cmpd # | Structure | MS |
|---|---|---|
| 103 | 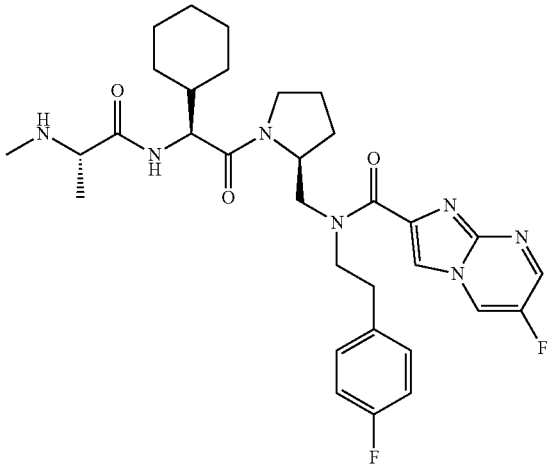 [SMILES: CN[C@@H](C)C(=O)N[C@H](C(=O)N1CCC[C@H]1CN(CCc1ccc(F)cc1)C(=O)c1cn2cc(F)cnc2n1)C1CCCCC1] | M + 1 = 610.3 |
| 104 | 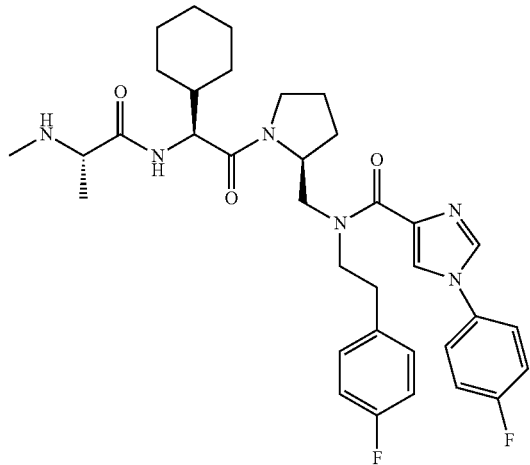 [SMILES: CN[C@@H](C)C(=O)N[C@H](C(=O)N1CCC[C@H]1CN(CCc1ccc(F)cc1)C(=O)c1cn(-c2ccc(F)cc2)cn1)C1CCCCC1] | M + 1 = 635.3 |
| 105 | 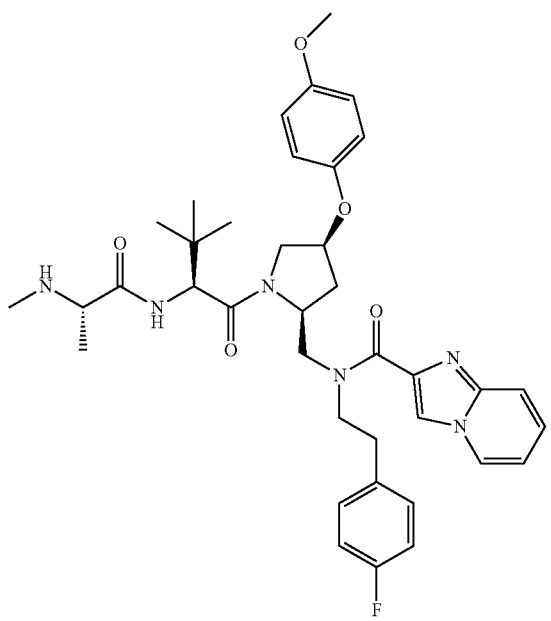 [SMILES: CN[C@@H](C)C(=O)N[C@H](C(=O)N1C[C@@H](Oc2ccc(OC)cc2)C[C@H]1CN(CCc1ccc(F)cc1)C(=O)c1cn2ccccc2n1)C(C)(C)C] | M + 1 = 687.1 |

TABLE 1-continued
| Cmpd # | Structure | MS |
|---|---|---|
| 106 | 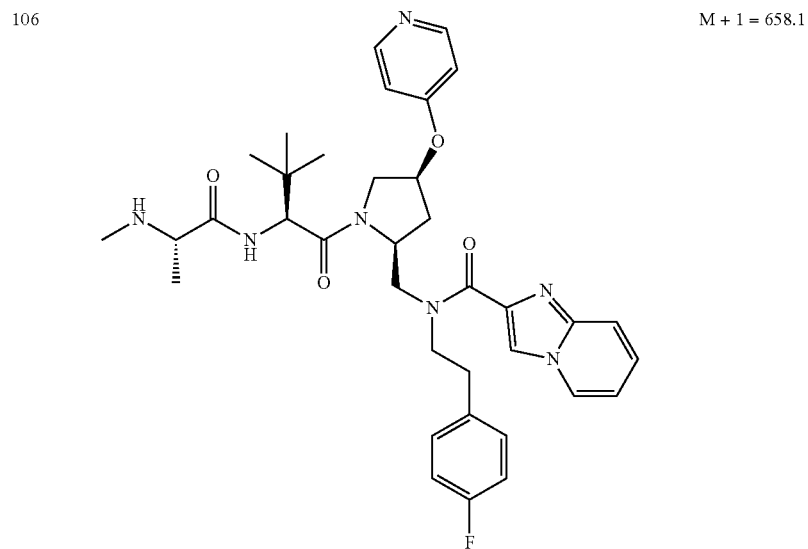 | M + 1 = 658.1 |
| 107 | 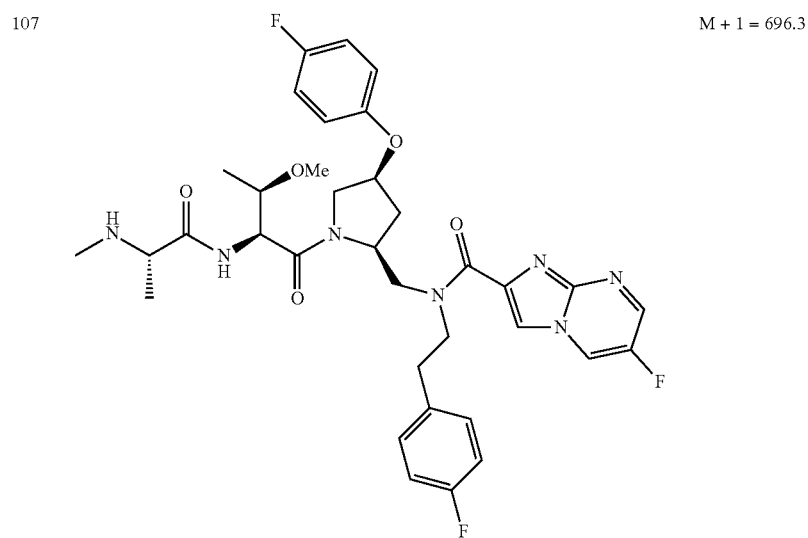 | M + 1 = 696.3 |

TABLE 1-continued

| Cmpd # | Structure | MS |
|---|---|---|
| 108 | 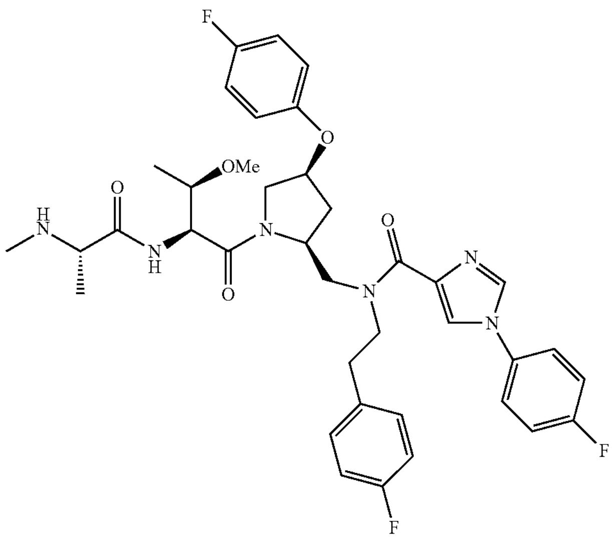 [SMILES: CN[C@@H](C)C(=O)N[C@H](C(=O)N1C[C@@H](Oc2ccc(F)cc2)C[C@H]1CN(CCc1ccc(F)cc1)C(=O)c1cn(-c2ccc(F)cc2)cn1)[C@@H](C)OC] | M + 1 = 721.1 |
| 109 | 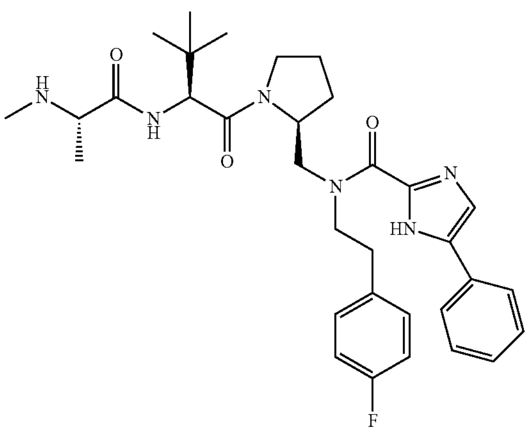 [SMILES: CN[C@@H](C)C(=O)N[C@H](C(=O)N1CCC[C@H]1CN(CCc1ccc(F)cc1)C(=O)c1ncc(-c2ccccc2)[nH]1)C(C)(C)C] | M + 1 = 591.2 |
| 110 | 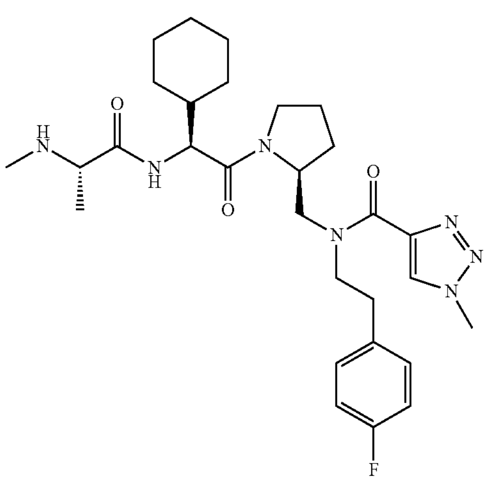 [SMILES: CN[C@@H](C)C(=O)N[C@H](C(=O)N1CCC[C@H]1CN(CCc1ccc(F)cc1)C(=O)c1cn(C)nn1)C1CCCCC1] | M + 1 = 556.3 |

TABLE 1-continued
| Cmpd # | Structure | MS |
|---|---|---|
| 111 | 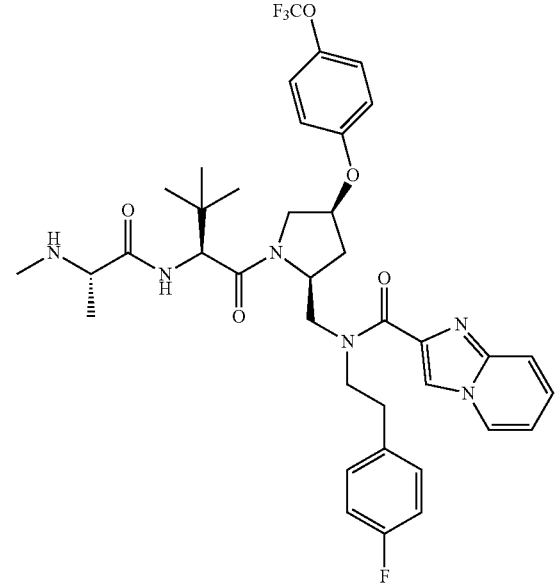 [SMILES: CN[C@@H](C)C(=O)N[C@H](C(=O)N1C[C@@H](Oc2ccc(OC(F)(F)F)cc2)C[C@H]1CN(CCc1ccc(F)cc1)C(=O)c1cn2ccccc2n1)C(C)(C)C] | M + 1 = 741.3 |
| 112 | 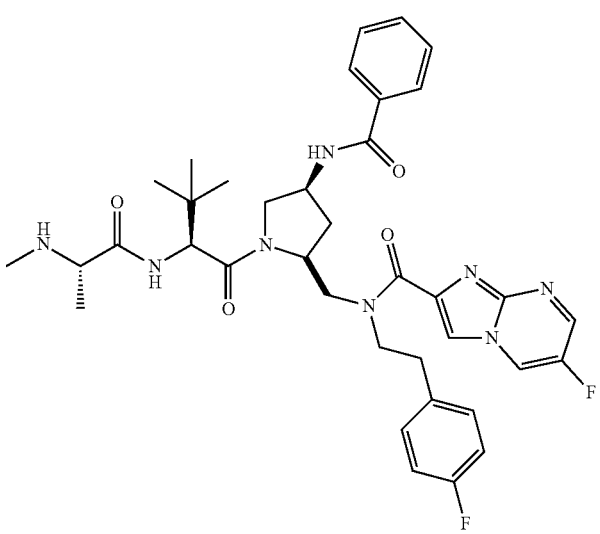 [SMILES: CN[C@@H](C)C(=O)N[C@H](C(=O)N1C[C@@H](NC(=O)c2ccccc2)C[C@H]1CN(CCc1ccc(F)cc1)C(=O)c1cn2cc(F)cnc2n1)C(C)(C)C] | M + 1 = 703.1 |
| 113 | 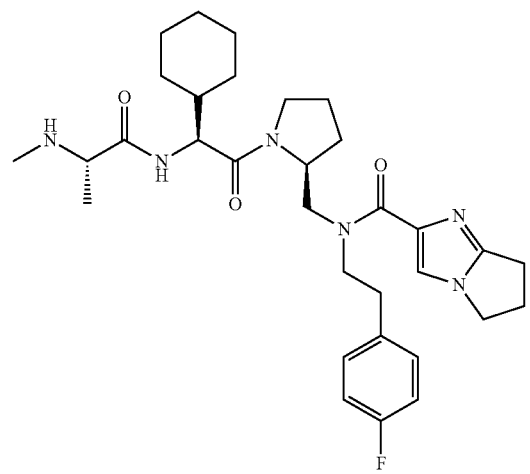 [SMILES: CN[C@@H](C)C(=O)N[C@H](C(=O)N1CCC[C@H]1CN(CCc1ccc(F)cc1)C(=O)c1cn2c(n1)CCC2)C1CCCCC1] | M + 1 = 581.3 |

TABLE 1-continued

| Cmpd # | Structure | MS |
|---|---|---|
| 114 | 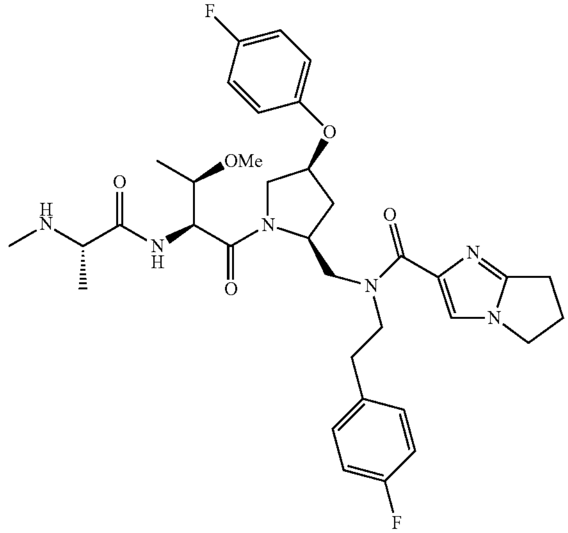 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2c(n1)CCC2)[C@@H](C)OC] | M + 1 = 667.1 |
| 115 | 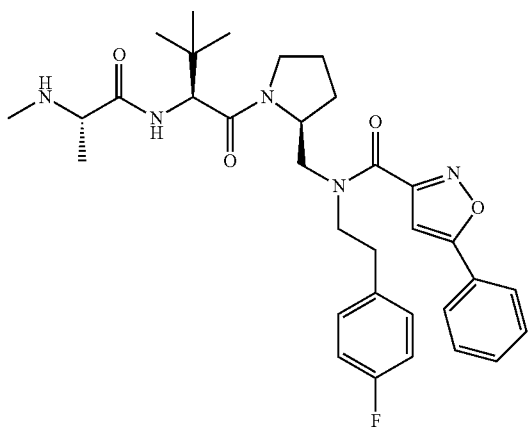 [SMILES: CN[C@@H](C)C(=O)N[C@H](C(=O)N1CCC[C@H]1CN(CCc1ccc(F)cc1)C(=O)c1cc(-c2ccccc2)on1)C(C)(C)C] | M + 1 = 592.1 |
| 116 | 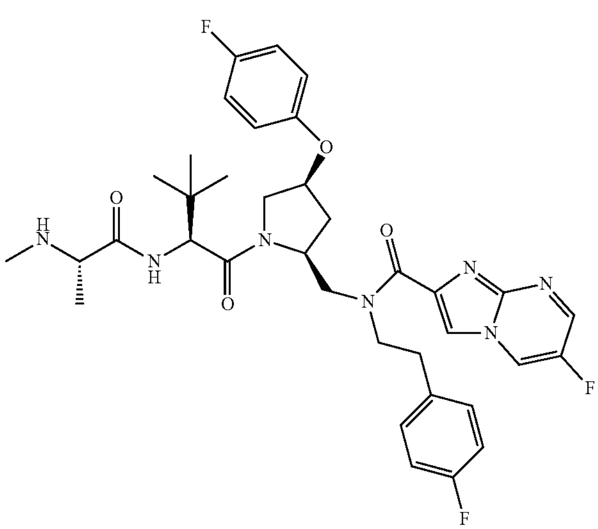 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2cc(F)cnc2n1)C(C)(C)C] | M + 1 = 694.0 |

TABLE 1-continued

| Cmpd # | Structure | MS |
|---|---|---|
| 117 | 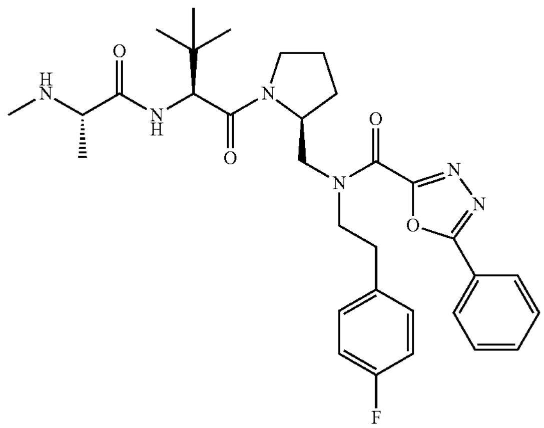 [SMILES: CN[C@@H](C)C(=O)N[C@H](C(=O)N1CCC[C@H]1CN(CCc1ccc(F)cc1)C(=O)c1nnc(-c2ccccc2)o1)C(C)(C)C] | M + 1 = 593.2 |
| 118 | 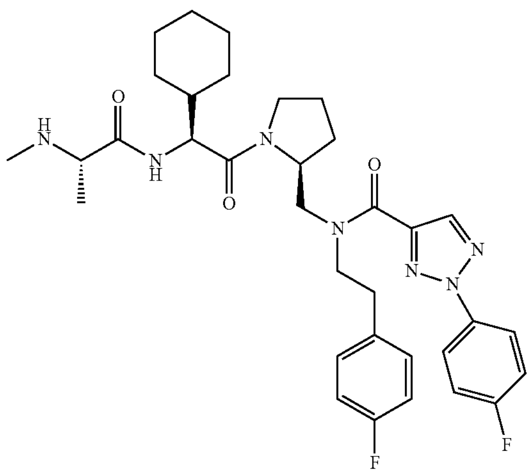 [SMILES: CN[C@@H](C)C(=O)N[C@H](C(=O)N1CCC[C@H]1CN(CCc1ccc(F)cc1)C(=O)c1cnn(-c2ccc(F)cc2)n1)C1CCCCC1] | M + 1 = 636.2 |
| 119 | 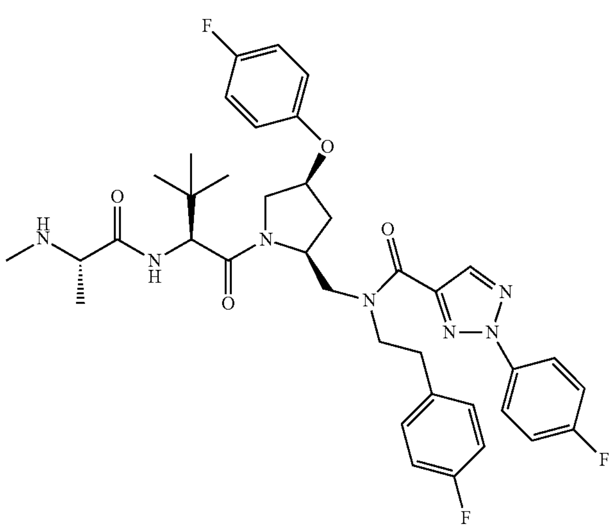 [SMILES: CN[C@@H](C)C(=O)N[C@H](C(=O)N1C[C@@H](Oc2ccc(F)cc2)C[C@H]1CN(CCc1ccc(F)cc1)C(=O)c1cnn(-c2ccc(F)cc2)n1)C(C)(C)C] | M + 1 = 720.1 |

TABLE 1-continued

| Cmpd # | Structure | MS |
|---|---|---|
| 120 | 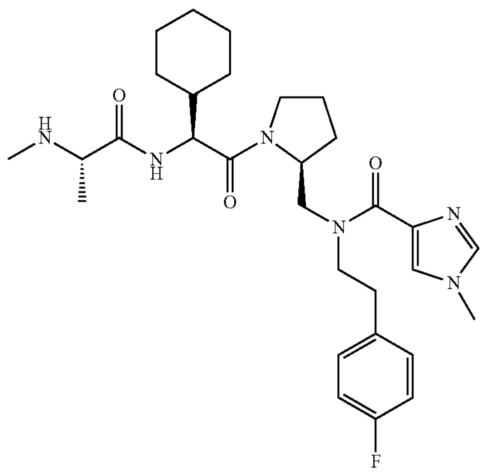 [SMILES: CN[C@@H](C)C(=O)N[C@H](C(=O)N1CCC[C@H]1CN(CCc1ccc(F)cc1)C(=O)c1cn(C)cn1)C1CCCCC1] | M + 1 = 555.3 |
| 121 | 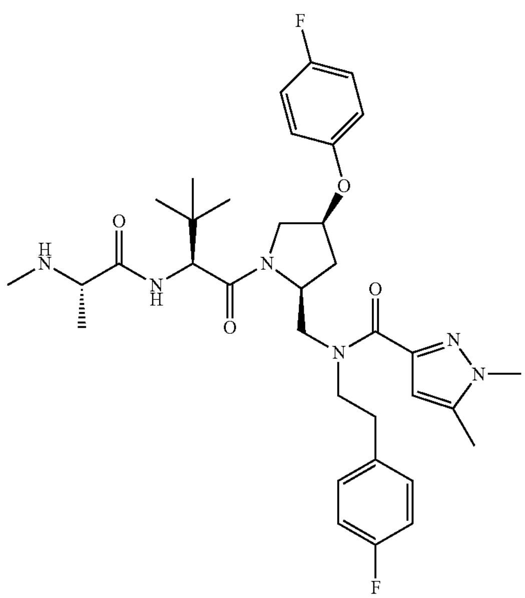 | M + 1 = 653.1 |
| 122 | 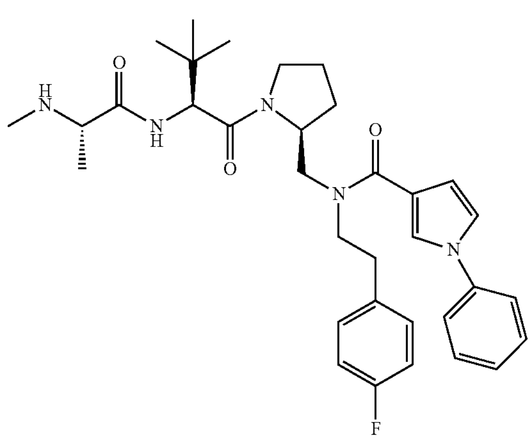 [SMILES: CN[C@@H](C)C(=O)N[C@H](C(=O)N1CCC[C@H]1CN(CCc1ccc(F)cc1)C(=O)c1ccn(-c2ccccc2)c1)C(C)(C)C] | M + 1 = 590.2 |

TABLE 1-continued
| Cmpd # | Structure | MS |
|---|---|---|
| 123 | 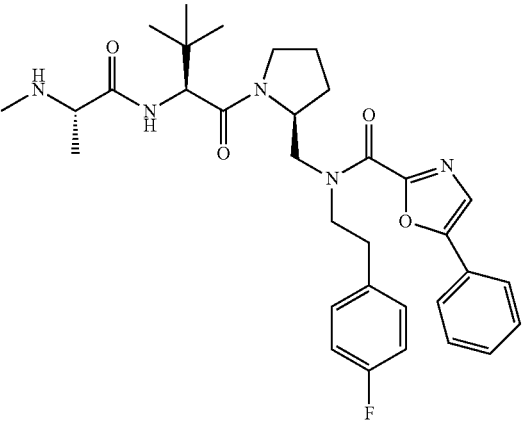 [SMILES: CN[C@@H](C)C(=O)N[C@H](C(=O)N1CCC[C@H]1CN(CCc1ccc(F)cc1)C(=O)c1ncc(-c2ccccc2)o1)C(C)(C)C] | M + 1 = 592.2 |
| 124 | 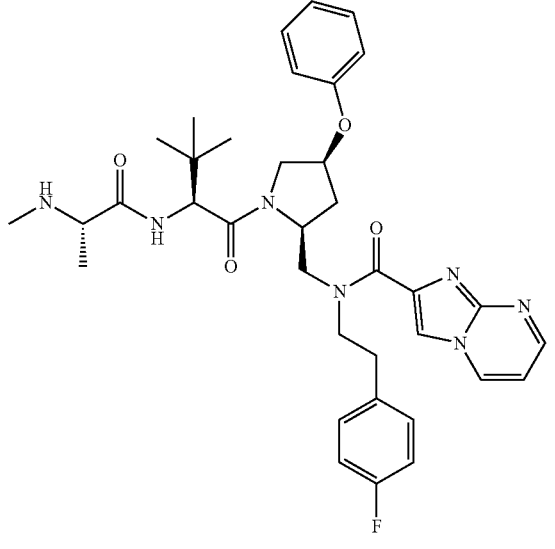 [SMILES: CN[C@@H](C)C(=O)N[C@H](C(=O)N1C[C@@H](Oc2ccccc2)C[C@H]1CN(CCc1ccc(F)cc1)C(=O)c1cn2cccnc2n1)C(C)(C)C] | M + 1 = 658.5 |
| 125 | 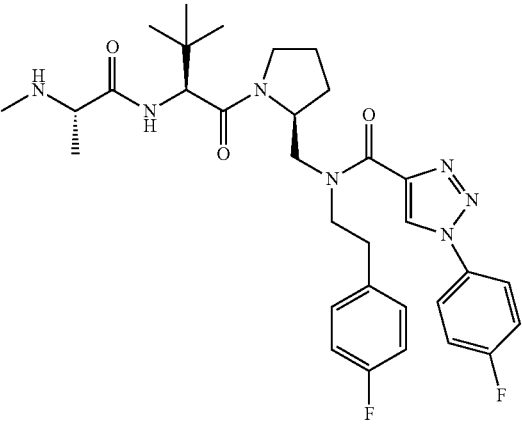 [SMILES: CN[C@@H](C)C(=O)N[C@H](C(=O)N1CCC[C@H]1CN(CCc1ccc(F)cc1)C(=O)c1cn(-c2ccc(F)cc2)nn1)C(C)(C)C] | M + 1 = 610.1 |

TABLE 1-continued

| Cmpd # | Structure | MS |
|---|---|---|
| 126 | 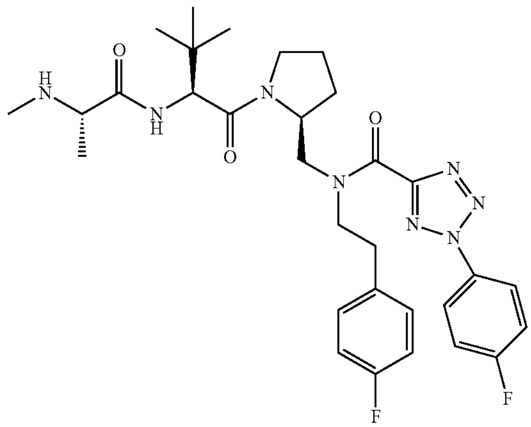 [SMILES: CN[C@@H](C)C(=O)N[C@H](C(=O)N1CCC[C@H]1CN(CCc1ccc(F)cc1)C(=O)c1nnn(-c2ccc(F)cc2)n1)C(C)(C)C] | M + 1 = 611.1 |

Example 9

The following example illustrates the use of a compound of Formula 1 or salt thereof.

Fluorescence Polarization-Based Competition Assay

Binding of compounds of Formula 1 to target BIR domains was measured using a fluorescence-polarization (FP) assay. Fluorescence-polarization was evaluated using a GENios microplate reader (TECAN) Pro instrument with the excitation filter set at 485 nm and the emission filter set at 535 nm. The final amount of protein used in the assay corresponds to the amount of protein necessary to obtain 80% of the maximum FP value in a P1 or P2 fluorescent (FITC) probe saturation experiment. The compounds potency ($IC_{50}$) and selectivity, was assessed in the presence of the amount of target protein established, fluorescent probe, and a 10 point serial dilution in assay buffer (50 mM Hepes, pH 7.5, 250 mcg/mL γ-globulin, 2 mM DTT, 1% DMSO) of the selected compounds.

Assays were carried out in duplicate using untreated black 96-well plates (Corning #3915) and a total volume of 100 microliters, containing 25 microliters of fluorescent probe at a final concentration of 2 nM in assay buffer, 25 microliters of diluted compound, 25 microliters of BIR protein into assay buffer and 25 microliters of assay buffer. Buffer only (blank) or probe only in buffer (G-factor) were used as controls for calibration. The plate was incubated at room temperature in the dark for one hour and FP values in millipolarization units (mP) were recorded using Genios Pro FP reader.

The measured FP values (mP) were then plotted against compound concentration, and $IC_{50}$ values were calculated based on a sigmoidal dose-response (variable-slope) curve fit using GraphPad Prism version 4.02 for Windows, GraphPad Software, San Diego Calif. USA and/or CambridgeSoft Bio-Assay Enterprise Version 10.1. The $IC_{50}$ value is the concentration of test compound at which 50% of the tracer was displaced. $k_i$ values were derived from the calculated $IC_{50}$ values as described above and according to the equation described in Nikolovska-Coleska, Z. (2004) *Anal Biochem* 332, 261-273. The results are presented in Table 2, wherein A=less than 25 nM; B=less than 250 nM; C=less than 1000 nM; and D=greater than 1000 nM. Compounds are identified in Table 3 according to the compound numbers presented in Table 1. As the results show, compounds of Formula 1 demonstrating good binding affinity.

TABLE 2

| Cpd No. | XIAP $k_i$ (nM) | c-IAP1 $k_i$ (nM) | cIAP2 $k_i$ (nM) |
|---|---|---|---|
| 1 | C | A | — |
| 2 | D | B | B |
| 3 | B | A | — |
| 4 | C | B | B |
| 5 | B | A | — |
| 6 | B | A | A |
| 7 | B | A | A |
| 8 | A | A | — |
| 9 | B | A | — |
| 10 | B | A | A |
| 11 | B | A | — |
| 12 | C | A | B |
| 13 | B | A | — |
| 14 | C | A | B |
| 15 | B | A | — |
| 16 | B | A | — |
| 17 | B | A | A |
| 18 | B | A | A |
| 19 | B | A | — |
| 20 | B | A | A |
| 21 | B | A | — |
| 22 | B | A | — |
| 23 | A | A | — |
| 24 | B | A | — |
| 25 | B | A | — |
| 26 | B | A | — |
| 27 | B | A | — |
| 28 | B | A | — |
| 29 | C | A | — |
| 30 | B | A | — |
| 31 | B | A | — |
| 32 | B | A | A |
| 33 | B | A | — |
| 34 | B | A | — |
| 35 | A | A | — |
| 36 | B | A | A |
| 37 | B | A | A |
| 38 | — | — | — |
| 39 | B | A | — |
| 40 | B | A | A |
| 41 | B | A | — |
| 42 | B | A | — |
| 43 | B | A | — |
| 44 | B | A | A |
| 45 | A | A | — |

TABLE 2-continued

| Cpd No. | XIAP k$_i$ (nM) | c-IAP1 k$_i$ (nM) | cIAP2 k$_i$ (nM) |
|---|---|---|---|
| 46 | B | A | — |
| 47 | B | A | A |
| 48 | B | A | — |
| 49 | C | A | A |
| 50 | B | A | A |
| 51 | B | A | — |
| 52 | B | A | — |
| 53 | B | A | A |
| 54 | B | A | — |
| 55 | B | A | A |
| 56 | C | A | A |
| 57 | C | A | — |
| 58 | B | A | A |
| 59 | B | A | A |
| 60 | C | A | — |
| 61 | B | A | A |
| 62 | B | A | — |
| 63 | B | A | A |
| 64 | B | A | — |
| 65 | A | A | A |
| 66 | B | A | A |
| 67 | B | A | A |
| 68 | B | A | A |
| 69 | B | A | A |
| 70 | C | A | B |
| 71 | C | A | A |
| 72 | B | A | A |
| 73 | B | A | A |
| 74 | B | A | A |
| 75 | B | A | A |
| 76 | B | A | A |
| 77 | B | A | A |
| 78 | B | A | A |
| 79 | B | A | A |
| 80 | B | A | A |
| 81 | B | A | A |
| 82 | A | A | A |
| 83 | A | A | A |
| 84 | A | A | A |
| 85 | C | A | A |
| 86 | B | A | A |
| 87 | B | A | A |
| 88 | B | A | A |
| 89 | B | A | A |
| 90 | B | A | A |
| 91 | B | A | A |
| 92 | C | A | B |
| 93 | B | A | A |
| 94 | B | A | A |
| 95 | B | A | A |
| 96 | B | A | A |
| 97 | B | A | A |
| 98 | B | A | A |
| 99 | B | A | A |
| 100 | B | A | A |
| 101 | — | — | — |
| 102 | B | A | A |
| 103 | B | A | A |
| 104 | B | A | A |
| 105 | A | A | A |
| 106 | B | A | A |
| 107 | B | A | A |
| 108 | B | A | A |
| 109 | B | A | A |
| 110 | B | A | A |
| 111 | A | A | A |
| 112 | B | A | A |
| 113 | B | A | A |
| 114 | A | A | A |
| 115 | B | A | A |
| 116 | A | A | A |
| 117 | C | A | A |
| 118 | — | — | — |
| 119 | — | — | — |
| 120 | B | A | A |
| 121 | — | — | — |
| 122 | B | A | A |
| 123 | B | A | A |
| 124 | B | A | A |
| 125 | B | A | A |
| 126 | B | A | A |

Cell Culture and Cell Death Assays

Colorectal carcinoma HCT116 cells were cultured as monolayers in 96 well plates at a density of 2000 cells per well in McCoy's 5a medium (HyClone) supplemented with 2.2 g/L sodium bicarbonate, 10% FBS (HyClo$_{ne}$) and 1% penicillin/streptomycin (HyClone). 24 hours later, triplicate wells were treated with HGS ETR1 (30 ng/ml) in combination with compound. Cells were incubated in the presence of compound and HGS agonistic Trail receptor antibody, ETR1 (Mapatumamab, 30 ng/ml) for 72 hours. Metabolic viability of remaining cells was assessed by MTT (thiazolyl blue tetrazolium bromide, Sigma) assay.

$EC_{50}$ values (50% cell survival in the presence of compound as compared to untreated controls) were calculated from survival curves using BioAssay software (Cambridge-Soft) and GraphPad Prism (Graph Pad Software Inc.). The results are provided in Table 3, below, wherein A=less than 50 nM; B=less than 250 nM; C=less than 1000 nM; and D=greater than 1000 nM. Compounds are identified in Table 3 according to the compound numbers presented in Table 1. As the results show, tested compounds of Formula 1 demonstrated strong potency.

TABLE 3

| Compound Number | HCT116+ mapatubimap $EC_{50}$ (nM) |
|---|---|
| 1 | B |
| 2 | C |
| 3 | C |
| 4 | D |
| 5 | A |
| 6 | B |
| 7 | B |
| 8 | B |
| 9 | B |
| 10 | A |
| 11 | B |
| 12 | B |
| 13 | B |
| 14 | B |
| 15 | B |
| 16 | C |
| 17 | A |
| 18 | A |
| 19 | A |
| 20 | A |
| 21 | C |
| 22 | B |
| 23 | B |
| 24 | B |
| 26 | C |
| 27 | C |
| 28 | C |
| 29 | D |
| 30 | B |
| 31 | B |
| 32 | B |
| 33 | B |
| 34 | B |
| 35 | B |
| 36 | B |
| 37 | D |

TABLE 3-continued

| Compound Number | HCT116+ mapatubimap EC$_{50}$ (nM) |
|---|---|
| 38 | B |
| 39 | B |
| 40 | A |
| 41 | C |
| 42 | C |
| 43 | B |
| 44 | B |
| 45 | A |
| 46 | C |
| 47 | B |
| 48 | A |
| 49 | B |
| 50 | B |
| 51 | B |
| 52 | B |
| 53 | A |
| 54 | A |
| 55 | D |
| 56 | C |
| 57 | C |
| 58 | A |
| 59 | C |
| 60 | C |
| 61 | B |
| 62 | C |
| 63 | A |
| 64 | B |
| 65 | A |
| 66 | A |
| 67 | A |
| 68 | B |
| 69 | B |
| 70 | C |
| 71 | C |
| 72 | A |
| 73 | B |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | B |
| 88 | B |
| 89 | A |
| 90 | B |
| 91 | A |
| 92 | B |
| 93 | A |
| 94 | A |
| 95 | A |
| 96 | A |
| 97 | A |
| 98 | B |
| 99 | A |
| 100 | B |
| 101 | A |
| 102 | A |
| 103 | A |
| 104 | A |
| 105 | A |
| 106 | A |
| 107 | A |
| 108 | B |
| 109 | A |
| 110 | A |
| 111 | A |
| 112 | B |
| 113 | A |
| 114 | A |
| 115 | B |
| 116 | A |
| 117 | B |
| 118 | B |
| 119 | B |
| 120 | A |
| 121 | A |
| 122 | B |
| 123 | A |
| 124 | A |

Adjuvant Induced Arthritis (AIA) Model

Male Lewis rats (Charles River, 125-150 g) were habituated to the animal facility for one week prior to the day of challenge with synthetic adjuvant lipoidal amine (LA). On experimental day (d)=0, when the mean body weight (BW) of the cohort was 165-200 g, rats were anesthetized with isoflurane, the lower back was shaved and wiped with alcohol and then 0.1 mL of LA dissolved in Complete Freunds Adjuvant (CFA) (50 mg/mL LA in CFA) was injected subcutaneously at the base of the tail. On experimental d=7, BW was recorded for each animal and the ankle width measured using electronic calipers (QuantuMike micrometer; Mitutoyo). Balanced groups were formed based on ankle width and treatment was initiated. Animals were treated orally (PO) once a day (QD) or twice a day (BID) with test compounds 5, 6, 7, or 10 (see Table 1) at 10, 30 & 60 mg/kg, PO, dexamethasone (0.15 mg/kg, PO), or vehicle alone (5 mL/kg, PO) from d=7 until d=14, with BW and ankle width recorded daily.

The tested compounds at the highest doses demonstrated greater than 50% reduction in paw swelling as compared to controls. Some compounds showed similar efficacy at the lower tested dosages. These results indicate the effectiveness of the tested compounds for this indication.

Collagen-Induced Arthritis (CIA): Semi-Therapeutic Dosing

Male, B10 RIII mice (7-8 weeks old, Jackson Labs) were habituated to the animal facility for 1 wk. They were then challenged with collagen, which was emulsified in CFA supplemented with *mycobacterium tuberculosis*, on experimental day 0 and 15. From experimental day 12 onwards animals were dosed with test compound 6, 7, or 10 (see Table 1) at 3, 10, 30 mg/kg (PO BID), or dexamethasone (0.2 mg/kg, positive control). Clinical arthritis severity was assessed using an established scoring system for the duration of the study.

The tested compounds demonstrated greater than 50% reduction in Arthritic score at the highest doses. Some compounds showed similar efficacy at the lower tested dosages. These results indicate the effectiveness of the tested compounds for this indication.

CIA: Therapeutic Dosing

Male, B10 RIII mice (7-8 weeks old, Jackson Labs) were habituated to the animal facility for 1 wk. They were then challenged with collagen, which was emulsified in CFA supplemented with *mycobacterium tuberculosis*, on experimental day 0 and 15. From experimental day 15 onwards animals were dosed with test compound 10, 40, 45, or 66 (see Table 1) at 3, 10, 30 mg/kg (PO BID), or dexamethasone (0.2 mg/kg, positive control). Clinical arthritis severity was assessed using an established scoring system for the duration of the study.

The tested compounds reduced the mean arthritic score in the treated animals as compared to vehicle (water) control at the highest doses.

MDA-MB-231 Compound+Mapatubamab Xenograft Study

Female, nude mice received 5×10$^6$ MDA-MB-231 (CD) cells subcutaneously in the right flank (0.1 mL volume) on day 0 of the experiment. When the average tumor size reached ~100 mm$^3$, groups were formed using a balanced design based on tumor size, and dosing was initiated. Test compound 10 or 7 (see Table 1) (or corresponding vehicle alone) was given daily, and mapatubamab (or corresponding vehicle alone) was given twice weekly. Tumor size and body weight were measured twice weekly throughout the study.

Compounds 10 and 7 when dosed at (30 and 60 mg/kg, PO, QD) in combination with mapatubamab (10 mg/kg, IV) reduced tumor volume by 50% as compared to control, demonstrating combinational efficacy between the tested compounds and mapatubamab.

MDA-MB-231 Compound plus Taxol Xenograft Study

Female, CD-1, nude mice received 5×10$^6$ MDA-MB-231 (CD) cells subcutaneously in the right flank (0.1 mL volume, cells suspended in serum-free media) on day 1 of the experiment. When the average tumor size reached ~100 mm$^3$, groups were formed using a balanced design based on tumor size. Compounds 10, 7, 20, 40, 45, 58, 63, and 66 were then administered twice weekly at 30 and 100 mg/kg, PO, for two weeks. Taxol (20 mg/kg, IP) was co-administered with the initial treatment with test compound, and then once weekly for the duration of the study. Tumor size and body weight were measured twice weekly.

The tested compounds achieved stasis or tumor regression in the xenograft study.

Maximum Tolerated Dose (MTD) Study:

Male, CD-1 mice (20-25 g on arrival, Charles River) were habituated to the animal facility for four days and then randomly assigned to treatment groups. Animals were dosed by oral gavage twice weekly, for a total of six treatments, with compounds 63, 58, 45, 10, 20, 40, and 66 at 15, 70, or 350 mg/kg in water, PO, or water alone (5 ml/kg, PO). Body weight and general health were monitored throughout the experiment. Twenty four hours after the last dose (day 19), animals were anesthetized with isoflurane, and blood was collected for serum biochemistry. Serum biochemical parameters were restricted to random glucose, urea, creatinine, total protein, albumin, globulin, A:G ratio, total bilirubin, AST, ALT, alkaline phosphatase, GGT and amylase. Once exsanguinated the animals underwent full necropsy and organ weights were recorded for brain, heart, liver, spleen, kidneys, stomach (empty) and intestine (empty, from stomach to cecum). Because some treatments were suppressing weight gain (see below), organ weights were normalized to brain weight, and then expressed as percent change from the vehicle treated control group.

Mice showed positive growth curves and minimal or no clinical signs as a result of treatment, with slight weight loss observed for compounds 63 and 40 at the 350 mg/kg dose.

Pharmacokinetics (PK) of Compound in Plasma

CD-1 mice were dosed with compounds 5, 6, 7, 10, 17, 34, 58, 63, 66, 77, 78, 80, 81, 86, 87, 99, and 114 by IV or oral administration. Post-administration, the concentration of drug in the plasma of the treated mice was determined by HPLC-mass spectrometry, and drug concentrations were estimated relative to standard curves of the test compounds. The area under the time-concentration curve (AUC) was determined from the plasma concentrations, and the oral bioavailability (% F) was calculated.

Tested compounds of Formula 1 demonstrated good oral bioavailability (19% to 100% F) in CD-1 mice. Additionally, compounds selected from the tested group of compounds demonstrated positive allometric scaling to human equivalent doses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of Formula 1:

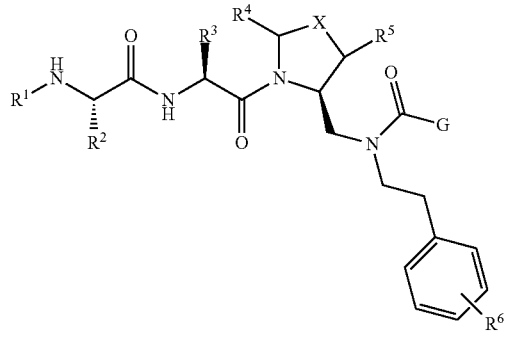

(1)

or a salt thereof, wherein

R¹ is H or alkyl;

R² is methyl or ethyl;

R³ is alkyl, cycloalkyl, heterocyclyl, heteroaryl, or aryl, any of which can be optionally further substituted with an amino, alkylamino, or alkoxy;

R⁴ and R⁵ are each, independently, H or alkyl;

R⁶ is H, halogen, or alkoxy;

X is O, S, CH₂, —(CH₂)₂— or CH—R⁷, wherein R⁷ is NR⁸, OR⁸, NC(O)OR⁸, NHC(O)R⁸ or NHSO₂R⁸, wherein R⁸ is alkyl, cycloalkyl, heterocyclyl, aryl, arylalkyl, or heteroaryl, any of which can be optionally further substituted with an alkyl, alkoxy, haloalkyl, or halogen; or X is

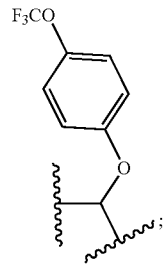

and G is

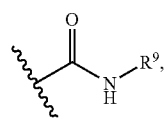

wherein R⁹ is substituted or unsubstituted alkyl, cycloalkyl, heterocyclyl, aryl or heteroaryl; or (2) a substituted or unsubstituted azole or pyrrole ring, optionally fused to a substituted or unsubstituted aryl, heteroaryl, cycloalkyl or heterocyclyl.

2. The compound of claim 1, wherein G is

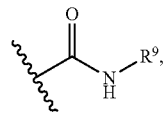

and R⁹ is substituted or unsubstituted alkyl, cycloalkyl, heterocyclyl, aryl, or heteroaryl.

3. The compound of claim 1, wherein G is

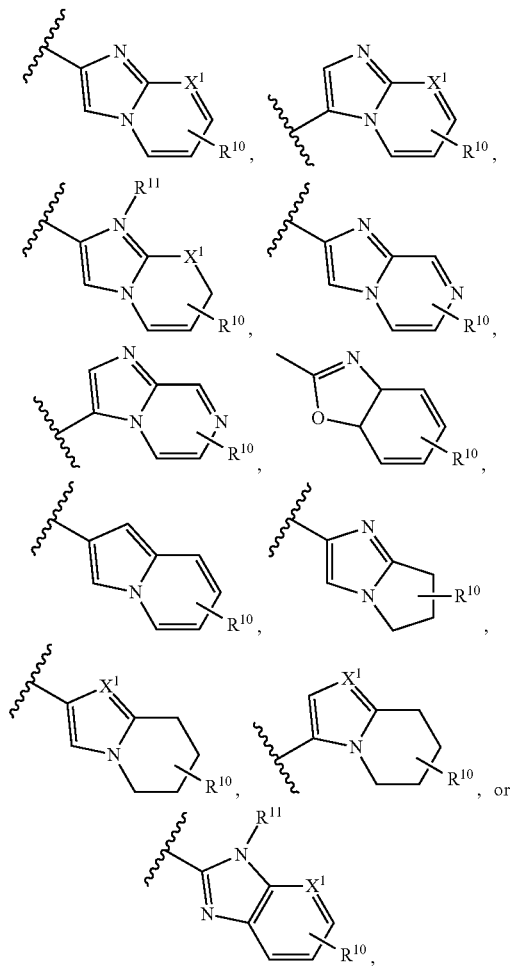

and X¹ is CH or N, R¹⁰ is H, halogen, hydroxyl, alkyl, alkoxy, aryl, amino, or NHC(O)-alkyl, and R¹¹ is hydrogen, alkyl, or NHC(O)CH₃;

or G is

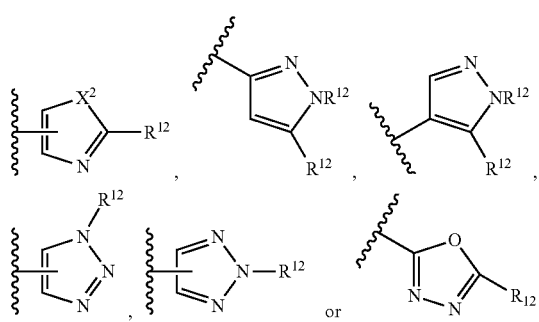

wherein X² is NH, NR¹², O, or S, and each R¹² is independently hydrogen, alkyl, cycloalkyl, heterocyclyl, NHC(O)CH₃, or phenyl optionally substituted with one or more alkyl, alkoxy, or halogen groups.

4. The compound of claim 1, wherein G is

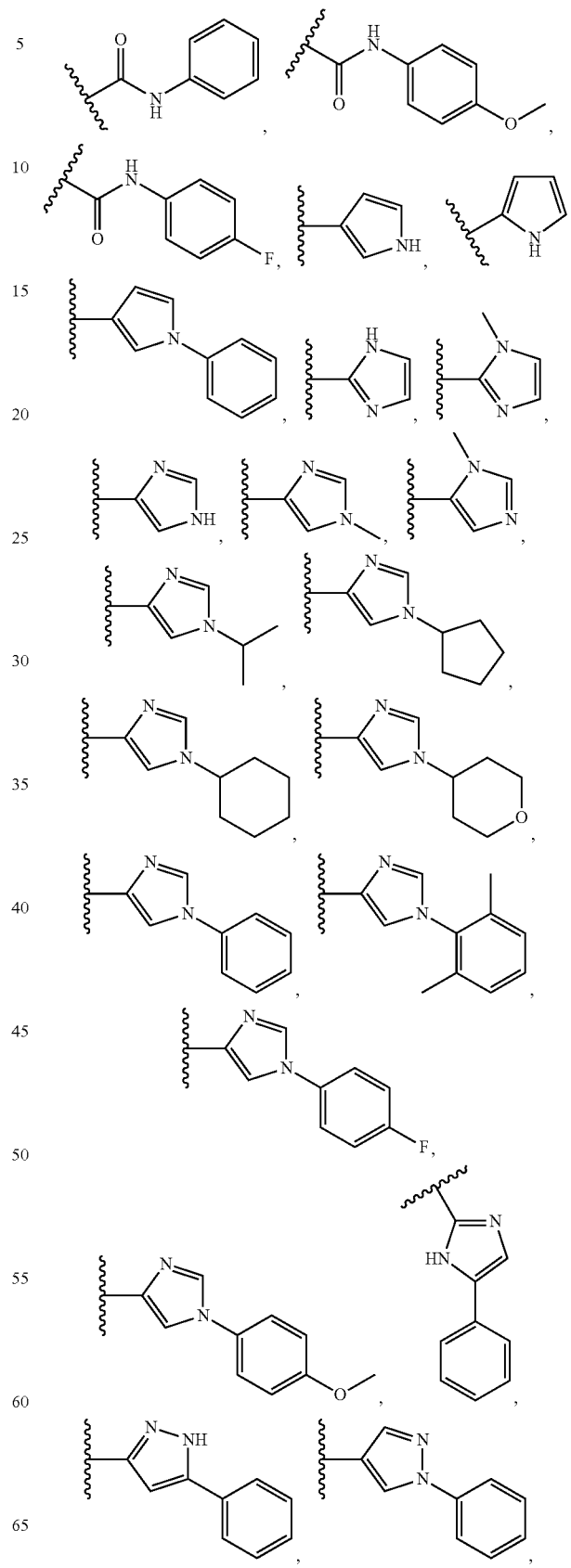

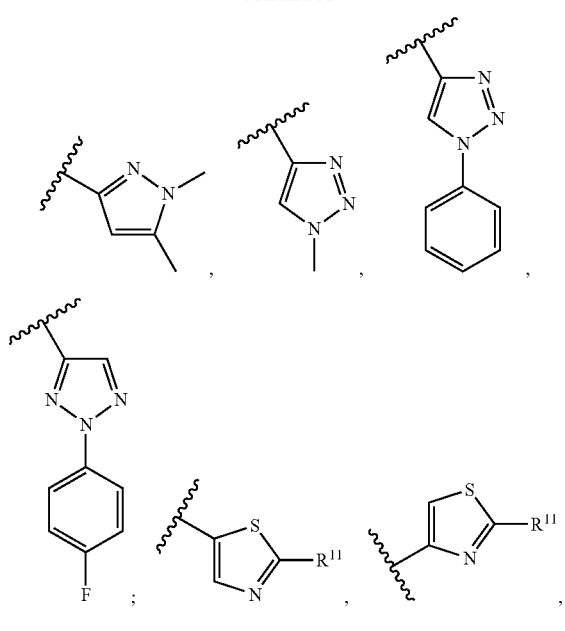
wherein R¹¹ is NHC(O)CH₃ or phenyl;
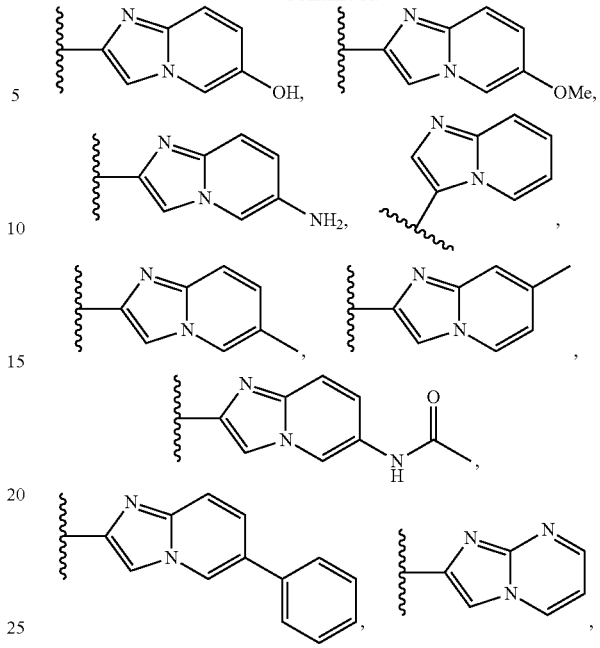
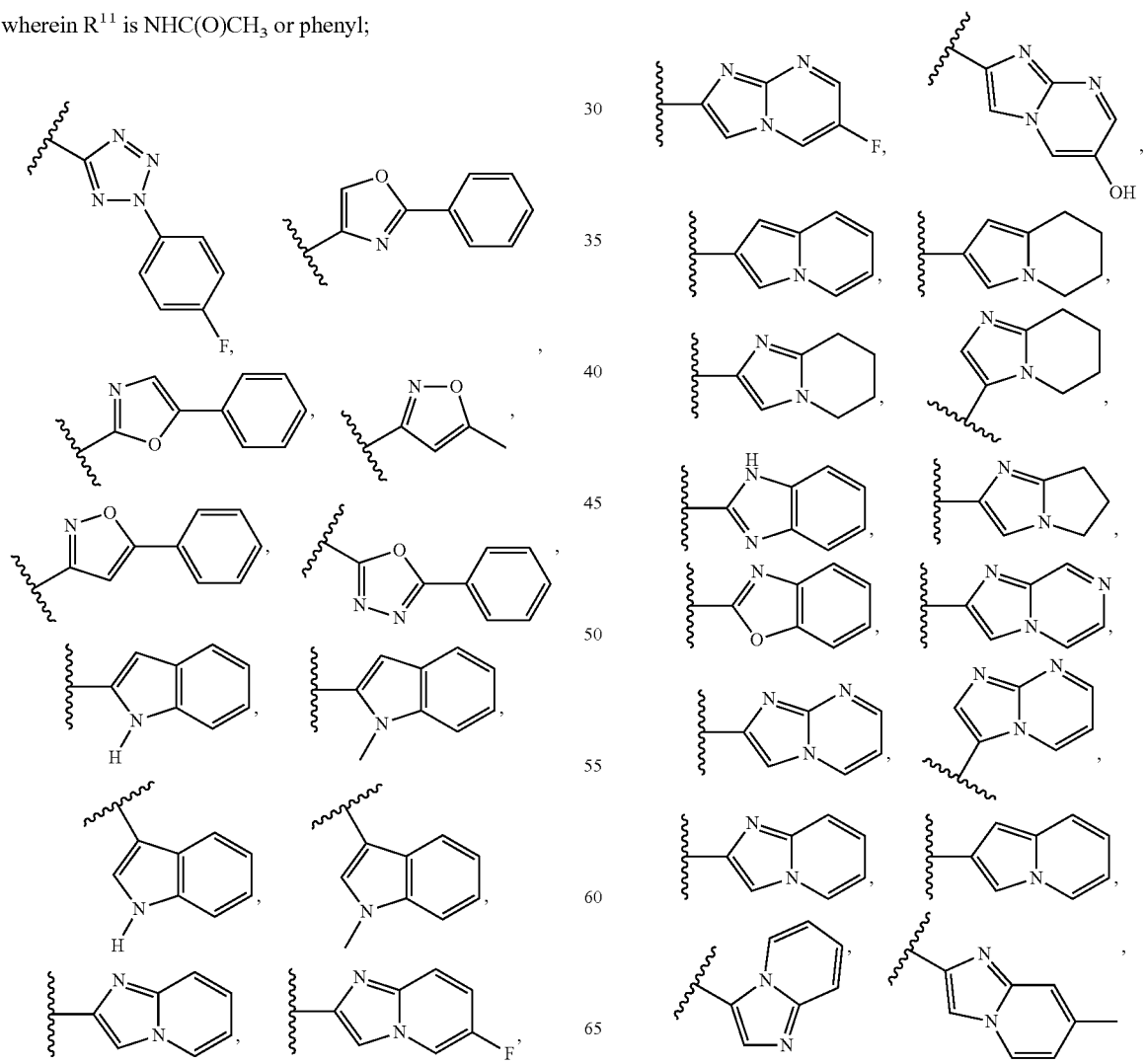

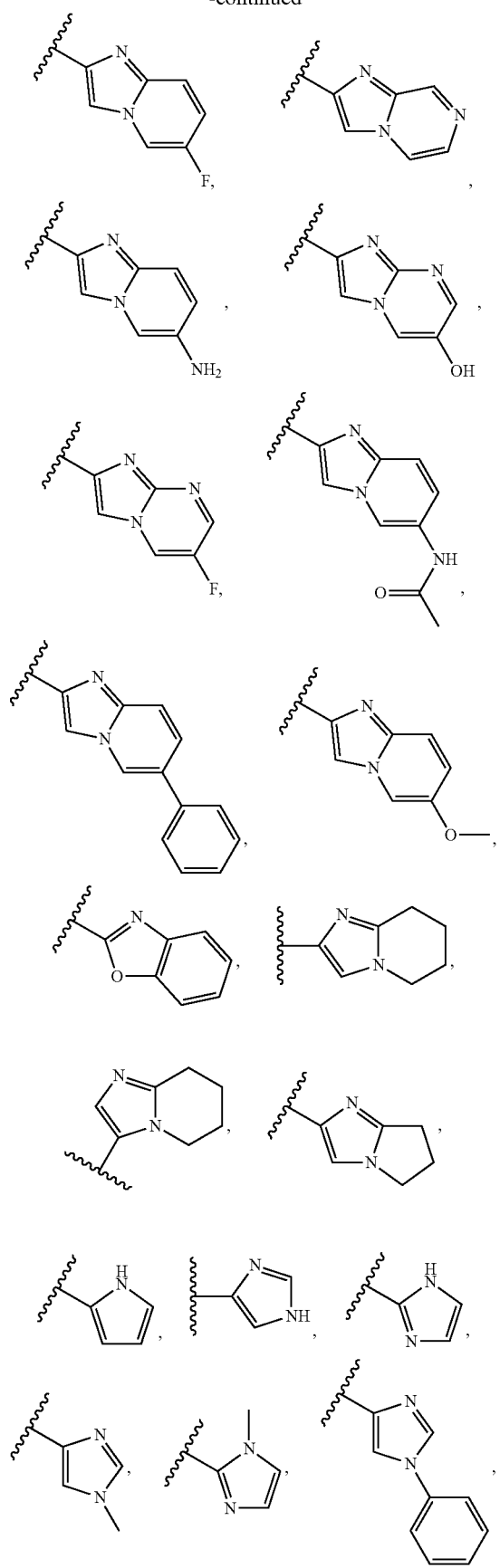

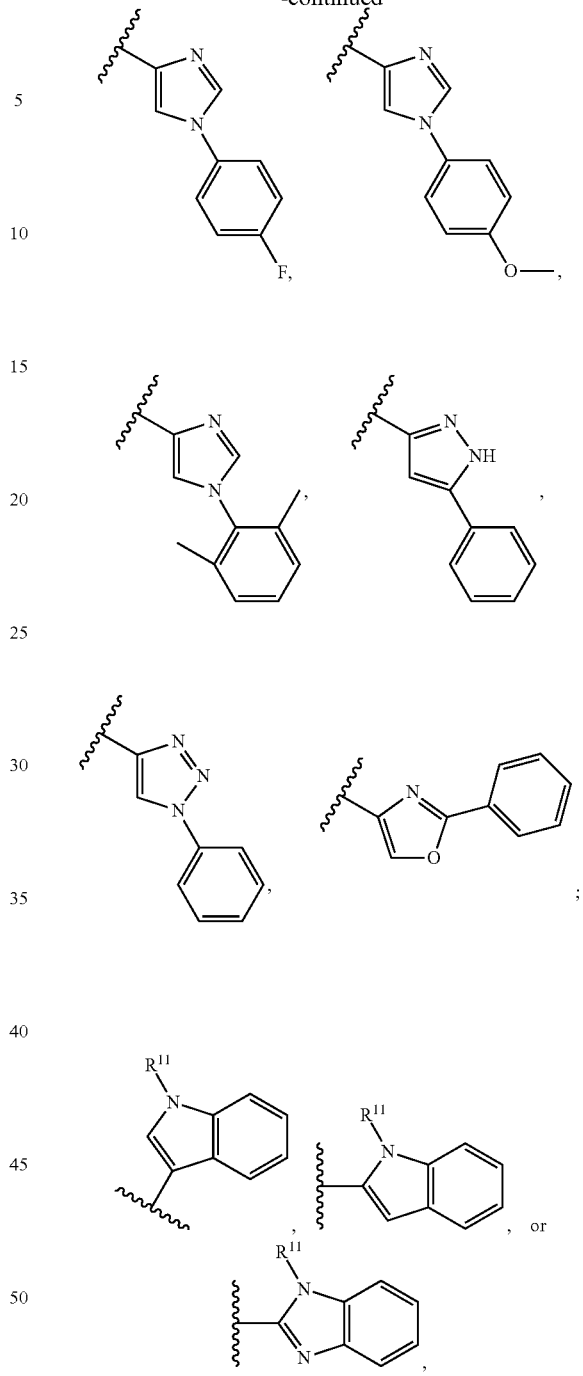

wherein R[11] is H or alkyl.

5. The compound of claim 1, wherein R[6] is H, F, or methoxy.

6. The compound of claim 1, wherein X is —CH$_2$—.

7. The compound of claim 1, wherein X is CH—NHC(O)R[8] and R[8] is alkyl, aryl, arylalkyl, alkoxy or heteroaryl, any of which can be optionally further substituted with an alkyl or halogen.

8. The compound of claim 1, wherein X is CH—OR[8] and R[8] is aryl or arylalkyl, which can be optionally further substituted with halogen.

9. The compound of claim 1, wherein X is:
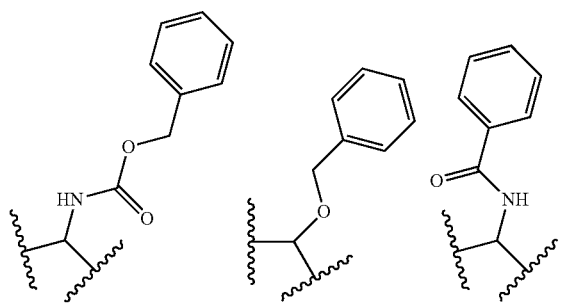
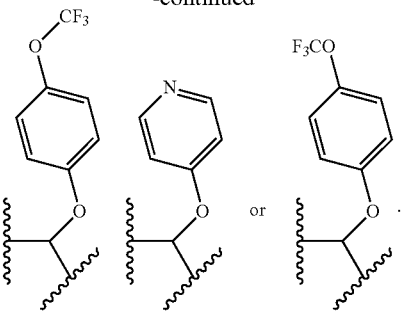
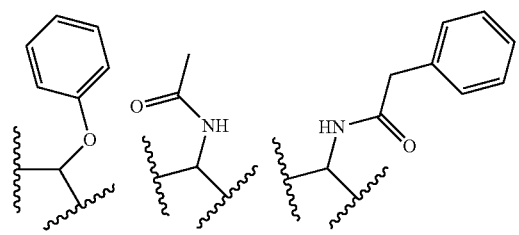
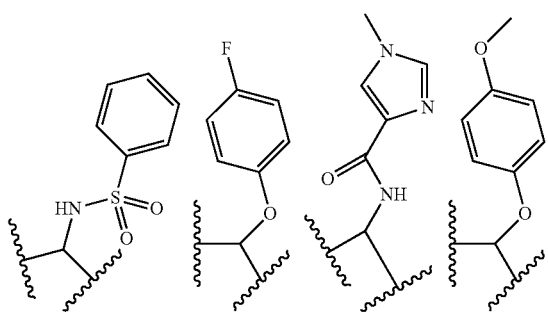
10. The compound of claim 1, wherein $R^4$ and $R^5$ both are hydrogen.
11. The compound of claim 1, wherein $R^1$ and $R^2$ both are methyl.
12. The compound of any of claim 1, wherein $R^3$ is tert-butyl, cyclohexyl, tetrahydropyranyl,
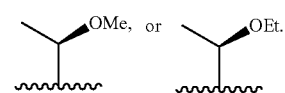
13. The compound of claim 1, wherein the compound is:
| No. | Structure |
|---|---|
| 1 | 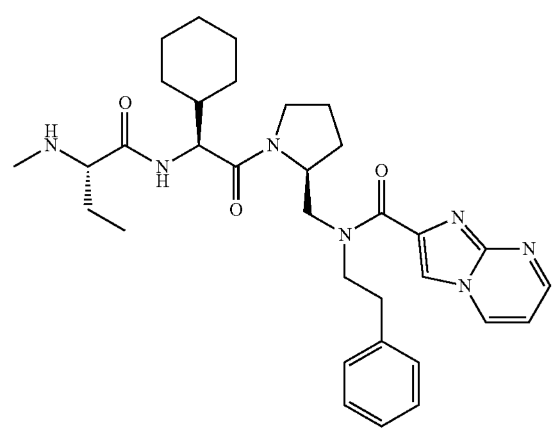 [SMILES: CC[C@H](NC)C(=O)N[C@H](C(=O)N1CCC[C@H]1CN(CCc1ccccc1)C(=O)c1cn2cccnc2n1)C1CCCCC1] |

| No. | Structure |
|---|---|
| 2 | 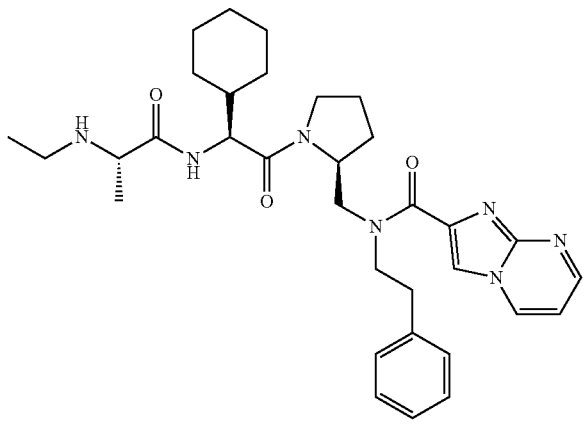 [SMILES: CCN[C@@H](C)C(=O)N[C@H](C(=O)N1CCC[C@H]1CN(CCc1ccccc1)C(=O)c1cn2cccnc2n1)C1CCCCC1] |
| 3 | 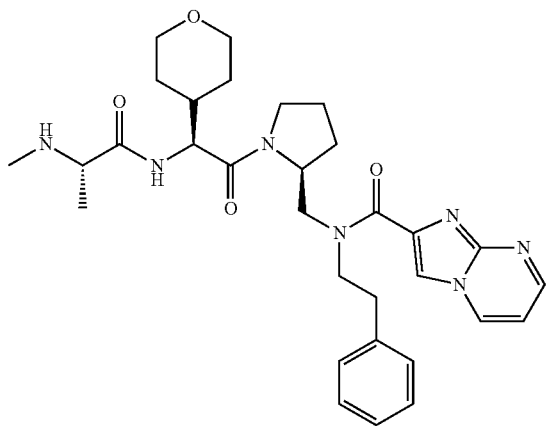 [SMILES: CN[C@@H](C)C(=O)N[C@H](C(=O)N1CCC[C@H]1CN(CCc1ccccc1)C(=O)c1cn2cccnc2n1)C1CCOCC1] |
| 4 | 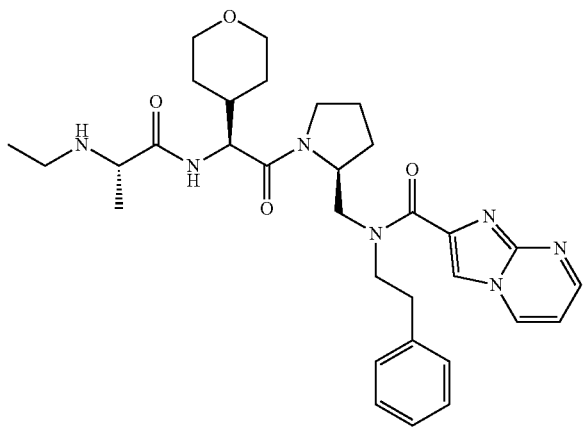 [SMILES: CCN[C@@H](C)C(=O)N[C@H](C(=O)N1CCC[C@H]1CN(CCc1ccccc1)C(=O)c1cn2cccnc2n1)C1CCOCC1] |

-continued
| No. | Structure |
|---|---|
| 5 | 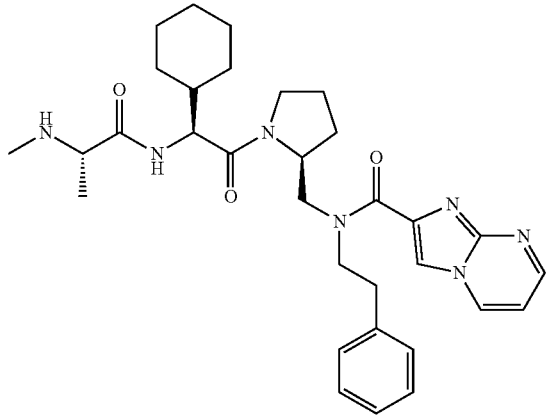 [SMILES: CN[C@@H](C)C(=O)N[C@H](C(=O)N1CCC[C@H]1CN(CCc1ccccc1)C(=O)c1cn2cccnc2n1)C1CCCCC1] |
| 6 | 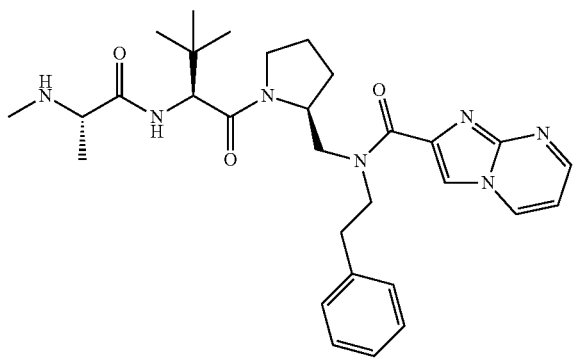 [SMILES: CN[C@@H](C)C(=O)N[C@H](C(=O)N1CCC[C@H]1CN(CCc1ccccc1)C(=O)c1cn2cccnc2n1)C(C)(C)C] |
| 7 | 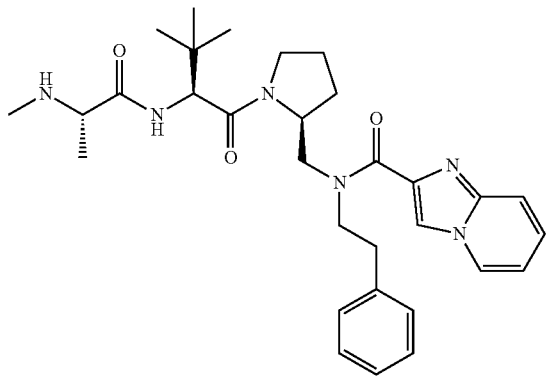 |
| 8 | 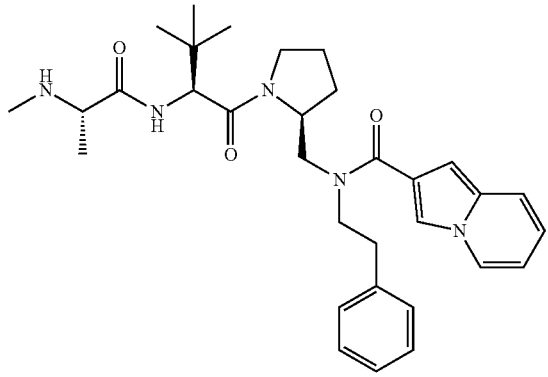 [SMILES: CN[C@@H](C)C(=O)N[C@H](C(=O)N1CCC[C@H]1CN(CCc1ccccc1)C(=O)c1cc2ccccn2c1)C(C)(C)C] |

| No. | Structure |
|---|---|
| 9 | 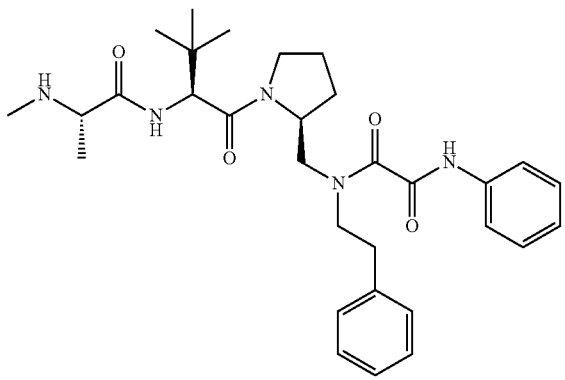 [SMILES: CN[C@@H](C)C(=O)N[C@H](C(=O)N1CCC[C@H]1CN(CCc1ccccc1)C(=O)C(=O)Nc1ccccc1)C(C)(C)C] |
| 10 | 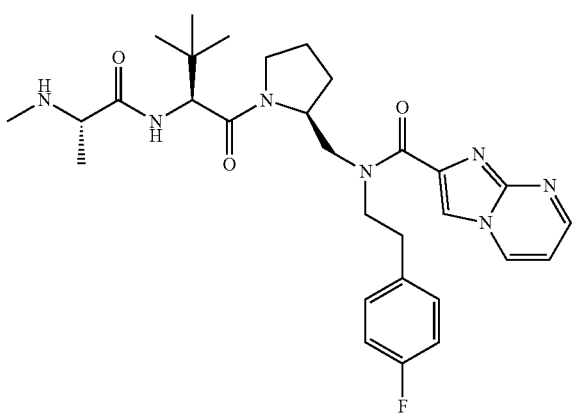 [SMILES: CN[C@@H](C)C(=O)N[C@H](C(=O)N1CCC[C@H]1CN(CCc1ccc(F)cc1)C(=O)c1cn2cccnc2n1)C(C)(C)C] |
| 11 | 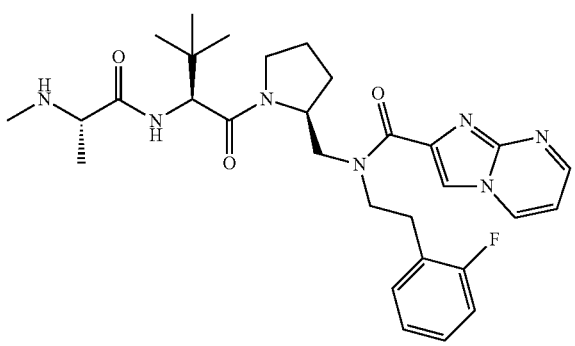 [SMILES: CN[C@@H](C)C(=O)N[C@H](C(=O)N1CCC[C@H]1CN(CCc1ccccc1F)C(=O)c1cn2cccnc2n1)C(C)(C)C] |
| 12 | 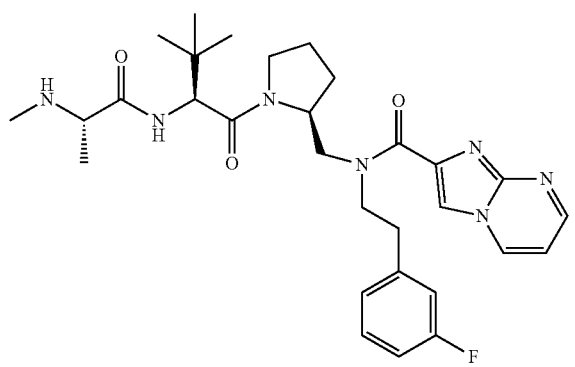 [SMILES: CN[C@@H](C)C(=O)N[C@H](C(=O)N1CCC[C@H]1CN(CCc1cccc(F)c1)C(=O)c1cn2cccnc2n1)C(C)(C)C] |

| No. | Structure |
|---|---|
| 13 | 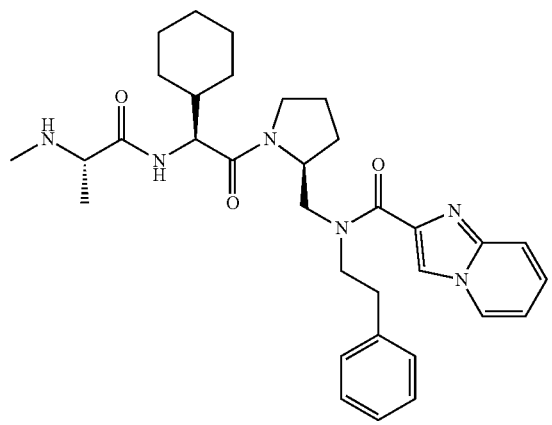 [SMILES: CN[C@@H](C)C(=O)N[C@H](C(=O)N1CCC[C@H]1CN(CCc1ccccc1)C(=O)c1cn2ccccc2n1)C1CCCCC1] |
| 14 | 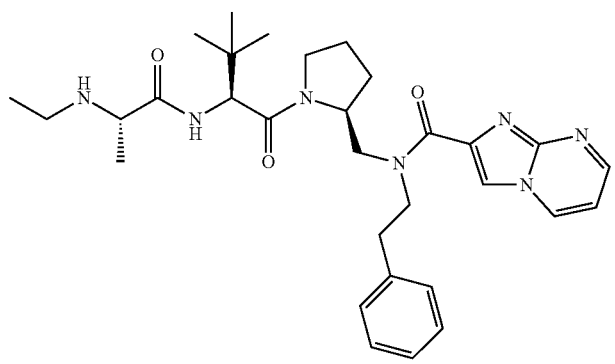 [SMILES: CCN[C@@H](C)C(=O)N[C@H](C(=O)N1CCC[C@H]1CN(CCc1ccccc1)C(=O)c1cn2cccnc2n1)C(C)(C)C] |
| 15 | 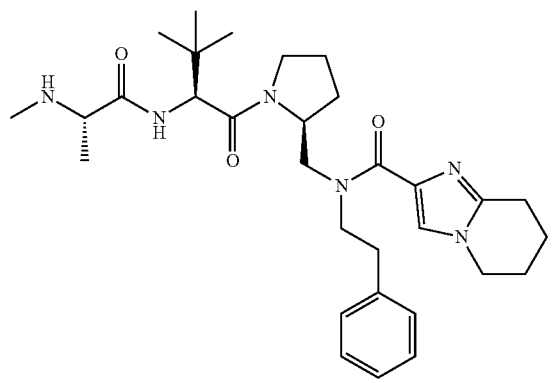 [SMILES: CN[C@@H](C)C(=O)N[C@H](C(=O)N1CCC[C@H]1CN(CCc1ccccc1)C(=O)c1cn2c(n1)CCCC2)C(C)(C)C] |
| 16 | 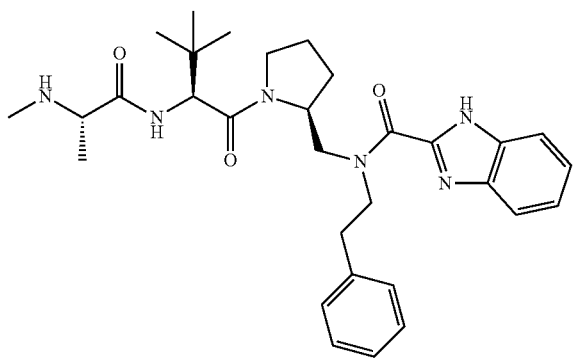 [SMILES: CN[C@@H](C)C(=O)N[C@H](C(=O)N1CCC[C@H]1CN(CCc1ccccc1)C(=O)c1nc2ccccc2[nH]1)C(C)(C)C] |

| No. | Structure |
|---|---|
| 17 | 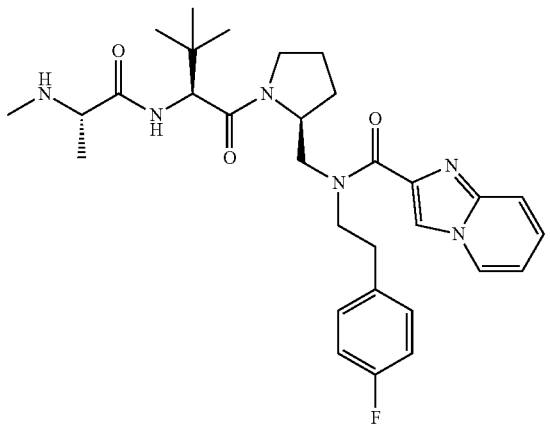 [SMILES: CN[C@@H](C)C(=O)N[C@H](C(=O)N1CCC[C@H]1CN(CCc1ccc(F)cc1)C(=O)c1cn2ccccc2n1)C(C)(C)C] |
| 18 | 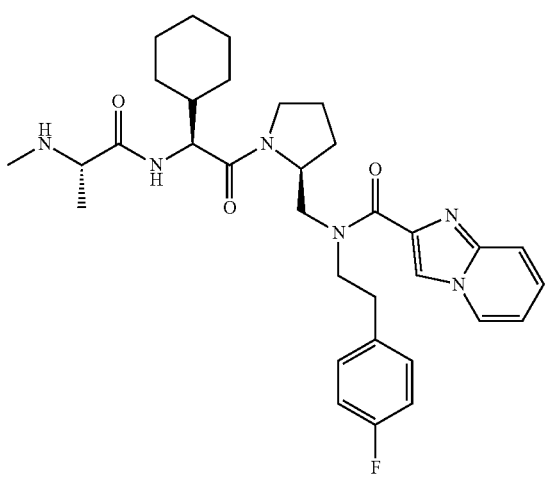 [SMILES: CN[C@@H](C)C(=O)N[C@H](C(=O)N1CCC[C@H]1CN(CCc1ccc(F)cc1)C(=O)c1cn2ccccc2n1)C1CCCCC1] |
| 19 | 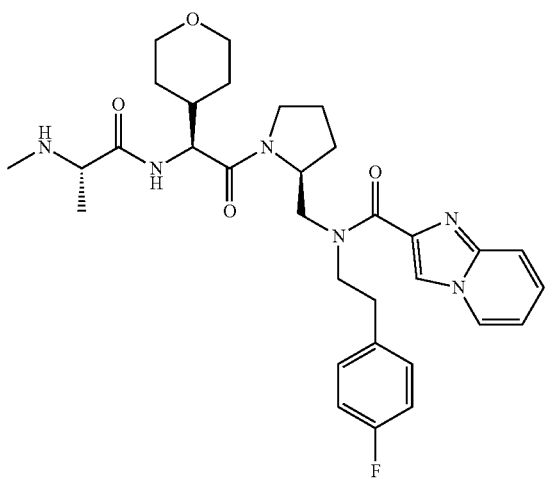 [SMILES: CN[C@@H](C)C(=O)N[C@H](C(=O)N1CCC[C@H]1CN(CCc1ccc(F)cc1)C(=O)c1cn2ccccc2n1)C1CCOCC1] |

-continued
| No. | Structure |
|---|---|
| 20 | 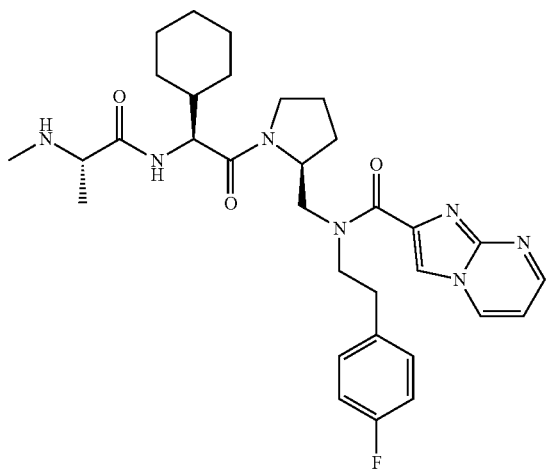 [SMILES: CN[C@@H](C)C(=O)N[C@H](C(=O)N1CCC[C@H]1CN(CCc1ccc(F)cc1)C(=O)c1cn2cccnc2n1)C1CCCCC1] |
| 21 | 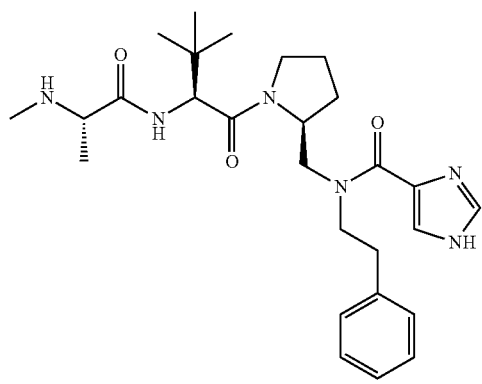 [SMILES: CN[C@@H](C)C(=O)N[C@H](C(=O)N1CCC[C@H]1CN(CCc1ccccc1)C(=O)c1c[nH]cn1)C(C)(C)C] |
| 22 | 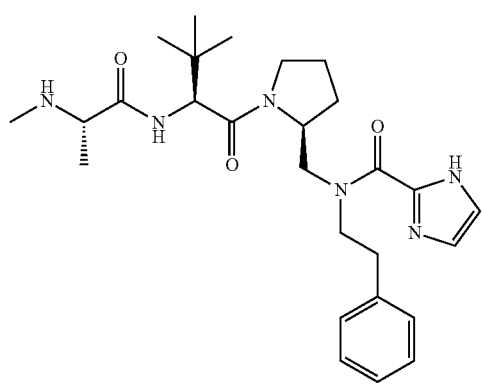 |
| 23 | 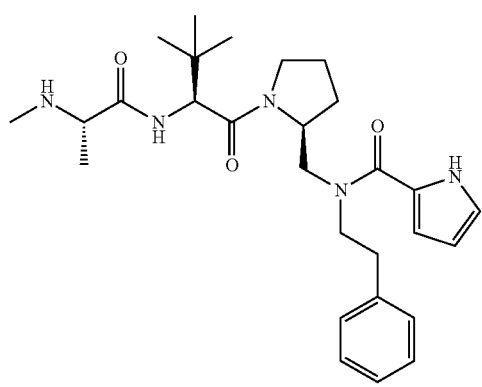 [SMILES: CN[C@@H](C)C(=O)N[C@H](C(=O)N1CCC[C@H]1CN(CCc1ccccc1)C(=O)c1ccc[nH]1)C(C)(C)C] |

-continued
| No. | Structure |
|---|---|
| 24 | 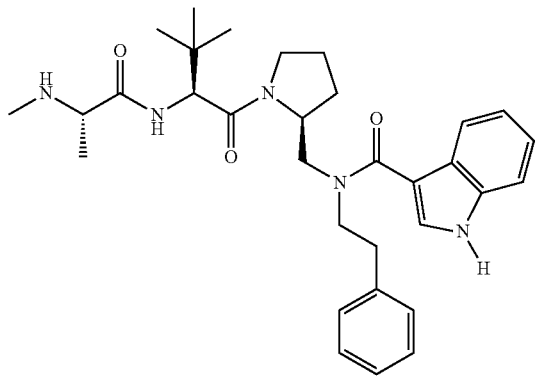 [SMILES: CN[C@@H](C)C(=O)N[C@H](C(=O)N1CCC[C@H]1CN(CCc1ccccc1)C(=O)c1c[nH]c2ccccc12)C(C)(C)C] |
| 25 | 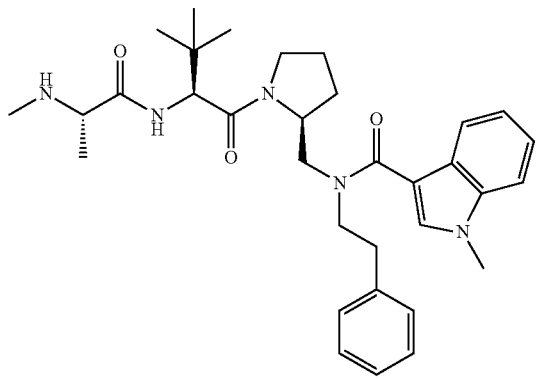 [SMILES: CN[C@@H](C)C(=O)N[C@H](C(=O)N1CCC[C@H]1CN(CCc1ccccc1)C(=O)c1cn(C)c2ccccc12)C(C)(C)C] |
| 26 | 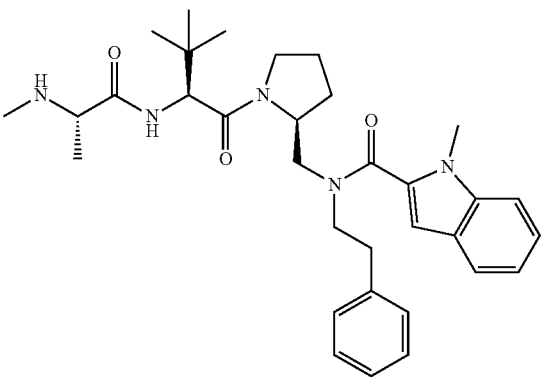 [SMILES: CN[C@@H](C)C(=O)N[C@H](C(=O)N1CCC[C@H]1CN(CCc1ccccc1)C(=O)c1cc2ccccc2n1C)C(C)(C)C] |
| 27 | 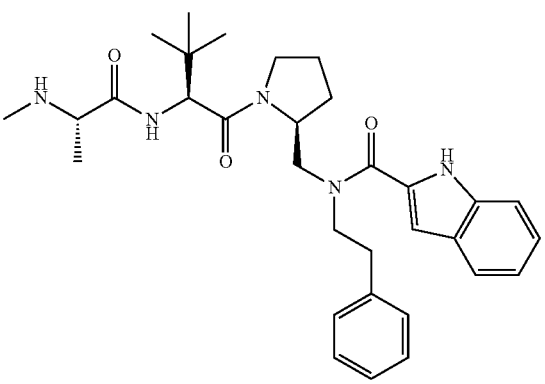 [SMILES: CN[C@@H](C)C(=O)N[C@H](C(=O)N1CCC[C@H]1CN(CCc1ccccc1)C(=O)c1cc2ccccc2[nH]1)C(C)(C)C] |

| No. | Structure |
|---|---|
| 28 | 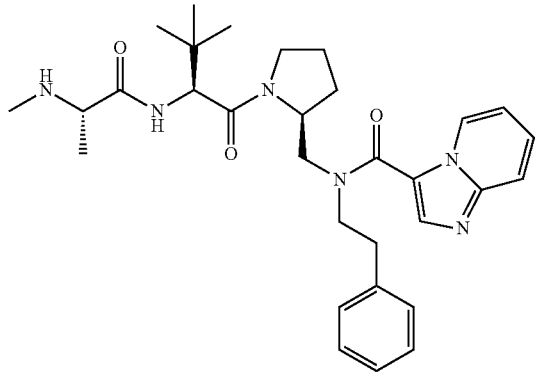 [SMILES: CN[C@@H](C)C(=O)N[C@H](C(=O)N1CCC[C@H]1CN(CCc1ccccc1)C(=O)c1cnc2ccccn12)C(C)(C)C] |
| 29 | 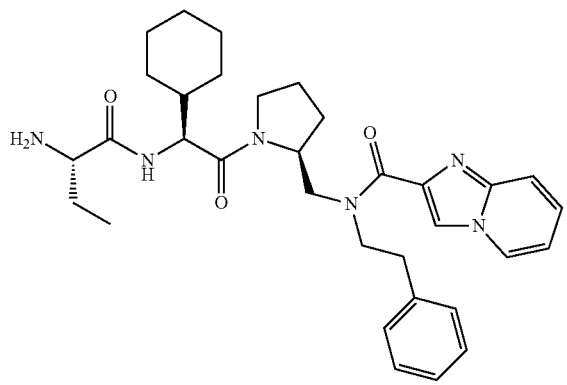 [SMILES: CC[C@H](N)C(=O)N[C@H](C(=O)N1CCC[C@H]1CN(CCc1ccccc1)C(=O)c1cn2ccccc2n1)C1CCCCC1] |
| 30 | 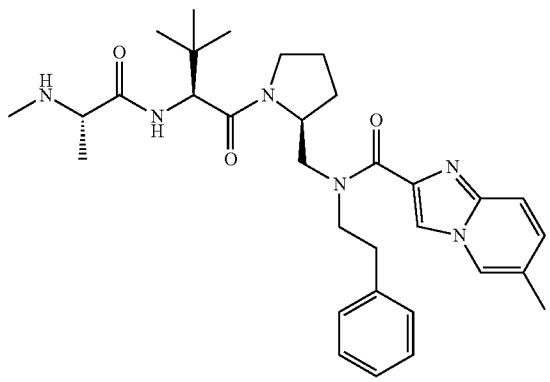 |
| 31 | 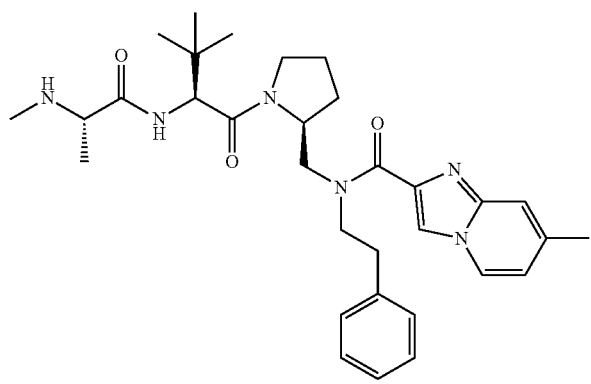 |

| No. | Structure |
|---|---|
| 32 | 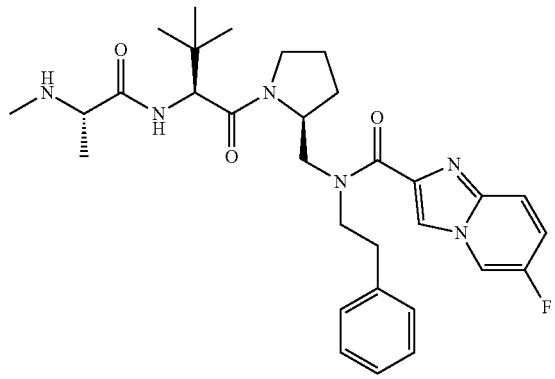 [SMILES: CN[C@@H](C)C(=O)N[C@H](C(=O)N1CCC[C@H]1CN(CCc1ccccc1)C(=O)c1cn2cc(F)ccc2n1)C(C)(C)C] |
| 33 | 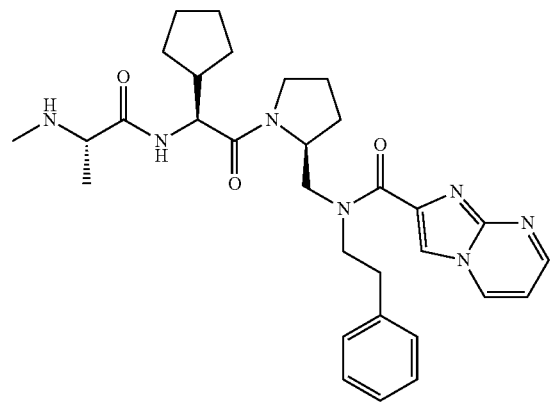 [SMILES: CN[C@@H](C)C(=O)N[C@H](C(=O)N1CCC[C@H]1CN(CCc1ccccc1)C(=O)c1cn2cccnc2n1)C1CCCC1] |
| 34 | 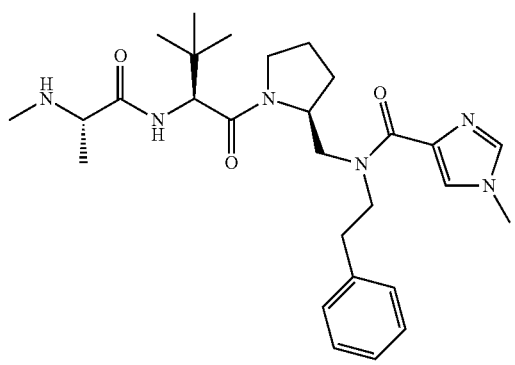 |
| 35 | 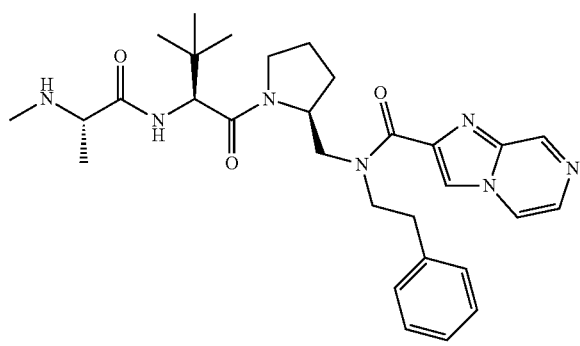 [SMILES: CN[C@@H](C)C(=O)N[C@H](C(=O)N1CCC[C@H]1CN(CCc1ccccc1)C(=O)c1cn2ccncc2n1)C(C)(C)C] |

| No. | Structure |
|---|---|
| 36 | 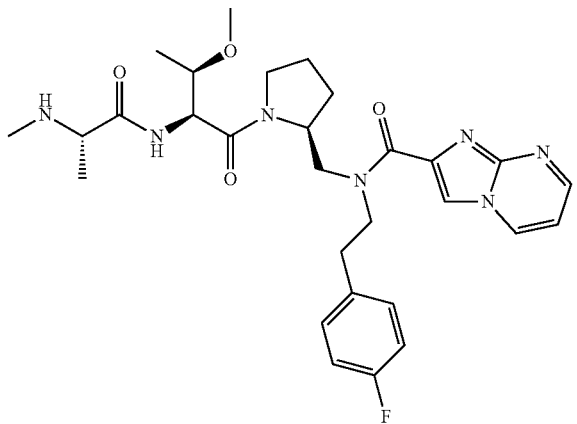 [SMILES: CN[C@@H](C)C(=O)N[C@H](C(=O)N1CCC[C@H]1CN(CCc1ccc(F)cc1)C(=O)c1cn2cccnc2n1)[C@@H](C)OC] |
| 37 | 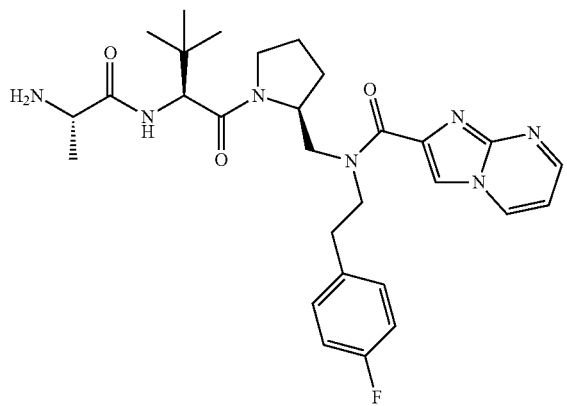 [SMILES: C[C@H](N)C(=O)N[C@H](C(=O)N1CCC[C@H]1CN(CCc1ccc(F)cc1)C(=O)c1cn2cccnc2n1)C(C)(C)C] |
| 38 | 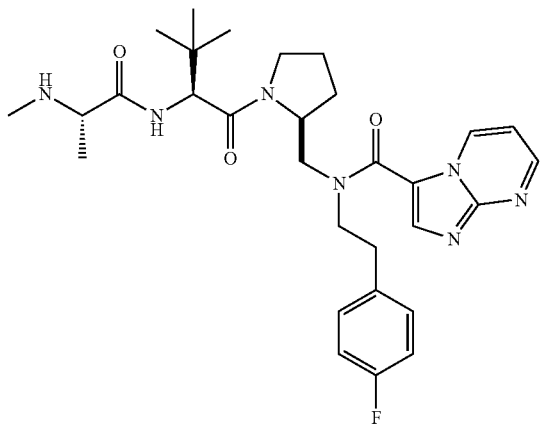 [SMILES: CN[C@@H](C)C(=O)N[C@H](C(=O)N1CCC[C@H]1CN(CCc1ccc(F)cc1)C(=O)c1cnc2ncccn12)C(C)(C)C] |

| No. | Structure |
|---|---|
| 39 | 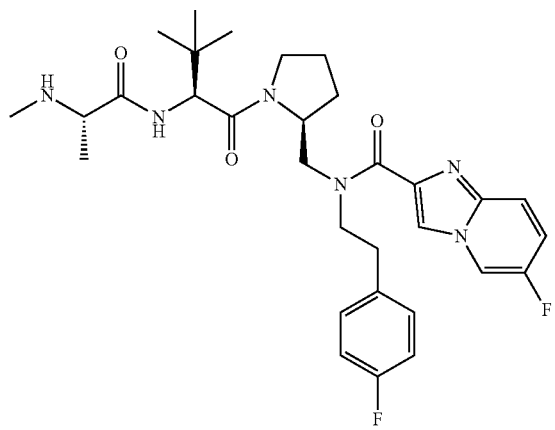 [SMILES: CN[C@@H](C)C(=O)N[C@H](C(=O)N1CCC[C@H]1CN(CCc1ccc(F)cc1)C(=O)c1cn2cc(F)ccc2n1)C(C)(C)C] |
| 40 | 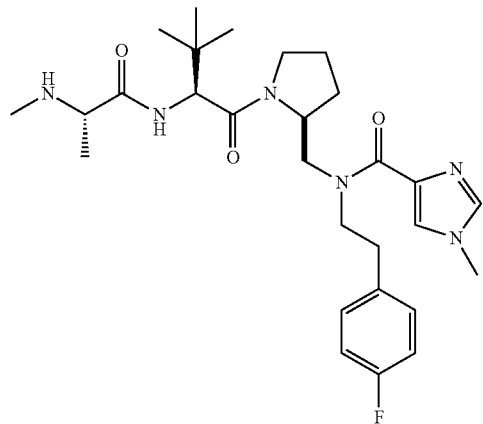 [SMILES: CN[C@@H](C)C(=O)N[C@H](C(=O)N1CCC[C@H]1CN(CCc1ccc(F)cc1)C(=O)c1cn(C)cn1)C(C)(C)C] |
| 41 | 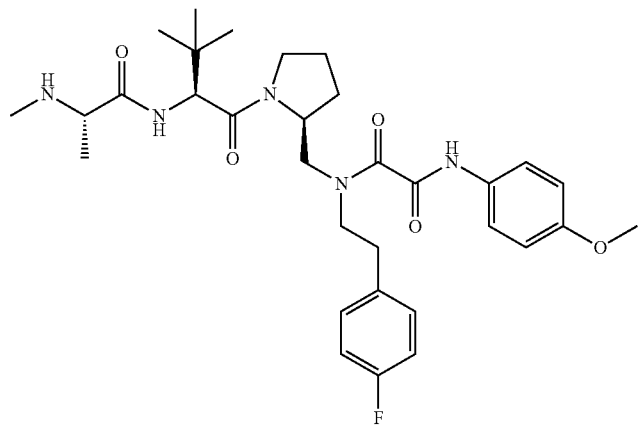 |

| No. | Structure |
|---|---|
| 42 | 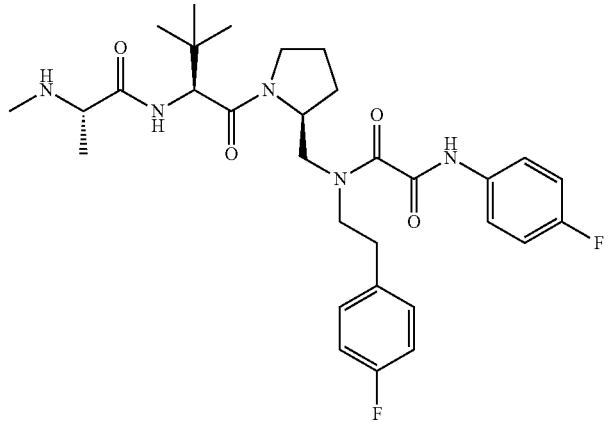 [SMILES: CN[C@@H](C)C(=O)N[C@H](C(=O)N1CCC[C@H]1CN(CCc1ccc(F)cc1)C(=O)C(=O)Nc1ccc(F)cc1)C(C)(C)C] |
| 43 | 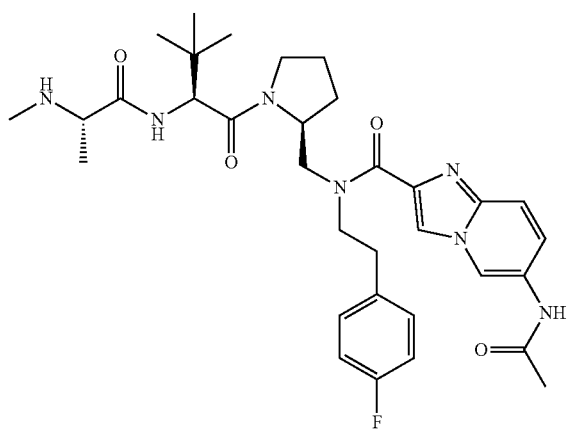 [SMILES: CN[C@@H](C)C(=O)N[C@H](C(=O)N1CCC[C@H]1CN(CCc1ccc(F)cc1)C(=O)c1cn2cc(NC(C)=O)ccc2n1)C(C)(C)C] |
| 44 | 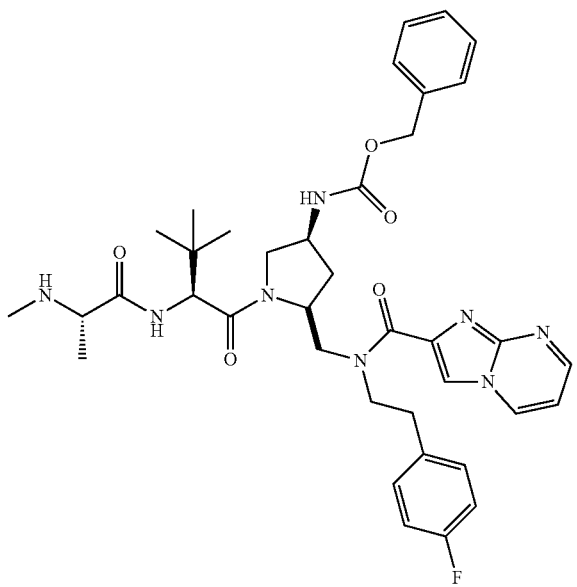 [SMILES: CN[C@@H](C)C(=O)N[C@H](C(=O)N1C[C@@H](NC(=O)OCc2ccccc2)C[C@H]1CN(CCc1ccc(F)cc1)C(=O)c1cn2cccnc2n1)C(C)(C)C] |

-continued
| No. | Structure |
|---|---|
| 45 | 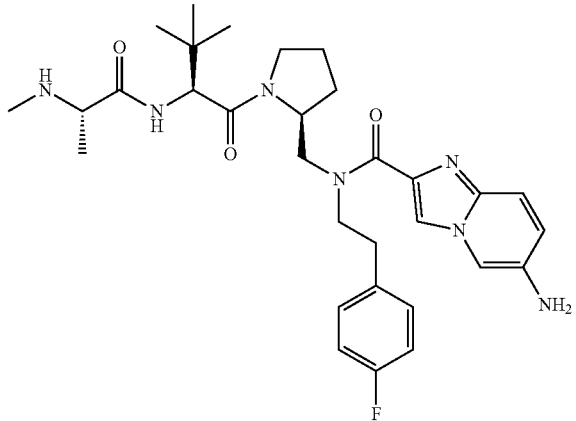 [SMILES: CN[C@@H](C)C(=O)N[C@H](C(=O)N1CCC[C@H]1CN(CCc1ccc(F)cc1)C(=O)c1cn2cc(N)ccc2n1)C(C)(C)C] |
| 46 | 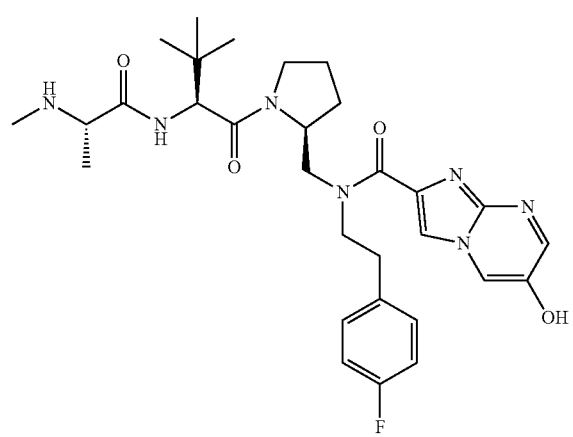 [SMILES: CN[C@@H](C)C(=O)N[C@H](C(=O)N1CCC[C@H]1CN(CCc1ccc(F)cc1)C(=O)c1cn2cc(O)cnc2n1)C(C)(C)C] |
| 47 | 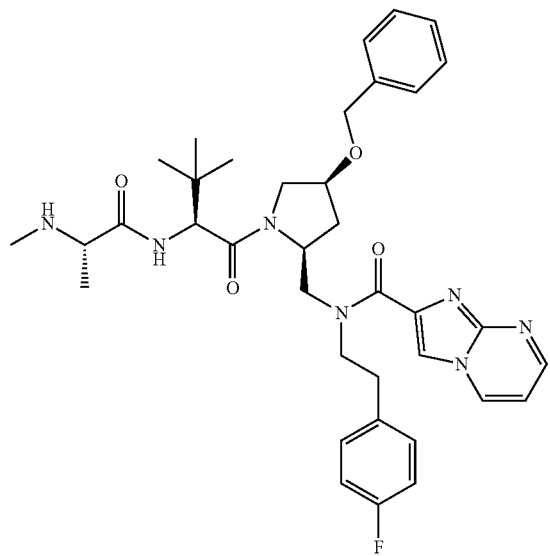 [SMILES: CN[C@@H](C)C(=O)N[C@H](C(=O)N1C[C@@H](OCc2ccccc2)C[C@H]1CN(CCc1ccc(F)cc1)C(=O)c1cn2cccnc2n1)C(C)(C)C] |

| No. | Structure |
|---|---|
| 48 | 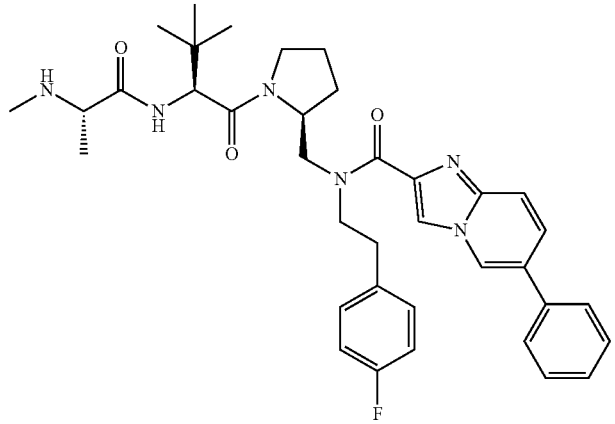 [SMILES: CN[C@@H](C)C(=O)N[C@H](C(=O)N1CCC[C@H]1CN(CCc1ccc(F)cc1)C(=O)c1cn2cc(-c3ccccc3)ccc2n1)C(C)(C)C] |
| 49 | 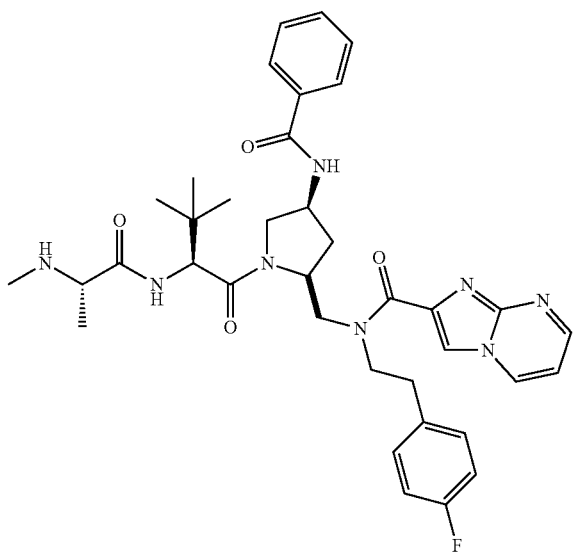 [SMILES: CN[C@@H](C)C(=O)N[C@H](C(=O)N1C[C@@H](NC(=O)c2ccccc2)C[C@H]1CN(CCc1ccc(F)cc1)C(=O)c1cn2cccnc2n1)C(C)(C)C] |
| 50 | 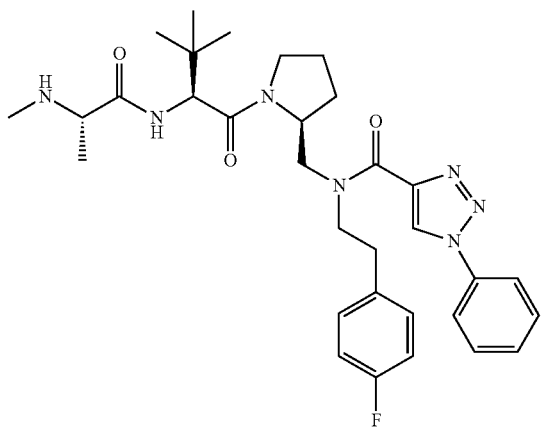 |

-continued
| No. | Structure |
|---|---|
| 51 | 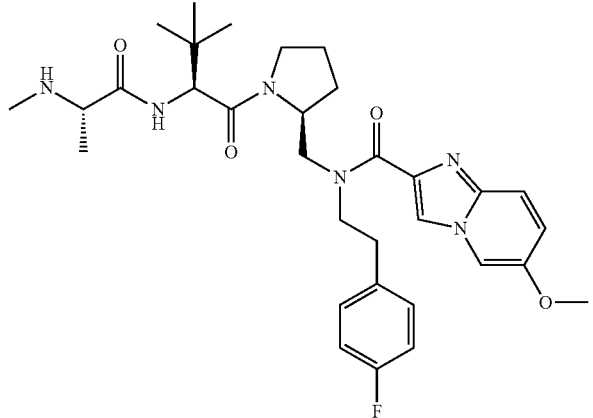 |
| 52 | 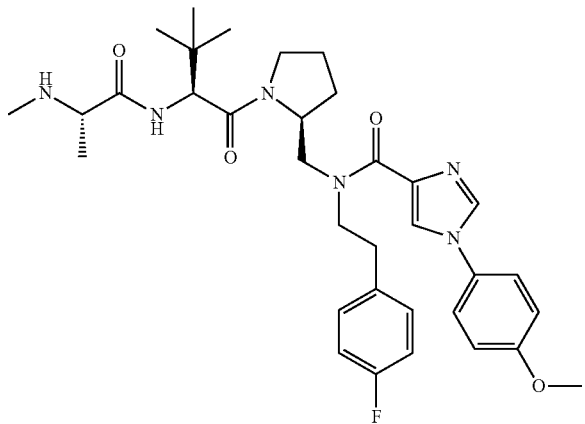 |
| 53 | 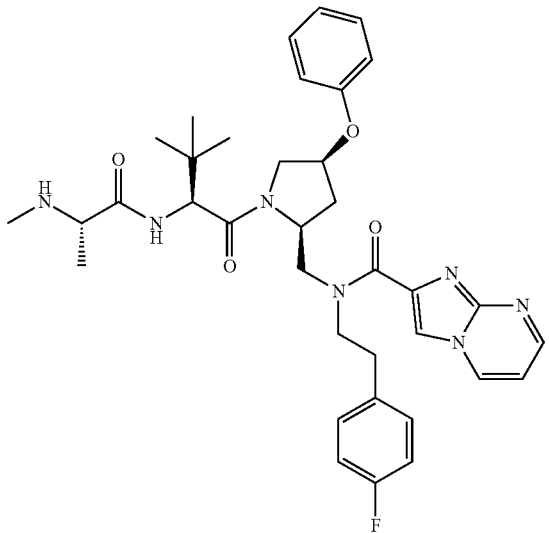 [SMILES: CN[C@@H](C)C(=O)N[C@H](C(=O)N1C[C@@H](Oc2ccccc2)C[C@H]1CN(CCc1ccc(F)cc1)C(=O)c1cn2cccnc2n1)C(C)(C)C] |

| No. | Structure |
|---|---|
| 54 | 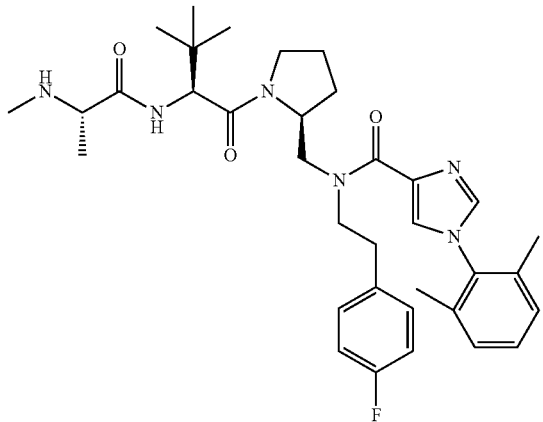 |
| 55 | 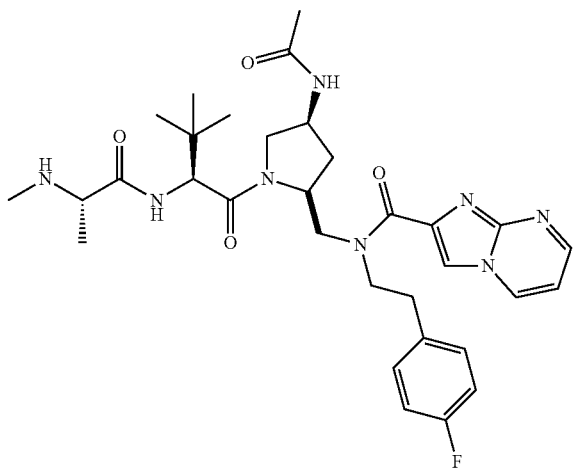 [SMILES: CN[C@@H](C)C(=O)N[C@H](C(=O)N1C[C@@H](NC(C)=O)C[C@H]1CN(CCc1ccc(F)cc1)C(=O)c1cn2cccnc2n1)C(C)(C)C] |
| 56 | 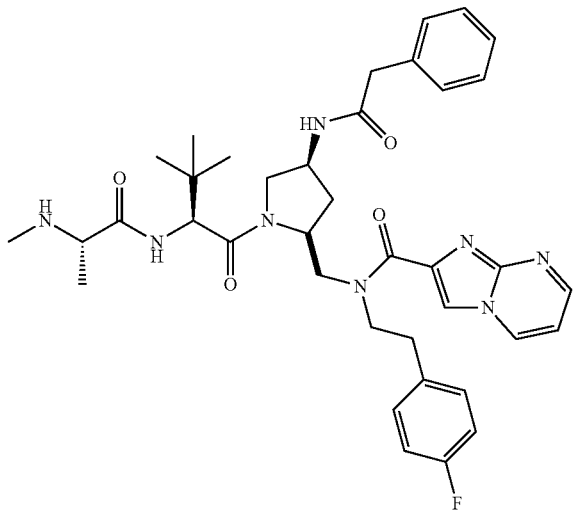 [SMILES: CN[C@@H](C)C(=O)N[C@H](C(=O)N1C[C@@H](NC(=O)Cc2ccccc2)C[C@H]1CN(CCc1ccc(F)cc1)C(=O)c1cn2cccnc2n1)C(C)(C)C] |

| No. | Structure |
|---|---|
| 57 | 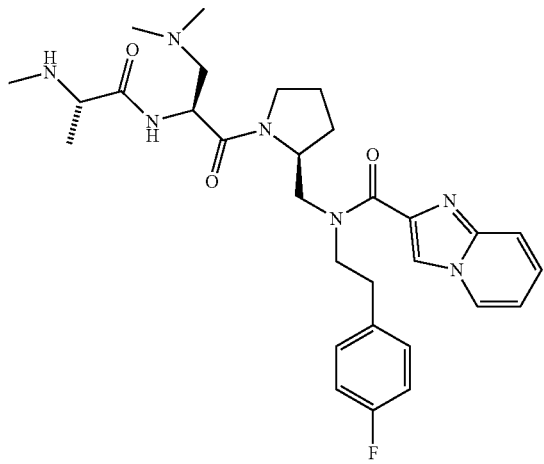 [SMILES: CN[C@@H](C)C(=O)N[C@@H](CN(C)C)C(=O)N1CCC[C@H]1CN(CCc1ccc(F)cc1)C(=O)c1cn2ccccc2n1] |
| 58 | 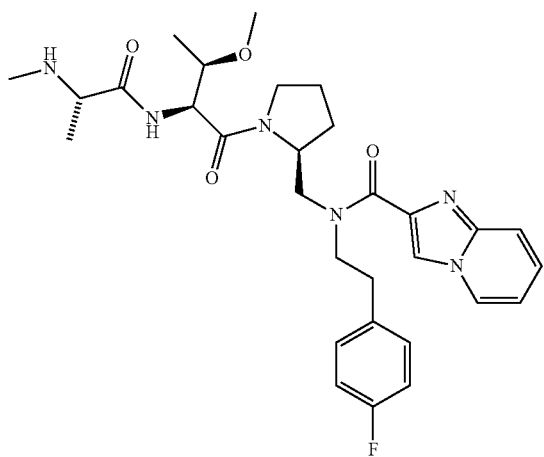 [SMILES: CN[C@@H](C)C(=O)N[C@H](C(=O)N1CCC[C@H]1CN(CCc1ccc(F)cc1)C(=O)c1cn2ccccc2n1)[C@@H](C)OC] |
| 59 | 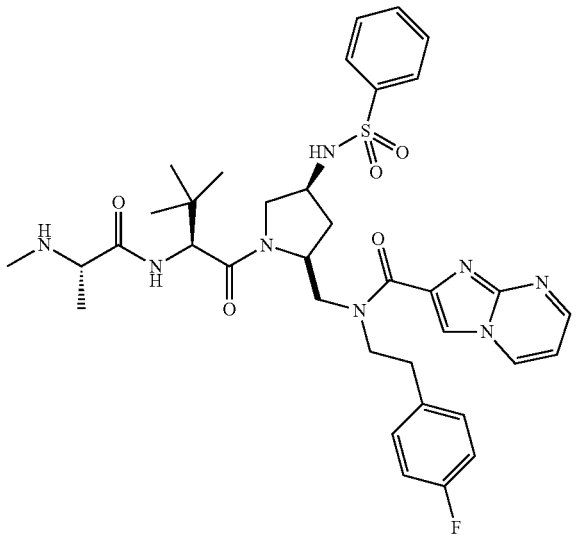 [SMILES: CN[C@@H](C)C(=O)N[C@H](C(=O)N1C[C@@H](NS(=O)(=O)c2ccccc2)C[C@H]1CN(CCc1ccc(F)cc1)C(=O)c1cn2cccnc2n1)C(C)(C)C] |

| No. | Structure |
|---|---|
| 60 | 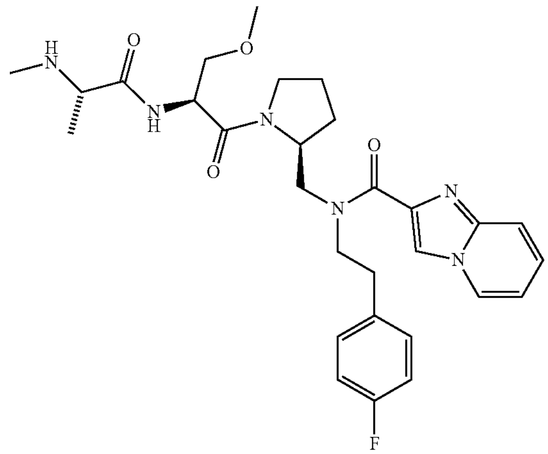 [SMILES: CN[C@@H](C)C(=O)N[C@@H](COC)C(=O)N1CCC[C@H]1CN(CCc1ccc(F)cc1)C(=O)c1cn2ccccc2n1] |
| 61 | 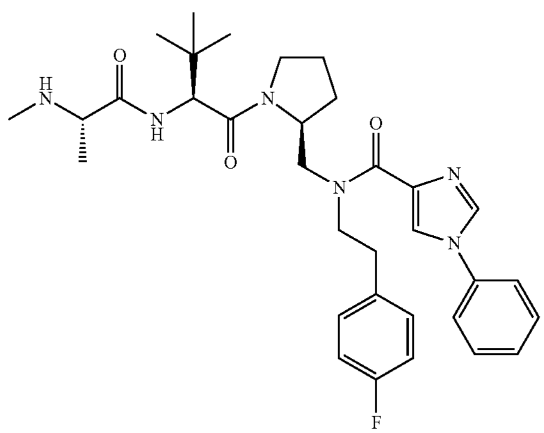 [SMILES: CN[C@@H](C)C(=O)N[C@H](C(=O)N1CCC[C@H]1CN(CCc1ccc(F)cc1)C(=O)c1cn(-c2ccccc2)cn1)C(C)(C)C] |
| 62 | 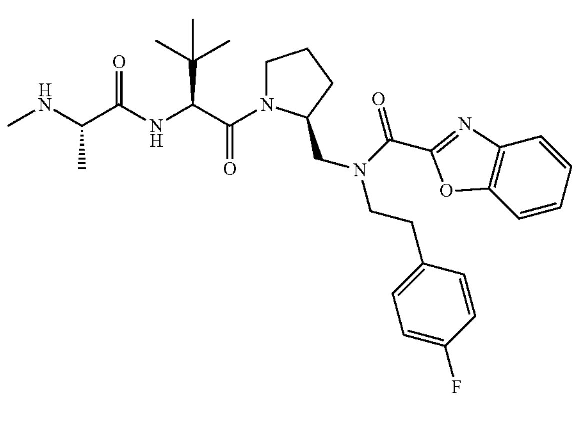 [SMILES: CN[C@@H](C)C(=O)N[C@H](C(=O)N1CCC[C@H]1CN(CCc1ccc(F)cc1)C(=O)c1nc2ccccc2o1)C(C)(C)C] |

-continued
| No. | Structure |
|---|---|
| 63 | 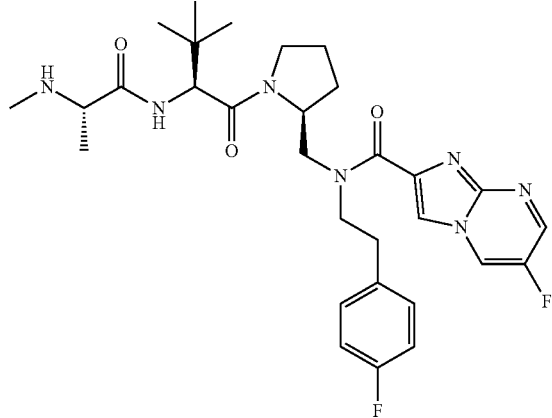 [SMILES: CN[C@@H](C)C(=O)N[C@H](C(=O)N1CCC[C@H]1CN(CCc1ccc(F)cc1)C(=O)c1cn2cc(F)cnc2n1)C(C)(C)C] |
| 64 | 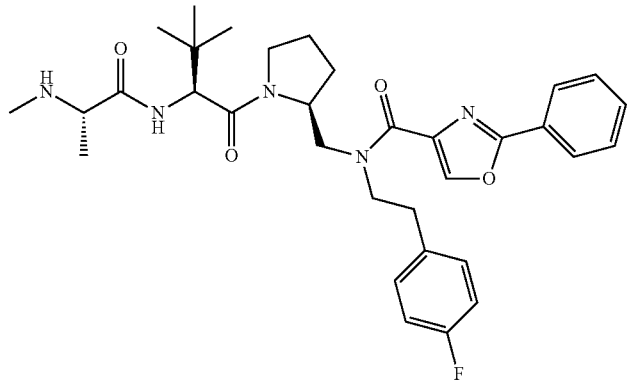 [SMILES: CN[C@@H](C)C(=O)N[C@H](C(=O)N1CCC[C@H]1CN(CCc1ccc(F)cc1)C(=O)c1coc(-c2ccccc2)n1)C(C)(C)C] |
| 65 | 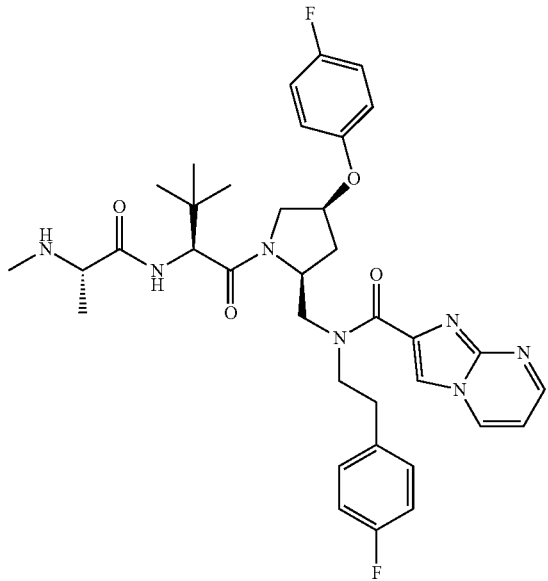 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2cccnc2n1)C(C)(C)C] |

| No. | Structure |
|---|---|
| 66 | 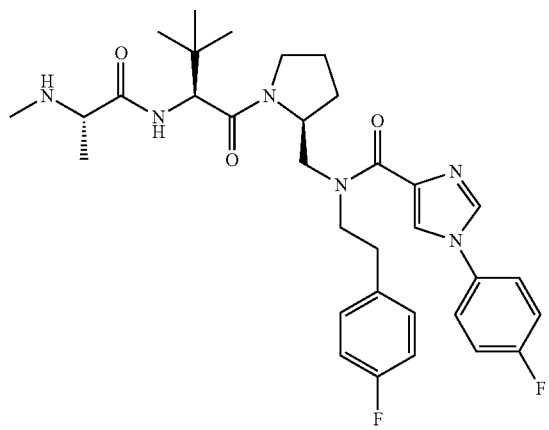 [SMILES: CN[C@@H](C)C(=O)N[C@H](C(=O)N1CCC[C@H]1CN(CCc1ccc(F)cc1)C(=O)c1cn(-c2ccc(F)cc2)cn1)C(C)(C)C] |
| 67 | 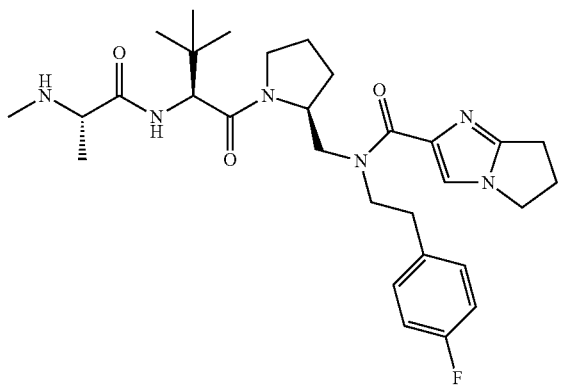 [SMILES: CN[C@@H](C)C(=O)N[C@H](C(=O)N1CCC[C@H]1CN(CCc1ccc(F)cc1)C(=O)c1cn2c(n1)CCC2)C(C)(C)C] |
| 68 | 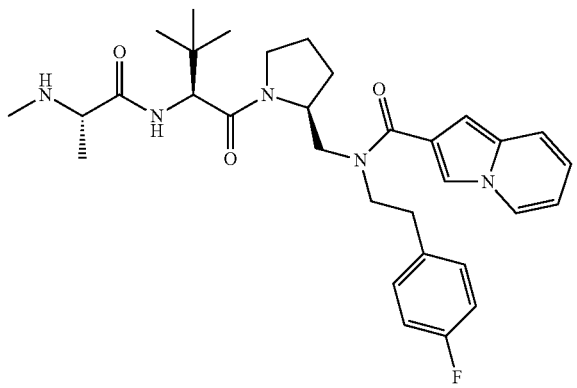 [SMILES: CN[C@@H](C)C(=O)N[C@H](C(=O)N1CCC[C@H]1CN(CCc1ccc(F)cc1)C(=O)c1cc2ccccn2c1)C(C)(C)C] |

-continued
| No. | Structure |
|---|---|
| 69 | 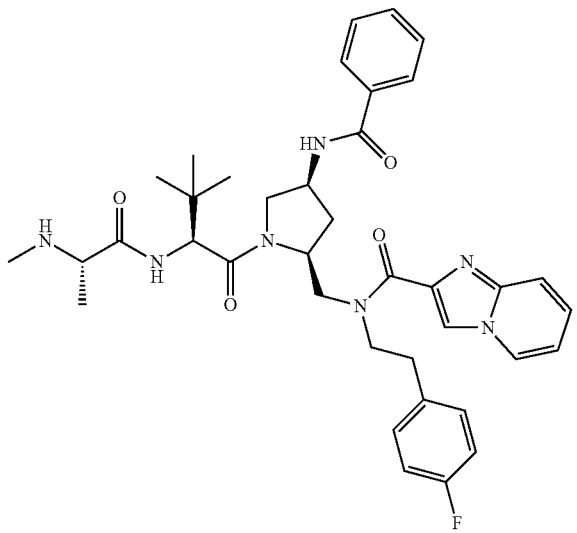 [SMILES: CN[C@@H](C)C(=O)N[C@H](C(=O)N1C[C@@H](NC(=O)c2ccccc2)C[C@H]1CN(CCc1ccc(F)cc1)C(=O)c1cn2ccccc2n1)C(C)(C)C] |
| 70 | 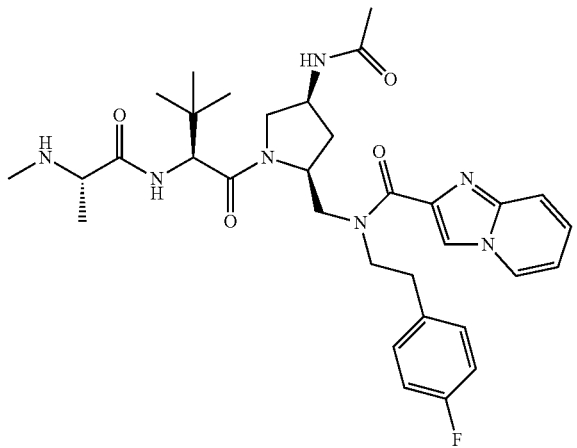 [SMILES: CN[C@@H](C)C(=O)N[C@H](C(=O)N1C[C@@H](NC(C)=O)C[C@H]1CN(CCc1ccc(F)cc1)C(=O)c1cn2ccccc2n1)C(C)(C)C] |
| 71 | 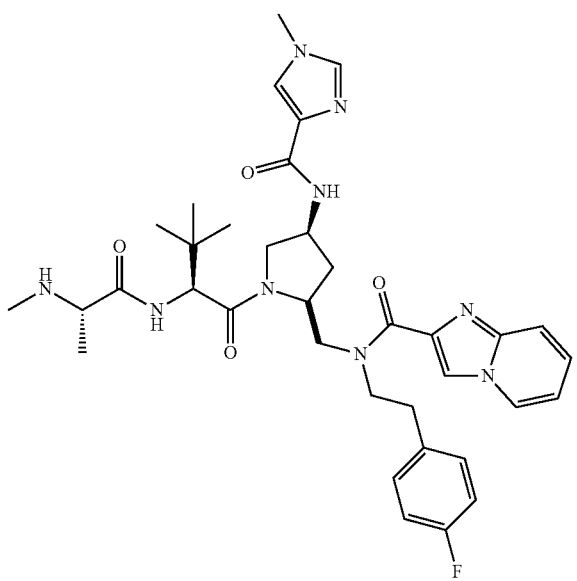 [SMILES: CN[C@@H](C)C(=O)N[C@H](C(=O)N1C[C@@H](NC(=O)c2cn(C)cn2)C[C@H]1CN(CCc1ccc(F)cc1)C(=O)c1cn2ccccc2n1)C(C)(C)C] |

-continued
| No. | Structure |
|---|---|
| 72 | 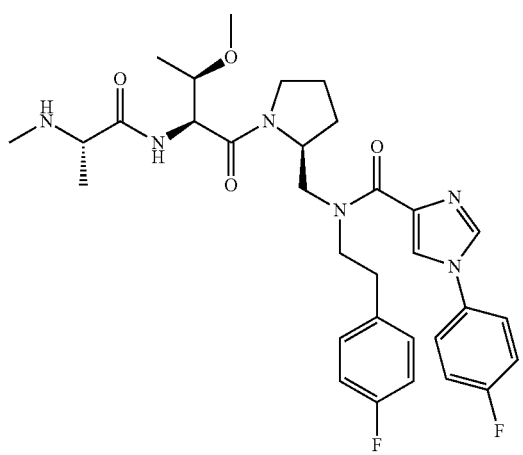 [SMILES: CN[C@@H](C)C(=O)N[C@H](C(=O)N1CCC[C@H]1CN(CCc1ccc(F)cc1)C(=O)c1cn(-c2ccc(F)cc2)cn1)[C@@H](C)OC] |
| 73 | 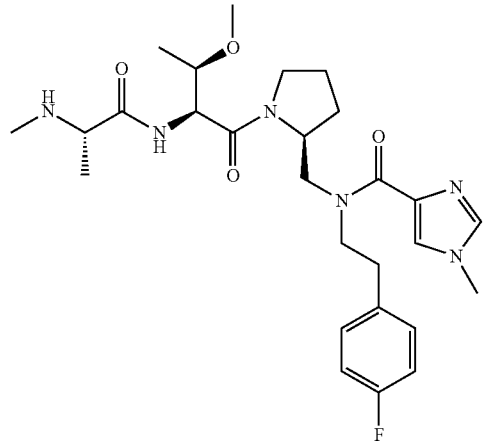 [SMILES: CN[C@@H](C)C(=O)N[C@H](C(=O)N1CCC[C@H]1CN(CCc1ccc(F)cc1)C(=O)c1cn(C)cn1)[C@@H](C)OC] |
| 74 | 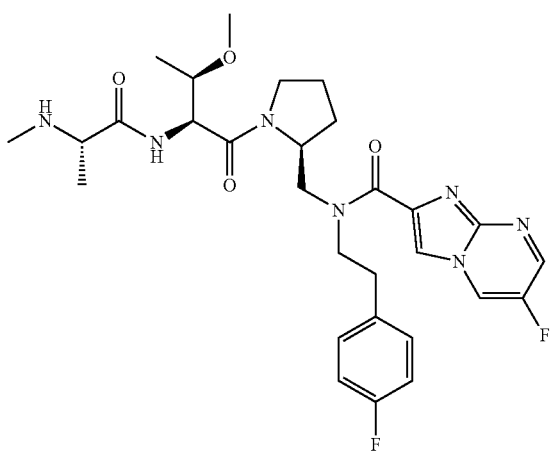 [SMILES: CN[C@@H](C)C(=O)N[C@H](C(=O)N1CCC[C@H]1CN(CCc1ccc(F)cc1)C(=O)c1cn2cc(F)cnc2n1)[C@@H](C)OC] |

| No. | Structure |
|---|---|
| 75 | 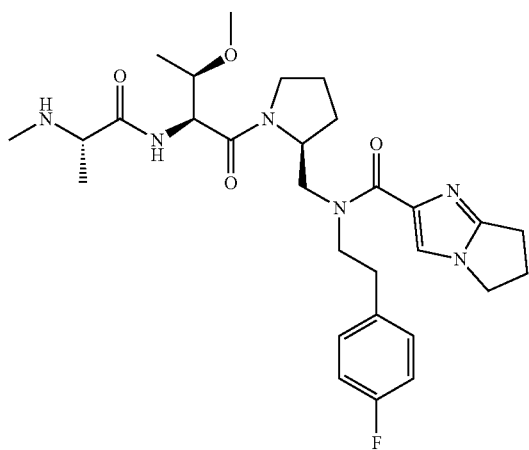 [SMILES: CN[C@@H](C)C(=O)N[C@H](C(=O)N1CCC[C@H]1CN(CCc1ccc(F)cc1)C(=O)c1cn2c(n1)CCC2)[C@@H](C)OC] |
| 76 | 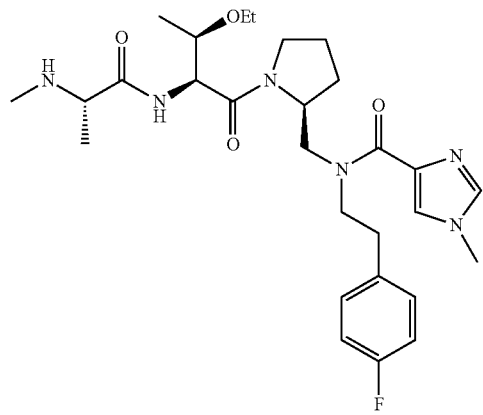 [SMILES: CCO[C@H](C)[C@H](NC(=O)[C@H](C)NC)C(=O)N1CCC[C@H]1CN(CCc1ccc(F)cc1)C(=O)c1cn(C)cn1] |
| 77 | 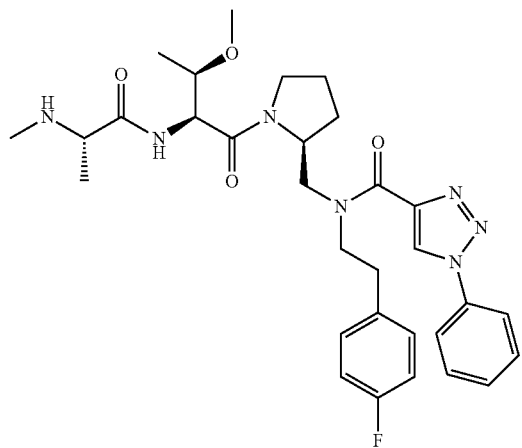 [SMILES: CN[C@@H](C)C(=O)N[C@H](C(=O)N1CCC[C@H]1CN(CCc1ccc(F)cc1)C(=O)c1cn(-c2ccccc2)nn1)[C@@H](C)OC] |

| No. | Structure |
|---|---|
| 78 | 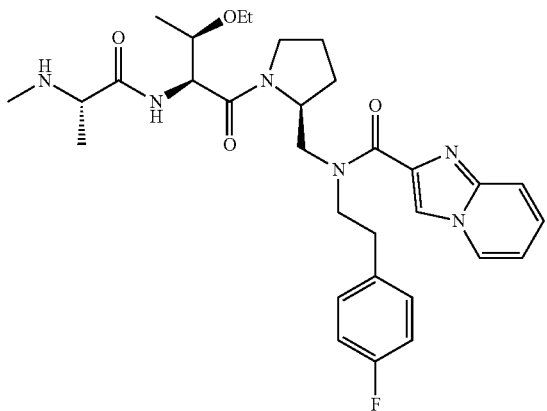 [SMILES: CCO[C@H](C)[C@H](NC(=O)[C@H](C)NC)C(=O)N1CCC[C@H]1CN(CCc1ccc(F)cc1)C(=O)c1cn2ccccc2n1] |
| 79 | 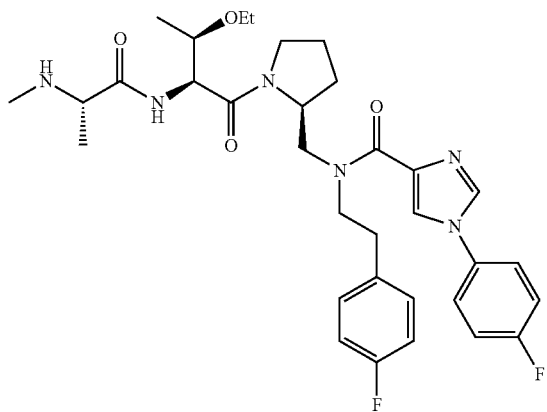 [SMILES: CCO[C@H](C)[C@H](NC(=O)[C@H](C)NC)C(=O)N1CCC[C@H]1CN(CCc1ccc(F)cc1)C(=O)c1cn(-c2ccc(F)cc2)cn1] |
| 80 | 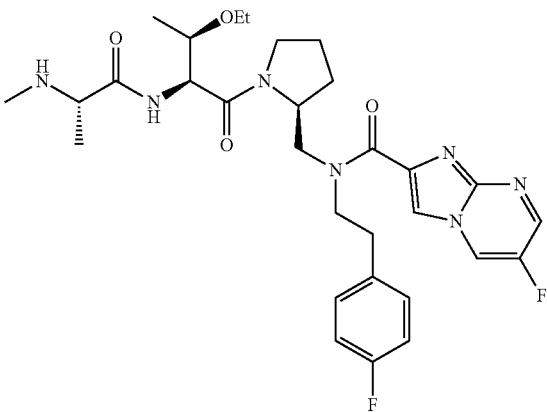 |

-continued
| No. | Structure |
|---|---|
| 81 | 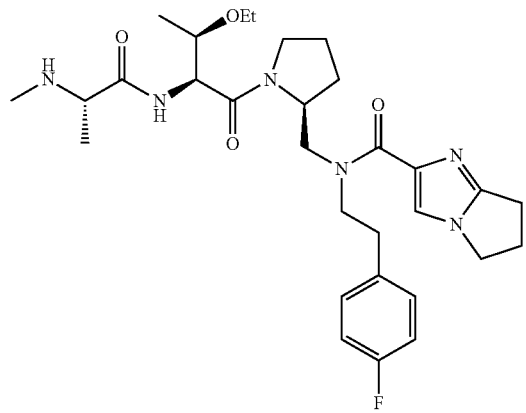 [SMILES: CCO[C@H](C)[C@H](NC(=O)[C@H](C)NC)C(=O)N1CCC[C@H]1CN(CCc1ccc(F)cc1)C(=O)c1cn2c(n1)CCC2] |
| 82 | 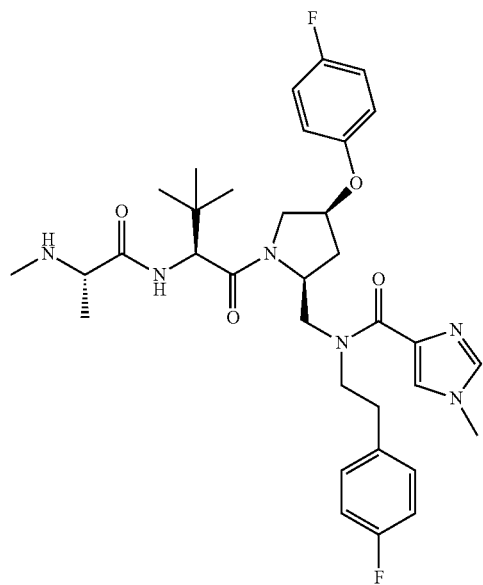 [SMILES: CN[C@@H](C)C(=O)N[C@H](C(=O)N1C[C@@H](Oc2ccc(F)cc2)C[C@H]1CN(CCc1ccc(F)cc1)C(=O)c1cn(C)cn1)C(C)(C)C] |
| 83 | 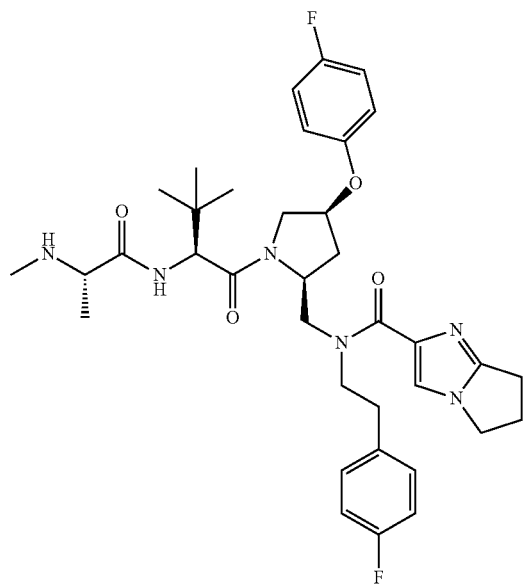 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2c(n1)CCC2)C(C)(C)C] |

| No. | Structure |
|---|---|
| 84 | 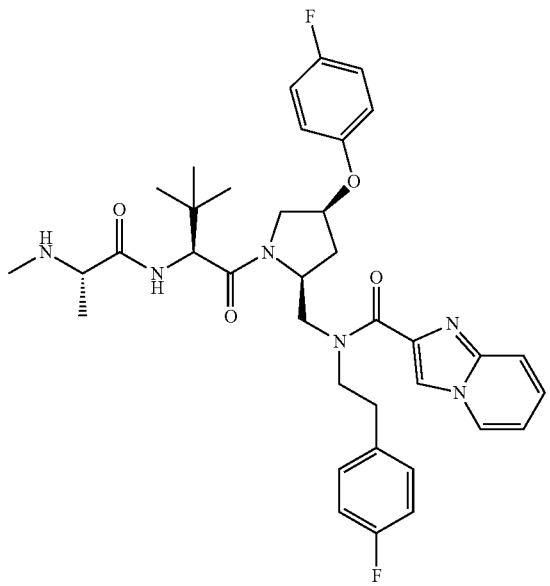 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2ccccc2n1)C(C)(C)C] |
| 85 | 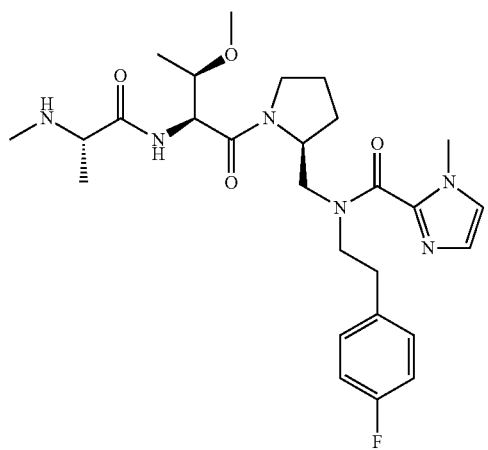 [SMILES: CN[C@@H](C)C(=O)N[C@H](C(=O)N1CCC[C@H]1CN(CCc1ccc(F)cc1)C(=O)c1nccn1C)[C@@H](C)OC] |
| 86 | 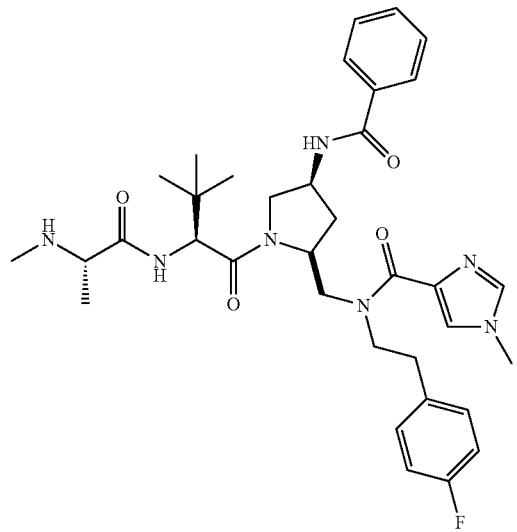 |

-continued
| No. | Structure |
|---|---|
| 87 | 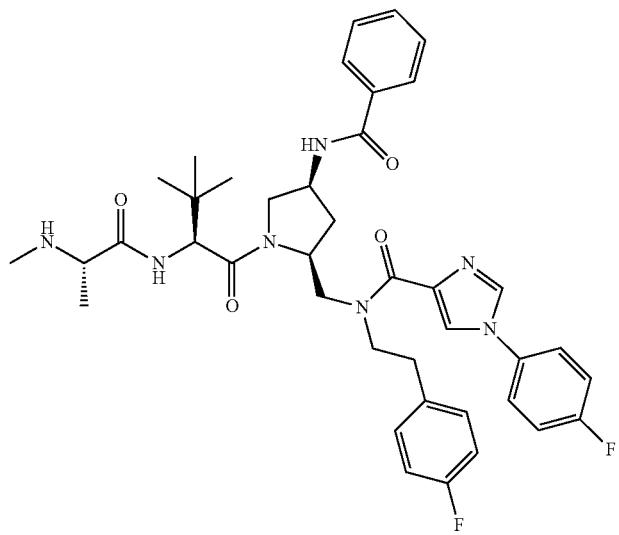 [SMILES: CN[C@@H](C)C(=O)N[C@H](C(=O)N1C[C@@H](NC(=O)c2ccccc2)C[C@H]1CN(CCc1ccc(F)cc1)C(=O)c1cn(-c2ccc(F)cc2)cn1)C(C)(C)C] |
| 88 | 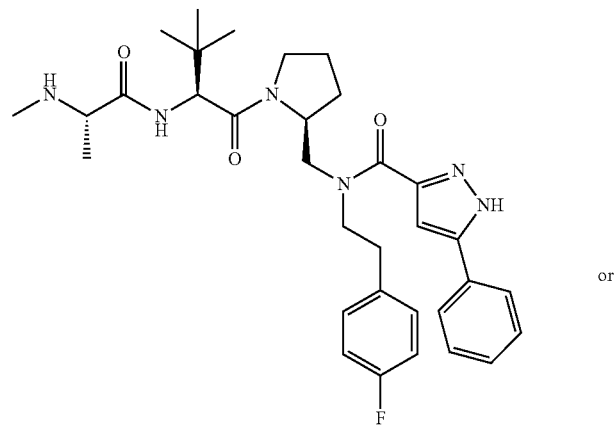 [SMILES: CN[C@@H](C)C(=O)N[C@H](C(=O)N1CCC[C@H]1CN(CCc1ccc(F)cc1)C(=O)c1cc(-c2ccccc2)[nH]n1)C(C)(C)C] or |
| 89 | 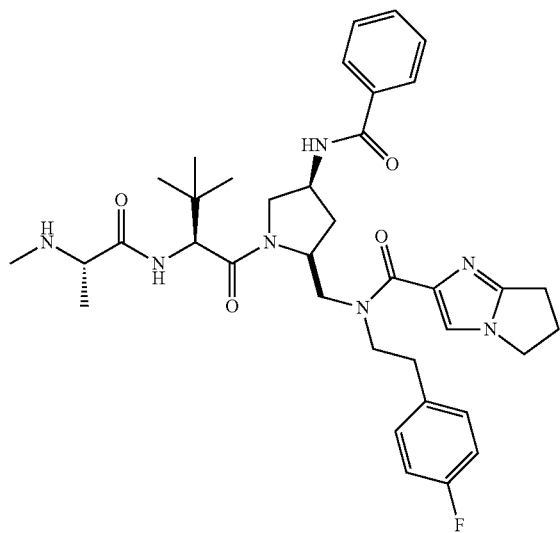 [SMILES: CN[C@@H](C)C(=O)N[C@H](C(=O)N1C[C@@H](NC(=O)c2ccccc2)C[C@H]1CN(CCc1ccc(F)cc1)C(=O)c1cn2c(n1)CCC2)C(C)(C)C] |

| No. | Structure |
|---|---|
| 90 | 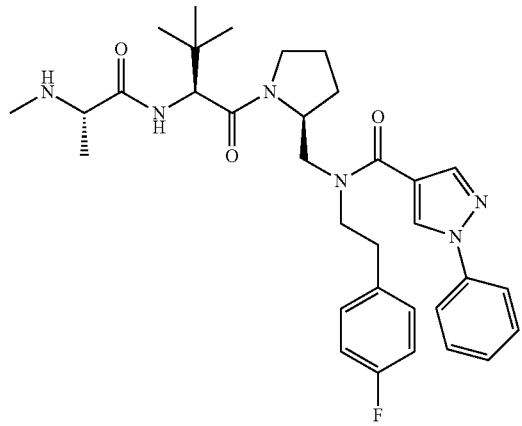 [SMILES: CN[C@@H](C)C(=O)N[C@H](C(=O)N1CCC[C@H]1CN(CCc1ccc(F)cc1)C(=O)c1cnn(-c2ccccc2)c1)C(C)(C)C] |
| 91 | 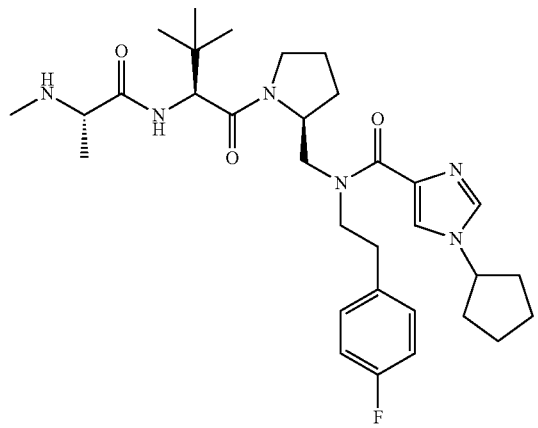 [SMILES: CN[C@@H](C)C(=O)N[C@H](C(=O)N1CCC[C@H]1CN(CCc1ccc(F)cc1)C(=O)c1cn(C2CCCC2)cn1)C(C)(C)C] |
| 92 | 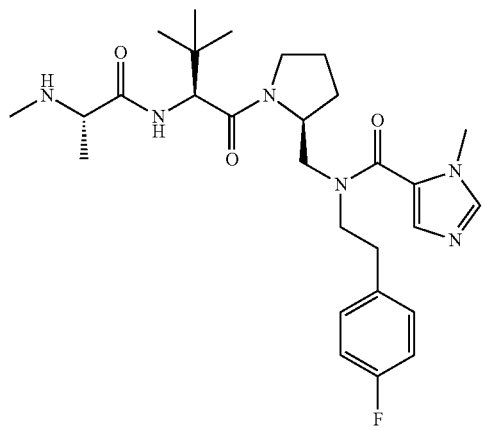 [SMILES: CN[C@@H](C)C(=O)N[C@H](C(=O)N1CCC[C@H]1CN(CCc1ccc(F)cc1)C(=O)c1cncn1C)C(C)(C)C] |

| No. | Structure |
|---|---|
| 93 | 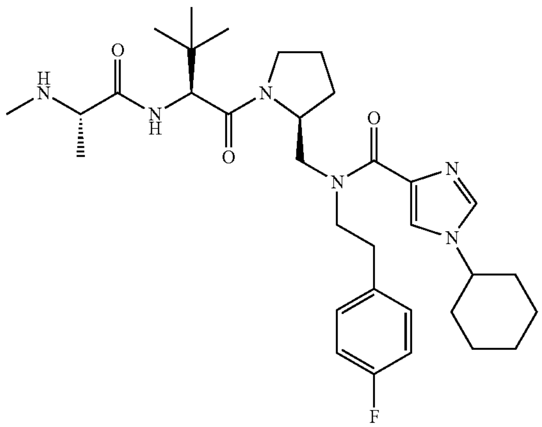 [SMILES: CN[C@@H](C)C(=O)N[C@H](C(=O)N1CCC[C@H]1CN(CCc1ccc(F)cc1)C(=O)c1cn(C2CCCCC2)cn1)C(C)(C)C] |
| 94 | 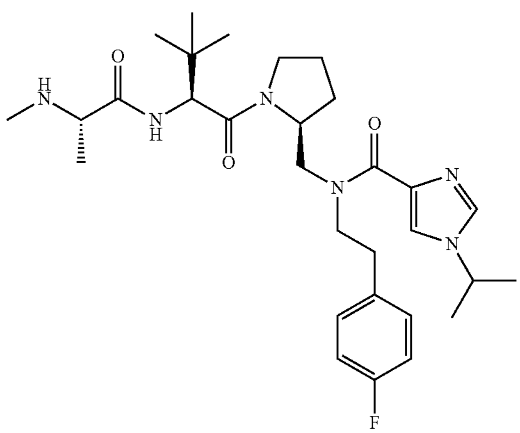 [SMILES: CN[C@@H](C)C(=O)N[C@H](C(=O)N1CCC[C@H]1CN(CCc1ccc(F)cc1)C(=O)c1cn(C(C)C)cn1)C(C)(C)C] |
| 95 | 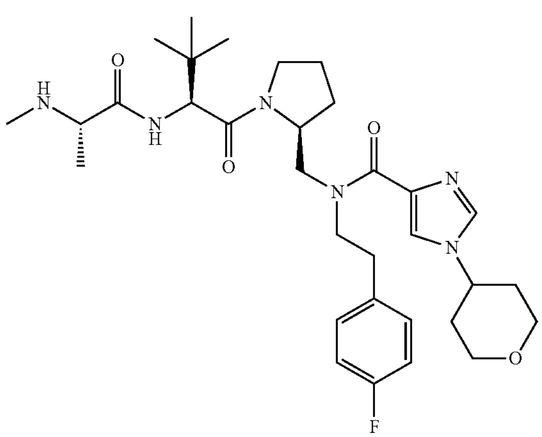 [SMILES: CN[C@@H](C)C(=O)N[C@H](C(=O)N1CCC[C@H]1CN(CCc1ccc(F)cc1)C(=O)c1cn(C2CCOCC2)cn1)C(C)(C)C] |

| No. | Structure |
|---|---|
| 96 | 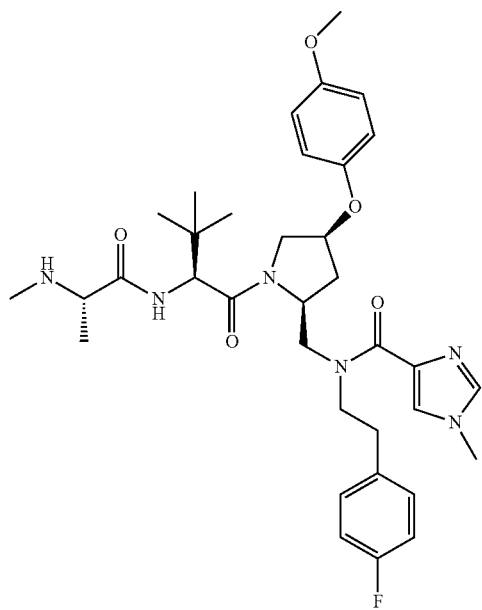 [SMILES: CN[C@@H](C)C(=O)N[C@H](C(=O)N1C[C@@H](Oc2ccc(OC)cc2)C[C@H]1CN(CCc1ccc(F)cc1)C(=O)c1cn(C)cn1)C(C)(C)C] |
| 97 | 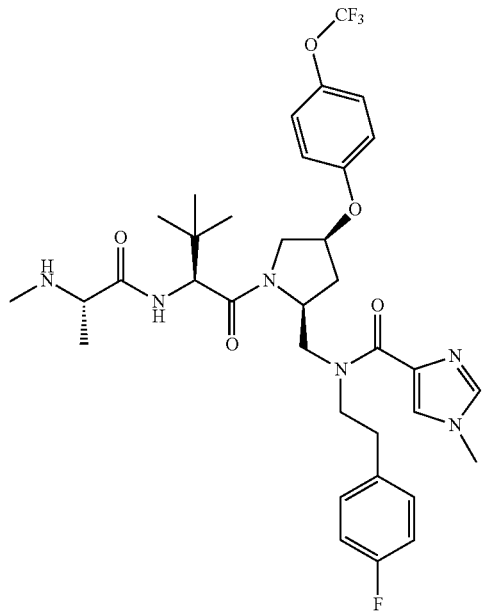 [SMILES: CN[C@@H](C)C(=O)N[C@H](C(=O)N1C[C@@H](Oc2ccc(OC(F)(F)F)cc2)C[C@H]1CN(CCc1ccc(F)cc1)C(=O)c1cn(C)cn1)C(C)(C)C] |

| No. | Structure |
|---|---|
| 98 | 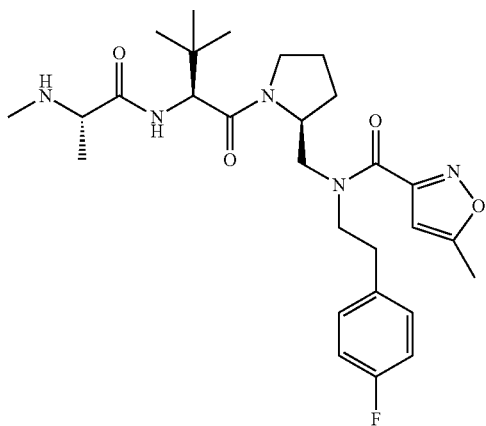 [SMILES: CN[C@@H](C)C(=O)N[C@H](C(=O)N1CCC[C@H]1CN(CCc1ccc(F)cc1)C(=O)c1cc(C)on1)C(C)(C)C] |
| 99 | 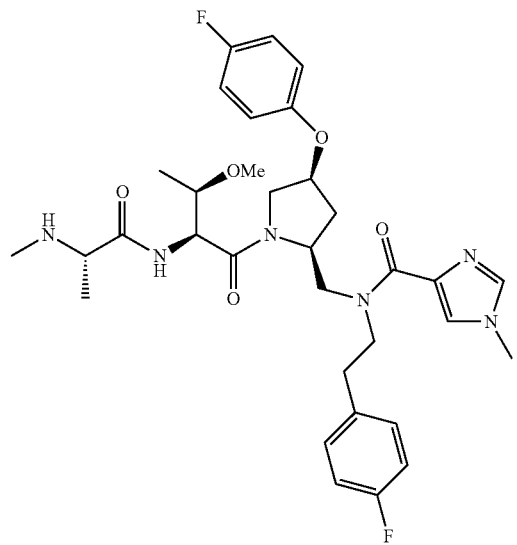 |
| 100 | 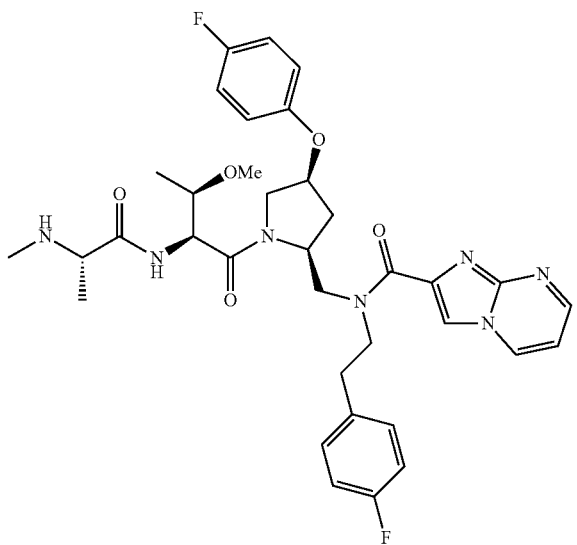 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2cccnc2n1)[C@@H](C)OC] |

-continued
| No. | Structure |
|---|---|
| 101 | 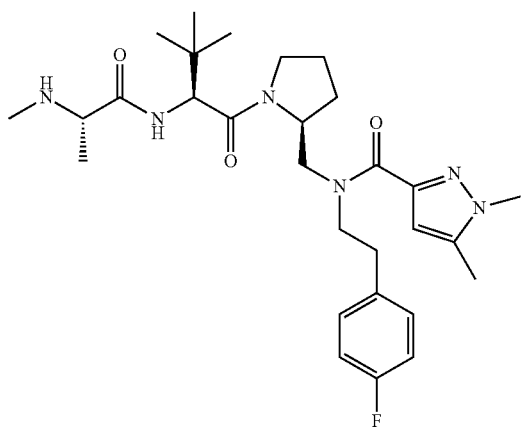 |
| 102 | 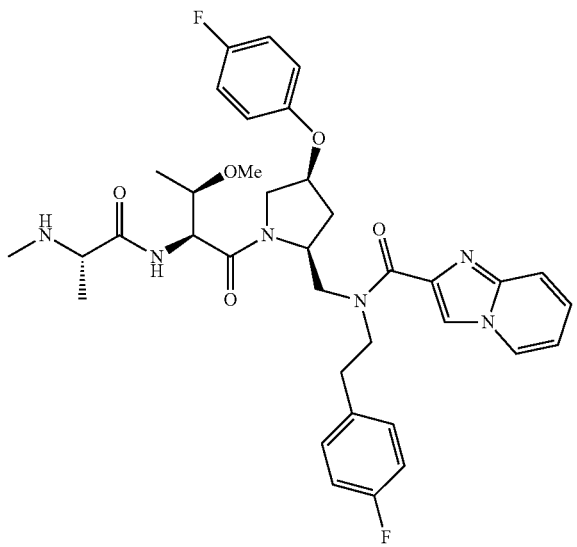 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2ccccc2n1)[C@@H](C)OC] |
| 103 | 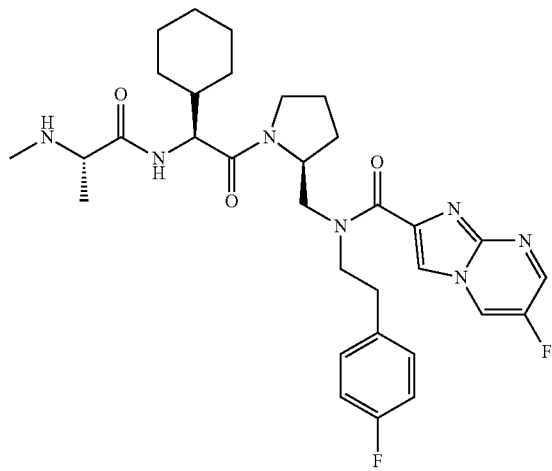 [SMILES: CN[C@@H](C)C(=O)N[C@H](C(=O)N1CCC[C@H]1CN(CCc1ccc(F)cc1)C(=O)c1cn2cc(F)cnc2n1)C1CCCCC1] |

-continued
| No. | Structure |
|---|---|
| 104 | 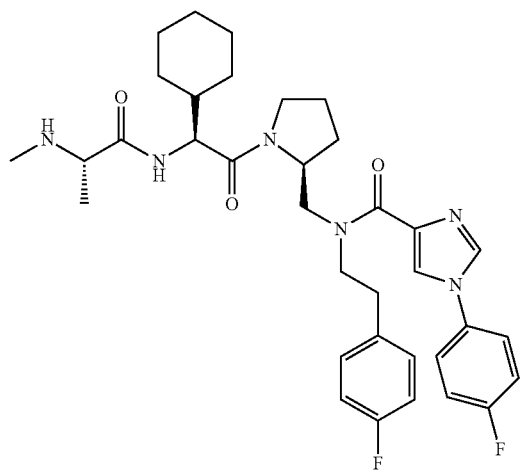 [SMILES: CN[C@@H](C)C(=O)N[C@H](C(=O)N1CCC[C@H]1CN(CCc1ccc(F)cc1)C(=O)c1cn(-c2ccc(F)cc2)cn1)C1CCCCC1] |
| 105 | 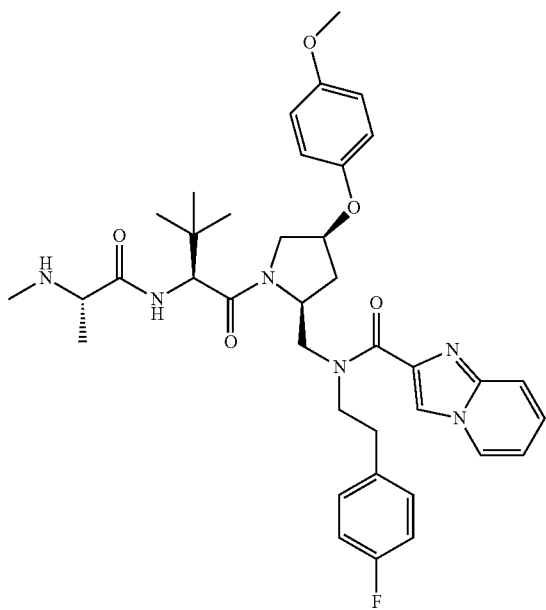 [SMILES: CN[C@@H](C)C(=O)N[C@H](C(=O)N1C[C@@H](Oc2ccc(OC)cc2)C[C@H]1CN(CCc1ccc(F)cc1)C(=O)c1cn2ccccc2n1)C(C)(C)C] |
| 106 | 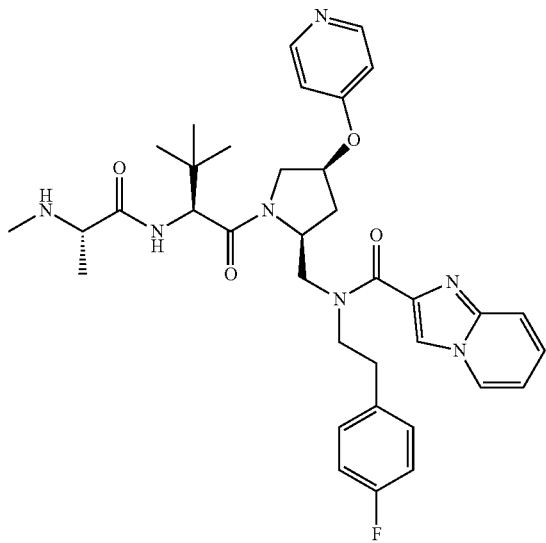 [SMILES: CN[C@@H](C)C(=O)N[C@H](C(=O)N1C[C@@H](Oc2ccncc2)C[C@H]1CN(CCc1ccc(F)cc1)C(=O)c1cn2ccccc2n1)C(C)(C)C] |

-continued
| No. | Structure |
|---|---|
| 107 | 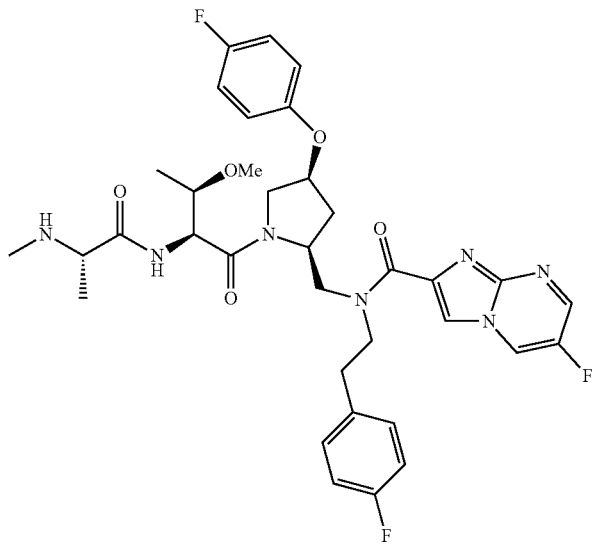 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2cc(F)cnc2n1)[C@@H](C)OC] |
| 108 | 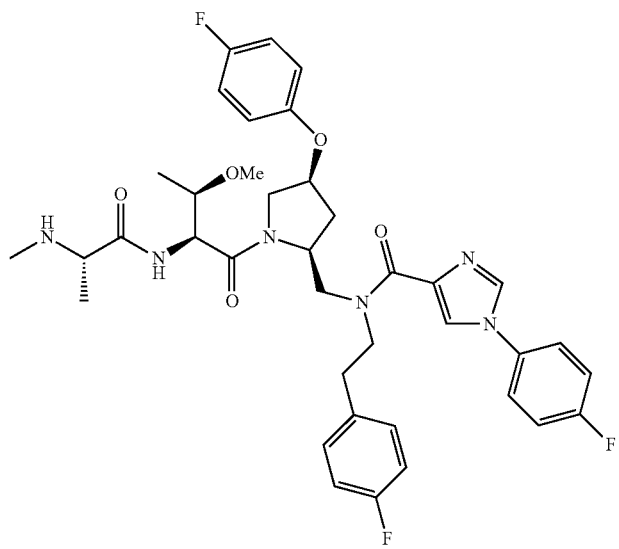 [SMILES: CN[C@@H](C)C(=O)N[C@H](C(=O)N1C[C@@H](Oc2ccc(F)cc2)C[C@H]1CN(CCc1ccc(F)cc1)C(=O)c1cn(-c2ccc(F)cc2)cn1)[C@@H](C)OC] |
| 109 | 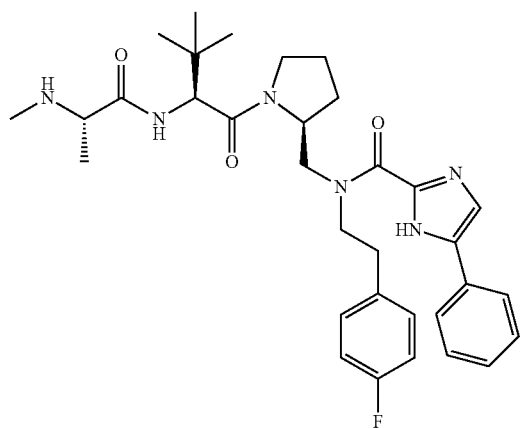 [SMILES: CN[C@@H](C)C(=O)N[C@H](C(=O)N1CCC[C@H]1CN(CCc1ccc(F)cc1)C(=O)c1ncc(-c2ccccc2)[nH]1)C(C)(C)C] |

-continued
| No. | Structure |
|---|---|
| 110 | 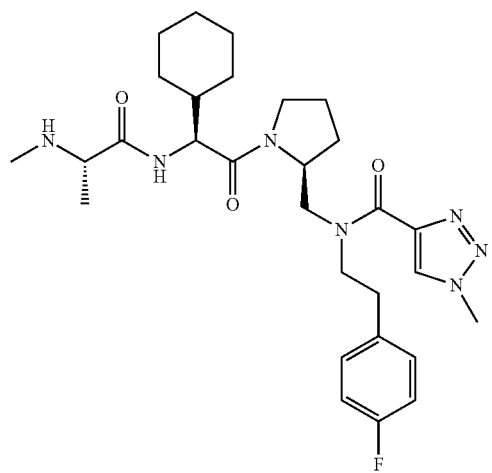 [SMILES: CN[C@@H](C)C(=O)N[C@H](C(=O)N1CCC[C@H]1CN(CCc1ccc(F)cc1)C(=O)c1cn(C)nn1)C1CCCCC1] |
| 111 | 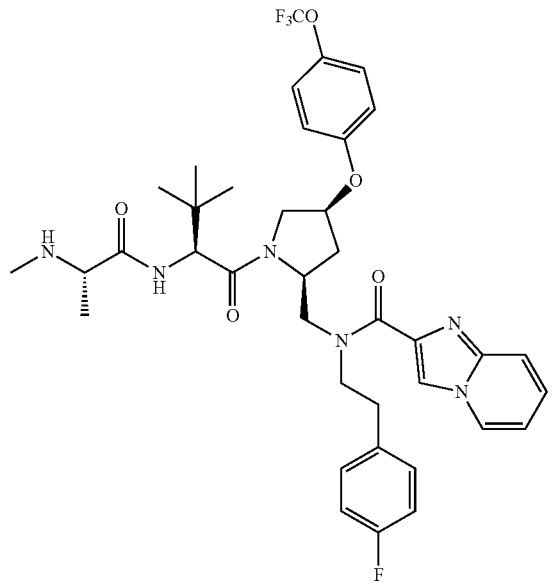 [SMILES: CN[C@@H](C)C(=O)N[C@H](C(=O)N1C[C@@H](Oc2ccc(OC(F)(F)F)cc2)C[C@H]1CN(CCc1ccc(F)cc1)C(=O)c1cn2ccccc2n1)C(C)(C)C] |
| 112 | 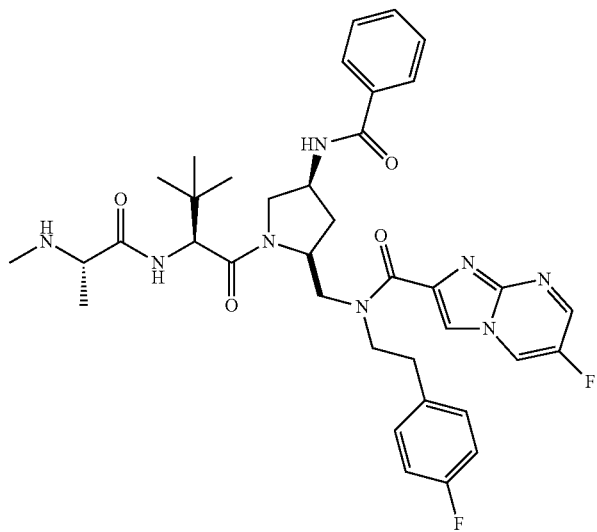 [SMILES: CN[C@@H](C)C(=O)N[C@H](C(=O)N1C[C@@H](NC(=O)c2ccccc2)C[C@H]1CN(CCc1ccc(F)cc1)C(=O)c1cn2cc(F)cnc2n1)C(C)(C)C] |

| No. | Structure |
|---|---|
| 113 | 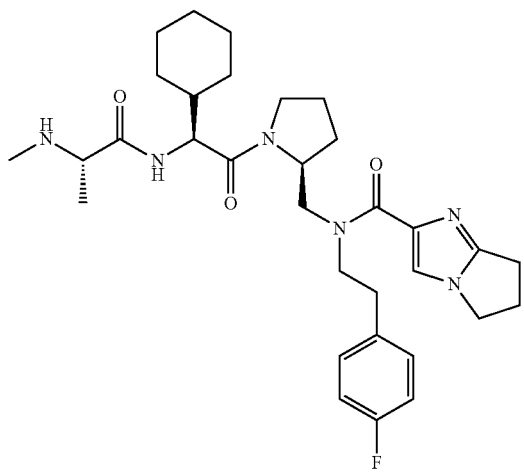 [SMILES: CN[C@@H](C)C(=O)N[C@H](C(=O)N1CCC[C@H]1CN(CCc1ccc(F)cc1)C(=O)c1cn2c(n1)CCC2)C1CCCCC1] |
| 114 | 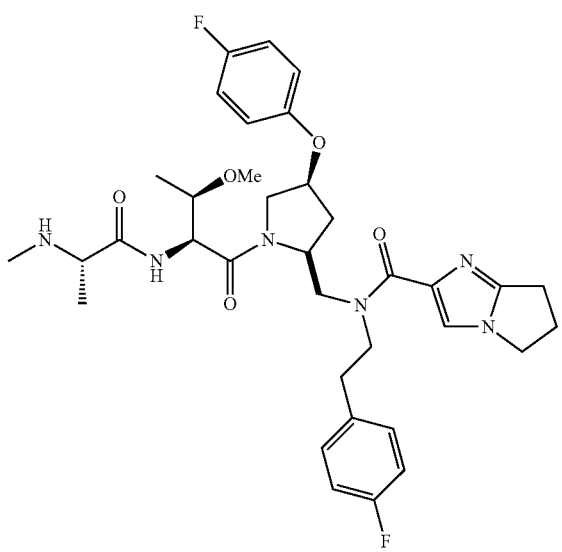 [SMILES: CN[C@@H](C)C(=O)N[C@H](C(=O)N1C[C@@H](Oc2ccc(F)cc2)C[C@H]1CN(CCc1ccc(F)cc1)C(=O)c1cn2c(n1)CCC2)[C@@H](C)OC] |
| 115 | 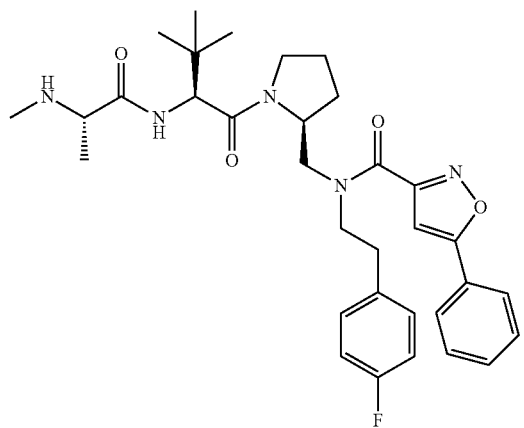 [SMILES: CN[C@@H](C)C(=O)N[C@H](C(=O)N1CCC[C@H]1CN(CCc1ccc(F)cc1)C(=O)c1cc(-c2ccccc2)on1)C(C)(C)C] |

| No. | Structure |
|---|---|
| 116 | 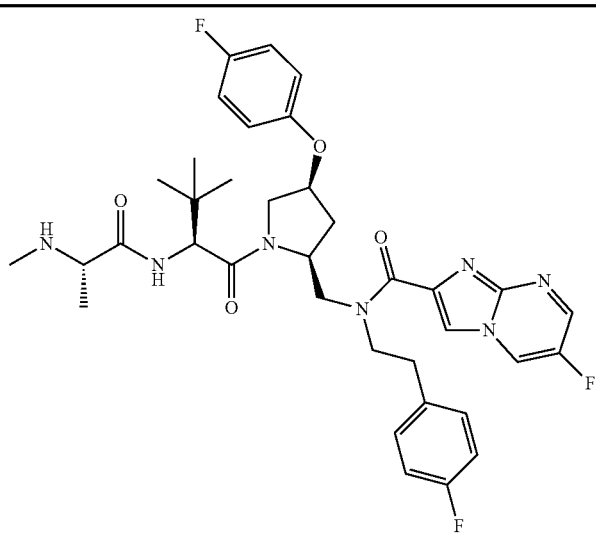 |
| 117 | 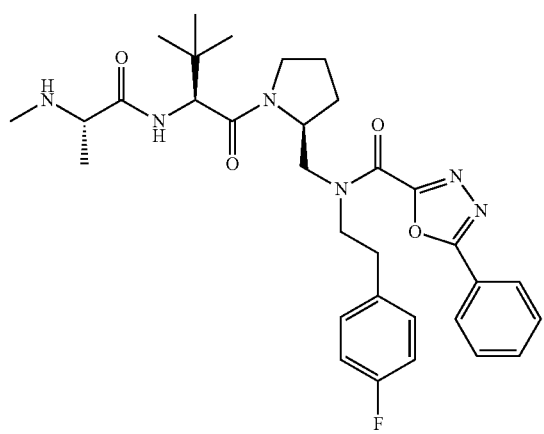 [SMILES: CN[C@@H](C)C(=O)N[C@H](C(=O)N1CCC[C@H]1CN(CCc1ccc(F)cc1)C(=O)c1nnc(-c2ccccc2)o1)C(C)(C)C] |
| 118 | 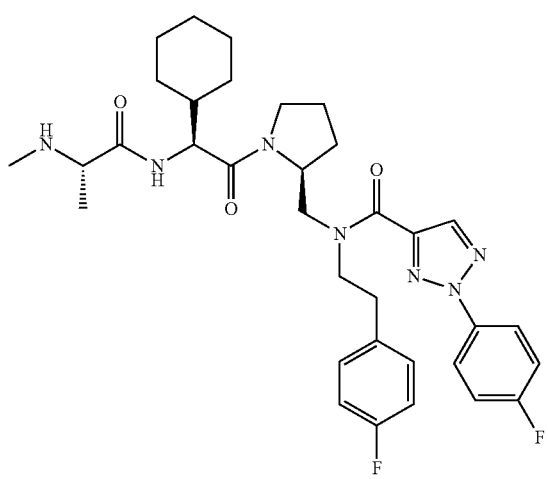 [SMILES: CN[C@@H](C)C(=O)N[C@H](C(=O)N1CCC[C@H]1CN(CCc1ccc(F)cc1)C(=O)c1cnn(-c2ccc(F)cc2)n1)C1CCCCC1] |

| No. | Structure |
|---|---|
| 119 | 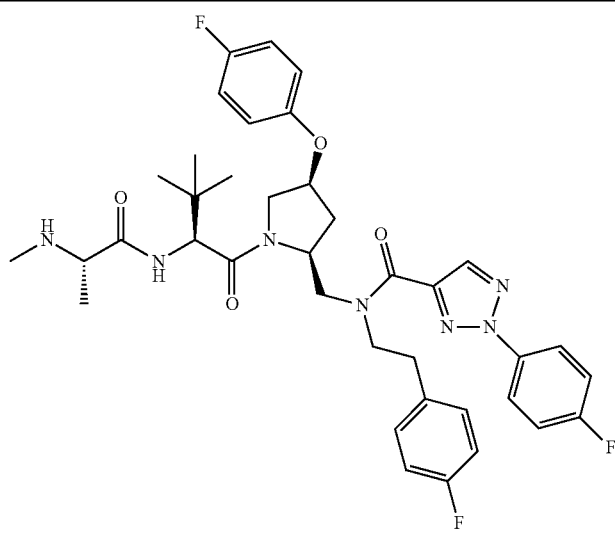 |
| 120 | 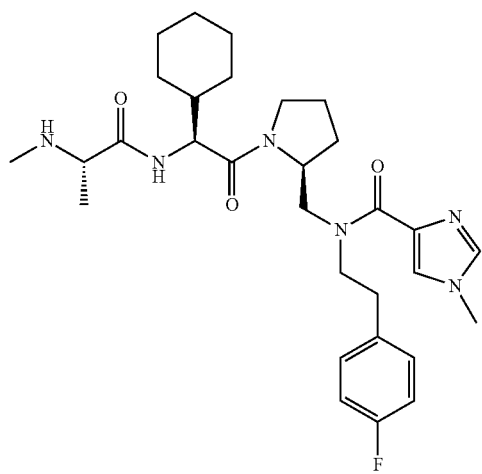 [SMILES: CN[C@@H](C)C(=O)N[C@H](C(=O)N1CCC[C@H]1CN(CCc1ccc(F)cc1)C(=O)c1cn(C)cn1)C1CCCCC1] |
| 121 | 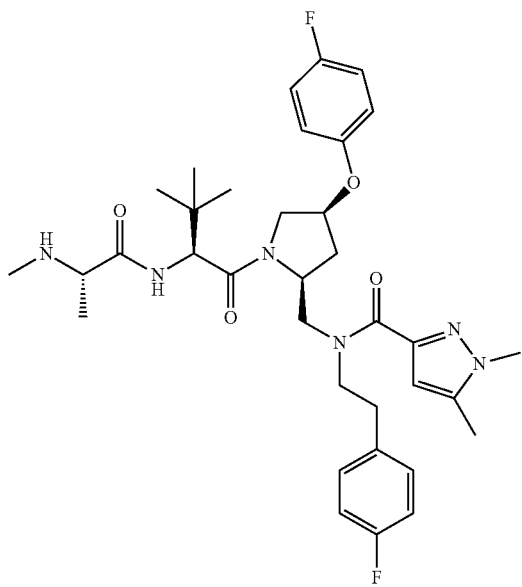 |

| No. | Structure |
|---|---|
| 122 | 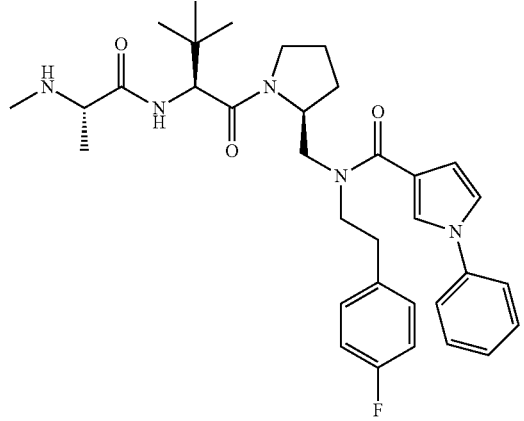 [SMILES: CN[C@@H](C)C(=O)N[C@H](C(=O)N1CCC[C@H]1CN(CCc1ccc(F)cc1)C(=O)c1ccn(-c2ccccc2)c1)C(C)(C)C] |
| 123 | 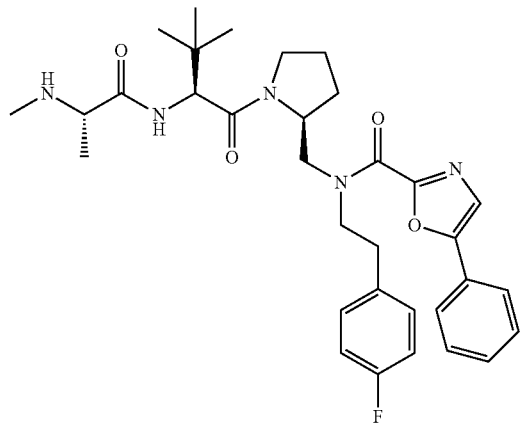 [SMILES: CN[C@@H](C)C(=O)N[C@H](C(=O)N1CCC[C@H]1CN(CCc1ccc(F)cc1)C(=O)c1ncc(-c2ccccc2)o1)C(C)(C)C] |
| 124 | 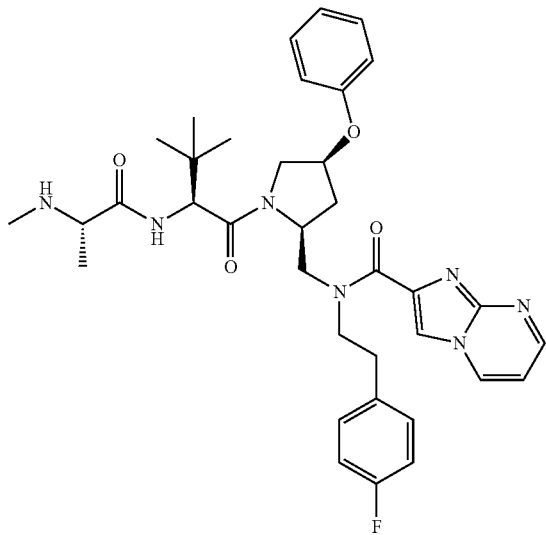 [SMILES: CN[C@@H](C)C(=O)N[C@H](C(=O)N1C[C@@H](Oc2ccccc2)C[C@H]1CN(CCc1ccc(F)cc1)C(=O)c1cn2cccnc2n1)C(C)(C)C] |

-continued

| No. | Structure |
|---|---|
| 125 | 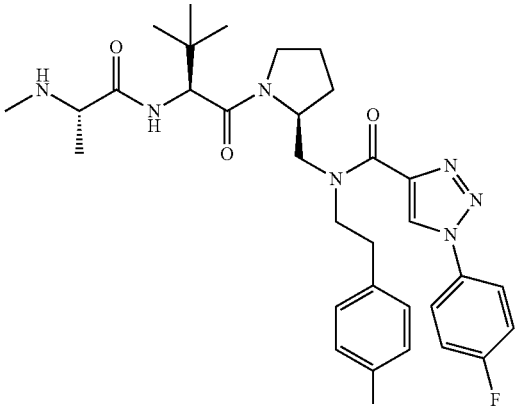 |
| 126 | 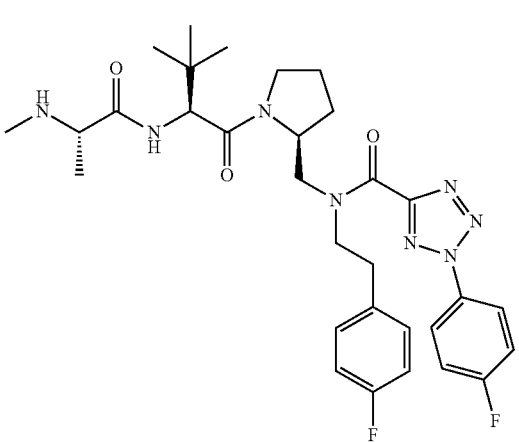 [SMILES: CN[C@@H](C)C(=O)N[C@H](C(=O)N1CCC[C@H]1CN(CCc1ccc(F)cc1)C(=O)c1nnn(-c2ccc(F)cc2)n1)C(C)(C)C] | or pharmaceutically acceptable salt thereof.

14. A method of enhancing apoptosis in a cell or altering the release of inflammatory cytokines from a cell comprising contacting a cell with a compound of claim 1.

15. The method of claim 14, wherein the cell is a lymphocyte, granulocyte or an antigen presenting cell.

16. The method of claim 14, wherein the cell is in a subject, and the cell is contacted with the compound of claim 1 by administering the compound to the subject.

17. The method of claim 14, wherein the cell is in a human.

18. The method of claim 14, further comprising administering to the subject a chemotherapeutic agent and/or a death receptor agonist prior to, simultaneously with, or after administration of the compound of claim 1.

19. The method of claim 18, wherein the death receptor agonist is administered in an amount that produces a synergistic effect.

20. The method of claim 14 further comprising administering TRAIL or a TRAIL receptor antibody prior to, simultaneously with, or after administration of a compound of claim 1.

21. The method of claim 16, wherein the subject is afflicted with a proliferative disease.

22. The method of claim 21, wherein the proliferative disease is cancer or an autoimmune disease or inflammatory disorder.

23. A compound of any of Formulas 2-ii through 2-iv, 4-i, or 4-ii:

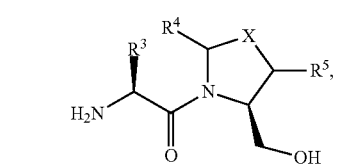

2-ii

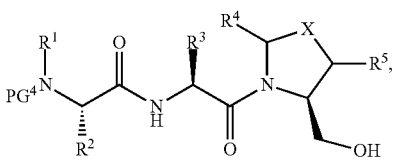

2-iii

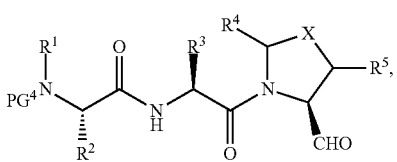

2-iv

-continued

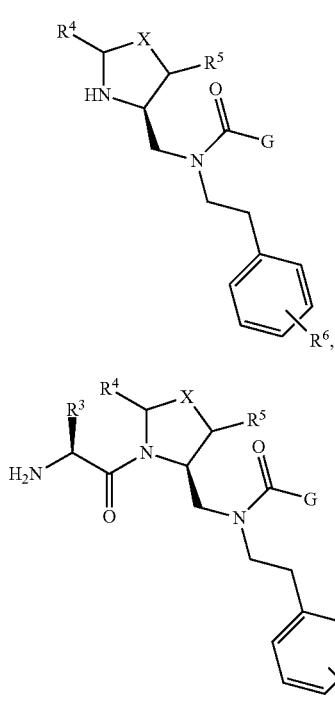

4-ii wherein PG¹, PG², and PG⁴ are protecting groups, and X, G, R¹, R², R³, R⁴, R⁵, and R⁶ are as defined in claim 1.

24. A method of preparing a compound of claim 1 comprising
   (I) combining compound 1-vi with a compound of formula LG-C(O)-G, wherein LG is a leaving group and PG⁴ is a protecting group, followed by deprotection of PG⁴ to provide a compound of Formula 1:

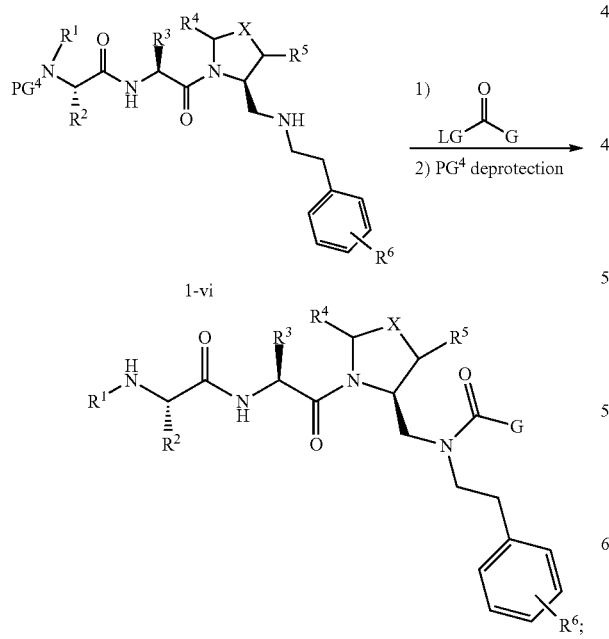

wherein the method optionally further comprises
(a) deprotection of PG² of compound 1-v to provide compound 1-vi, wherein PG² is a protecting group;

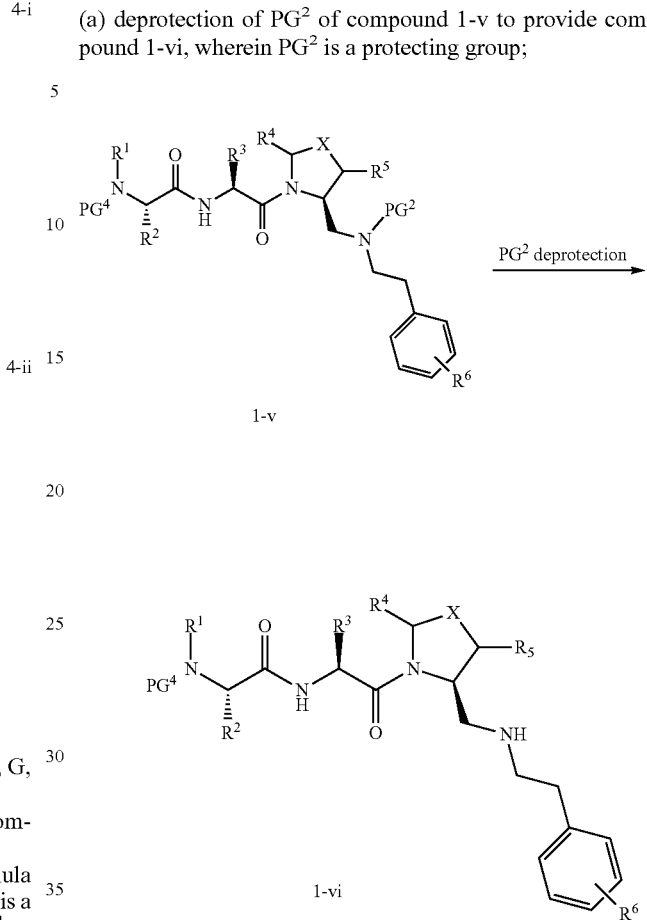

wherein the method optionally further comprises
(b) coupling compound 1-iv with PG⁴(R¹)N(R²)CHCO₂H, wherein PG⁴ is a protecting group that is different from PG², to provide compound 1-v;

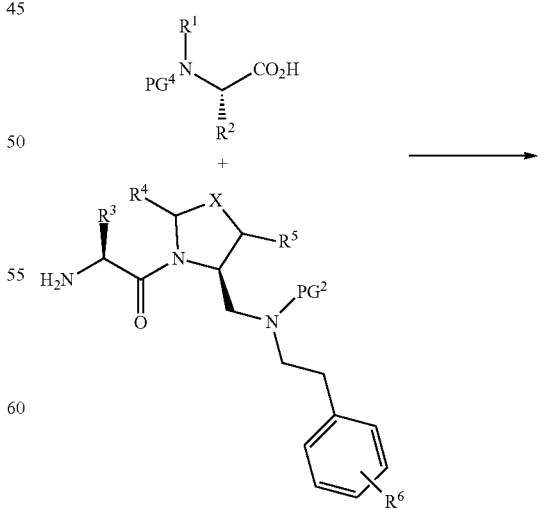

-continued

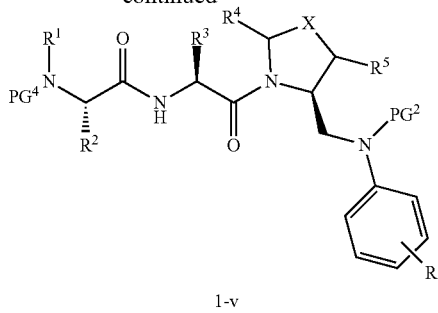

1-v wherein the method optionally further comprises (c) coupling compound 1-iii with $PG^3(H)N(R^3)CHCO_2H$, wherein $PG^3$ is a protecting group that is different from $PG^2$, followed by deprotection of $PG^3$ to provide compound 1-iv;

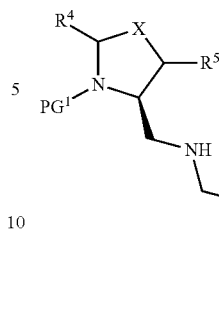

1) coupling
2) $PG^3$ deprotection

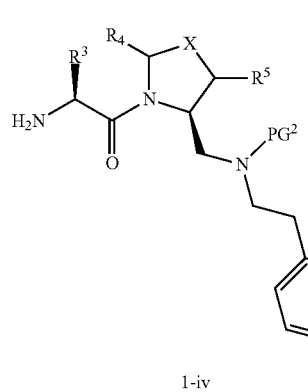

1-iii

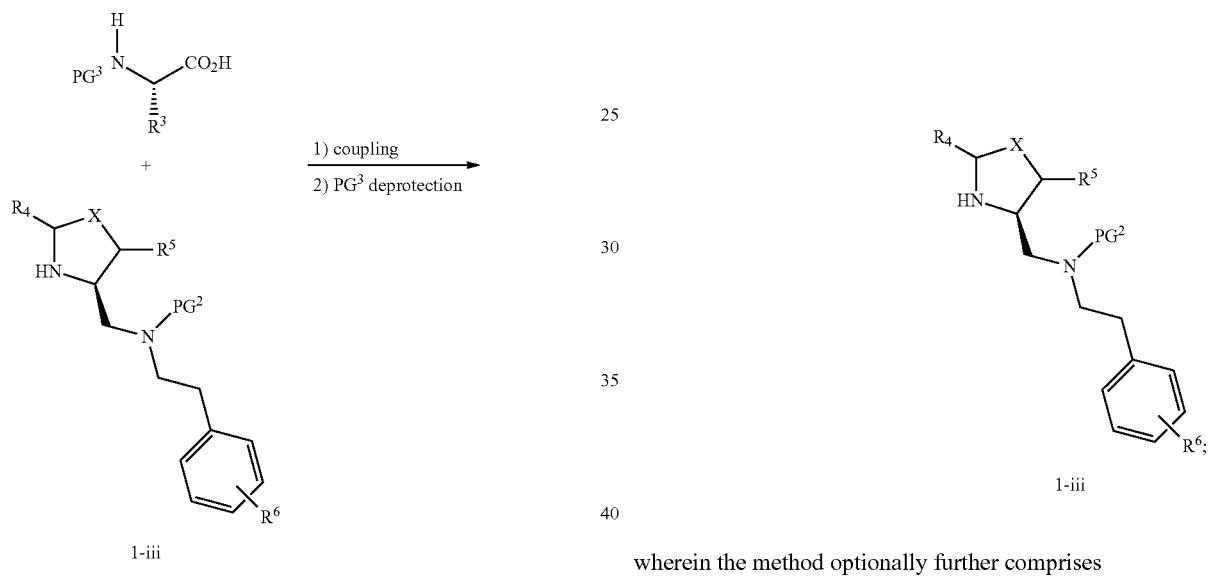

1-ii

1) $PG^2$ protection
2) $PG^1$ protection 1-iii wherein the method optionally further comprises (e) combining compound 1-i with an amine having the formula

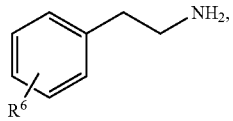

followed by reduction with a hydride, to provide compound 1-ii, wherein $PG^1$ is a protecting group:

1-i 1) 
2) hyride 1-iv wherein the method optionally further comprises (d) protecting the amine group of compound 1-ii with a protecting group ($PG^2$) that is different from $PG^1$, followed by deprotection of $PG^1$ to provide compound 1-iii;

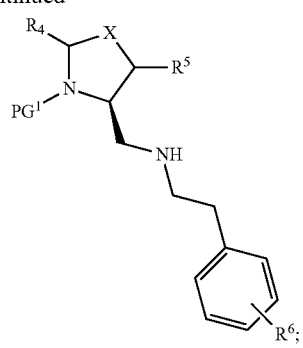

1-ii or (II) combining compound 1-vi with a compound of formula LG-C(O)-G, wherein LG is a leaving group, followed by deprotection of $PG^4$, to provide a compound of Formula 1:

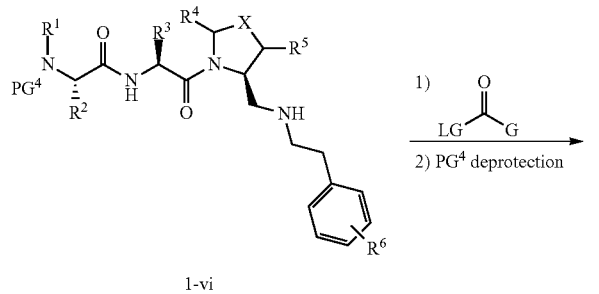

1-vi

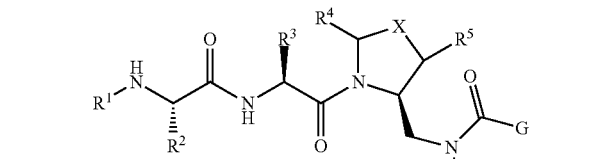

1 wherein the method optionally further comprises
(a) reductive amination of compound 2-iv to provide compound 1-vi:

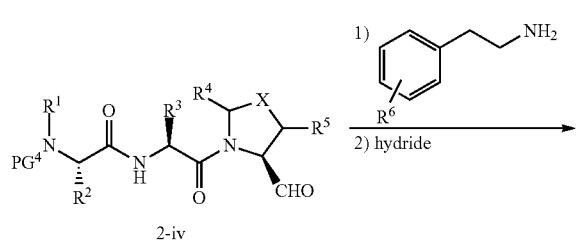

2-iv

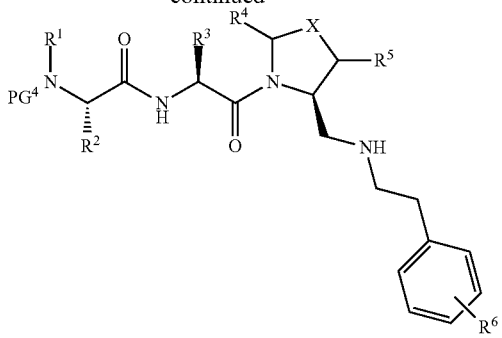

1-vi wherein the method optionally further comprises
(b) oxidizing compound 2-iii to provide compound 2-iv:

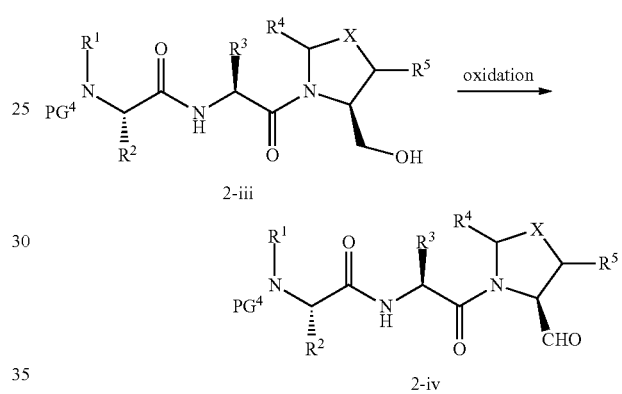

wherein the method optionally further comprises
(c) coupling compound 2-ii with a compound of the formula $PG^4(R^1)N(R^2)CHCO_2H$ to provide compound 2-iii, wherein $PG^4$ is a protecting group:

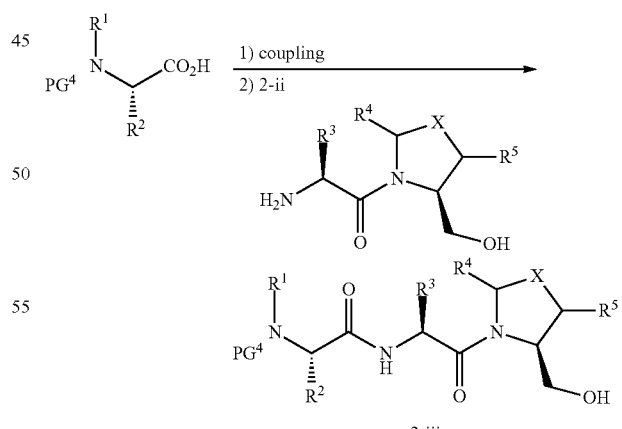

2-iii wherein the method optionally further comprises
(d) coupling compound 2-i with a compound of the formula $PG^3(H)N(R^3)CHCO_2H$, wherein $PG^3$ is a protecting group, followed by deprotection of $PG^3$ to provide intermediate compound 2-ii:

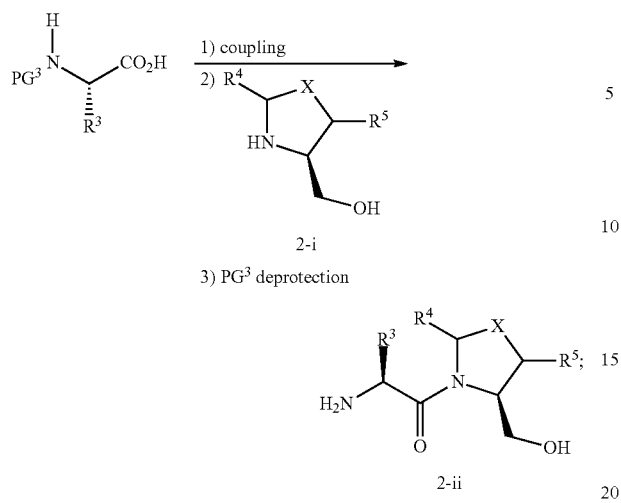

2-i

3) PG³ deprotection

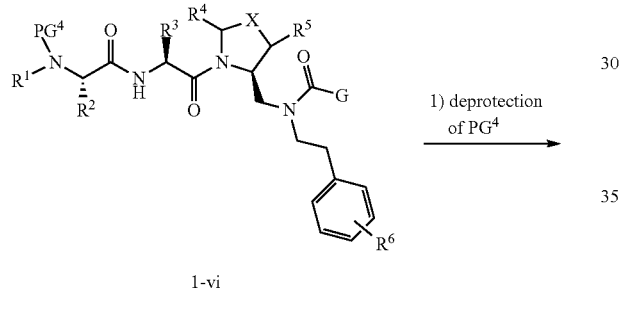

2-ii or (III) deprotecting compound 1-vi to provide a compound of Formula 1:

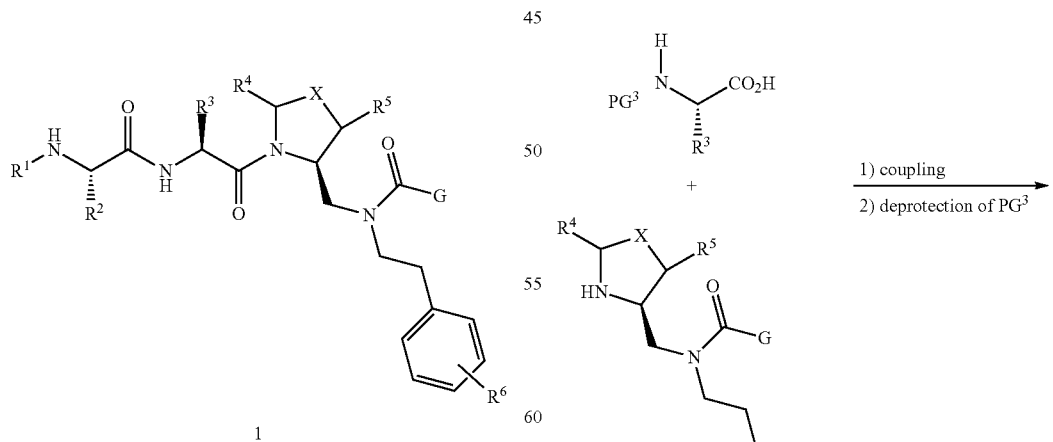

1-vi

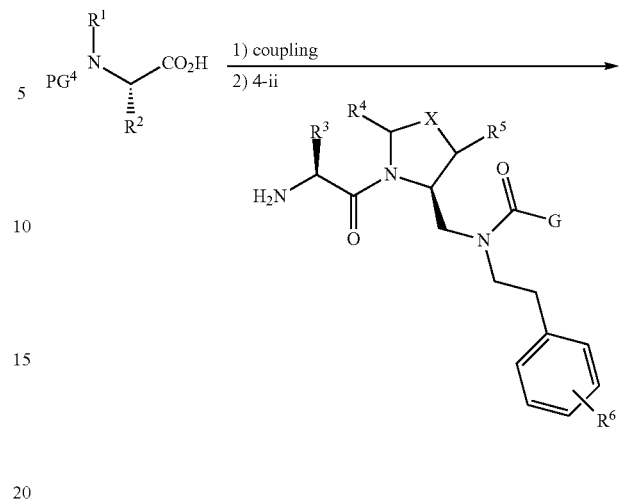

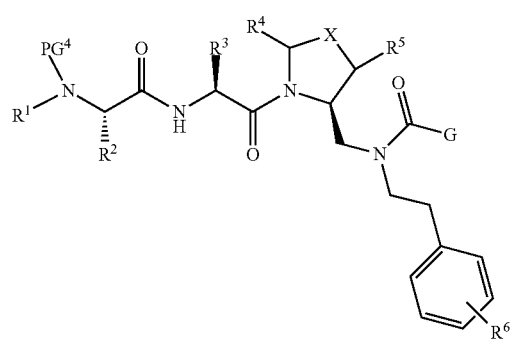

wherein the method optionally further comprises (b) coupling compound 4-i with a compound having the formula PG³(H)N(R³)CHCO₂H, wherein PG³ is a protecting group, followed by deprotection of PG³ to provide compound 4-ii:

wherein the method optionally further comprises (a) coupling compound 4-ii with a compound having the formula PG⁴(R¹)N(R²)CHCO₂H to provide compound 1-vi, wherein PG⁴ is a protecting group:

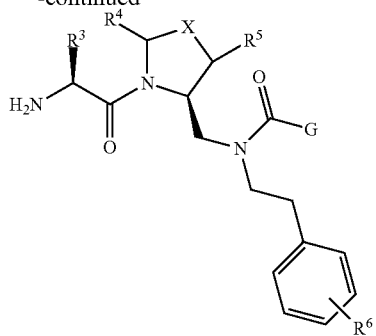

4-ii wherein the method optionally further comprises (c) combining compound 1-ii with a compound of formula LG-C(O)-G, wherein PG$^1$ is a protecting group, followed by deprotection of PG$^1$ to provide intermediate compound 4-i:

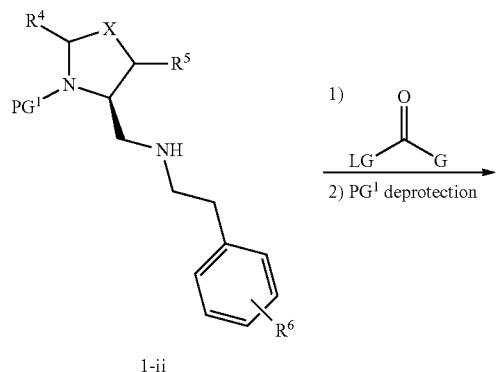

1-ii

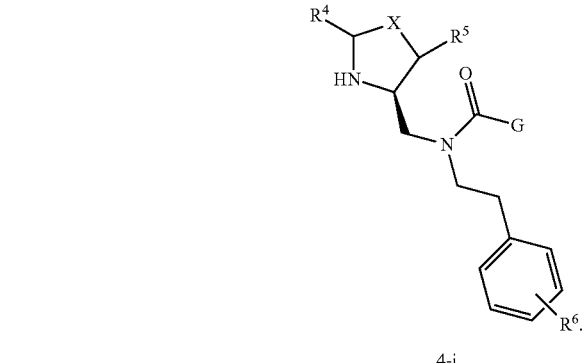

4-i

25. The method of claim 24, wherein the method comprises combining compound 1-vi with a compound of formula LG-C(O)-G, wherein LG is a leaving group and PG$^4$ is a protecting group, followed by deprotection of PG$^4$ to provide a compound of Formula 1:

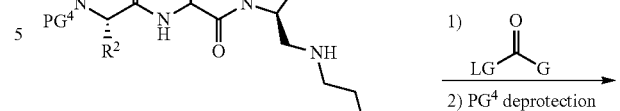

1-vi

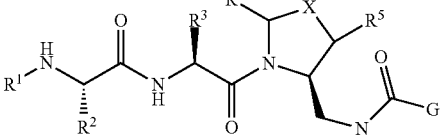

1

26. The method of claim 25, wherein the method further comprises deprotection of PG$^2$ of compound 1-v to provide compound 1-vi, wherein PG$^2$ is a protecting group:

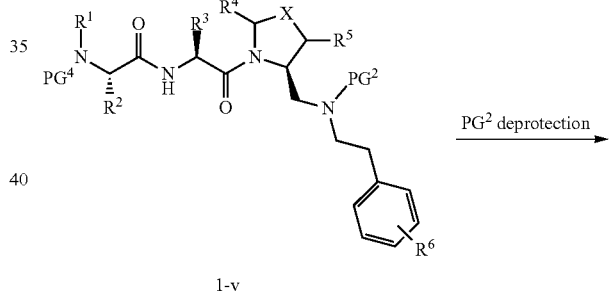

1-v

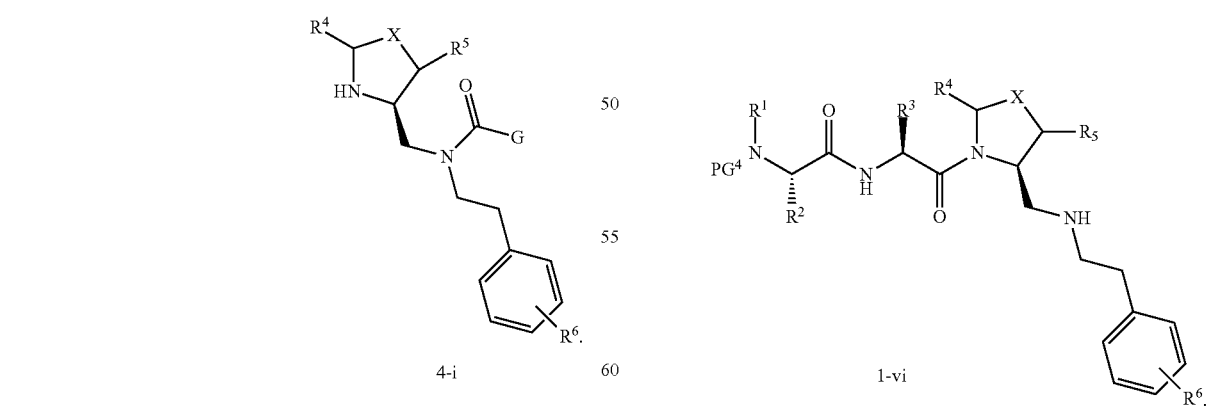

1-vi

27. The method of claim 26, wherein the method further comprises coupling compound 1-iv with PG$^4$(R$^1$)N(R$^2$)CHCO$_2$H, wherein PG$^4$ is a protecting group that is different from PG$^2$, to provide compound 1-v:

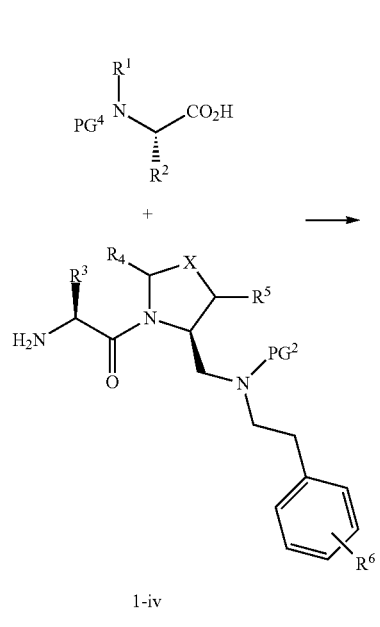

1-iv

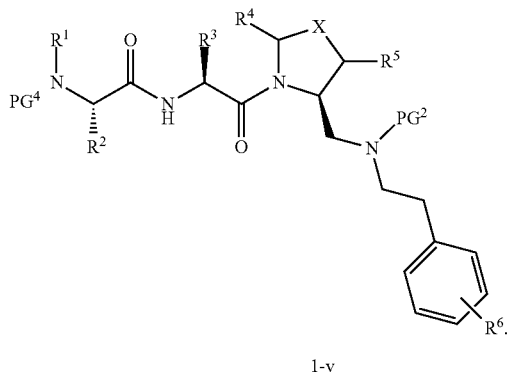

1-v

28. The method of claim 27, wherein the method further comprises coupling compound 1-iii with PG³(H)N(R³)CHCO₂H, wherein PG³ is a protecting group that is different from PG², followed by deprotection of PG³ to provide compound 1-iv;

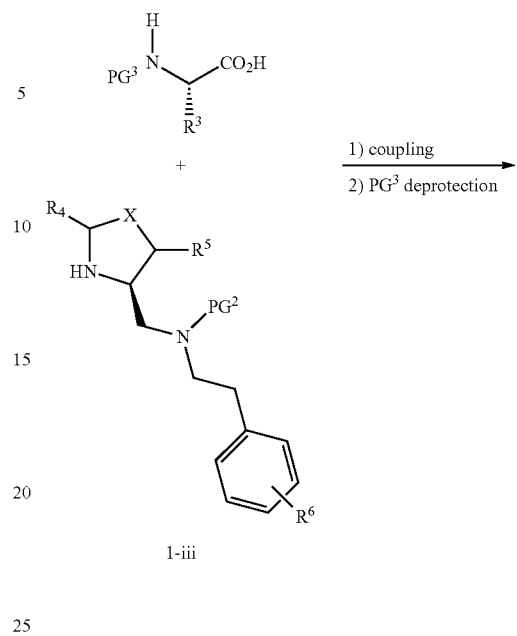

1-iii

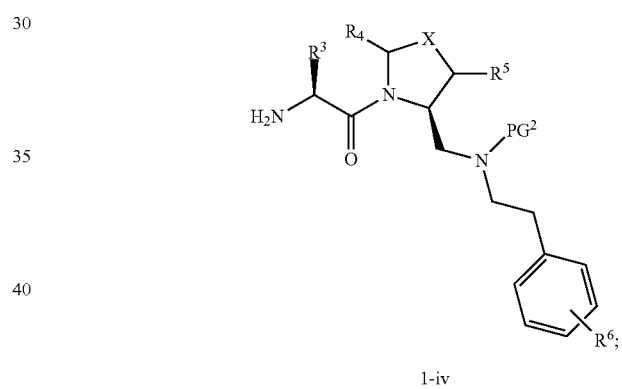

1-iv;

29. The method of claim 28, wherein the method further comprises protecting the amine group of compound 1-ii with a protecting group (PG²) that is different from PG¹, followed by deprotection of PG¹ to provide compound 1-iii:

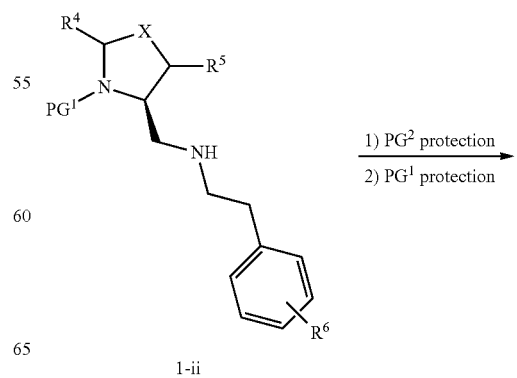

1-ii

-continued

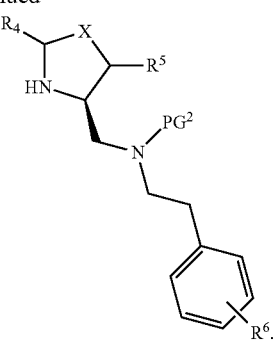

1-iii

30. The method of claim 29, wherein the method further comprises combining compound 1-i with an amine having the formula

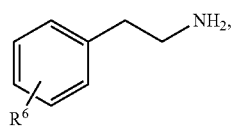

followed by reduction with a hydride, to provide compound 1-ii, wherein $PG^1$ is a protecting group:

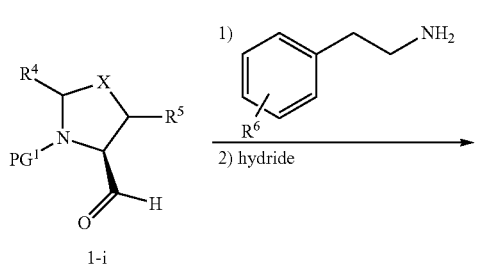

31. The method of claim 24, wherein the method comprises combining a compound of formula 1-vi with a compound of formula LG-C(O)-G, wherein LG is a leaving group, followed by deprotection of $PG^4$, to provide a compound of Formula 1:

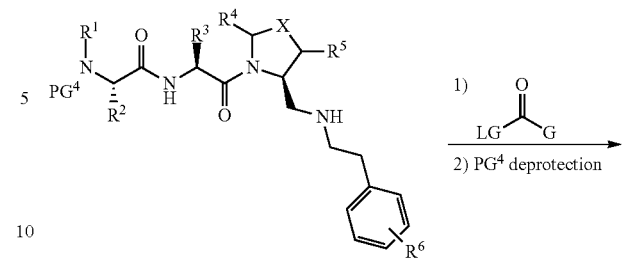

1-vi

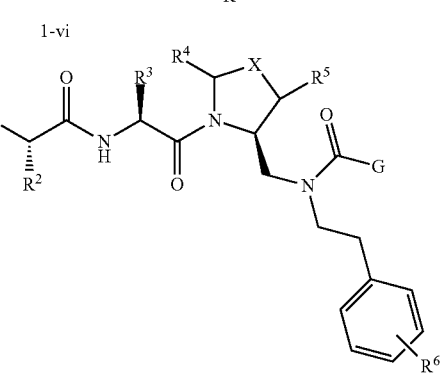

1

32. The method of claim 31, wherein the method further comprises reductive amination of compound 2-iv to provide compound 1-vi:

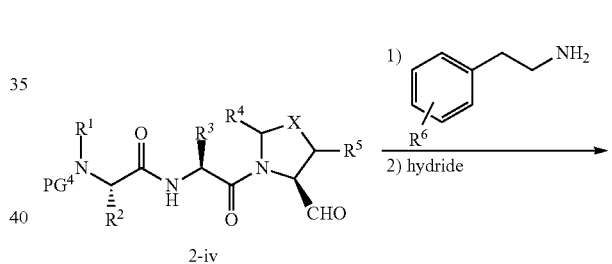

2-iv

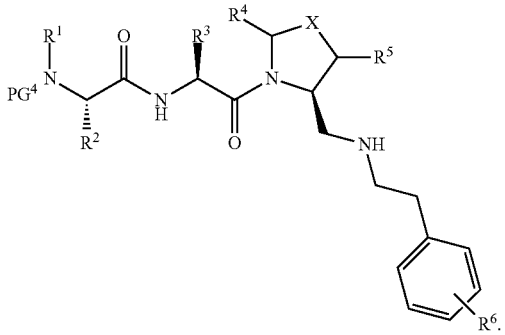

1-vi

33. The method of claim 32, wherein the method further comprises oxidizing compound 2-iii to provide compound 2-iv:

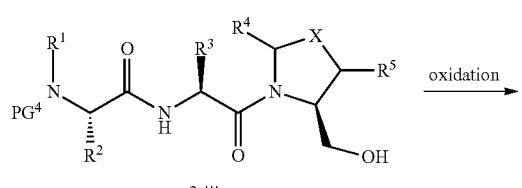

2-iii

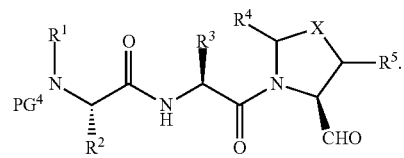

2-iv

34. The method of claim 33, wherein the method further comprises coupling compound 2-ii with a compound of the formula PG$^4$(R$^1$)N(R$^2$)CHCO$_2$H to provide compound 2-iii, wherein PG$^4$ is a protecting group:

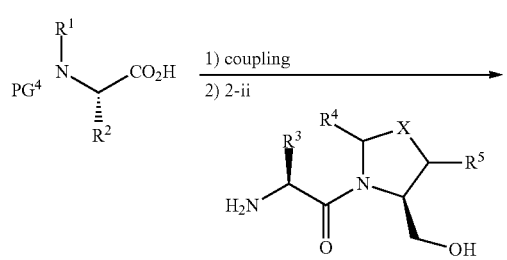

2-iii

35. The method of claim 34, wherein the method further comprises coupling compound 2-i with a compound of the formula PG$^3$(H)N(R$^3$)CHCO$_2$H, wherein PG$^3$ is a protecting group, followed by deprotection of PG$^3$ to provide intermediate compound 2-ii:

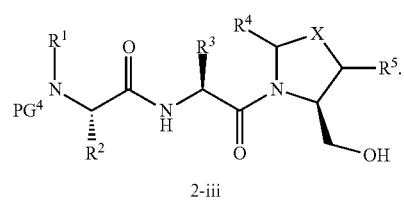

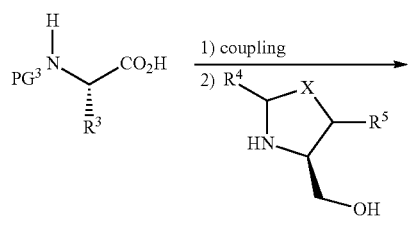

-continued

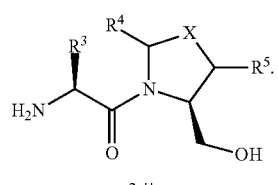

2-ii

36. The method of claim 24, wherein the method comprises deprotecting compound 1-vi to provide a compound of Formula 1:

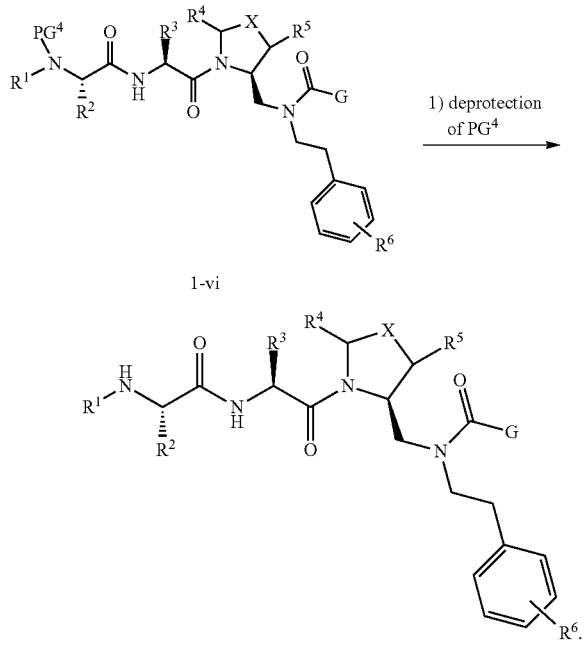

37. The method of claim 36, wherein the method further comprises coupling compound 4-ii with a compound having the formula PG$^4$(R$^1$)N(R$^2$)CHCO$_2$H to provide compound 1-vi, wherein PG$^4$ is a protecting group:

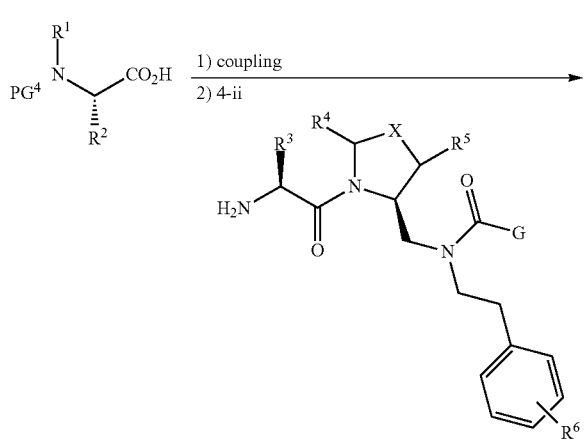

-continued

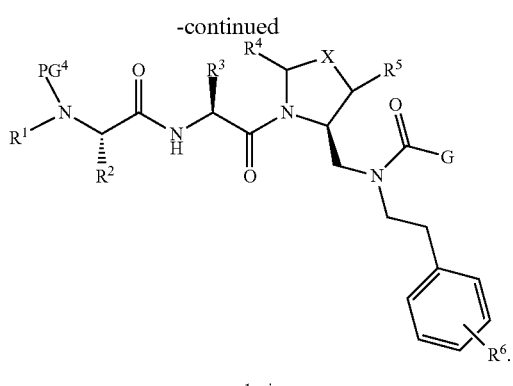

1-vi

38. The method of claim 37, wherein the method further comprises coupling compound 4-i with a compound having the formula $PG^3(H)N(R^3)CHCO_2H$, wherein $PG^3$ is a protecting group, followed by deprotection of $PG^3$ to provide compound 4-ii:

39. The method of claim 38, wherein the method further comprises combining compound 1-ii with a compound of formula LG-C(O)-G, wherein $PG^1$ is a protecting group, followed by deprotection of $PG^1$ to provide intermediate compound 4-i:

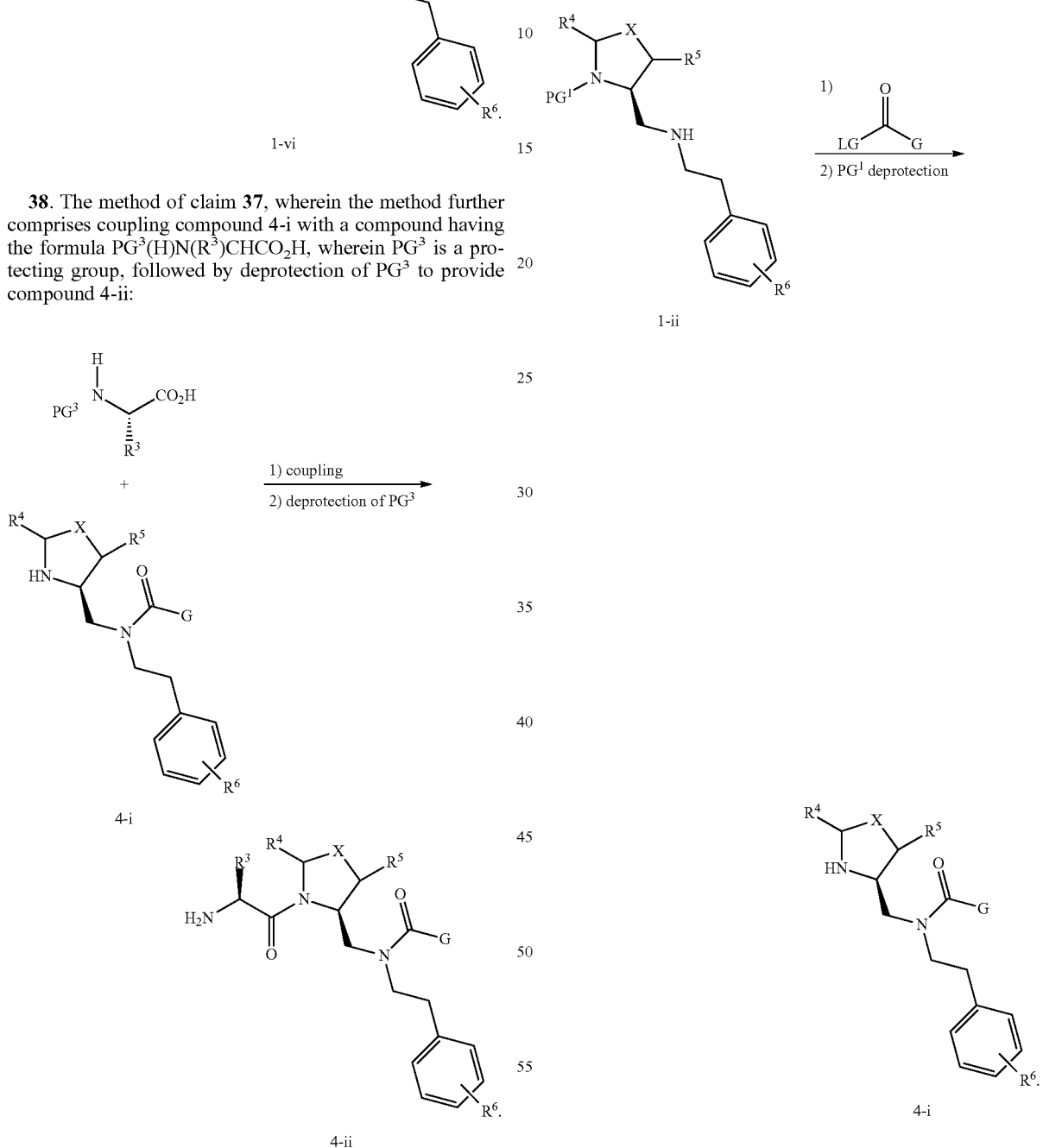

* * * * *

SEQUENCE LISTING

<160> NUMBER OF SEQ ID NOS: 3

<210> SEQ ID NO 1
<211> LENGTH: 28
<212> TYPE: DNA

```
<213> ORGANISM: Artificial Sequence
<220> FEATURE:
<223> OTHER INFORMATION: Synthetic

<400> SEQUENCE: 1
ttaataggat ccatcaacgg cttttatc                                           28

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
gctgcatgtg tgtcagagg                                                     19

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Ala Val Pro Phe Tyr Leu Pro Gly Gly
1               5
```